(12) United States Patent
Schmidt et al.

(10) Patent No.: US 7,723,566 B2
(45) Date of Patent: May 25, 2010

(54) REGENERATION

(75) Inventors: Eduard Daniel Leendert Schmidt, Oosterbeek (NL); Anne Douwe de Boer, Dreumel (NL); Dianne Antoinette Maria van der Kop, Wageningen (NL)

(73) Assignee: Expressive Research, B.V., Wageningen (NL)

(*) Notice: Subject to any disclaimer, the term of this patent is extended or adjusted under 35 U.S.C. 154(b) by 247 days.

(21) Appl. No.: 11/515,613

(22) Filed: Sep. 5, 2006

(65) Prior Publication Data
US 2007/0089182 A1    Apr. 19, 2007

Related U.S. Application Data

(62) Division of application No. 10/111,018, filed as application No. PCT/NL00/00765 on Oct. 22, 1999, now abandoned.

(30) Foreign Application Priority Data
Oct. 22, 1999   (EP) .................................. 99203480

(51) Int. Cl.
*C12N 15/29* (2006.01)
*C12N 15/82* (2006.01)
*C12N 15/87* (2006.01)

(52) U.S. Cl. .................. 800/278; 536/23.6; 435/320.1; 435/419

(58) Field of Classification Search ....................... None
See application file for complete search history.

(56) References Cited

OTHER PUBLICATIONS

Schmidt et al (1997, Development 124:2049-2062).*
Wang et al (2007, Journal of Plant Physiology 164(5):655-664).*
Bowie et al, Science 247:1306-1310, 1990.*
McConnell et al, Nature 411 (6838):709-713, 2001.*
Fourgoux-Nicol et al (1999, Plant Molecular Biology 40 :857-872).*

* cited by examiner

*Primary Examiner*—Stuart F. Baum
(74) *Attorney, Agent, or Firm*—Hoffmann & Baron, LLP

(57) ABSTRACT

The invention relates to the filed of regeneration of cells, self-renewal of (micro-organisms), and the vegetative propagation of plant parts such as plant tissues or organs.

6 Claims, 58 Drawing Sheets

Figure 1

Figure 2:
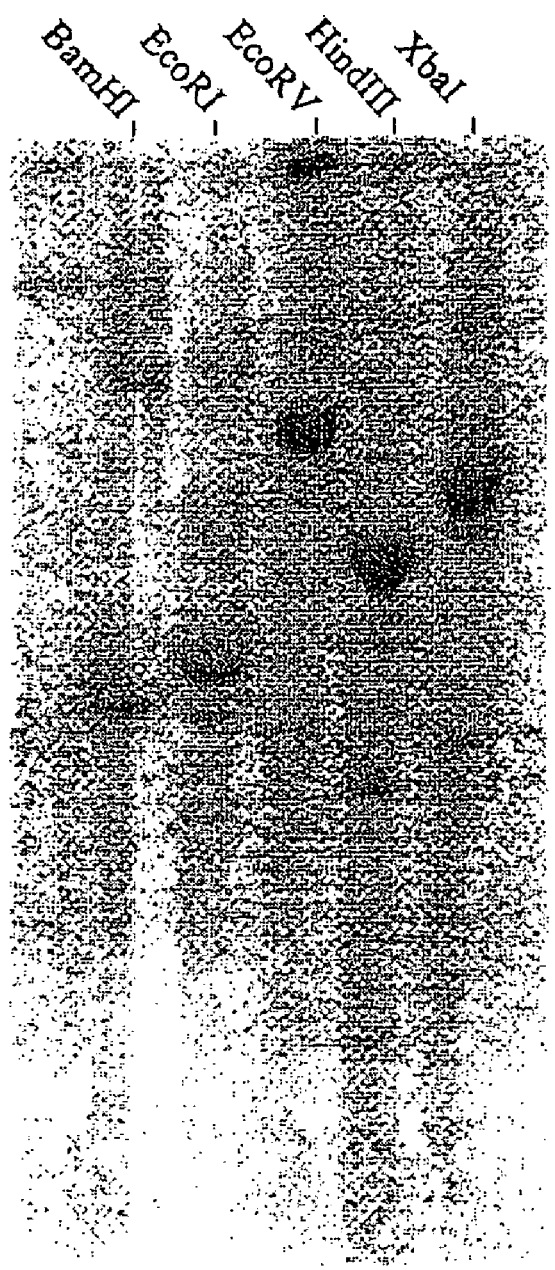

RKS1
TGAGGACTGACCCGTGGATAAGTACTCAGGTGCAATGTGGCCAACAGTTCCACGGACTGCAGTTGTGACATGAGAG
TCTCTATGGTCTAGAAGCTTAGCTAACCCGAAATCACCAACAACTGCTTCGAAGTCCTCATCTAACAGAATGTTAG
CT (SEQ ID NO. 6)

RKS2
TGACGATTTCCCTGTGGATATACATTCTGGTGCAATATGACCCATTGTTCCTCGGACCTGAGTGGTTACATTAGTC
CTTCTAACATCTACCAACTTGGCTAAACCAAAATCACCAACCACTGCTTCAAAGTCTTCATCTAGTAACACATTTG
CA (SEQ ID NO. 7)

RKS3
AGATGATTTTCCTGTGCAGAGATACTCTGGCGCAATGTGACCCATTGTGCCTCGGACTTGAGTTGTGACATGAGTC
AGAGATGTGTCCACAAGCTTAGCTAAACCGAAATCTCCAAGAACTGGCTCAAAATTGTTGTCTAAAAGTATGTTTG
CA (SEQ ID NO. 8)

RKS4
AGATGACTGACCAGTGGAGAGATACTCGGGTGCAATGTGACCAACAGTTCCTCTAACCGCGGTTGTGACATGTGAA
TCCTCGTGGTTGAGTAGCTTTGCTAGTCCAAAATCCCCAACAACTGCTTCAAAATACTCATCTAGGAGAATGTTTG
CT (SEQ ID NO. 9)

RKS5
TGAGGACTGTCCAGTGGAAAGGTACTCGGGAGCGATGTGTCCAATGGTTCCTCGGACTGCGGTAGTGACATGTGAA
TCTCTCTGGTCTAAAAGCTTTGCTAGACCAAAATCGCCAACTATTGCTTCAAAGCTCTCATCAAGTAGAATATTTG
CA (SEQ ID NO. 10)

RKS6
TGATGATTTCCCTGTTGATAAATATTCTGGTGCAATGTGACCCATTGTTCCTCGAACTTGAGTAGTCACATTAGTC
CTTCTAACATCTACTAGCTTGGCTAAACCAAAATCACCAACCACTGCTTCAAAATCTTCATCTAGTAACACGTTAG
CT  (SEQ ID NO. 11)

RKS7
AGAGGATTGACCAGTTGAGAGATACTCTGGAGCAATGTGACCCACCGTGCCTCTAACCGCGGTTGTCACATGAGAA
TCTTGATGATCCAAGAGTTTAGCTAAACCAAAATCGCCAACCACAGCTTCACAGTAGTCATCAAGAAGTATATTCG
CT (SEQ ID NO. 12)

RKS8
TGAAGATTTTCCAGTTGAGAGATACTCAGGAGCAATGTGTCCAATAGTTCCACGCACAGCCGTTGTGACATGTGTA
TCTTTATAATCCATAAGCCTAGCTAACCCGAAATCACCTACCACCGCCTCAAATTCCTCGTCCAACAGAATATTAG
CA (SEQ ID NO. 13)

RKS10
TGATGATTTTCCAGTGGAAAGGTACTCAGGGGCTATATGACCAATTGTCCCACGCACTGCGGTTGTCACATGTGTG
TCTTTGTAGTCCATGAGTTTTGCAAGTCCAAAATCCCCAACCACGGCTTCAAACTCTTCATCCAACAAAATATTTG
CA (SEQ ID NO. 14)

RKS11
AGAAGACTGACCAGTGGAGAGATATTCAGGTGCAATGTGGCCAACCGTACCACGGACCGCAGTTGTGACATGAGAA
TCCGCATGGTTAAGGAGCTTTGCGAGTCCAAAGTCACCAACAACAGCTTCAAAGCACTCGTCTAAGAGAATATTAG
CT (SEQ ID NO. 15)

RKS12
AGAAGATTTTCCTGTCGAGAGGTACTCGGGAGCTATATGGCCAATCGTACCGCGTACAGCAGTTGTCACATGGGAG
TCATTGTAATTCATTAATTTTGCTAGCCCAAAGTCTCCAACAACAGCTTCAAACTCTTCATCTAACAGTATATTTG
CA (SEQ ID NO. 16)

Fig. 1 CONTD.

RKS13
TGCTAATATATTGTTAGATGAAGAGTTTGAAGCTGTTGTTGGAGATTTTGGGCTCGCAAAATTAATGAATTATAAT
GACTCCCATGTGACAACTGCTGTACGCGGTACAATTGGCCATATAGCGCCCGAGTACCTCTCGACAGGAAAATCTT
CT (SEQ ID NO. 17)

RKS14
TGCGAACATACTTCTTGACGATTACTTTGAAGCTGTTGTCGGAGATTTCGGGTTGGCTAAGCTTTTGGATCATGAG
GAGTCGCATGTGACAACCGCCGTGAGAGGAACAGTGGGTCACATTGCACCTGAGTATCTCTCAACAGGACAATCTT
CT (SEQ ID NO. 18)

RKS0
TGAAGATTTTCCGGTTGAGAGATATTCTGGAGCGATGTGACCGATGGTGCCACGGACTGCTGTTGTCACGTGAGTG
TCTTTATAGTCCATAAGCTTTGCCAACCCGAAATCTCCAACAACCGCTTCGAATTCTTCGTCTAAGAGGATGTTTG
CT (SEQ ID NO. 19)

5 x SSC

Figure 4a
Arabidopsis thaliana RKS0 cDNA

1/1                                       31/11
att ttt att tta ttt ttt act ctt tgt ttg ttt taa tgc taa tgg gtt ttt aaa agg gtt 61/21                                     91/31
atc gaa aaa atg agt gag ttt gtg ttg agg ttg tct ctg taa agt gtt aat ggt ggt gat 121/41                                    151/51
ttt cgg aag tta ggg ttt tct cgg atc tga aga gat caa atc aag att cga aat tta cca 181/61                                    211/71
ttg ttg ttt gaa ATG GAG TCG AGT TAT GTG GTG TTT ATC TTA CTT TCA CTG ATC TTA CTT 241/81                                    271/91
CCG AAT CAT TCA CTG TGG CTT GCT TCT GCT AAT TTG GAA GGT GAT GCT TTG CAT ACT TTG 301/101                                   331/111
AGG GTT ACT CTA GTT GAT CCA AAC AAT GTC TTG CAG AGC TGG GAT CCT ACG CTA GTG AAT 361/121                                   391/131
CCT TGC ACA TGG TTC CAT GTC ACT GCA AAC AAC GAG AAC AGT GTC ATA AGA GTT GAT TTG 421/141                                   451/151
GGG AAT GCA GAG TTA TCT GGC CAT TTA GTT CCA GAG CTT GGT GTG CTC AAG AAT TTG CAG 481/161                                   511/171
TAT TTG GAG CTT TAC AGT AAC AAC ATA ACT GGC CCG ATT CCT AGT AAT CTT GGA AAT CTG 541/181                                   571/191
ACA AAC TTA GTG AGT TTG GAT CTT TAC TTA AAC AGC TTC TCC GGT CCT ATT CCG GAA TCA 601/201                                   631/211
TTG GGA AAG CTT TCA AAG CTG AGA TTT CTC CGG CTT AAC AAC AAC AGT CTC ACT GGG TCA 661/221                                   691/231
ATT CCT ATG TCA CTG ACC AAT ATT ACT ACC CTT CAA GTG TTA GAT CTA TCA AAT AAC AGA 721/241                                   751/251
CTC TCT GGT TCA GTT CCT GAC AAT GGC TCC TTC TCA CTC TTC ACA CCC ATC AGT TTT GCT 781/261                                   811/271
AAT AAC TTA GAC CTA TGT GGA CCT GTT ACA AGT CAC CCA TGT CCT GGA TCT CCC CCG TTT 841/281                                   871/291
TCT CCT CCA CCA CCT TTT ATT CAA CCT CCC CCA GTT TCC ACC CCG AGT GGG TAT GGT ATA 901/301                                   931/311
ACT GGA GCA ATA GCT GGT GGA GTT GCT GCA GGT GCT GCT TTG CCC TTT GCT GCT CCT GCA 961/321                                   991/331
ATA GCC TTT GCT TGG TGG CGA CGA AGA AGC CCA CTA GAT ATT TTC TTC GAT GTC CCT GCC 1021/341                                  1051/351
GAA GAA GAT CCA GAA GTT CAT CTG GGA CAG CTC AAG AGG TTT TCT TTG CGG GAG CTA CAA 1081/361                                  1111/371
GTG GCG AGT GAT GGG TTT AGT AAC AAG AAC ATT TTG GGC AGA GGT GGG TTT GGG AAA GTC 1141/381                                  1171/391
TAC AAG GGA CGC TTG GCA GAC GGA ACT CTT GTT GCT GTC AAG AGA CTG AAG GAA GAG CGA 1201/401                                  1231/411
ACT CCA GGT GGA GAG CTC CAG TTT CAA ACA GAA GTA GAG ATG ATA AGT ATG GCA GTT CAT 1261/421                                  1291/431
CGA AAC CTG TTG AGA TTA CGA GGT TTC TGT ATG ACA CCG ACC GAG AGA TTG CTT GTG TAT 1321/441                                  1351/451
CCT TAC ATG GCC AAT GGA AGT GTT GCT TCG TGT CTC AGA GAG AGG CCA CCG TCA CAA CCT

Fig. 4a CONTD.

```
1381/461                                1411/471
CCG CTT GAT TGG CCA ACG CGG AAG AGA ATC GCG CTA GGC TCA GCT CGA GGT TTG TCT TAC

1441/481                                1471/491
CTA CAT GAT CAC TGC GAT CCG AAG ATC ATT CAC CGT GAC GTA AAA GCA GCA AAC ATC CTC

1501/501                                1531/511
TTA GAC GAA GAA TTC GAA GCG GTT GTT GGA GAT TTC GGG TTG GCA AAG CTT ATG GAC TAT

1561/521                                1591/531
AAA GAC ACT CAC GTG ACA ACA GCA GTC CGT GGC ACC ATC GGT CAC ATC GCT CCA GAA TAT

1621/541                                1651/551
CTC TCA ACC GGA AAA TCT TCA GAG AAA ACC GAC GTT TTC GGA TAC GGA ATC ATG CTT CTA

1681/561                                1711/571
GAA CTA ATC ACA GGA CAA AGA GCT TTC GAT CTC GCT CGG CTA GCT AAC GAC GAC GAC GTC

1741/581                                1771/591
ATG TTA CTT GAC TGG GTG AAA GGA TTG TTG AAG GAG AAG AAG CTA GAG ATG TTA GTG GAT

1801/601                                1831/611
CCA GAT CTT CAA ACA AAC TAC GAG GAG AGA GAA CTG GAA CAA GTG ATA CAA GTG GCG TTG

1861/621                                1891/631
CTA TGC ACG CAA GGA TCA CCA ATG GAA AGA CCA AAG ATG TCT GAA GTT GTA AGG ATG CTG

1921/641                                1951/651
GAA GGA GAT GGG CTT GCG GAG AAA TGG GAC GAA TGG CAA AAA GTT GAG ATT TTG AGG GAA

1981/661                                2011/671
GAG ATT GAT TTG AGT CCT AAT CCT AAC TCT GAT TGG ATT CTT GAT TCT ACT TAC AAT TTG

2041/681                                2071/691
CAC GCC GTT GAG TTA TCT GGT CCA AGG taa aaa aaa aaa aaa aaa aa (SEQ ID NO. 20)
```

Figure 4B

MESSYVVFILLSLILLPNHSL
WLASANLEG

DALHTLRVTLVDP
NNVLQSWDPTLVN

PCTWFHVTCNNENSVIRV

DLGNAELSGHLV
P ELGVLKNLQYLELYSNNITGPI
PSNLGNLTNLVSLDLYLNSFSGPI
PESLGKLSKLRFLRLNNNSLTGSI
PMSLTNITTLQVLDLSNNRLSGSV
PDNGSFSLFTPISFANNLDLCGPV

TSHPCPGSPPFSPPPP
FIQPPPVSTPSGYGITG

AIAGGVAAGAAL
PFAAPAIAFAWW

RRRSPLDIFFDVPAEEDPE
VHLGQLKRFSLRELQVAS

DGFSNKNILGRGGFGKVYKGRLAD
GTLVAVKRLKEERTPGGELQFQ
TEVEMISMAVHRNLLRLRGFCM
TPTERLLVYPYMANGSVASCLR
ERPPSQPPLDWPTRKRIALGSA
RGLSYLHDHCDPKIIHRDVKAA
NILLDEEFEAVVGDFGLAKLMD
YKDTHVTTAVRGTIGHIAPEYL
STGKSSEKTDVFGYGIMLLELI
TGQRAFDLARLANDDDVMLLDW
VKGLLKEKKLEMLVDPDLQTNY
EERELEQVIQVALLCTQGSPME
RPKMSEVVRMLE

GDGLAEKWDEWQKVEILREEIDLS

PNPNSDWILDSTYNLHAVELSGPR (SEQ ID NO. 21)

Figure 6C
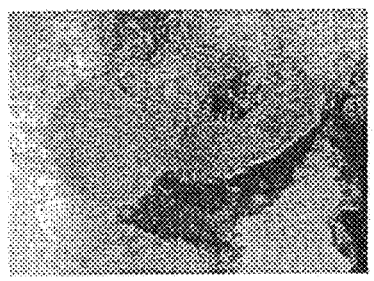 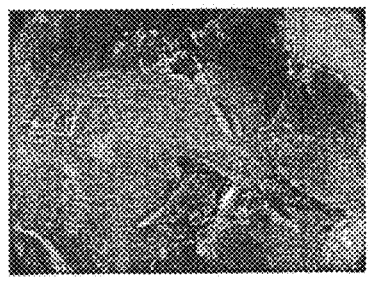
plant 1      plant 2

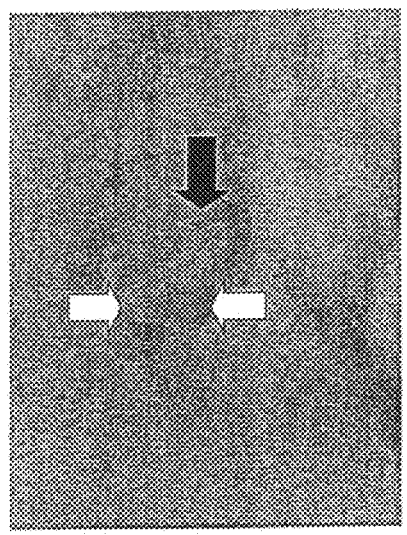
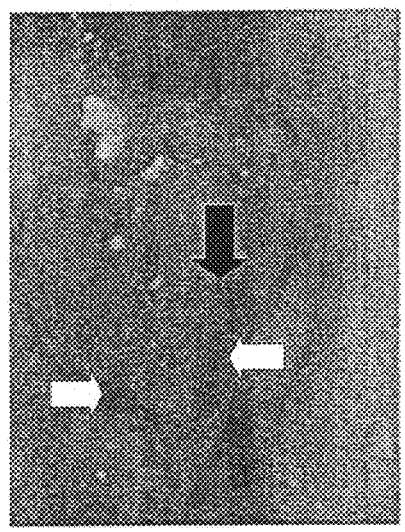
Figure 6F

Figure 7. Predicted protein domains of the RKS subfamily I rks6

MRMFSL
QKMAMAFTLLFFACLCSFVSPDAQG

DALFALRISLRALP
NQLSDWNQNQVN

PCTWSQVICDDKNFVTSL

TLSDMNFSGTLSSRV
GILENLKTLTLKGNGITGEI
PEDFGNLTSLTSLDLEDNQLTGRI
PSTIGNLKKLQFLTLSRNKLNGTI
PESLTGLPNLLNLLLDSNSLSGQI
PQSLFEIPKYNFTSNNLNCGG

RQPHPCVSAVAHSGDSSKPKTG

IIAGVVAGVTVVL
FGILLFLFC

KDRHKGYRRDVFVDVAGE
VDRRIAFGQLKRFAWRELQLAT

DNFSEKNVLGQGGFGKVYKGVLPD
TPKVAVKRLTDFESPGGDAAFQ
REVEMISVAVHRNLLRLIGFCT
TQTERLLVYPFMQNLSLAHRLR
EIKAGDPVLDWETRKRIALGAA
RGFEYLHEHCNPKIIHRDVKAA
NVLLDEDFEAVVGDFGLAKLVD
VRRTNVTTQVRGTMGHIAPEYL
STGKSSERTDVFGYGIMLLELV
TGQRAIDFSRLEEEDDVLLLDH
VKKLEREKRLGAIVDKNLDGEY
IKEEVEMMIQVALLCTQGSPED
RPVMSEVVRMLE

GEGLAERWEEWQNVEVTRRHEFE

RLQRRFDWGEDSMHNQDAIELSGGR
SEQ ID NO. 23 rks2

MALLIITALVFSSL
WSSVSPDAQG

DALFALRSSLR
ASPEQLSDWNQNQVD

PCTWSQVICDDKKHVTSV

TLSYMNFSSGTLSSGI
G ILTTLKTLTLKGNGIMGGI
PESIGNLSSLTSLDLEDNHLTDRI
PSTLGNLKNLQFFFTANNLSCGG

TFPQPCVTESSPSGDSSSRKTG

IIAGVVSGIAVIL
LGFFFFFFC

KDKHKGYKRDVFVDVAGTNFKKGLISGE
VDRRIAFGQLRRFAWRELQLAT

DEFSEKNVLGQGGFGKVYKGLLSD
GTKVAVKRLTDFERPGGDEAFQ
REVEMISVAVHRNLLRLIGFCT
TQTERLLVYPFMQNLSVAYCLR
EIKPGDPVLDWFRRKQIALGAA
RGLEYLHEHCNPKIIHRDVKAA
NVLLDEDFEAVVGDFGLAKLVD
VRRTNVTTQVRGTMGHIAPECI
STGKSSEKTDVFGYGIMLLELV
TGQRAIDFSRLEEEDDVLLLDH
VKKLEREKRLEDIVDKKLDEDY
IKEEVEMMIQVALLCTQAAPEE
RPAMSEVVRMLE

GEGLAERWEEWQNLEVTRQEEFQ

RLQRRFDWGEDSINNQDAIELSGGR
SEQ ID NO. 24 rks3

MALAFVGITSS
TTQPDIEG

GALLQLRDSLNDSSNRL
KWTRDFVS

PCYSWSYVTCRGQSVVAL

NLASSGFTGTLS
P AITKLKFLVTLELQNNSLSGAL
PDSLGNMVNLQTLNLSVNSFSGSI
PASWSQLSNLKHLDLSSNNLTGSI
PTQFFSIPTFEFSGTQLICGKS

LNQPCSSSRLPVTSSKKKLRD

ITLTASCVASIIL
FLGAMVMYHHH

RVRRTKYDIPFDVAGEDDR
KISFGQLKRFSLREIQLAT

DSFNESNLIGQGGFGKVYRGLLPD
KTKVAVKRLADYFSPGGEAAFQ
REIQLISVAVHKNLLRLIGFCT
TSSERILVYPYMENLSVAYRLR
DLKAGEEGLDWPTRKRVAFGSA
HGLEYLHEHCNPKIIHRDLKAA
NILLDNNFEPVLGDFGLAKLVD
TSLTHVTTQVRGTMGHIAPEYL
CTGKSSEKTDVFGYGITLLELV
TGQRAIDFSRLEEEENILLLD
HIKKLLREQRLRDIVDSNLTTY
DSKEVETIVQVALLCTQGSPED
RPAMSEVVKMLQ

GTGGLAEKWTEWEQLEEVRNKEALLL

PTLPATWDEEETTVDQESIRLSTAR
SEQ ID NO. 25

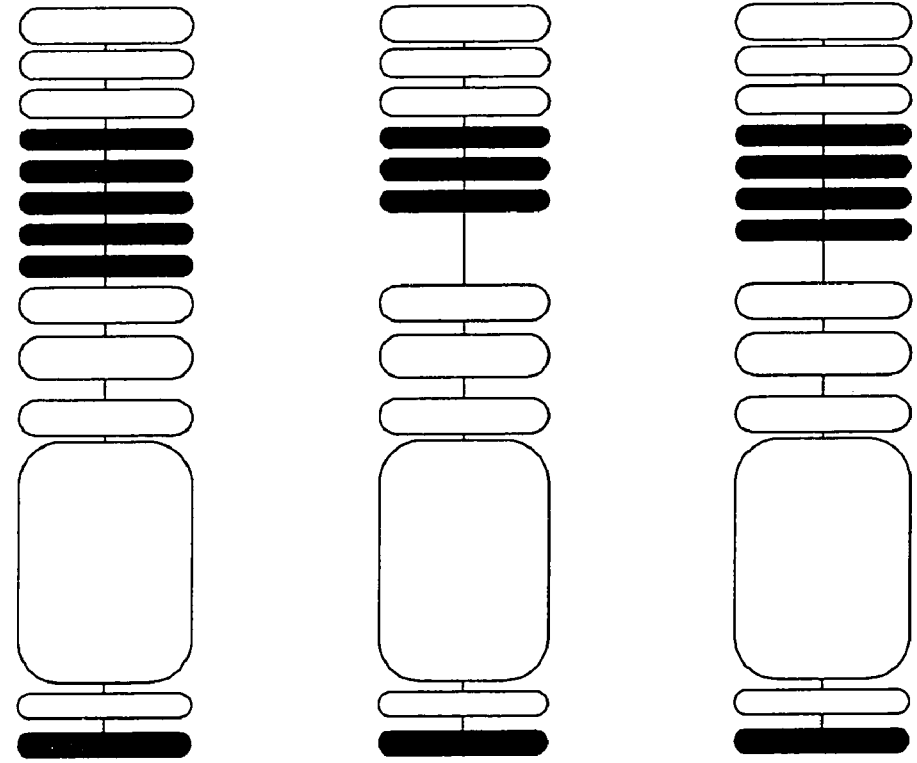

Figure 7. Predicted protein domains of the RKS subfamily II
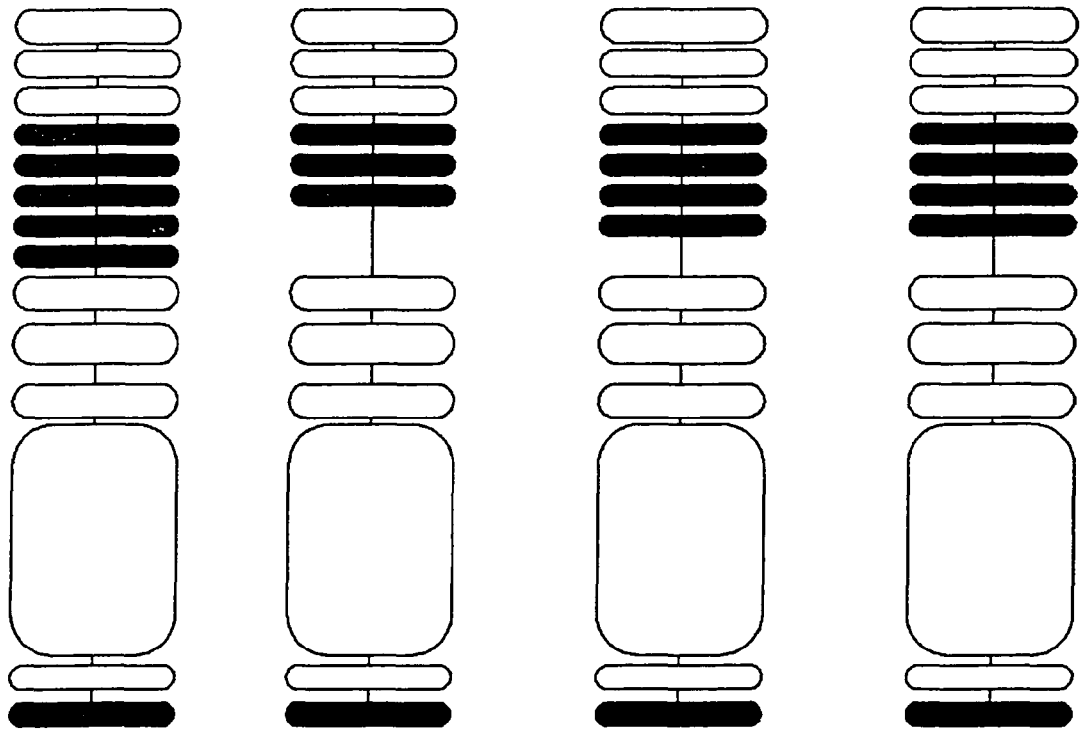

Figure 7. Predicted protein domains of the RKS subfamily III
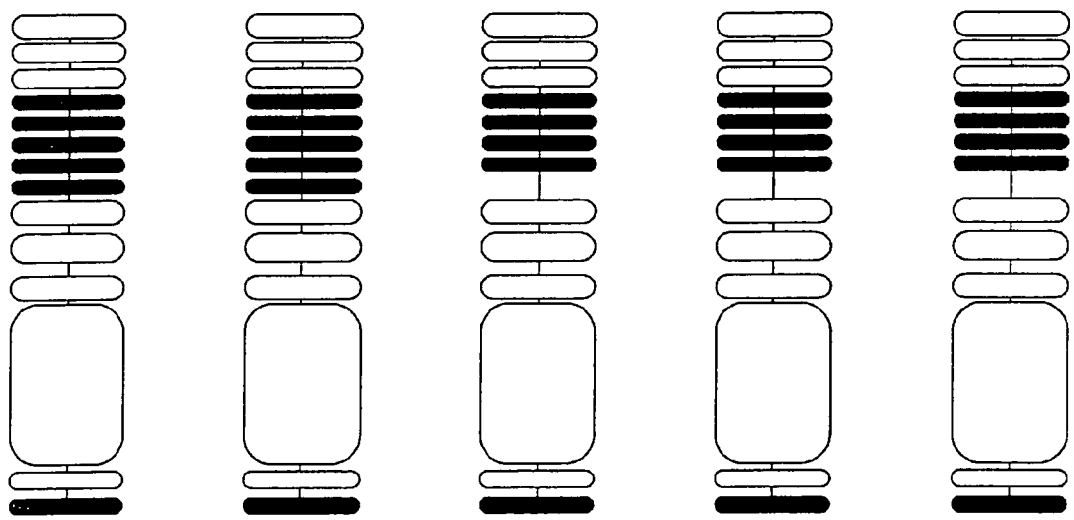

Figure 8a
Arabidopsis thaliana RKS1 cDNA

```
1/1                             31/11
cca aag ttg att gct tta aga agg gat ATG gaa ggt gtg aga ttt gtg gtg tgg aga tta 61/21                           91/31
gga ttt ctg gtt ttt gta tgg ttc ttt gat atc tct tct gct aca ctt tct cct act ggt 121/41                          151/51
gta aac tat gaa gtg aca gct ttg gtt gct gtg aag aat gaa ttg aat gat ccg tac aaa 181/61                          211/71
gtt ctt gag aat tgg gat gtg aat tca gtt gat cct tgt agc tgg aga atg gtt tct tgc 241/81                          271/91
act gat ggc tat gtc tct tca ctg gtg ttg caa aac aat gca atc act ggt cca att ccg 301/101                         331/111
gaa acg att ggg agg ttg gag aag ctt cag tca ctt gat ctt tcg aac aat tca ttc acc 361/121                         391/131
ggg gag ata ccg gcc tca ctt gga gaa ctc aag aac ttg aat tac ttg cgg tta aac aat 421/141                         451/151
aac agt ctt ata gga act tgc cct gag tct cta tcc aag att gag gga ctc act cta gtg 481/161                         511/171
gta att ggt aat gcg tta atc tgt ggc cca aaa gct gtt tca aac tgt tct gct gtt ccc 541/181                         571/191
gag cct ctc acg ctt cca caa gat ggt cca gat gaa tca gga act cgt acc aat ggc cat 601/201                         631/211
cac gtt gct ctt gca ttt gcc gca agc ttc agt gca gca ttt ttt gtt ttc ttt aca agc 661/221                         691/231
gga atg ttt ctt tgg tgg aga tat cgc cgt aac aag caa ata ttt ttt gac gtt aat gaa 721/241                         751/251
caa tat gat cca gaa gtg agt tta ggg cac ttg aag agg tat aca ttc aaa gag ctt aga 781/261                         811/271
tct gcc acc aat cat ttc aac tcg aag aac att ctc gga aga ggc gga tac ggg att gtg 841/281                         871/291
tac aaa gga cac tta aac gat gga act ttg gtg gct gtc aaa cgt ctc aag gac tgt aac 901/301                         931/311
att gcg ggt gga gaa gtc cag ttt cag aca gaa gta gag act ata agt ttg gct ctt cat 961/321                         991/331
cgc aat ctc ctc cgg ctc cgc ggt ttc tgt agt agc aac cag gag aga att tta gtc tac 1021/341                        1051/351
cct tac atg cca aat ggg agt gtc gca tca cgc tta aaa gat aat atc cgt gga gag cca 1081/361                        1111/371
gca tta gac tgg tcg aga agg aag aag ata gcg gtt ggg aca gcg aga gga cta gtt tac 1141/381                        1171/391
cta cac gag caa tgt gac ccg aag att ata cac cgc gat gtg aaa gca gct aac att ctg 1201/401                        1231/411
tta gat gag gac ttc gaa gca gtt gtt ggt gat ttt ggg tta gct aag ctt cta gac cat 1261/421                        1291/431
aga gac tct cat gtc aca act gca gtc cgt gga act gtt ggc cac att gca cct gag tac 1321/441                        1351/451
tta tcc acg ggt cag tcc tca gag aag act gat gtc ttt ggc ttt ggc ata ctt ctc ctt
```

Fig. 8a CONTD.

```
1381/461                          1411/471
gag ctc att act ggt cag aaa gct ctt gat ttt ggc aga tcc gca cac cag aaa ggt gta 1441/481                          1471/491
atg ctt gac tgg gtg aag aag ctg cac caa gaa ggg aaa cta aag cag tta ata gac aaa 1501/501                          1531/511
gat cta aat gac aag ttc gat aga gta gaa ctc gaa gaa atc gtt caa gtt gcg cta ctc 1561/521                          1591/531
tgc act caa ttc aat cca tct cat cga ccg aaa atg tca gaa gtt atg aag atg ctt gaa 1621/541                          1651/551
ggt gac ggt ttg gct gag aga tgg gaa gcg acg cag aac ggt act ggt gag cat cag cca 1681/561                          1711/571
ccg cca ttg cca ccg ggg atg gtg agt tct tcg ccg cgt gtg agg tat tac tcg gat tat 1741/581                          1771/591
att cag gaa tcg tct ctt gta gta gaa gcc att gag ctc tcg ggt cct cga tga (SEQ ID NO. 34)
```

Figure 8b

MEGVRFVVWRLGFL
VFVWFFDISSATLSPTGVNYEV

TALVAVKNELNDP
YKVLENWDVNSVD

PCSWRMVSCTDGYVSS

LVLQNNAITGPI
P ETIGRLEKLQSLDLSNNSFTGEI
PASLG ELKNLNYLRLNNNSLIGTC
PESLS KIEGLTLVVIGNALICGPK

AVSNCSAVPEPLTL
PQDGPDESGTRTNG

HHVALAFAASFS
AAFFVFFTSGMFLWW

RYRRNKQIFFDVNEQYDPE
VSLGHLKRYTFKELRSAT

NHFNSKNILGRGGYGIVYKGHLND
GTLVAVKRLKDCNIAGGEVQFQ
TEVETISLALHRNLLRLRGFCS
SNQERILVYPYMPNGSVASRLK
DNIRGEPALDWSRRKKIAVGTA
RGLVYLHEQCDPKIIHRDVKAA
NILLDEDFEAVVGDFGLAKLLD
HRDSHVTTAVRGTVGHIAPEYL
STGQSSEKTDVFGFGILLLELI
TGQKALDFGRSAHQKGVMLDW
VKKLHQEGKLKQLIDKDLNDKF
DRVELEEIVQVALLCTQFNPSH
RPKMSEVMKMLE

GDGLAERWEATQNGTGEHQPPPLPPGMVSSS

PRVRYYSDYIQESSLVVEAIELSGPR (SEQ ID NO. 35)

Figure 9a
Arabidopsis thaliana RKS2 cDNA

```
1/1                              31/11
tca att ttg gta gct ctt aga aaa ATG gct ctg ctt att atc act gcc tta gtt ttt agt 61/21                            91/31
agt tta tgg tca tct gtg tca cca gat gct caa ggg gat gca tta ttt gcg ttg agg agc 121/41                           151/51
tcg tta cgt gca tct cct gaa cag ctt agt gat tgg aac cag aat caa gtc gat cct tgt 181/61                           211/71
act tgg tct caa gtt att tgt gat gac aag aaa cat gtt act tct gta acc ttg tct tac 241/81                           271/91
atg aac ttc tcc tcg gga aca ctg tct tca gga ata gga atc ttg aca act ctc aag act 301/101                          331/111
ctt aca ttg aag gga aat gga ata atg ggt gga ata cca gaa tcc att gga aat ctg tct 361/121                          391/131
agc ttg acc agc tta gat ttg gag gat aat cac tta act gat cgc att cca tcc act ctc 421/141                          451/151
ggt aat ctc aag aat cta cag ttc ttt ttc aca gca aac aac ttg agc tgt ggt ggc act 481/161                          511/171
ttc ccg caa cct tgt gta acc gag tcc agt cct tca ggt gat tca agc agt aga aaa act 541/181                          571/191
gga atc atc gct gga gtt gtt agc gga ata gcg gtt att cta cta gga ttc ttc ttc ttt 601/201                          631/211
ttc ttc tgc aag gat aaa cat aaa gga tat aaa cga gac gta ttt gtg gat gtt gca gga 661/221                          691/231
acg aac ttt aaa aaa ggt ttg att tca ggt gaa gtg gac aga agg att gct ttt gga cag 721/241                          751/251
ttg aga aga ttt gca tgg aga gag ctt cag ttg gct aca gat gag ttc agt gaa aag aat 781/261                          811/271
gtt ctc gga caa gga ggc ttt ggg aaa gtt tac aaa gga ttg ctt tcg gat ggc acc aaa 841/281                          871/291
gtc gct gta aaa aga ttg act gat ttt gaa cgt cca gga gga gat gaa gct ttc cag aga 901/301                          931/311
gaa gtt gag atg ata agt gta gct gtt cat agg aat ctg ctt cgc ctt atc ggc ttt tgt 961/321                          991/331
aca aca caa act gaa cga ctt ttg gtg tat cct ttc atg cag aat cta agt gtt gca tat 1021/341                         1051/351
tgc tta aga gag att aaa ccc ggg gat cca gtt ctg gat tgg ttc agg agg aaa cag att 1081/361                         1111/371
gcg tta ggt gca gca cga gga ctc gaa tat ctt cat gaa cat gca aac ccg aag atc ata 1141/381                         1171/391
cac aga gat gtg aaa gct gca aat gtg tta cta gat gaa gac ttt gaa gca gtg gtt ggt 1201/401                         1231/411
gat ttt ggt tta gcc aag ttg gta gat gtt aga agg act aat gta acc act cag gtc cga 1261/421                         1291/431
gga aca atg ggt cat att gca cca gaa tgt ata tcc aca ggg aaa tcg tca gag aaa acc 1321/441                         1351/451
gat gtt ttc ggg tac gga att atg ctt ctg gag ctt gta act gga caa aga gca att gat

1381/461                         1411/471
```

Fig. 9a CONTD.

```
ttc tcg cgg tta gag gaa gaa gat gat gtc tta ttg cta gac cat gtg aag aaa ctg gaa
1441/481                             1471/491
aga gag aag aga tta gaa gac ata gta gat aag aag ctt gat gag gat tat ata aag gaa
1501/501                             1531/511
gaa gtt gaa atg atg ata caa gta gct ctg cta tgc aca caa gca gca ccg gaa gaa cga
1561/521                             1591/531
cca gcg atg tcg gaa gta gta aga atg cta gaa gga gaa ggg ctt gca gag aga tgg gaa
1621/541                             1651/551
gag tgg cag aat ctt gaa gtg acg aga caa gaa gag ttt cag agg ttg cag agg aga ttt
1681/561                             1711/571
gat tgg ggt gaa gat tcc att aat aat caa gat gct att gaa tta tct ggt gga aga tag
```

(SEQ ID NO. 36)

Figure 9b

MALLIITALVFSSL
WSSVSPDAQG

DALFALRSSLR
ASPEQLSDWNQNQVD

PCTWSQVICDDKKHVTSV

TLSYMNFSSGTLSSGI
G ILTTLKTLTLKGNGIMGGI
PESIGNLSSLTSLDLEDNHLTDRI
PSTLGNLKNLQFFFTANNLSCGG

TFPQPCVTESSPSGDSSSRKTG

IIAGVVSGIAVIL
LGFFFFFFC

KDKHKGYKRDVFVDVAGTNFKKGLISGE
VDRRIAFGQLRRFAWRELQLAT

DEFSEKNVLGQGGFGKVYKGLLSD
GTKVAVKRLTDFERPGGDEAFQ
REVEMISVAVHRNLLRLIGFCT
TQTERLLVYPFMQNLSVAYCLR
EIKPGDPVLDWFRRKQIALGAA
RGLEYLHEHCNPKIIHRDVKAA
NVLLDEDFEAVVGDFGLAKLVD
VRRTNVTTQVRGTMGHIAPECI
STGKSSEKTDVFGYGIMLLELV
TGQRAIDFSRLEEEDDVLLLDH
VKKLEREKRLEDIVDKKLDEDY
IKEEVEMMIQVALLCTQAAPEE
RPAMSEVVRMLE

GEGLAERWEEWQNLEVTRQEEFQ

RLQRRFDWGEDSINNQDAIELSGGR    (SEQ ID NO. 37)

Figure 10a
Arabidopsis thaliana RKS3 cDNA

```
1/1                             31/11
aac ggt gaa agt ttc cat gat cct ctt cga gga ttc att caa aga aat tgc ttt aga tgg 61/21                           91/31
aac aat cag aaa ttg atc tta caa tgt ttc ATG gcc tta gct ttt gtg gga atc act tcg 121/41                          151/51
tca aca act caa cca gat atc gaa gga gga gct ctg ttg cag ctc aga gat tcg ctt aat 181/61                          211/71
gat tcg agc aat cgt cta aaa tgg aca cgc gat ttt gtg agc cct tgc tat agt tgg tct 241/81                          271/91
tat gtt acc tgc aga ggc cag agt gtt gtg gct cta aat ctt gcc tcg agt gga ttc aca 301/101                         331/111
gga aca ctc tct cca gct att aca aaa ctg aag ttc ttg gtt acc tta gag tta cag aac 361/121                         391/131
aat agt tta tct ggt gcc tta cca gat tct ctt ggg aac atg gtt aat cta cag act tta 421/141                         451/151
aac cta tca gtg aat agt ttc agc gga tcg ata cca gcg agc tgg agt cag ctc tcg aat 481/161                         511/171
cta aag cac ttg gat ctc tca tcc aat aat tta aca gga agc atc cca aca caa ttc ttc 541/181                         571/191
tca atc cca aca ttc gat ttt tca gga act cag ctt ata tgc ggt aaa agt ttg aat cag 601/201                         631/211
cct tgt tct tca agt tct cgt ctt cca gtc aca tcc tcc aag aaa aag ctg aga gac att 661/221                         691/231
act ttg act gca agt tgt gtt gct tct ata atc tta ttc ctt gga gca atg gtt atg tat 721/241                         751/251
cat cac cat cgc gtc cgc aga acc aaa tac gac atc ttt ttt gat gta gct ggg gaa gat 781/261                         811/271
gac agg aag att tcc ttt gga caa cta aaa cga ttc tct tta cgt gaa atc cag ctc gca 841/281                         871/291
aca gat agt ttc aac gag agc aat ttg ata gga caa gga gga ttt ggt aaa gta tac aga 901/301                         931/311
ggt ttg ctt cca gac aaa aca aaa gtt gca gtg aaa cgc ctt gcg gat tac ttc agt cct 961/321                         991/331
gga gga gaa gct gct ttc caa aga gag att cag ctc ata agc gtt gcg gtt cat aaa aat 1021/341                        1051/351
ctc tta cgc ctt att ggc ttc tgc aca act tcc tct gag aga atc ctt gtt tat cca tac 1081/361                        1111/371
atg gaa aat ctt agt gtt gca tat cga cta aga gat ttg aaa gcg gga gag gaa gga tta 1141/381                        1171/391
gac tgg cca aca agg aag cgt gta gct ttt ggt tca gct cac ggt tta gag tat cta cac 1201/401                        1231/411
gaa cat tgt aac ccg aag atc ata cac cgc gat ctc aag gct gca aac ata ctt tta gac 1261/421                        1291/431
aac aat ttt gag cca gtt ctt gga gat tcg ggt tta gct aag ctt gtg gac aca tct ctg 1321/441                        1351/451
act cat gtc aca act caa gtc cga ggc aca atg ggt cac att gcg cca gag tat ctc tgc
```

Fig. 10a CONTD.

```
1381/461                            1411/471
aca gga aaa tca tct gaa aaa acc gat gtt ttt ggt tac ggt ata acg ctt ctt gag ctt 1441/481                            1471/491
gtt act ggt cag cgc gca atc gat ttt tca cgc ttg gaa gaa gag gaa aat att ctc ttg 1501/501                            1531/511
ctt gat cat ata aag aag ttg ctt aga gaa cag aga ctt aga gac att gtt gat agc aat 1561/521                            1591/531
ttg act aca tat gac tcc aaa gaa gtt gaa aca atc gtt caa gtg gct ctt ctc tgc aca 1621/541                            1651/551
caa ggc tca cca gaa gat aga cca gcg atg tct gaa gtg gtc aaa atg ctt caa ggg act 1681/561                            1711/571
ggt ggt ttg gct gag aaa tgg act gaa tgg gaa caa ctt gaa gaa gtt agg aac aaa gaa 1741/581                            1771/591
gca ttg ttg ctt ccg act tta ccg gct act tgg gat gaa gaa gaa acc acc gtt gat caa 1801/601
gaa tct atc cga tta tcg aca gca aga tga (SEQ ID NO. 38)
```

Figure 10b

MALAFVGITSSTTQPDIEG

GALLQLRDSLNDSSNRL
KWTRDFVS

PCYSWSYVTCRGQSVVAL

NLASSGFTGTLS
P AITKLKFLVTLELQNNSLSGAL
PDSLGNMVNLQTLNLSVNSFSGSI
PASWSQLSNLKHLDLSSNNLTGSI
PTQFFSIPTFEFSGTQLICGKS

LNQPCSSSRLPVTSSKKKLRD

ITLTASCVASIIL
FLGAMVMYHHH

RVRRTKYDIFFDVAGEDDR
KISFGQLKRFSLREIQLAT

DSFNESNLIGQGGFGKVYRGLLPD
KTKVAVKRLADYFSPGGEAAFQ
REIQLISVAVHKNLLRLIGFCT
TSSERILVYPYMENLSVAYRLR
DLKAGEEGLDWPTRKRVAFGSA
HGLEYLHEHCNPKIIHRDLKAA
NILLDNNFEPVLGDFGLAKLVD
TSLTHVTTQVRGTMGHIAPEYL
CTGKSSEKTDVFGYGITLLELV
TGQRAIDFSRLEEEENILLLD
HIKKLLREQRLRDIVDSNLTTY
DSKEVETIVQVALLCTQGSPED
RPAMSEVVKMLQ

GTGGLAEKWTEWEQLEEVRNKEALLL

PTLPATWDEEETTVDQESIRLSTAR     (SEQ ID NO. 39)

Figure 11a
Arabidopsis thaliana RKS4 cDNA

```
1/1                              31/11
tct tcc ttc tcc ttc tgg taa tct aat cta aag ctt ttc ATG gtg gtg atg aag ata ttc 61/21                            91/31
tct gtt ctg tta cta cta tgt ttc ttc gtt act tgt tct ctc tct tct gaa ccc aga aac 121/41                           151/51
cct gaa gtc att aat ggt gac aaa ttc ttc atc ttt gtt ttg ttt ttt ccc aat tcc aga 181/61                           211/71
gga gct cca agt cag tct ctt tca gga act tta tct ggg tct att gga aat ctc act aat 241/81                           271/91
ctt cga caa gtg tca tta cag aac aat aac atc tcc ggt aaa atc cca ccg gag att tgt 301/101                          331/111
tct ctt ccc aaa tta cag act ctg gat tta tcc aat aac cgg ttc tcc ggt gaa atc ccc 361/121                          391/131
ggt tct gtt aac cag ctg agt aat ctc caa tat ctt gtt gct ggg aac cct ttg att tgt 421/141                          451/151
aaa aac agc cta ccg gag att tgt tca gga tca atc agt gca agc cct ctt tct gtc tct 481/161                          511/171
tta cgt tct tca tca gac aag caa gag gaa ggg tta ctt ggg ttg gga aat cta aga agc 541/181                          571/191
ttc aca ttc agg gaa ctt cat gta gct acg gat ggt ttt agt tcc aag agt att ctt ggt 601/201                          631/211
gct ggt ggg ttt ggt aat gtc tac aga gga aaa ttc ggg gat ggg aca gtg gtt gca gtg 661/221                          691/231
aaa cga ttg aaa gat gtg aat gga acc tcc ggg aac tca cag ttt cgt act gag ctt gag 721/241                          751/251
atg atc agc tta gct gtt cat agg aat ttg ctt cgg tta atc ggt tat tgt gcg agt tct 781/261                          811/271
agc gaa aga ctt ctt gtt tac cct tac atg tcc aat ggc agc gtc gcc tct agg ctc aaa 841/281                          871/291
gct aag cca gcg ttg gac tgg aac aca agg aag aag ata gcg att gga gct gca aga ggg 901/301                          931/311
ttg ttt tat cta cac gag caa tgc gat ccc aag att att cac cga gat gtc aag gca gca 961/321                          991/331
aac att ctc cta gat gag tat ttt gaa gca gtt gtt ggg gat ttt gga cta gca aag cta 1021/341                         1051/351
ctc aac cac gag gat tca cat gtc aca acc gcg gtt aga gga act gtt ggt cac att gca 1081/361                         1111/371
cct gag tat ctc tcc acc ggt cag tca tct gag aaa acc gat gtc ttt ggg ttc ggt ata 1141/381                         1171/391
ctt ttg cta gag ctc atc aca gga atg aga gct ctc gag ttt ggc aag tct gtt agc cag 1201/401                         1231/411
aaa gga gct atg cta gaa tgg gtg agg aag cta cac aag gaa atg aaa gta gag gag cta 1261/421                         1291/431
gta gac cga gaa ctg ggg aca acc tac gat aga ata gaa gtt gga gag atg cta caa gtg 1321/441                         1351/451
gca ctg ctc tgc act cag ttt ctt cca gct cac aga ccc aaa atg tct gaa gta gtt cag
```

Fig. 11a CONTD.

```
1381/461                              1411/471
atg ctt gaa gga gat gga tta gct gag aga tgg gct gct tca cat gac cat tca cat ttc 1441/481                              1471/491
tac cat gcc aac atg tct tac agg act att acc tct act gat ggc aac aac caa acc aaa 1501/501                              1531/511
cat ctg ttt ggc tcc tca gga ttt gaa gat gaa gat gat aat caa gcg tta gat tca ttc 1561/521
gcc atg gaa cta tct ggt cca agg tag   (SEQ ID NO. 40)
```

Figure 11b

MVVMKLITMKIFSVLLLL
CFFVTCSLSSEPRNPEV

EALINIKNELHDP
HGVFKNWDEFSVD

PCSWTMISCSSDNLVIGL

GAPSQSLSGTLS
G SIGNLTNLRQVSLQNNNISGKI
PPEICSLPKLQTLDLSNNRFSGEI
PGSVNQLSNLQYLRLNNNSLSGPF
PASLSQIPHLSFLDLSYNNLRGPV
PKFPARTFNVAGNPLICKNS

LPEICSGSISASPL
SVSLRSSSGRRN

ILAVALGVSLGFAVSVIL
SLGFIWY

RKKQRRLTMLRISDKQEE
GLLGLGNLRSFTFRELHVAT

DGFSSKSILGAGGFGNVYRGKFGD
GTVVAVKRLKDVNGTSGNSQFR
TELEMISLAVHRNLLRLIGYCA
SSSERLLVYPYMSNGSVASRLK
AKPALDWNTRKKIAIGAA
RGLFYLHEQCDPKIIHRDVKAA
NILLDEYFEAVVGDFGLAKLLN
HEDSHVTTAVRGTVGHIAPEYL
STGQSSEKTDVFGFGILLLELI
TGMRALEFGKSVSQKGAMLEW
VRKLHKEMKVEELVDRELGTTY
DRIEVGEMLQVALLCTQFLPAH
RPKMSEVVQMLE

GDGLAERWAASHDHSHFYHANM
SYRTITSTDGNNQTKHLFG

SSGFEDEDDNQALDSFAMELSGPR    (SEQ ID NO. 41)

Figure 12a
Arabidopsis thaliana RKS5 cDNA

```
1/1                              31/11
cta gag aat tct tat act ttt tct acg ATG gag att tct ttg atg aag ttt ctg ttt tta
61/21                            91/31
gga atc tgg gtt tat tat tac tct gtt ctt gac tct gtt tct gcc atg gat agt ctt tta 121/41                           151/51
tct ccc aag ggt gtt aac tat gaa gtg gct gcg tta atg tca gtg aag aac aag atg aaa 181/61                           211/71
gat gag aaa gag gtt ttg tct ggt tgg gat att aac tct gtt gat cct tgt act tgg aac 241/81                           271/91
atg gtt ggt tgt tct tct gaa ggt ttt gtg gtt tct ctg tta ctt cag aat aat cag tta 301/101                          331/111
act ggt ccg att cct tct gag tta ggc caa ctc tct gag ctt gaa acg ctt gat tta tcg 361/121                          391/131
ggg aat cgg ttt agt ggt gaa atc cca gct tct tta ggg ttc tta act cac tta aac tac 421/141                          451/151
ttg cgg ctt agc agg aat ctt tta tct ggg caa gtc cct cac ctc gtc gct ggc ctc tca 481/161                          511/171
ggt ctt tct ttc ttg gat cta tct ttc aac aat cta agc gga cca act ccg aat ata tca 541/181                          571/191
gca aaa gat tac agg att gta gga aat gca ttt ctt tgt ggt cca gct tcc caa gag ctt 601/201                          631/211
tgc tca gat gct aca cct gtg aga aat gtg cag caa gac tac gaa ttt gaa atc ggc cat 661/221                          691/231
ctg aaa agg ttc agt ttt cgc gaa ata caa acc gca aca agc aat ttt agt cca aag aac 721/241                          751/251
att ttg gga caa gga ggg ttt ggg atg gtt tat aaa ggg tat ctc cca aat gga act gtg 781/261                          811/271
gtg gca gtt aaa aga ttg aaa gat ccg att tat aca gga gaa gtt cag ttt caa acc gaa 841/281                          871/291
gta gag atg att ggc tta gct gtt cac cgt aac ctt tta cgc ctc ttt gga ttc tgt atg 901/301                          931/311
acc ccg gaa gag aga atg ctt gtg tat ccg tac atg cca aat gga agc gta gct gat cgt 961/321                          991/331
ctg aga gat tgg aat cgg agg ata agc att gca ctc ggc gca gct cga gga ctt gtt tac 1021/341                         1051/351
ttg cac gag caa tgc aat cca aag att att cac aga gac gtc aaa gct gca aat att cta 1081/361                         1111/371
ctt gat gag agc ttt gaa gca ata gtt ggc gat ttt ggt cta gca aag ctt tta gac cag 1141/381                         1171/391
aga gat tca cat gtc act acc gca gtc cga gga acc att gga cac atc gct ccc gag tac 1201/401                         1231/411
ctt tcc act gga cag tcc tca gag aaa acc gat gtt ttc gga ttc gga gta cta atc ctt 1261/421                         1291/431
gaa ctc ata aca ggt cat aag atg att gat caa ggc aat ggt caa gtt cga aaa gga atg 1321/441                         1351/451
ata ttg agc tgg gta agg aca ttg aaa gca gag aag aga ttt gca gag atg gtg gac aga 1381/461                         1411/471
gat ttg aag gga gag ttt gat gat ttg gtg ttg gag gaa gta gtg gaa ttg gct ttg ctt
```

Fig. 12a CONTD.

```
1441/481                            1471/491
tgt aca cag cca cat ccg aat cta aga ccg agg atg tct caa gtg ttg aag gta cta gaa 1501/501                            1531/511
ggt tta gtg gaa cag tgt gaa gga ggg tat gaa gct aga gct cca agt gtc tct agg aac 1561/521                            1591/531
tac agt aat ggt cat gaa gag cag tcc ttt att att gaa gcc att gag ctc tct gga cca 1621/541
cga tga tag   (SEQ ID NO. 42)
```

Figure 12b

MEISLMKFLFLGIWVYYY
SVLDSVSAM

DSLLSPKWAALMSVKNKMKDE
KEVLSGWDINSVD

PCTWNMVGCSSEGFVVS

LLLQNNQLTGPI
PSELGQLSELETLDLSGNRFSGEI
PASLGFLTHLNYLRLSRNLLSGQV
PHLVAGLSGLSFLDLSFNNLSGPT
P     NISAKDYRIVGNAFLCGPA

SQELCSDATPVRNGMLLRKFFAKLYL
KHGFVYLTSCNRSAATGLSEKDNSK

HHSLVLSFAFGIVVA
FIISLMFLFFWVLWH

RSRLSRSHGTYLIVSLCLSYTIYVKTLLKSA
LLFMDFLVQQDYEFEIGHLKRFSFREIQTAT

SNFSPKNILGQGGFGMVYKGYLPN
GTVVAVKRLKDPIYTGEVQFQ
TEVEMIGLAVHRNLLRLFGFCM
TPEERMLVYPYMPNGSVADRLR
DWNRRISIALGAA
RGLVYLHEQCNPKIIHRDVKAA
NILLDESFEAIVGDFGLAKLLD
QRDSHVTTAVRGTIGHIAPEYL
STGQSSEKTDVFGFGVLILELI
TGHKMIDQGNGQVRKGMILSW
VRTLKAEKRFAEMVDRDLKGEF
DDLVLEEVVELALLCTQPHPNL
RPRMSQVLKV

LEGLVEQCEGGYEARA

PASVSRNYSNGHEEQSFIIEAIELSGPR    (SEQ ID NO. 43)

Figure 13a
Arabidopsis thaliana RKS6 cDNA

```
1/1                             31/11
ATT GTT TCC TTC TTT TGG GAT TTT CTC CTT GGA TGG AAC CAG CTC AAT TAA TGA GAT GAG

61/21                           91/31
ATG AGA ATG TTC AGC TTG CAG AAG ATG GCT ATG GCT TTT ACT CTC TTG TTT TTT GCC TGT
121/41
                                151/51
TTA TGC TCA TTT GTG TCT CCA GAT GCT CAA GGG GAT GCA CTG TTT GCG TTG AGG ATC TCC

181/61                          211/71
TTA CGT GCA TTA CCG AAT CAG CTA AGT GAC TGG AAT CAG AAC CAA GTT AAT CCT TGC ACT

241/81                          271/91
TGG TCC CAA GTT ATT TGT GAT GAC AAA AAC TTT GTC ACT TCT CTT ACA TTG TCA GAT ATG

301/101                         331/111
AAC TTC TCG GGA ACC TTG TCT TCA AGA GTA GGA ATC CTA GAA AAT CTC AAG ACT CTT ACT

361/121                         391/131
TTA AAG GGA AAT GGA ATT ACG GGT GAA ATA CCA GAA GAC TTT GGA AAT CTG ACT AGC TTG

421/141                         451/151
ACT AGT TTG GAT TTG GAG GAC AAT CAG CTA ACT GGT CGT ATA CCA TCC ACT ATC GGT AAT

481/161                         511/171
CTC AAG AAA CTT CAG TTC TTG ACC TTG AGT AGG AAC AAA CTT AAT GGG ACT ATT CCG GAG

541/181                         571/191
TCA CTC ACT GGT CTT CCA AAC CTG TTA AAC CTG CTG CTT GAT TCC AAT AGT CTC AGT GGT

601/201                         631/211
CAG ATT CCT CAA AGT CTG TTT GAG ATC CCA AAA TAT AAT TTC ACG TCA AAC AAC TTG AAT

661/221                         691/231
TGT GGC GGT CGT CAA CCT CAC CCT TGT GTA TCC GCG GTT GCC CAT TCA GGT GAT TCA AGC

721/241                         751/251
AAG CCT AAA ACT GGC ATT ATT GCT GGA GTT GTT GCT GGA GTT ACA GTT GTT CTC TTT GGA

781/261                         811/271
ATC TTG TTG TTT CTG TTC TGC AAG GAT AGG CAT AAA GGA TAT AGA CGT GAT GTG TTT GTG

841/281                         871/291
GAT GTT GCA GGT GAA GTG GAC AGG AGA ATT GCA TTT GGA CAG TTG AAA AGG TTT GCA TGG

901/301                         931/311
AGA GAG CTC CAG TTA GCG ACA GAT AAC TTC AGC GAA AAG AAT GTA CTT GGT CAA GGA GGC

961/321                         991/331
TTT GGG AAA GTT TAC AAA GGA GTG CTT CCG GAT ACA CCC AAA GTT GCT GTG AAG AGA TTG

1021/341                        1051/351
ACG GAT TTC GAA AGT CCT GGT GGA GAT GCT GCT TTC CAA AGG GAA GTA GAG ATG ATA AGT

1081/361                        1111/371
GTA GCT GTT CAT AGG AAT CTA CTC CGT CTT ATC GGG TTC TGC ACC ACA CAA ACA GAA CGC

1141/381                        1171/391
CTT TTG GTT TAT CCC TTC ATG CAG AAT CTA AGT CTT GCA CAT CGT CTG AGA GAG ATC AAA

1201/401                        1231/411
GCA GGC GAC CCG GTT CTA GAT TGG GAG ACG AGG AAA CGG ATT GCC TTA GGA GCA GCG CGT

1261/421                        1291/431
GGT TTT GAG TAT CTT CAT GAA CAT TGC AAT CCG AAG ATC ATA CAT CGT GAT GTG AAA GCA

1321/441                        1351/451
GCT AAT GTG TTA CTA GAT GAA GAT TTT GAA GCA GTG GTT GGT GAT TTT GGT TTA GCC AAG

1381/461                        1411/471
```

Fig. 13a CONTD.

```
CTA GTA GAT GTT AGA AGG ACT AAT GTG ACT ACT CAA GTT CGA GGA ACA ATG GGT CAC ATT
1441/481                                 1471/491
GCA CCA GAA TAT TTA TCA ACA GGG AAA TCA TCA GAG AGA ACC GAT GTT TTC GGG TAT GGA
1501/501                                 1531/511
ATT ATG CTT CTT GAG CTT GTT ACA GGA CAA CGC GCA ATA GAC TTT TCA CGT TTG GAG GAA
1561/521                                 1591/531
GAA GAT GAT GTC TTG TTA CTT GAC CAC GTG AAG AAA CTG AAA GAG AAG AGA TTA GGA
1621/541                                 1651/551
GCA ATC GTA GAT AAG AAT TTG GAT GGA GAG TAT ATA AAA GAA GAA GTA GAG ATG ATG ATA
A
1681/561                                 1711/571
CAA GTG GCT TTG CTT TGT ACA CAA GGT TCA CCA GAA GAC CGA CCA GTG ATG TCT GAA GTT
1741/581                                 1771/591
GTG AGG ATG TTA GAA GGA GAA GGG CTT GCG GAG AGA TGG GAA GAG TGG CAA AAC GTG GAA
1801/601                                 1831/611
GTC ACG AGA CGT CAT GAG TTT GAA CGG TTG CAG AGG AGA TTT GAT TGG GGT GAA GAT TCT
1861/621                                 1891/631
ATG CAT AAC CAA GAT GCC ATT GAA TTA TCT GGT GGA AGA TGA CCA AAA ACA TCA AAC CTT
```

(SEQ ID NO. 44)

Figure 13b

MRMFSL
QKMAMAFTLLFFACLCSFVSPDAQG

DALFALRISLRALP
NQLSDWNQNQVN

PCTWSQVICDDKNFVTSL

TLSDMNFSGTLSSRV
GILENLKTLTLKGNGITGEI
PEDFGNLTSLTSLDLEDNQLTGRI
PSTIGNLKKLQFLTLSRNKLNGTI
PESLTGLPNLLNLLLDSNSLSGQI
PQSLFEIPKYNFTSNNLNCGG

RQPHPCVSAVAHSGDSSKPKTG

IIAGVVAGVTVVL
FGILLFLFC

KDRHKGYRRDVFVDVAGE
VDRRIAFGQLKRFAWRELQLAT

DNFSEKNVLGQGGFGKVYKGVLPD
TPKVAVKRLTDFESPGGDAAFQ
REVEMISVAVHRNLLRLIGFCT
TQTERLLVYPFMQNLSLAHRLR
EIKAGDPVLDWETRKRIALGAA
RGFEYLHEHCNPKIIHRDVKAA
NVLLDEDFEAVVGDFGLAKLVD
VRRTNVTTQVRGTMGHIAPEYL
STGKSSERTDVFGYGIMLLELV
TGQRAIDFSRLEEEDDVLLLDH
VKKLEREKRLGAIVDKNLDGEY
IKEEVEMMIQVALLCTQGSPED
RPVMSEVVRMLE

GEGLAERWEEWQNVEVTRRHEFE

RLQRRFDWGEDSMHNQDAIELSGGR (SEQ ID NO. 45)

Figure 14a
Arabidopsis thaliana RKS8 cDNA

```
1/1                                31/11
GTT TTT TTT TTT TTA CCC TCT TGG AGG ATC TGG GAG GAG AAA TTT GCT TTT TTT TGG TAA

61/21                              91/31
ATG GGG AGA AAA AAG TTT GAA GCT TTT GGT TTT GTC TGC TTA ATC TCA CTG CTT CTT CTG

121/41                             151/51
TTT AAT TCG TTA TGG CTT GCC TCT TCT AAC ATG GAA GGT GAT GCA CTG CAC AGT TTG AGA

181/61                             211/71
GCT AAT CTA GTT GAT CCA AAT AAT GTC TTG CAA AGC TGG GAT CCT ACG CTT GTT AAT CCG

241/81                             271/91
TGT ACT TGG TTT CAC GTA ACG TGT AAC AAC GAG AAC AGT GTT ATA AGA GTC GAT CTT GGG

301/101                            331/111
AAT GCA GAC TTG TCT GGT CAG TTG GTT CCT CAG CTA GGT CAG CTC AAG AAC TTG CAG TAC

361/121                            391/131
TTG GAG CTT TAT AGT AAT AAC ATA ACC GGG CCG GTT CCA AGC GAT CTT GGG AAT CTG ACA

421/141                            451/151
AAC TTA GTG AGC TTG GAT CTT TAC TTG AAC AGC TTC ACT GGT CCA ATT CCA GAT TCT CTA

481/161                            511/171
GGA AAG CTA TTC AAG CTT CGC TTT CTT CGG CTC AAC AAT AAC AGT CTC ACC GGA CCA ATT

541/181                            571/191
CCC ATG TCA TTG ACT AAT ATC ATG ACC CTT CAA GTT TTG GAT CTG TCG AAC AAC CGA TTA

601/201                            631/211
TCC GGA TCT GTT CCT GAT AAT GGT TCC TTC TCG CTC TTC ACT CCC ATC AGT TTT GCT AAC

661/221                            691/231
AAC TTG GAT CTA TGC GGC CCA GTT ACT AGC CGT CCT TGT CCT GGA TCT CCC CCG TTT TCT

721/241                            751/251
CCT CCA CCA CCT TTT ATA CCA CCT CCC ATA GTT CCT ACA CCA GGT GGG TAT AGT GCT ACT

781/261                            811/271
GGA GCC ATT GCG GGA GGA GTT GCT GCT GGT GCT GCT TTA CTA TTT GCT GCC CCT GCT TTA

841/281                            871/291
GCT TTT GCT TGG TGG CGT AGA AGA AAA CCT CAA GAA TTC TTC TTT GAT GTT CCT GCC GAA

901/301                            931/311
GAG GAC CCT GAG GTT CAC TTG GGG CAG CTT AAG CGG TTC TCT CTA CGG GAA CTT CAA GTA

961/321                            991/331
GCA ACT GAT AGC TTC AGC AAC AAG AAC ATT TTG GGC CGA GGT GGG TTC GGA AAA GTC TAC

1021/341                           1051/351
AAA GGC CGT CTT GCT GAT GGA ACA CTT GTT GCA GTC AAA CGG CTT AAA GAA GAG CGA ACC

1081/361                           1111/371
CCA GGT GGC GAG CTC CAG TTT CAG ACA GAA GTG GAG ATG ATA AGC ATG GCC GTT CAC AGA

1141/381                           1171/391
AAT CTC CTC AGG CTA CGC GGT TTC TGT ATG ACC CCT ACC GAG AGA TTG CTT GTT TAT CCT

1201/401                           1231/411
TAC ATG GCT AAT GGA AGT GTC GCT TCC TGT TTG AGA GAA CGT CCA CCA TCA CAG TTG CCT

1261/421                           1291/431
CTA GCC TGG TCA ATA AGA CAG CAA ATC GCG CTA GGA TCA GCG AGG GGT TTG TCT TAT CTT

1321/441                           1351/451
CAT GAT CAT TGC GAC CCC AAA ATT ATT CAC CGT GAT GTG AAA GCT GCT AAT ATT CTG TTG
```

Fig. 14a CONTD.

```
1381/461                           1411/471
GAC GAG GAA TTT GAG GCG GTG GTA GGT GAT TTC GGG TTA GCT AGA CTT ATG GAC TAT AAA

1441/481                           1471/491
GAT ACT CAT GTC ACA ACG GCT GTG CGT GGG ACT ATT GGA CAC ATT GCT CCT GAG TAT CTC

1501/501                           1531/511
TCA ACT GGA AAA TCT TCA GAG AAA ACT GAT GTT TTT GGC TAC GGG ATC ATG CTT TTG GAA

1561/521                           1591/531
CTG ATT ACA GGT CAG AGA GCT TTT GAT CTT GCA AGA CTG GCG AAT GAC GAT GAC GTT ATG

1621/541                           1651/551
CTC CTA GAT TGG GTG AAA GGG CTT TTG AAG GAG AAG AAG CTG GAG ATG CTT GTG GAT CCT

1681/561                           1711/571
GAC CTG CAA AGC AAT TAC ACA GAA GCA GAA GTA GAA CAG CTC ATA CAA GTG GCT CTT CTC

1741/581                           1771/591
TGC ACA CAG AGC TCA CCT ATG GAA CGA CCT AAG ATG TCT GAG GTT GTT CGA ATG CTT GAA

1801/601                           1831/611
GGT GAC GGT TTA GCG GAG AAA TGG GAC GAG TGG CAG AAA GTG GAA GTT CTC AGG CAA GAA

1861/621                           1891/631
GTG GAG CTC TCT TCT CAC CCC ACC TCT GAC TGG ATC CTT GAT TCG ACT GAT AAT CTT CAT

1921/641
GCT ATG GAG TTG TCT GGT CCA AGA TAA AC    (SEQ ID NO. 46)
```

Figure 14b

MGRKKFEAFGFVCLISLLLLFNSL
WLASSNMEG

DALHSLRANLVDP
NNVLQSWDPTLVN

PCTWFHVTCNNENSVIRV

DLGNADLSGQLV
P QLGQLKNLQYLELYSNNITGPV
PSDLGNLTNLVSLDLYLNSFTGPI
PDSLGKLFKLRFLRLNNNSLTGPI
PMSLTNIMTLQVLDLSNNRLSGSV
PDNGSFSLFTPISFANNLDLCGPV

TLRPCPGSPPFSPPPP
FIPPPIVPTPGGYSATG

AIAGGVAAGAAL
LFAAPALAFAWW

RRRKPQEFFFDVPAEEDPE
VHLGQLKRFSLRELQVAT

DSFSNKNILGRGGFGKVYKGRLAD
GTLVAVKRLKEERTPGGELQFQ
TEVEMISMAVHRNLLRLRGFCM
TPTERLLVYPYMANGSVASCLR
ERPPSQLPLAWSIRQQIALGSA
RGLSYLHDHCDPKIIHRDVKAA
NILLDEEFEAVVGDFGLARLMD
YKDTHVTTAVRGTIGHIAPEYL
STGKSSEKTDVFGYGIMLLELI
TGQRAFDLARLANDDDVMLLDW
VKGLLKEKKLEMLVDPDLQSNY
TEAEVEQLIQVALLCTQSSPME
RPKMSEVVRMLE

GDGLAEKWDEWQKVEVLRQEVELS

SHPTSDWILDSTDNLHAMELSGPR        (SEQ ID NO. 47)

Figure 15a
Arabidopsis thaliana RKS10 cDNA

```
1/1                                  31/11
atc agg ggt ttt aac aat gat gga ttt tct ctg atg agg gat agt tct agg gtt tgt ttt 61/21                                91/31
taa tct ctt gag gat aaa ATG gaa cga aga tta atg atc cct tgc ttc ttt tgg ttg att 121/41                               151/51
ctc gtt ttg gat ttg gtt ctc aga gtc tcg ggc aac gcc gaa ggt gat gct cta agt gca 181/61                               211/71
ctg aaa aac agt tta gcc gac cct aat aag gtg ctt caa agt tgg gat gct act ctt gtt 241/81                               271/91
act cca tgt aca tgg ttt cat gtt act tgc aat agc gac aat agt gtt aca cgt gtt gac 301/101                              331/111
ctt ggg aat gca aat cta tct gga cag ctc gta atg caa ctt ggt cag ctt cca aac ttg 361/121                              391/131
cag tac ttg gag ctt tat agc aat aac att act ggg aca atc cca gaa cag ctt gga aat 421/141                              451/151
ctg acg gaa ttg gtg agc ttg gat ctt tac ttg aac aat tta agc ggg cct att cca tca 481/161                              511/171
act ctc ggc cga ctt aag aaa ctc cgt ttc ttg cgt ctt aat aac aat agc tta tct gga 541/181                              571/191
gaa att cca agg tct ttg act gct gtc ctg acg cta caa gtt ctt ttt gcc aac acc aag 601/201                              631/211
ttg act ccc ctt cct gca tct cca ccg cct cct atc tct cct aca ccg cca tca cct gca 661/221                              691/231
ggg agt aat aga att act gga gcg att gcg gga gga gtt gct gca ggt gct gca ctt cta 721/241                              751/251
ttt gct gtt ccg gcc att gca cta gct tgg tgg cga agg aaa aag ccg cag gac cac ttc 781/261                              811/271
ttt gat gta cca gct gaa gag gac cca gaa gtt cat tta gga caa ctg aag agg ttt tca 841/281                              871/291
ttg cgt gaa cta caa gtt gct tcg gat aat ttt agc aac aag aac ata ttg ggt aga ggt 901/301                              931/311
ggt ttt ggt aaa gtt tat aaa gga cgg tta gct gat ggt act tta gtg gcc gtt aaa agg 961/321                              991/331
cta aaa gag gag cgc acc caa ggt ggc gaa ctg cag ttc cag aca gag gtt gag atg att 1021/341                             1051/351
agt atg gcg gtt cac aga aac ttg ctt cgg ctt cgt gga ttt gca tga act cca acc gaa 1081/361                             1111/371
aga ttg ctt gtt tat ccc tac atg gct aat gga agt gtt gcc tcc tgt tta aga gaa cgt 1141/381                             1171/391
ccc gag tcc cag cca cca ctt gat tgg cca aag aga cag cgt att gcg ttg gga tct gca 1201/401                             1231/411
aga ggg ctt gcg tat tta cat gat cat tgc gac cca aag att att cat cga gat gtg aaa 1261/421                             1291/431
gct gca aat att ttg ttg gat gaa gag ttt gaa gcc gtg gtt ggg gat ttt gga ctt gca 1321/441                             1351/451
aaa ctc atg gac tac aaa gac aca cat gtg aca acc gca gtg cgt ggg aca att ggt cat

1381/461                             1411/471
```

Fig. 15a CONTD.

```
ata gcc cct gag tac ctt tcc act gga aaa tca tca gag aaa acc gat gtc ttt ggg tat
1441/481                             1471/491
gga gtc atg ctt ctt gag ctt atc act gga caa agg gct ttt gat ctt gct cgc ctc gcg
1501/501                             1531/511
aat gat gat gat gtc atg tta cta gac tgg gtg aaa ggg ttg tta aaa gag aag aaa ttg
1561/521                             1591/531
gaa gca cta gta gat gtt gat ctt cag ggt aat tac aaa gac gaa gaa gtg gag cag cta
1621/541                             1651/551
atc caa gtg gct tta ctc tgc act cag agt tca cca atg gaa aga ccc aaa atg tct gaa
1681/561                             1711/571
gtt gta aga atg ctt gaa gga gat ggt tta gct gag aga tgg gaa gag tgg caa aag gag
1741/581                             1771/591
gaa atg ttc aga caa gat ttc aac tac cca acc cac cat cca gcc gtg tct ggc tgg atc
1801/601                             1831/611
att ggc gat tcc act tcc cag atc gaa aac gaa tac ccc tcg ggt cca aga taa gat tcg
1861/621                             1891/631
aaa cac gaa tgt ttt ttc tgt att ttg ttt ttc tct gta ttt att gag ggt ttt agc ttc
```

(SEQ ID NO. 48)

Figure 15b

MERRLMIPCFFWLILVL
DLVLRVSGNAEG

DALSALKNSLADP
NKVLQSWDATLVT

PCTWFHVTCNSDNSVTRV

DLGNANLSGQLV
M QLGQLPNLQYLELYSNNITGTI
PEQLGNLTELVSLDLYLNNLSGPI
PSTLGRLKKLRFLRLNNNSLSGEI
PRSLTAVLTLQVLFANTK LTPL

PASPPPPISPTPPSPAGSNRITG

AIAGGVAAGAAL
LFAVPAIALAWW

RRKKPQDHFFDVPAEEDPE
VHLGQLKRFSLRELQVAS

DNFSNKNILGRGGFGKVYKGRLAD
GTLVAVKRLKEERTQGGELQFQ
TEVEMISMAVHRNLLRLRGFCM
TPTERLLVYPYMANGSVASCLR
ERPESQPPLDWPKRQRIALGSA
RGLAYLHDHCDPKIIHRDVKAA
NILLDEEFEAVVGDFGLAKLMD
YKDTHVTTAVRGTIGHIAPEYL
STGKSSEKTDVFGYGVMLLELI
TGQRAFDLARLANDDDVMLLDW
VKGLLKEKKLEALVDVDLQGNY
KDEEVEQLIQVALLCTQSSPME
RPKMSEVVRMLE

GDGLAERWEEWQKEEMFRQDFNYPTHH

PAVSGWIIGDSTSQIENEYPSGPR    (SEQ ID NO. 49)

Figure 16a
Arabidopsis thaliana RKS11 cDNA

```
tgttaacctctcgtaactaaaatcttcc
ATGaagattcaaattcatctcctttactcgttcttgttcctctgtttctctactctcact
ctatcttctgagcccagaaaccctgaagttgaggcgttgataagtataaggaacaatttg
catgatcctcatggagctttgaacaattgggacgagttttcagttgatccttgtagctgg
gctatgatcacttgctctcccgacaacctcgtcattggactgtcattgcaaaataacaac
atctccggcaaaattccaccggagctcggttttctacccaaattacaaaccttggatctt
tccaacaaccgattctccggtgacatccctgtttccatcgaccagctaagcagccttcaa
tatctgagactcaacaacaactctttgtctgggcccttccctgcttctttgtcccaaatt
Cctcacctctccttcttggacttgtcttacaacaatctcagtggccctgttcctaaattc
ccagcaaggactttcaa
cgttgctggtaatcctttgatttgtagaagcaacccacctgagatttgttctgga
tcaatcaatgcaagtccacttctgtttctttgagctcttcatcagcagataaacaagag
gaagggcttcaaggacttgggaatctaagaagcttcacattcagagaactccatgtttat
acagatggtttcagttccaagaacattctcggcgctggtggattcggtaatgtgtacaga
ggcaagcttggagatgggacaatggtggcagtgaaacggttgaaggatattaatggaacc
tcagggattcacagtttcgtatggagctagagatgattagcttagctgttcataagaat
ctgcttcggttaattggttattgcgcaacttctggtgaaaggcttcttgtttacccttac
atgcctaatggaagcgtcgcctctaagcttaaatctaaaccggcattggactggaacatg
aggaagaggatagcaattggtgcagcgagagtttgttgtatctacatgagcaatgtgat
cccaagatcattcatagagatgtaaaggcagctaatattctcttagacgagtgctttgaa
gctgttgttggtgactttggactcgcaaagctccttaaccatgcggattctcatgtcaca
actgcggtccgtgcgtacggttggccacattgcacctgaatatctctccactggtcagtct
tctgagaaaaccgatgtgtttgggttcggtatactattgctcgagctcataaccggactg
agagctcttgagtttggtaaaaccgttagccagaaaggagctatgcttgaatgggtgagg
aaattacatgaagagatgaaagtagaggaactattggatcgagaactcggaactaactac
gataagattgaagttggagagatgttgcaagtggctttgctatgcacacaatatctgcca
gctcatcgtcctaaaatgtctgaagttgttttgatgcttgaaggcgatggattagccgag
agatgggctgcttcgcataaccattcacatttctaccatgccaatatctctttcaagaca
atctcttctctgtctactacttctgtctcaaggcttgacgcacattgcaatgatccaact
tatcaaatgtttggatcttcggctttcgatgatgacgatgatcatcagcctttagattcc
tttgccatggaactatccggtccaagataacacaatgaaaaaaaaaaaaaaaaaaaaa
```

(SEQ ID NO. 50)

Figure 16b

MKIQIHLLYSFLFLCFSTL
TLSSEPRNPEV

EALISIRNNLHDP
HGALNNWDEFSVD

PCSWAMITCSPDNLVIGL

SLQNNNISGKI
PPELGFLPKLQTL DLSNNRFSGDI
PVSIDQLSSLQYLDLSYNNLSGPV
PKFPARTFNVAGNPLICRSN

PPEICSGSINASPL
SVSLSSSSGTRSNR

LAIALSVSLGSVVILVLALGSFCWY

RKKQRRLLILNLNADKQEE
GLQGLGNLRSFTFRELHVYT

DGFSSKNILGAGGFGNVYRGKLGD
GTMVAVKRLKDINGTSGDSQFR
MELEMISLAVHKNLLRLIGYCA
TSGERLLVYPYMPNGSVASKLK
SKPALDWNMRKRIAIGAA
RGLLYLHEQCDPKIIHRDVKAA
NILLDECFEAVVGDFGLAKLLN
HADSHVTTAVRGTVGHIAPEYL
STGQSSEKTDVFGFGILLLELI
TGLRALEFGKTVSQKGAMLEW
VRKLHEEMKVEELLDRELGTNY
DKIEVGEMLQVALLCTQYLPAH
RPKMSEVVLMLE

GDGLAERWAASHNHSHFYHANISFKT
ISSLSTTSVSRLDAHCND

PTYQMFGSSAFDDDDDHQPLDSFAMELSGPR (SEQ ID NO. 51)

Figure 17a
Arabidopsis thaliana RKS12 cDNA

```
1/1                                 31/11
ttt aaa aac ctt gct agt tct caa ttc tca tga ctt tgc ttt tag tct tag aag tgg aaa 61/21                               91/31
ATG gaa cat gga tca tcc cgt ggc ttt att tgg ctg att cta ttt ctc gat ttt gtt tcc 121/41                              151/51
aga gtc acc gga aaa aca caa gtt gat gct ctc att gct cta aga agc agt tta tca tca 181/61                              211/71
ggt gac cat aca aac aat ata ctc caa agc tgg aat gcc act cac gtt act cca tgt tca 241/81                              271/91
tgg ttt cat gtt act tgc aat act gaa aac agt gtt act cgt ctg gaa ctt ttt aac aat 301/101                             331/111
aat att act ggg gag ata cct gag gag ctt ggc gac ttg atg gaa cta gta agc ttg gac 361/121                             391/131
ctt ttt gca aac aac ata agc ggt ccc atc cct tcc tct ctt ggc aaa cta gga aaa ctc 421/141                             451/151
cgc ttc ttg cgt ctt tat aac aac agc tta tct gga gaa att cca agg tct ttg act gct 481/161                             511/171
ctg ccg ctg gat gtt ctt gat atc tca aac aat cgg ctc agt gga gat att cct gtt aat 541/181                             571/191
ggt tcc ttt tcg cag ttc act tct atg agt ttt gcc aat aat aaa tta agg ccg cga cct 601/201                             631/211
gca tct cct tca cca tca cct tca gga acg tct gca gca ata gta gtg gga gtt gct gcg 661/221                             691/231
ggt gca gca ctt cta ttt gcg ctt gct tgg tgg ctg aga aga aaa ctg cag ggt cac ttt 721/241                             751/251
ctt gat gta cct gct gaa gaa gac cca gag gtt tat tta gga caa ttt aaa agg ttc tcc 781/261                             811/271
ttg cgt gaa ctg cta gtt gct aca gag aaa ttt agc aaa aga aat gta ttg ggc aaa gga 841/281                             871/291
cgt ttt ggt ata ttg tat aaa gga cgt tta gct gat gac act cta gtg gct gtg aaa cgg 901/301                             931/311
cta aat gaa gaa cgt acc aag ggt ggg gaa ctg cag ttt caa acc gaa gtt gag atg atc 961/321                             991/331
agt atg gcc gtt cat agg aac ttg ctt cgg ctt cgt ggc ttt tgc atg act cca act gaa 1021/341                            1051/351
aga tta ctt gtt tat ccc tac atg gct aat gga agt gtt gct tct tgt tta aga gag cgt 1081/361                            1111/371
cct gaa ggc aat cca gcc ctt gac tgg cca aaa aga aag cat att gct ctg gga tca gca 1141/381                            1171/391
agg ggg ctc gca tat tta cac gat cat tgc gac caa aag atc att cac ctg gat gtg aaa 1201/401                            1231/411
gct gca aat ata ctg tta gat gaa gag ttt gaa gct gtt gtt gga gat ttt ggg cta gca 1261/421                            1291/431
aaa tta atg aat tat aac gac tcc cat gtg aca act gct gta cgg ggt acg att ggc cat 1321/441                            1351/451
ata gcg ccc gag tac ctc tcg aca gga aaa tct tct gag aag act gat gtt ttt ggg tac
```

Fig.17a CONTD.

```
1381/461                                 1411/471
ggg gtc atg ctt ctc gag ctc atc act gga caa aag gct ttc gat ctt gct cgg ctt gca 1441/481                                 1471/491
aat gat gat gat atc atg tta ctc gac tgg gtg aaa gag gtt ttg aaa gag aag aag ttg 1501/501                                 1531/511
gaa agc ctt gtg gat gca gaa ctc gaa gga aag tac gtg aaa aca gaa gtg gag cag ctg 1561/521                                 1591/531
ata caa atg gct ctg ctc tgc act caa agt tct gca atg gaa cgt cca aag atg tca gaa 1621/541                                 1651/551
gta gtg aga atg ctg gaa gga gat ggt tta gct gag aga tgg gaa gaa tgg caa aag gag 1681/561                                 1711/571
gag atg cca ata cat gat ttt aac tat caa gcc tat cct cat gct ggc act gac tgg ctc 1741/581                                 1771/591
atc ccc tat tcc aat tcc ctt atc gaa aac gat tac ccc tcg ggg cca aga taa cct ttt 1801/601                                 1831/611
aga aag ggt cat ttc ttg tgg gtt ctt caa caa gta tat ata tag gta gtg aag ttg taa 1861/621                                 1891/631
gaa gca aaa ccc cac att cac ctt tga ata tca cta ctc tat aaaaaaaaaaaaaaaaaaaaaaa
```

(SEQ ID NO. 52)

Figure 17b

MEHGSSRGFI
WLILFLDFVSRVTGKTQV

DALIALRSSLSSGDHTNNILQ
SWNATHVT

PCSWFHVTCNTENSVTRL

ELFNNNITGEI
PEELGDLMELVSLDLFANNISGPI
PSSLGKLGKLRFLRLYNNSLSGEI
PRSLTALP LDVLDISNNRLSGDI
PVNGSFSQFTSMRFA NNKLRPR

PASPSPSPSGGTS

AAIVVGVAAGAALLFALAWWL

RRKLQGHFLDVPAAEEDPE
VYLGQFKRFSLRELLVAT

EKFSKRNVLGKGRFGILYKGRLAD
DTLVAVKRLNEERTKGGELQFQ
TEVEMISMAVHRNLLRLRGFCM
TPTERLLVYPYMANGSVASCLR
ERPEGNPALDWPKRKHIALGSA
RGLAYLHDHCDQKIIHLDVKAA
NILLDEEFEAVVGDFGLAKLMN
YNDSHVTTAVRGTIGHIAPEYL
STGKSSEKTDVFGYGVMLLELI
TGQKAFDLARLANDDDIMLLDW
VKEVLKEKKLESLVDAELEGKY
VETEVEQLIQMALLCTQSSAME
RPKMSEVVRMLE

GDGLAERWEEWQKEEMPIHDFNYQAY

PHAGTDWLIPYSNSLIENDYPSGPR (SEQ ID NO. 53)

Figure 18a
Arabidopsis thaliana RKS13 cDNA

```
1/1                              31/11
taa taa acc tct aat aat aat ggc ttt gct ttt act ctg ATG aca agt tca aaa atg gaa 61/21                            91/31
caa aga tca ctc ctt tgc ttc ctt tat ctg ctc cta cta ttc aat ttc act ctc aga gtc 121/41                           151/51
gct gga aac gct gaa ggt gat gct ttg act cag ctg aaa aac agt ttg tca tca ggt gac 181/61                           211/71
cct gca aac aat gta ctc caa agc tgg gat gct act ctt gtt act cca tgt act tgg ttt 241/81                           271/91
cat gtt act tgc aat cct gag aat aaa gtt act cgt gtg gag ctt tat agc aat aac att 301/101                          331/111
aca ggg gag ata cct gag gag ctt ggc gac ttg gtg gaa cta gta agc ttg gat ctt tac 361/121                          391/131
gca aac agc ata agc ggt ccc atc cct tcg tct ctt ggc aaa cta gga aaa ctc cgg ttc 421/141                          451/151
ttg cgt ctt aac aac aat agc tta tca ggg gaa att cca atg act ttg act tct gtg cag 481/161                          511/171
ctg caa gtt ctg gat atc tca aac aat cgg ctc agt gga gat att cct gtt aat ggt tct 541/181                          571/191
ttt tcg ctc ttc act cct atc agt ttt gcg aat aat agc tta acg gat ctt ccc gaa cct 601/201                          631/211
ccg cct act tct acc tct cct acg cca cca cca cct tca ggg ggg caa atg act gca gca 661/221                          691/231
ata gca ggg gga gtt gct gca ggt gca gca ctt cta ttt gct gtt cca gcc att gcg ttt 721/241                          751/251
gct tgg tgg ctc aga aga aaa cca cag gac cac ttt ttt gat gta cct gct gaa gaa gac 781/261                          811/271
cca gag gtt cat tta gga caa ctc aaa agg ttt acc ttg cgt gaa ctg tta gtt gct act 841/281                          871/291
gat aac ttt agc aat aaa aat gta ttg ggt aga ggt ggt ttt ggt aaa gtg tat aaa gga 901/301                          931/311
cgt tta gcc gat ggc aat cta gtg gct gtc aaa agg cta aaa gaa gaa cgt acc aag ggt 961/321                          991/331
ggg gaa ctg cag ttt caa acc gaa gtt gag atg atc agt atg gcc gtt cat agg aac ttg 1021/341                         1051/351
ctt cgg ctt cgt ggc ttt tgc atg act cca act gaa aga tta ctt gtt tat ccc tac atg 1081/361                         1111/371
gct aat gga agt gtt gct tct tgt tta aga gag cgt cct gaa ggc aat cca gca ctt gat 1141/381                         1171/391
tgg cca aaa aga aag cat att gct ctg gga tca gca agg ggg ctt gcg tat tta cat gat 1201/401                         1231/411
cat tgc gac caa aaa atc att cac cgg gat gtt aaa gct gct aat ata ttg tta gat gaa 1261/421                         1291/431
gag ttt gaa gct gtt gtt gga gat ttt ggg ctc gca aaa tta atg aat tat aat gac tcc 1321/441                         1351/451
cat gtg aca act gct gta cgc ggt aca att ggc cat ata gcg ccc gag tac ctc tcg aca 1381/461                         1411/471
gga aaa tct tct gag aag act gat gtt ttt ggg tac ggg gtc atg ctt ctc gag ctc atc
```

Fig. 18a CONTD.

```
1441/481                            1471/491
act gga caa aag gct ttc gat ctt gct cgg ctt gca aat gat gat gat atc atg tta ctc 1501/501                            1531/511
gac tgg gtg aaa gag gtt ttg aaa gag aag aag ttg gaa agc ctt gtg gat gca gaa ctc 1561/521                            1591/531
gaa gga aag tac gtg gaa aca gaa gtg gag cag ctg ata caa atg gct ctc tgc act 1621/541                            1651/551
caa agt tct gca atg gaa cgt cca aag atg tca gaa gta gtg aga atg ctg gaa gga gat 1681/561                            1711/571
ggt tta gct gag aga tgg gaa gaa tgg caa aag gag gag atg cca ata cat gat ttt aac 1741/581                            1771/591
tat caa gcc tat cct cat gct ggc act gac tgg ctc atc ccc tat tcc aat tcc ctt atc 1801/601.                           1831/611
gaa aac gat tac ccc tcg ggt cca aga taa cct ttt aga aag ggt ctt ttc ttg tgg gtt 1861/621
ctt caa caa gta tat ata tag att ggt gaa gtt tta aga tgc aaa aaa aa    (SEQ ID NO. 54)
```

Figure 18b

MEQRSLLCFLYLL
LLFNFTLRVAGNAEG

DALTQLKNSLSSGDP
ANNVLQSWDATLVT

PCTWFHVTCNPENKVTRV

ELYSNNITGEI
PEELGDLVELVSLDLYANSISGPI
PSSLGKLGKLRFLRLNNNSLSGEI
PMTLTSVQLQVLDISNNRLSGDI
PVNGSFSLFTPISFANNSLTDLPE

PPPTSTSPTPPPPSG

GQMTAAIAGGVAAGAAL
LFAVPAIAFAWWL

RRKPQDHFFDVPGAEEDPE
VHLGQLKRFTLRELLVAT

DNFSNKNVLGRGGFGKVYKGRLAD
GNLVAVKRLKEERTKGGELQFQ
TEVEMISMAVHRNLLRLRGFCM
TPTERLLVYPYMANGSVASCLR
ERPEGNPALDWPKRKHIALGSA
RGLAYLHDHCDQKIIHRDVKAA
NILLDEEFEAVVGDFGLAKLMN
YNDSHVTTAVRGTIGHIAPEYL
STGKSSEKTDVFGYGVMLLELI
TGQKAFDLARLANDDDIMLLDW
VKEVLKEKKLESLVDAELEGKY
VETEVEQLIQMALLCTQSSAME
RPKMSEVVRMLE

GDGLAERWEEWQKEEMPIHDFNYQA

YPHAGTDWLIPYSNSLIENDYPSGPR    (SEQ ID NO. 55)

Figure 19a
Arabidopsis thaliana RKS14 cDNA

```
1/1                                   31/11
ctg cac ctt aga gat taa tac tct caa gaa aaa caa gtt ttg att cgg aca aag ATG ttg 61/21                                 91/31
caa gga aga aga gaa gca aaa aag agt tat gct ttg ttc tct tca act ttc ttc ttc ttc 121/41                                151/51
ttt atc tgt ttt ctt tct tct tct gca gaa ctc aca gac aaa gtt gtt gcc tta ata 181/61                                211/71
gga atc aaa agc tca ctg act gat cct cat gga gtt cta atg aat tgg gat gac aca gca 241/81                                271/91
gtt gat cca tgt agc tgg aac atg atc act tgt tct gat ggt ttt gtc ata agg cta tac 301/101                               331/111
agg tta ttg cag aac aat tac ata aca gga aac atc cct cat gag att ggg aaa ttg atg 361/121                               391/131
aaa ctc aaa aca ctt gat ctc tct acc aat aac ttc act ggt caa atc cca ttc act ctt 421/141                               451/151
tct tac tcc aaa aat ctt cac agg agg gtt aat aat aac agc ctg aca gga aca att cct 481/161                               511/171
agc tca ttg gca aac atg acc caa ctc act ttt ttg gat ttg tcg tat aat aac ttg agt 541/181                               571/191
gga cca gtt cca aga tca ctt gcc aaa aca ttc aat gtt atg ggc aat tct cag att tgt 601/201                               631/211
cca aca gga act gag aaa gac tgt aat ggg act cag cct aag cca atg tca atc acc ttg 661/221                               691/231
aac agt tct caa aga act aaa aac cgg aaa atc gcg gta gtc ttc ggt gta agc ttg aca 721/241                               751/251
tgt gtt tgc ttg ttg atc att ggc ttt ggt ttt ctt ctt tgg tgg aga aga aga cat aac 781/261                               811/271
aaa caa gta tta ttc ttt gac att aat gag caa aac aag gaa gaa atg tgt cta ggg aat 841/281                               871/291
cta agg agg ttt aat ttc aaa gaa ctt caa tcc gca act agt aac ttc agc agc aag aat 901/301                               931/311
ctg gtc gga aaa gga ggg ttt gga aat gtg tat aaa ggt tgt ctt cat gat gga agt atc 961/321                               991/331
atc gcg gtg aag aga tta aag gat ata aac aat ggt ggt gga gag gtt cag ttt cag aca 1021/341                              1051/351
gag ctt gaa atg ata agc ctt gcc gtc cac cgg aat ctc ctc cgc tta tac ggt ttc tgt 1081/361                              1111/371
act act tcc tct gaa cgg ctt ctc gtt tat cct tac atg tcc aat ggc agt gtc gct tct 1141/381                              1171/391
cgt ctc aaa gct aaa ccg gta ttg gat tgg ggc aca aga aag cga ata gca tta gga gca 1201/401                              1231/411
gga aga ggg ttg ctg tat ttg cat gag caa tgt gat cca aag atc att cac cgt gat gtc 1261/421                              1291/431
aaa gct gcg aac ata ctt ctt gac gat tac ttt gaa gct gtt gtc gga gat tcg ggg ttg 1321/441                              1351/451
gct aag ctt ttg gat cat gag gag tcg cat gtg aca acc gcc gtg aga gga aca gtg ggt

1381/461                              1411/471
```

Fig. 19a CONTD.

```
cac att gca cct gag tat ctc tca aca gga caa tct tct gag aag aca gat gtg ttc ggt
1441/481                                        1471/491
ttc ggg att ctt ctt ctc gaa ttg att act gga ttg aga gct ctt gaa ttc gga aaa gca
1501/501                                        1531/511
gca aac caa aga gga gcg ata ctt gat tgg gta aag aaa cta caa caa gag aag aag cta
1561/521                                        1591/531
gaa cag ata gta gac aag gat ttg aag agc aac tac gat aga ata gaa gtg gaa gaa atg
1621/541                                        1651/551
gtt caa gtg gct ttg ctt tgt aca cag tat ctt ccc att cac cgt cct aag atg tct gaa
1681/561                                        1711/571
gtt gtg aga atg ctt gaa ggc gat ggt ctt gtt gag aaa tgg gaa gct tct tct cag aga
1741/581                                        1771/591
gca gaa acc aat aga agt tac agt aaa cct aac gag ttt tct tcc tct gaa cgt tat tcg
1801/601                                        1831/611
gat ctt aca gat gat tcc tcg gtg ctg gtt caa gcc atg gag tta tca ggt cca aga tga
1861/621                                        1891/631
caa gag aaa cta tat gaa tgg ctt tgg gtt tgt aaa aaa     (SEQ ID NO. 56)
```

Figure 19b

MLQGRREAKKSYALFSSTFF
FFFICFLSSSSAELTDKV

VALIGIKSSLTDP
HGVLMNWDDTAVD

PCSWNMITCSDGFVIR

LYRLLQNNYITGNI
PHEIGKLMKLKTLDLSTNNFTGQI
PFTLSYSKNLHRRVNNNSLTGTI
PSSLANMTQLTFLLDLSYNNLSGPV
PRSLA       KTFNVMGNSQICPT

GTEKDCNGTQPKPMSITLNSSQRGTKNRK

IAVVFGVSLTCVCLLIIGFGFLLWW

RRRHNKQVLFFDINEQNKE
EMCLGNLRRFNFKELQSAT

SNFSSKNLVGKGGFGNVYKGCLHD
GSIIAVKRLKDINNGGGEVQFQ
TELEMISLAVHRNLLRLYGFCT
TSSERLLVYPYMSNGSVA
SRLKAKPVLDWGTRKRIALGAG
RGLLYLHEQCDPKIIHRDVKAA
NILLDDYFEAVVGDFGLAKLLD
HEESHVTTAVRGTVGHIAPEYL
STGQSSEKTDVFGFGILLLELI
TGLRALEFGKAANQRGAILDW
VKKLQQEKKLEQIVDKDLKSNY
DRIEVEEMVQVALLCTQYLPIH
RPKMSEVVRMLE

GDGLVEKWEASSQRAET
NRSYSKPNEFSSS

ERYSDLTDDSSVLVQAMELSGPR    (SEQ ID NO. 57)

Figure 20 A
Arabidopsis thaliana RKS 7 partial cDNA sequence.

AGCGAATATACTTCTTGATGACTACTGTGAAGCTGTGGTTGGCGATTTTGG
TTTAGCTAAACTCTTGGATCATCAAGATTCTCATGTGACAACCGCGGTTAG
AGGCACGGTGGGTCACATTGCTCCAGAGTATCTCTCAACTGGTCAATCCTC
T (SEQ ID NO. 58)
AACAGATGTTTTTTGGCTTTGGGATTCTTCTTCTTGAGCTTGTAACCGGAC
AAGGAGCTTTTGAGTCTGTTAAAGCGGCTAACCGGAAAGGTGTGATGCTTG
ATTGGGTTAAAAAGATTCATCAAGAGAAGAAACTTGAGCTACTTGTGGATA
AAGAGTTGTTGAAGAAGAAGAGCTACGATGAGATTGAGTTAGACGAAATGG
TAAGAGTAGCTTTGTTGTGCACACAGTACCTGCCAGGACATAGACCAAAAA
TGTCTGAAGTTGTTCGAATGCTGGAAGGAGATGGACTTGCAGAGAAATGGG
AAGCTTCTCAAAGATCAGACAGTGTTTCAAAATGTAGCAACAGGATAAATG
AATTGATGTCATCTTCAGACAGATACTCTGATCTTACCGATGACTCTAGTT
TACTTGTGCAAGCAATGGAGCTCTCTGGTCCTAGATGAAATCTATACATGA
ATCTGAAGAAGAAGAAGAACATGCATCTGTTTCTTGAATCAAGAGGGATTC
TTGTTTTTTTGTATAATAGAGAGGTTTTTGGAGGGAAATGTTGTGTCTCT
GTAACTGTATAGGCTTGTTGTGTAAGAAGTTATTACTGCACTTAGGGTTAA
TTCAAAGTTCTTTACATAAAAAATGATTAGTTGCGTTGAATAGAGGGAACA
CTTTGGGAGATTTCATGTATGAAATTTGG (SEQ ID NO. 59)

Figure 20B
Predicted partial amino acid sequences of the Arabidopsis thaliana RKS-7 protein.

A
NILLDDYCEAVVGDFGLAKLLD
HQDSHVTTAVRGTVGHIAPEYL
STGQSS (SEQ ID NO. 60)

QMFFGFGILLLELV
TGQGAFE SVKAANRKGVMLDW
VKKIHQEKKLELLVDKELLKKKSY
DEIELDEMVRVALLCTQYLPGH
RPKMS EVVRMLE

GDGLAEKWEASQRSDS
VSKCSNRINELMSSS

DRYSDLTDDSSLLVQAMELSGPR*
( SEQ ID NO. 61)

Figure 21 A
Arabidopsis thaliana RKS 9 partial cDNA sequence.

```
GAAATGGTAAGAGTAGCTTTGTTGTGCACACAGTACCTGCCAGGACATAGA
CCAAGAGTGTCTGAAGTTGTTCGAATGCTGGAAGGAGATGGACTTGCAGAG
AAGTGGGAAGCTTCTCAAGGATCAGACAGTGTTTCAAAATGTAGCAACAG
GATAAATGAAGTGATGTCATCTTCAGACAGATACTCTGATGTTACCGATGA
CTCTAGTTTACGTGTGCAAGCAATGGAGCTCTCTGGTCCTAGATGAAGTCT
ATACATGAATCTGAAGAAGAAGAACATGCATCTGTTTCTTGAATCAAG
AGGGATTCTTGTTTTTTTGTATAATAGAGAGGTTTTTTGGAGGGAAATGTT
GTGTCTCTGTAACTGTATAGGCTTGTTGTGTAAGAAGTTATTACTGCACTT
AGGGTTAAGTCAAAGTTCTTTACATAAGGGGGATTAGTTGCGTTGAATAG
AGGGAACACTTTGGGAGATTTCATGTGTGAAAGTTGGGAAGTCATGTTTGA
GAATGAAGGTTATCTTATTATTGAA (SEQ ID NO. 62)
```

Figure 21B
Predicted amino acid sequence of the Arabidopsis thaliana RKS-9 protein

```
              VDKELLKKKSY
DEIELDEMVRVALLCTQYLPGH
RPRVSEVVRMLE

GDGLAEKWEASQGSDS
VSKCSNRINEVMSSS

DRYSDVTDDSSLRVQAMELSGPR*
( SEQ ID NO. 63)
```

Figure 22A
Arabidopsis thaliana RKS 15 partial cDNA sequence.

GTGGATAAAGAGTTGTTGAAGAAGAAGAGCTACGATGAGATTGAGTTAGA
CGAAATGGTAAGAGTAGCTTTGTTGTGCACACAGTACCTGCCAGGACATA
GACCAAGAGTGTCTGAAGTTGTTCGAATGCTGGAAGGAGATGGACTTGCA
GAGAAGTGGGGAAGCTTCTCAAGGATCAGACAGTGTTTCAAAATGTAGCA
ACAGGATAAATGAAGTGATGTCATCTTCAGACAGATACTCTGATGTTACC
GATGACTCTAGTTTACGTGTGCAAGCAATGGAGCTCTCTGGTCCTAGATG
AAGTCTATACATGAATCTGAAGAAGAAGAACATGCATCTGTTTCTTG
AATCAAGAGGGATTCTTGTTTTTTGTATAATAGAGAGGTTTTTTGGAGG
GAAATGTTGTGTCTCTGTAACTGTATAGGCTTGTTGTGTAAGAAGTTATT
ACTGCACTTAGGGTTAAGTCAAAGTTCTTTACATAAGGGGGATTAGTTG
CGTTGAATAGAGGGAACACTTTGGGAGATTTCATGTGTGAAAGTTGGGAA
GTCATGTTTGAGAATGAAGGTTATCTTATTATTGAA ( SEQ ID NO. 64)

Figure 22B
Predicted amino acid sequence of the Arabidopsis thaliana RKS-15 protein.

VDKELLKKKSY
KEIELDEMVRVALLCTQYLPGH
RPRVSEVVRMLE

GDGLAEKWEASQGSDSVSKCSNRINEVMSSS

DRYSDVTDDSSLRVQAMELSGPR* (SEQ ID NO. 65)

Figure 23A
Arabidopsis thaliana RKS 16 partial cDNA sequence.

AAAGTACGTGGAAGCAGAAGTGGAGCAGCTGATACGAATGGCTCTGCTCTG
CACTCAAAGTTCTGCAATGGAACGTCCAAAGATGTCAGAAGTAGTGAGAAT
GCTGGAAGGAGATGGTTTAGCTGAGAGATGGGAAGAATGGCAAAAGGAGGA
GATGCCAATACATGATTTTAACTATCAAGCCTATCCTCATGCTGGCACTGA
CTGGCTCATCCCCTATTCCAAGTCCCTTATCGAAGGCGATTACCCCTCGGG
TCCAAGATAACCTTTTAGAAAGGGTCTTTTCTTGTGGGTTCTTCAACAAGT
ATATATATAGATTGGTGAAGTTTTAAGATGCAAGAGGGGCCATGCACTTT
TGAATATCACCTCCTCTATAAGTAGTATTGTGTCTCTTG   SEQ ID NO. 66

Figure 23B
Predicted amino acid sequence of the Arabidopsis thaliana RKS-16 protein.

KY
VEAEVEQLIRMALLCTQSSAME
RPKMSEVVRMLE

GDGLAERWEEWQKEEMPIHDFNYQAY

PHAGTDWLIPYSKSLIEGDYPSGPR*
SEQ ID NO. 67

SEQUENCE LISTING

```
<160> NUMBER OF SEQ ID NOS: 67

<210> SEQ ID NO 1
<211> LENGTH: 29
<212> TYPE: DNA
<213> ORGANISM: Arabidopsis thaliana
<220> FEATURE:
<223> OTHER INFORMATION: Description of Artificial Sequence: primer RKS
      B forward
<220> FEATURE:
<223> OTHER INFORMATION: /note=""S" stands for C/G, "Y" stands for C/T,
      "W" stands for A/T, "H" stands for A/C/T, "V" stands
      for A/C/G, "R" stands for A/G.

<400> SEQUENCE: 1
ccsaagatya twcaccghga tgtvaargc                                           29

<210> SEQ ID NO 2
<211> LENGTH: 26
<212> TYPE: DNA
<213> ORGANISM: Arabidopsis thaliana
<220> FEATURE:
```

```
<223> OTHER INFORMATION: Description of Artificial Sequence: primer RKS
      E reverse
<220> FEATURE:
<223> OTHER INFORMATION: /note=""R" stands for A/G, "W" stands for A/T,
      "N" stands for A/C/G/T.

<400> SEQUENCE: 2
ccrwanccra aracatcggt tttctc                                              26

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 3
gactcgagtc gacatcgatt tttttttttt tt                                       32

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: forward
      oligo

<400> SEQUENCE: 4
gccatggtga acaagatgga tgg                                                 23

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: reverse
      oligo

<400> SEQUENCE: 5
ggatcctcag aagaactcgt caag                                                24

<210> SEQ ID NO 6
<211> LENGTH: 154
<212> TYPE: DNA
<213> ORGANISM: Arabidopsis thaliana
<220> FEATURE:
<223> OTHER INFORMATION: /note="Amplified receptor kinase fragment RKS1"

<400> SEQUENCE: 6
tgaggactga cccgtggata agtactcagg tgcaatgtgg ccaacagttc cacggactgc         60
agttgtgaca tgagagtctc tatggtctag aagcttagct aacccgaaat caccaacaac        120
tgcttcgaag tcctcatcta acagaatgtt agct                                    154

<210> SEQ ID NO 7
<211> LENGTH: 154
<212> TYPE: DNA
<213> ORGANISM: Arabidopsis thaliana
<220> FEATURE:
<223> OTHER INFORMATION: /note="Amplified receptor kinase fragment RKS2"

<400> SEQUENCE: 7
tgacgatttc cctgtggata tacattctgg tgcaatatga cccattgttc ctcggacctg         60
agtggttaca ttagtccttc taacatctac caacttggct aaaccaaaat caccaaccac        120
tgcttcaaag tcttcatcta gtaacacatt tgca                                    154
```

<210> SEQ ID NO 8
<211> LENGTH: 154
<212> TYPE: DNA
<213> ORGANISM: Arabidopsis thaliana
<220> FEATURE:
<223> OTHER INFORMATION: /note="Amplified receptor kinase fragment RKS3"

<400> SEQUENCE: 8

```
agatgatttt cctgtgcaga gatactctgg cgcaatgtga cccattgtgc ctcggacttg     60
agttgtgaca tgagtcagag atgtgtccac aagcttagct aaaccgaaat ctccaagaac    120
tggctcaaaa ttgttgtcta aaagtatgtt tgca                                154
```

<210> SEQ ID NO 9
<211> LENGTH: 154
<212> TYPE: DNA
<213> ORGANISM: Arabidopsis thaliana
<220> FEATURE:
<223> OTHER INFORMATION: /note="Amplified receptor kinase fragment RKS4"

<400> SEQUENCE: 9

```
agatgactga ccagtggaga gatactcggg tgcaatgtga ccaacagttc ctctaaccgc     60
ggttgtgaca tgtgaatcct cgtggttgag tagctttgct agtccaaaat ccccaacaac    120
tgcttcaaaa tactcatcta ggagaatgtt tgct                                154
```

<210> SEQ ID NO 10
<211> LENGTH: 154
<212> TYPE: DNA
<213> ORGANISM: Arabidopsis thaliana
<220> FEATURE:
<223> OTHER INFORMATION: /note="Amplified receptor kinase fragment RKS5"

<400> SEQUENCE: 10

```
tgaggactgt ccagtggaaa ggtactcggg agcgatgtgt ccaatggttc ctcggactgc     60
ggtagtgaca tgtgaatctc tctggtctaa aagctttgct agaccaaaat cgccaactat    120
tgcttcaaag ctctcatcaa gtagaatatt tgca                                154
```

<210> SEQ ID NO 11
<211> LENGTH: 154
<212> TYPE: DNA
<213> ORGANISM: Arabidopsis thaliana
<220> FEATURE:
<223> OTHER INFORMATION: /note="Amplified receptor kinase fragment RKS6"

<400> SEQUENCE: 11

```
tgatgatttc cctgttgata aatattctgg tgcaatgtga cccattgttc ctcgaacttg     60
agtagtcaca ttagtccttc taacatctac tagcttggct aaaccaaaat caccaaccac    120
tgcttcaaaa tcttcatcta gtaacacgtt agct                                154
```

<210> SEQ ID NO 12
<211> LENGTH: 154
<212> TYPE: DNA
<213> ORGANISM: Arabidopsis thaliana
<220> FEATURE:
<223> OTHER INFORMATION: /note="Amplified receptor kinase fragment RKS7"

<400> SEQUENCE: 12

```
agaggattga ccagttgaga gatactctgg agcaatgtga cccaccgtgc ctctaaccgc     60
ggttgtcaca tgagaatctt gatgatccaa gagtttagct aaaccaaaat cgccaaccac    120
```
agcttcacag tagtcatcaa gaagtatatt cgct                                     154

<210> SEQ ID NO 13
<211> LENGTH: 154
<212> TYPE: DNA
<213> ORGANISM: Arabidopsis thaliana
<220> FEATURE:
<223> OTHER INFORMATION: /note="Amplified receptor kinase fragment RKS8"

<400> SEQUENCE: 13
tgaagatttt ccagttgaga gatactcagg agcaatgtgt ccaatagttc cacgcacagc        60
cgttgtgaca tgtgtatctt tataatccat aagcctagct aacccgaaat cacctaccac       120
cgcctcaaat tcctcgtcca acagaatatt agca                                    154

<210> SEQ ID NO 14
<211> LENGTH: 154
<212> TYPE: DNA
<213> ORGANISM: Arabidopsis thaliana
<220> FEATURE:
<223> OTHER INFORMATION: /note="Amplified receptor kinase fragment
      RKS10"

<400> SEQUENCE: 14
tgatgatttt ccagtggaaa ggtactcagg ggctatatga ccaattgtcc cacgcactgc        60
ggttgtcaca tgtgtgtctt tgtagtccat gagttttgca agtccaaaat ccccaaccac       120
ggcttcaaac tcttcatcca acaaaatatt tgca                                    154

<210> SEQ ID NO 15
<211> LENGTH: 154
<212> TYPE: DNA
<213> ORGANISM: Arabidopsis thaliana
<220> FEATURE:
<223> OTHER INFORMATION: /note="Amplified receptor kinase fragment
      RKS11"

<400> SEQUENCE: 15
agaagactga ccagtggaga gatattcagg tgcaatgtgg ccaaccgtac cacggaccgc        60
agttgtgaca tgagaatccg catggttaag gagctttgcg agtccaaagt caccaacaac       120
agcttcaaag cactcgtcta agagaatatt agct                                    154

<210> SEQ ID NO 16
<211> LENGTH: 154
<212> TYPE: DNA
<213> ORGANISM: Arabidopsis thaliana
<220> FEATURE:
<223> OTHER INFORMATION: /note="Amplified receptor kinase fragment
      RKS12"

<400> SEQUENCE: 16
agaagatttt cctgtcgaga ggtactcggg agctatatgg ccaatcgtac cgcgtacagc        60
agttgtcaca tgggagtcat tgtaattcat taattttgct agcccaaagt ctccaacaac       120
agcttcaaac tcttcatcta acagtatatt tgca                                    154

<210> SEQ ID NO 17
<211> LENGTH: 154
<212> TYPE: DNA
<213> ORGANISM: Arabidopsis thaliana
<220> FEATURE:
<223> OTHER INFORMATION: /note="Amplified receptor kinase fragment
      RKS13"

<400> SEQUENCE: 17

-continued

```
tgctaatata ttgttagatg aagagtttga agctgttgtt ggagatttg ggctcgcaaa      60 attaatgaat tataatgact cccatgtgac aactgctgta cgcggtacaa ttggccatat    120
agcgcccgag tacctctcga caggaaaatc ttct                                154
```

<210> SEQ ID NO 18
<211> LENGTH: 154
<212> TYPE: DNA
<213> ORGANISM: Arabidopsis thaliana
<220> FEATURE:
<223> OTHER INFORMATION: /note="Amplified receptor kinase fragment RKS14"

<400> SEQUENCE: 18

```
tgcgaacata cttcttgacg attactttga agctgttgtc ggagatttcg ggttggctaa     60
gcttttggat catgaggagt cgcatgtgac aaccgccgtg agaggaacag tgggtcacat    120
tgcacctgag tatctctcaa caggacaatc ttct                                154
```

<210> SEQ ID NO 19
<211> LENGTH: 154
<212> TYPE: DNA
<213> ORGANISM: Arabidopsis thaliana
<220> FEATURE:
<223> OTHER INFORMATION: /note="Amplified receptor kinase fragment RKS0"

<400> SEQUENCE: 19

```
tgaagatttt ccggttgaga gatattctgg agcgatgtga ccgatggtgc cacggactgc     60
tgttgtcacg tgagtgtctt tatagtccat aagctttgcc aacccgaaat ctccaacaac    120
cgcttcgaat tcttcgtcta agaggatgtt tgct                                154
```

<210> SEQ ID NO 20
<211> LENGTH: 2087
<212> TYPE: DNA
<213> ORGANISM: Arabidopsis thaliana
<220> FEATURE:
<221> NAME/KEY: CDS
<222> LOCATION: (193)..(2067)
<223> OTHER INFORMATION: /note="Arabidopsis thaliana RKS0 cDNA"

<400> SEQUENCE: 20

```
attttatt tattttttac tctttgtttg ttttaatgct aatgggtttt taaaagggtt       60
atcgaaaaaa tgagtgagtt tgtgttgagg ttgtctctgt aaagtgttaa tggtggtgat    120
tttcggaagt tagggttttc tcggatctga agagatcaaa tcaagattcg aaatttacca   180
ttgttgtttg aa atg gag tcg agt tat gtg gtg ttt atc tta ctt tca ctg    231
              Met Glu Ser Ser Tyr Val Val Phe Ile Leu Leu Ser Leu
                1               5                  10 atc tta ctt ccg aat cat tca ctg tgg ctt gct tct gct aat ttg gaa      279
Ile Leu Leu Pro Asn His Ser Leu Trp Leu Ala Ser Ala Asn Leu Glu
     15                  20                  25 ggt gat gct ttg cat act ttg agg gtt act cta gtt gat cca aac aat      327
Gly Asp Ala Leu His Thr Leu Arg Val Thr Leu Val Asp Pro Asn Asn
 30                  35                  40                  45 gtc ttg cag agc tgg gat cct acg cta gtg aat cct tgc aca tgg ttc      375
Val Leu Gln Ser Trp Asp Pro Thr Leu Val Asn Pro Cys Thr Trp Phe
                 50                  55                  60 cat gtc act tgc aac aac gag aac agt gtc ata aga gtt gat ttg ggg      423
His Val Thr Cys Asn Asn Glu Asn Ser Val Ile Arg Val Asp Leu Gly
             65                  70                  75 aat gca gag tta tct ggc cat tta gtt cca gag ctt ggt gtg ctc aag      471
```

|  |  |
|---|---|
| Asn Ala Glu Leu Ser Gly His Leu Val Pro Glu Leu Gly Val Leu Lys<br>        80                     85                         90 | |
| aat ttg cag tat ttg gag ctt tac agt aac aac ata act ggc ccg att<br>Asn Leu Gln Tyr Leu Glu Leu Tyr Ser Asn Asn Ile Thr Gly Pro Ile<br>     95                    100                    105 | 519 |
| cct agt aat ctt gga aat ctg aca aac tta gtg agt ttg gat ctt tac<br>Pro Ser Asn Leu Gly Asn Leu Thr Asn Leu Val Ser Leu Asp Leu Tyr<br>110                    115                  120               125 | 567 |
| tta aac agc ttc tcc ggt cct att ccg gaa tca ttg gga aag ctt tca<br>Leu Asn Ser Phe Ser Gly Pro Ile Pro Glu Ser Leu Gly Lys Leu Ser<br>                    130                  135               140 | 615 |
| aag ctg aga ttt ctc cgg ctt aac aac aac agt ctc act ggg tca att<br>Lys Leu Arg Phe Leu Arg Leu Asn Asn Asn Ser Leu Thr Gly Ser Ile<br>             145                    150               155 | 663 |
| cct atg tca ctg acc aat att act acc ctt caa gtg tta gat cta tca<br>Pro Met Ser Leu Thr Asn Ile Thr Thr Leu Gln Val Leu Asp Leu Ser<br>                160                  165               170 | 711 |
| aat aac aga ctc tct ggt tca gtt cct gac aat ggc tcc ttc tca ctc<br>Asn Asn Arg Leu Ser Gly Ser Val Pro Asp Asn Gly Ser Phe Ser Leu<br>175                    180                  185 | 759 |
| ttc aca ccc atc agt ttt gct aat aac tta gac cta tgt gga cct gtt<br>Phe Thr Pro Ile Ser Phe Ala Asn Asn Leu Asp Leu Cys Gly Pro Val<br>190                    195                  200               205 | 807 |
| aca agt cac cca tgt cct gga tct ccc ccg ttt tct cct cca cca cct<br>Thr Ser His Pro Cys Pro Gly Ser Pro Pro Phe Ser Pro Pro Pro Pro<br>                    210                  215               220 | 855 |
| ttt att caa cct ccc cca gtt tcc acc ccg agt ggg tat ggt ata act<br>Phe Ile Gln Pro Pro Pro Val Ser Thr Pro Ser Gly Tyr Gly Ile Thr<br>             225                    230               235 | 903 |
| gga gca ata gct ggt gga gtt gct gca ggt gct gct ttg ccc ttt gct<br>Gly Ala Ile Ala Gly Gly Val Ala Ala Gly Ala Ala Leu Pro Phe Ala<br>                240                  245               250 | 951 |
| gct cct gca ata gcc ttt gct tgg tgg cga cga aga agc cca cta gat<br>Ala Pro Ala Ile Ala Phe Ala Trp Trp Arg Arg Arg Ser Pro Leu Asp<br>255                    260                  265 | 999 |
| att ttc ttc gat gtc cct gcc gaa gaa gat cca gaa gtt cat ctg gga<br>Ile Phe Phe Asp Val Pro Ala Glu Glu Asp Pro Glu Val His Leu Gly<br>270                    275                  280               285 | 1047 |
| cag ctc aag agg ttt tct ttg cgg gag cta caa gtg gcg agt gat ggg<br>Gln Leu Lys Arg Phe Ser Leu Arg Glu Leu Gln Val Ala Ser Asp Gly<br>                    290                  295               300 | 1095 |
| ttt agt aac aag aac att ttg ggc aga ggt ggg ttt ggg aaa gtc tac<br>Phe Ser Asn Lys Asn Ile Leu Gly Arg Gly Gly Phe Gly Lys Val Tyr<br>             305                    310               315 | 1143 |
| aag gga cgc ttg gca gac gga act ctt gtt gct gtc aag aga ctg aag<br>Lys Gly Arg Leu Ala Asp Gly Thr Leu Val Ala Val Lys Arg Leu Lys<br>                320                  325               330 | 1191 |
| gaa gag cga act cca ggt gga gag ctc cag ttt caa aca gaa gta gag<br>Glu Glu Arg Thr Pro Gly Gly Glu Leu Gln Phe Gln Thr Glu Val Glu<br>335                    340                  345 | 1239 |
| atg ata agt atg gca gtt cat cga aac ctg ttg aga tta cga ggt ttc<br>Met Ile Ser Met Ala Val His Arg Asn Leu Leu Arg Leu Arg Gly Phe<br>350                    355                  360               365 | 1287 |
| tgt atg aca ccg acc gag aga ttg ctt gtg tat cct tac atg gcc aat<br>Cys Met Thr Pro Thr Glu Arg Leu Leu Val Tyr Pro Tyr Met Ala Asn<br>                370                  375               380 | 1335 |
| gga agt gtt gct tcg tgt ctc aga gag agg cca ccg tca caa cct ccg<br>Gly Ser Val Ala Ser Cys Leu Arg Glu Arg Pro Pro Ser Gln Pro Pro<br>385                    390                  395 | 1383 |

-continued

```
ctt gat tgg cca acg cgg aag aga atc gcg cta ggc tca gct cga ggt   1431
Leu Asp Trp Pro Thr Arg Lys Arg Ile Ala Leu Gly Ser Ala Arg Gly
        400                 405                 410 ttg tct tac cta cat gat cac tgc gat ccg aag atc att cac cgt gac   1479
Leu Ser Tyr Leu His Asp His Cys Asp Pro Lys Ile Ile His Arg Asp
    415                 420                 425 gta aaa gca gca aac atc ctc tta gac gaa gaa ttc gaa gcg gtt gtt   1527
Val Lys Ala Ala Asn Ile Leu Leu Asp Glu Glu Phe Glu Ala Val Val
430                 435                 440                 445 gga gat ttc ggg ttg gca aag ctt atg gac tat aaa gac act cac gtg   1575
Gly Asp Phe Gly Leu Ala Lys Leu Met Asp Tyr Lys Asp Thr His Val
                450                 455                 460 aca aca gca gtc cgt ggc acc atc ggt cac atc gct cca gaa tat ctc   1623
Thr Thr Ala Val Arg Gly Thr Ile Gly His Ile Ala Pro Glu Tyr Leu
            465                 470                 475 tca acc gga aaa tct tca gag aaa acc gac gtt ttc gga tac gga atc   1671
Ser Thr Gly Lys Ser Ser Glu Lys Thr Asp Val Phe Gly Tyr Gly Ile
        480                 485                 490 atg ctt cta gaa cta atc aca gga caa aga gct ttc gat ctc gct cgg   1719
Met Leu Leu Glu Leu Ile Thr Gly Gln Arg Ala Phe Asp Leu Ala Arg
    495                 500                 505 cta gct aac gac gac gac gtc atg tta ctt gac tgg gtg aaa gga ttg   1767
Leu Ala Asn Asp Asp Asp Val Met Leu Leu Asp Trp Val Lys Gly Leu
510                 515                 520                 525 ttg aag gag aag aag cta gag atg tta gtg gat cca gat ctt caa aca   1815
Leu Lys Glu Lys Lys Leu Glu Met Leu Val Asp Pro Asp Leu Gln Thr
                530                 535                 540 aac tac gag gag aga gaa ctg gaa caa gtg ata caa gtg gcg ttg cta   1863
Asn Tyr Glu Glu Arg Glu Leu Glu Gln Val Ile Gln Val Ala Leu Leu
            545                 550                 555 tgc acg caa gga tca cca atg gaa aga cca aag atg tct gaa gtt gta   1911
Cys Thr Gln Gly Ser Pro Met Glu Arg Pro Lys Met Ser Glu Val Val
        560                 565                 570 agg atg ctg gaa gga gat ggg ctt gcg gag aaa tgg gac gaa tgg caa   1959
Arg Met Leu Glu Gly Asp Gly Leu Ala Glu Lys Trp Asp Glu Trp Gln
    575                 580                 585 aaa gtt gag att ttg agg gaa gag att gat ttg agt cct aat cct aac   2007
Lys Val Glu Ile Leu Arg Glu Glu Ile Asp Leu Ser Pro Asn Pro Asn
590                 595                 600                 605 tct gat tgg att ctt gat tct act tac aat ttg cac gcc gtt gag tta   2055
Ser Asp Trp Ile Leu Asp Ser Thr Tyr Asn Leu His Ala Val Glu Leu
                610                 615                 620 tct ggt cca agg taaaaaaaaa aaaaaaaaa                              2087
Ser Gly Pro Arg
            625

<210> SEQ ID NO 21
<211> LENGTH: 625
<212> TYPE: PRT
<213> ORGANISM: Arabidopsis thaliana

<400> SEQUENCE: 21

Met Glu Ser Ser Tyr Val Val Phe Ile Leu Leu Ser Leu Ile Leu Leu
 1               5                  10                  15

Pro Asn His Ser Leu Trp Leu Ala Ser Ala Asn Leu Glu Gly Asp Ala
                20                  25                  30

Leu His Thr Leu Arg Val Thr Leu Val Asp Pro Asn Asn Val Leu Gln
            35                  40                  45

Ser Trp Asp Pro Thr Leu Val Asn Pro Cys Thr Trp Phe His Val Thr
        50                  55                  60
```

```
Cys Asn Glu Asn Ser Val Ile Arg Val Asp Leu Gly Asn Ala Glu
 65                  70                  75                  80

Leu Ser Gly His Leu Val Pro Glu Leu Gly Val Leu Lys Asn Leu Gln
             85                  90                  95

Tyr Leu Glu Leu Tyr Ser Asn Asn Ile Thr Gly Pro Ile Pro Ser Asn
            100                 105                 110

Leu Gly Asn Leu Thr Asn Leu Val Ser Leu Asp Leu Tyr Leu Asn Ser
            115                 120                 125

Phe Ser Gly Pro Ile Pro Glu Ser Leu Gly Lys Leu Ser Lys Leu Arg
    130                 135                 140

Phe Leu Arg Leu Asn Asn Ser Leu Thr Gly Ser Ile Pro Met Ser
145                 150                 155                 160

Leu Thr Asn Ile Thr Thr Leu Gln Val Leu Asp Leu Ser Asn Asn Arg
                165                 170                 175

Leu Ser Gly Ser Val Pro Asp Asn Gly Ser Phe Ser Leu Phe Thr Pro
            180                 185                 190

Ile Ser Phe Ala Asn Asn Leu Asp Leu Cys Gly Pro Val Thr Ser His
        195                 200                 205

Pro Cys Pro Gly Ser Pro Pro Phe Ser Pro Pro Pro Phe Ile Gln
    210                 215                 220

Pro Pro Pro Val Ser Thr Pro Ser Gly Tyr Gly Ile Thr Gly Ala Ile
225                 230                 235                 240

Ala Gly Gly Val Ala Ala Gly Ala Ala Leu Pro Phe Ala Ala Pro Ala
                245                 250                 255

Ile Ala Phe Ala Trp Trp Arg Arg Ser Pro Leu Asp Ile Phe Phe
        260                 265                 270

Asp Val Pro Ala Glu Glu Asp Pro Glu Val His Leu Gly Gln Leu Lys
        275                 280                 285

Arg Phe Ser Leu Arg Glu Leu Gln Val Ala Ser Asp Gly Phe Ser Asn
    290                 295                 300

Lys Asn Ile Leu Gly Arg Gly Gly Phe Gly Lys Val Tyr Lys Gly Arg
305                 310                 315                 320

Leu Ala Asp Gly Thr Leu Val Ala Val Lys Arg Leu Lys Glu Glu Arg
                325                 330                 335

Thr Pro Gly Gly Glu Leu Gln Phe Gln Thr Glu Val Glu Met Ile Ser
            340                 345                 350

Met Ala Val His Arg Asn Leu Leu Arg Leu Arg Gly Phe Cys Met Thr
        355                 360                 365

Pro Thr Glu Arg Leu Leu Val Tyr Pro Tyr Met Ala Asn Gly Ser Val
370                 375                 380

Ala Ser Cys Leu Arg Glu Arg Pro Ser Gln Pro Pro Leu Asp Trp
385                 390                 395                 400

Pro Thr Arg Lys Arg Ile Ala Leu Gly Ser Ala Arg Gly Leu Ser Tyr
            405                 410                 415

Leu His Asp His Cys Asp Pro Lys Ile Ile His Arg Asp Val Lys Ala
            420                 425                 430

Ala Asn Ile Leu Leu Asp Glu Glu Phe Glu Ala Val Val Gly Asp Phe
        435                 440                 445

Gly Leu Ala Lys Leu Met Asp Tyr Lys Asp Thr His Val Thr Thr Ala
        450                 455                 460

Val Arg Gly Thr Ile Gly His Ile Ala Pro Glu Tyr Leu Ser Thr Gly
465                 470                 475                 480
```

```
Lys Ser Ser Glu Lys Thr Asp Val Phe Gly Tyr Gly Ile Met Leu Leu
            485                 490                 495

Glu Leu Ile Thr Gly Gln Arg Ala Phe Asp Leu Ala Arg Leu Ala Asn
            500                 505                 510

Asp Asp Asp Val Met Leu Leu Asp Trp Val Lys Gly Leu Leu Lys Glu
            515                 520                 525

Lys Lys Leu Glu Met Leu Val Asp Pro Asp Leu Gln Thr Asn Tyr Glu
            530                 535                 540

Glu Arg Glu Leu Glu Gln Val Ile Gln Val Ala Leu Leu Cys Thr Gln
545                 550                 555                 560

Gly Ser Pro Met Glu Arg Pro Lys Met Ser Glu Val Val Arg Met Leu
                565                 570                 575

Glu Gly Asp Gly Leu Ala Glu Lys Trp Asp Glu Trp Gln Lys Val Glu
            580                 585                 590

Ile Leu Arg Glu Glu Ile Asp Leu Ser Pro Asn Pro Asn Ser Asp Trp
            595                 600                 605

Ile Leu Asp Ser Thr Tyr Asn Leu His Ala Val Glu Leu Ser Gly Pro
            610                 615                 620

Arg
625

<210> SEQ ID NO 22
<211> LENGTH: 625
<212> TYPE: PRT
<213> ORGANISM: Arabidopsis thaliana
<220> FEATURE:
<223> OTHER INFORMATION: /note="Predicted amino acid sequence of the
      Arabidopsis thaliana RKS-0 protein"

<400> SEQUENCE: 22

Met Glu Ser Ser Tyr Val Val Phe Ile Leu Leu Ser Leu Ile Leu Leu
  1               5                  10                  15

Pro Asn His Ser Leu Trp Leu Ala Ser Ala Asn Leu Glu Gly Asp Ala
             20                  25                  30

Leu His Thr Leu Arg Val Thr Leu Val Asp Pro Asn Asn Val Leu Gln
         35                  40                  45

Ser Trp Asp Pro Thr Leu Val Asn Pro Cys Thr Trp Phe His Val Thr
     50                  55                  60

Cys Asn Asn Glu Asn Ser Val Ile Arg Val Asp Leu Gly Asn Ala Glu
 65                  70                  75                  80

Leu Ser Gly His Leu Val Pro Glu Leu Gly Val Leu Lys Asn Leu Gln
                 85                  90                  95

Tyr Leu Glu Leu Tyr Ser Asn Asn Ile Thr Gly Pro Ile Pro Ser Asn
            100                 105                 110

Leu Gly Asn Leu Thr Asn Leu Val Ser Leu Asp Leu Tyr Leu Asn Ser
            115                 120                 125

Phe Ser Gly Pro Ile Pro Glu Ser Leu Gly Lys Leu Ser Lys Leu Arg
            130                 135                 140

Phe Leu Arg Leu Asn Asn Asn Ser Leu Thr Gly Ser Ile Pro Met Ser
145                 150                 155                 160

Leu Thr Asn Ile Thr Thr Leu Gln Val Leu Asp Leu Ser Asn Asn Arg
                165                 170                 175

Leu Ser Gly Ser Val Pro Asp Asn Gly Ser Phe Ser Leu Phe Thr Pro
            180                 185                 190

Ile Ser Phe Ala Asn Asn Leu Asp Leu Cys Gly Pro Val Thr Ser His
            195                 200                 205
```

-continued

```
Pro Cys Pro Gly Ser Pro Pro Phe Ser Pro Pro Pro Phe Ile Gln
    210                 215                 220

Pro Pro Pro Val Ser Thr Pro Ser Gly Tyr Gly Ile Thr Gly Ala Ile
225                 230                 235                 240

Ala Gly Gly Val Ala Ala Gly Ala Ala Leu Pro Phe Ala Ala Pro Ala
                245                 250                 255

Ile Ala Phe Ala Trp Trp Arg Arg Ser Pro Leu Asp Ile Phe Phe
            260                 265                 270

Asp Val Pro Ala Glu Glu Asp Pro Glu Val His Leu Gly Gln Leu Lys
        275                 280                 285

Arg Phe Ser Leu Arg Glu Leu Gln Val Ala Ser Asp Gly Phe Ser Asn
    290                 295                 300

Lys Asn Ile Leu Gly Arg Gly Phe Gly Lys Val Tyr Lys Gly Arg
305                 310                 315                 320

Leu Ala Asp Gly Thr Leu Val Ala Val Lys Arg Leu Lys Glu Glu Arg
                325                 330                 335

Thr Pro Gly Gly Glu Leu Gln Phe Gln Thr Glu Val Glu Met Ile Ser
            340                 345                 350

Met Ala Val His Arg Asn Leu Leu Arg Leu Arg Gly Phe Cys Met Thr
        355                 360                 365

Pro Thr Glu Arg Leu Leu Val Tyr Pro Tyr Met Ala Asn Gly Ser Val
    370                 375                 380

Ala Ser Cys Leu Arg Glu Arg Pro Pro Ser Gln Pro Pro Leu Asp Trp
385                 390                 395                 400

Pro Thr Arg Lys Arg Ile Ala Leu Gly Ser Ala Arg Gly Leu Ser Tyr
                405                 410                 415

Leu His Asp His Cys Asp Pro Lys Ile Ile His Arg Asp Val Lys Ala
            420                 425                 430

Ala Asn Ile Leu Leu Asp Glu Glu Phe Glu Ala Val Val Gly Asp Phe
        435                 440                 445

Gly Leu Ala Lys Leu Met Asp Tyr Lys Asp Thr His Val Thr Thr Ala
    450                 455                 460

Val Arg Gly Thr Ile Gly His Ile Ala Pro Glu Tyr Leu Ser Thr Gly
465                 470                 475                 480

Lys Ser Ser Glu Lys Thr Asp Val Phe Gly Tyr Gly Ile Met Leu Leu
                485                 490                 495

Glu Leu Ile Thr Gly Gln Arg Ala Phe Asp Leu Ala Arg Leu Ala Asn
            500                 505                 510

Asp Asp Asp Val Met Leu Leu Asp Trp Val Lys Gly Leu Leu Lys Glu
        515                 520                 525

Lys Lys Leu Glu Met Leu Val Asp Pro Asp Leu Gln Thr Asn Tyr Glu
    530                 535                 540

Glu Arg Glu Leu Glu Gln Val Ile Gln Val Ala Leu Leu Cys Thr Gln
545                 550                 555                 560

Gly Ser Pro Met Glu Arg Pro Lys Met Ser Glu Val Val Arg Met Leu
                565                 570                 575

Glu Gly Asp Gly Leu Ala Glu Lys Trp Asp Glu Trp Gln Lys Val Glu
            580                 585                 590

Ile Leu Arg Glu Glu Ile Asp Leu Ser Pro Asn Pro Asn Ser Asp Trp
        595                 600                 605

Ile Leu Asp Ser Thr Tyr Asn Leu His Ala Val Glu Leu Ser Gly Pro
    610                 615                 620
```

Arg
625

```
<210> SEQ ID NO 23
<211> LENGTH: 613
<212> TYPE: PRT
<213> ORGANISM: Arabidopsis thaliana
<220> FEATURE:
<223> OTHER INFORMATION: /note="Predicted protein domain RKS-6 of the
      RKS subfamily I"

<400> SEQUENCE: 23
```

| Met | Arg | Met | Phe | Ser | Leu | Gln | Lys | Met | Ala | Met | Ala | Phe | Thr | Leu | Leu |
|---|---|---|---|---|---|---|---|---|---|---|---|---|---|---|---|
| 1 | | | | 5 | | | | | 10 | | | | | 15 | |

| Phe | Phe | Ala | Cys | Leu | Cys | Ser | Phe | Val | Ser | Pro | Asp | Ala | Gln | Gly | Asp |
| | | | 20 | | | | | 25 | | | | | 30 | | |

| Ala | Leu | Phe | Ala | Leu | Arg | Ile | Ser | Leu | Arg | Ala | Leu | Pro | Asn | Gln | Leu |
| | | | 35 | | | | | 40 | | | | | 45 | | |

| Ser | Asp | Trp | Asn | Gln | Asn | Gln | Val | Asn | Pro | Cys | Thr | Trp | Ser | Gln | Val |
| | 50 | | | | | 55 | | | | | 60 | | | | |

| Ile | Cys | Asp | Asp | Lys | Asn | Phe | Val | Thr | Ser | Leu | Thr | Leu | Ser | Asp | Met |
| 65 | | | | | 70 | | | | | 75 | | | | | 80 |

| Asn | Phe | Ser | Gly | Thr | Leu | Ser | Ser | Arg | Val | Gly | Ile | Leu | Glu | Asn | Leu |
| | | | | 85 | | | | | 90 | | | | | 95 | |

| Lys | Thr | Leu | Thr | Leu | Lys | Gly | Asn | Gly | Ile | Thr | Gly | Glu | Ile | Pro | Glu |
| | | | 100 | | | | | 105 | | | | | 110 | | |

| Asp | Phe | Gly | Asn | Leu | Thr | Ser | Leu | Thr | Ser | Leu | Asp | Leu | Glu | Asp | Asn |
| | | | 115 | | | | | 120 | | | | | 125 | | |

| Gln | Leu | Thr | Gly | Arg | Ile | Pro | Ser | Thr | Ile | Gly | Asn | Leu | Lys | Lys | Leu |
| | 130 | | | | | 135 | | | | | 140 | | | | |

| Gln | Phe | Leu | Thr | Leu | Ser | Arg | Asn | Lys | Leu | Asn | Gly | Thr | Ile | Pro | Glu |
| 145 | | | | | 150 | | | | | 155 | | | | | 160 |

| Ser | Leu | Thr | Gly | Leu | Pro | Asn | Leu | Leu | Asn | Leu | Leu | Leu | Asp | Ser | Asn |
| | | | | 165 | | | | | 170 | | | | | 175 | |

| Ser | Leu | Ser | Gly | Gln | Ile | Pro | Gln | Ser | Leu | Phe | Glu | Ile | Pro | Lys | Tyr |
| | | | 180 | | | | | 185 | | | | | 190 | | |

| Asn | Phe | Thr | Ser | Asn | Asn | Leu | Asn | Cys | Gly | Gly | Arg | Gln | Pro | His | Pro |
| | | | 195 | | | | | 200 | | | | | 205 | | |

| Cys | Val | Ser | Ala | Val | Ala | His | Ser | Gly | Asp | Ser | Ser | Lys | Pro | Lys | Thr |
| | 210 | | | | | 215 | | | | | 220 | | | | |

| Gly | Ile | Ile | Ala | Gly | Val | Val | Ala | Gly | Val | Thr | Val | Val | Leu | Phe | Gly |
| 225 | | | | | 230 | | | | | 235 | | | | | 240 |

| Ile | Leu | Leu | Phe | Leu | Phe | Cys | Lys | Asp | Arg | His | Lys | Gly | Tyr | Arg | Arg |
| | | | | 245 | | | | | 250 | | | | | 255 | |

| Asp | Val | Phe | Val | Asp | Val | Ala | Gly | Glu | Val | Asp | Arg | Arg | Ile | Ala | Phe |
| | | | 260 | | | | | 265 | | | | | 270 | | |

| Gly | Gln | Leu | Lys | Arg | Phe | Ala | Trp | Arg | Glu | Leu | Gln | Leu | Ala | Thr | Asp |
| | | | 275 | | | | | 280 | | | | | 285 | | |

| Asn | Phe | Ser | Glu | Lys | Asn | Val | Leu | Gly | Gln | Gly | Gly | Phe | Gly | Lys | Val |
| | 290 | | | | | 295 | | | | | 300 | | | | |

| Tyr | Lys | Gly | Val | Leu | Pro | Asp | Thr | Pro | Lys | Val | Ala | Val | Lys | Arg | Leu |
| 305 | | | | | 310 | | | | | 315 | | | | | 320 |

| Thr | Asp | Phe | Glu | Ser | Pro | Gly | Gly | Asp | Ala | Ala | Phe | Gln | Arg | Glu | Val |
| | | | | 325 | | | | | 330 | | | | | 335 | |

| Glu | Met | Ile | Ser | Val | Ala | Val | His | Arg | Asn | Leu | Leu | Arg | Leu | Ile | Gly |
| | | | 340 | | | | | 345 | | | | | 350 | | |

```
Phe Cys Thr Thr Gln Thr Glu Arg Leu Leu Val Tyr Pro Phe Met Gln
            355                 360                 365

Asn Leu Ser Leu Ala His Arg Leu Arg Glu Ile Lys Ala Gly Asp Pro
        370                 375                 380

Val Leu Asp Trp Glu Thr Arg Lys Arg Ile Ala Leu Gly Ala Ala Arg
385                 390                 395                 400

Gly Phe Glu Tyr Leu His Glu His Cys Asn Pro Lys Ile Ile His Arg
                405                 410                 415

Asp Val Lys Ala Ala Asn Val Leu Leu Asp Glu Asp Phe Glu Ala Val
            420                 425                 430

Val Gly Asp Phe Gly Leu Ala Lys Leu Val Asp Val Arg Arg Thr Asn
            435                 440                 445

Val Thr Thr Gln Val Arg Gly Thr Met Gly His Ile Ala Pro Glu Tyr
        450                 455                 460

Leu Ser Thr Gly Lys Ser Ser Glu Arg Thr Asp Val Phe Gly Tyr Gly
465                 470                 475                 480

Ile Met Leu Leu Glu Leu Val Thr Gly Gln Arg Ala Ile Asp Phe Ser
                485                 490                 495

Arg Leu Glu Glu Glu Asp Asp Val Leu Leu Leu Asp His Val Lys Lys
            500                 505                 510

Leu Glu Arg Glu Lys Arg Leu Gly Ala Ile Val Asp Lys Asn Leu Asp
        515                 520                 525

Gly Glu Tyr Ile Lys Glu Glu Val Glu Met Met Ile Gln Val Ala Leu
    530                 535                 540

Leu Cys Thr Gln Gly Ser Pro Glu Asp Arg Pro Val Met Ser Glu Val
545                 550                 555                 560

Val Arg Met Leu Glu Gly Gly Leu Ala Glu Arg Trp Glu Glu Trp
                565                 570                 575

Gln Asn Val Glu Val Thr Arg Arg His Glu Phe Glu Arg Leu Gln Arg
            580                 585                 590

Arg Phe Asp Trp Gly Glu Asp Ser Met His Asn Gln Asp Ala Ile Glu
        595                 600                 605

Leu Ser Gly Gly Arg
        610

<210> SEQ ID NO 24
<211> LENGTH: 571
<212> TYPE: PRT
<213> ORGANISM: Arabidopsis thaliana
<220> FEATURE:
<223> OTHER INFORMATION: /note="Predicted protein domain RKS-2 of the
      RKS subfamily I"

<400> SEQUENCE: 24

Met Ala Leu Leu Ile Ile Thr Ala Leu Val Phe Ser Ser Leu Trp Ser
1               5                   10                  15

Ser Val Ser Pro Asp Ala Gln Gly Asp Ala Leu Phe Ala Leu Arg Ser
            20                  25                  30

Ser Leu Arg Ala Ser Pro Glu Gln Leu Ser Asp Trp Asn Gln Asn Gln
        35                  40                  45

Val Asp Pro Cys Thr Trp Ser Gln Val Ile Cys Asp Asp Lys Lys His
    50                  55                  60

Val Thr Ser Val Thr Leu Ser Tyr Met Asn Phe Ser Ser Gly Thr Leu
65                  70                  75                  80

Ser Ser Gly Ile Gly Ile Leu Thr Thr Leu Lys Thr Leu Thr Leu Lys
```

-continued

```
                85                  90                  95
Gly Asn Gly Ile Met Gly Gly Ile Pro Glu Ser Ile Gly Asn Leu Ser
            100                 105                 110

Ser Leu Thr Ser Leu Asp Leu Glu Asp Asn His Leu Thr Asp Arg Ile
        115                 120                 125

Pro Ser Thr Leu Gly Asn Leu Lys Asn Leu Gln Phe Phe Thr Ala
    130                 135                 140

Asn Asn Leu Ser Cys Gly Gly Thr Phe Pro Gln Pro Cys Val Thr Glu
145                 150                 155                 160

Ser Ser Pro Ser Gly Asp Ser Ser Arg Lys Thr Gly Ile Ile Ala
            165                 170                 175

Gly Val Val Ser Gly Ile Ala Val Ile Leu Leu Gly Phe Phe Phe
        180                 185                 190

Phe Phe Cys Lys Asp Lys His Lys Gly Tyr Lys Arg Asp Val Phe Val
    195                 200                 205

Asp Val Ala Gly Thr Asn Phe Lys Lys Gly Leu Ile Ser Gly Glu Val
    210                 215                 220

Asp Arg Arg Ile Ala Phe Gly Gln Leu Arg Arg Phe Ala Trp Arg Glu
225                 230                 235                 240

Leu Gln Leu Ala Thr Asp Glu Phe Ser Glu Lys Asn Val Leu Gly Gln
                245                 250                 255

Gly Gly Phe Gly Lys Val Tyr Lys Gly Leu Leu Ser Asp Gly Thr Lys
            260                 265                 270

Val Ala Val Lys Arg Leu Thr Asp Phe Glu Arg Pro Gly Gly Asp Glu
        275                 280                 285

Ala Phe Gln Arg Glu Val Glu Met Ile Ser Val Ala Val His Arg Asn
    290                 295                 300

Leu Leu Arg Leu Ile Gly Phe Cys Thr Thr Gln Thr Glu Arg Leu Leu
305                 310                 315                 320

Val Tyr Pro Phe Met Gln Asn Leu Ser Val Ala Tyr Cys Leu Arg Glu
                325                 330                 335

Ile Lys Pro Gly Asp Pro Val Leu Asp Trp Phe Arg Arg Lys Gln Ile
            340                 345                 350

Ala Leu Gly Ala Ala Arg Gly Leu Glu Tyr Leu His Glu His Cys Asn
        355                 360                 365

Pro Lys Ile Ile His Arg Asp Val Lys Ala Ala Asn Val Leu Leu Asp
    370                 375                 380

Glu Asp Phe Glu Ala Val Val Gly Asp Phe Gly Leu Ala Lys Leu Val
385                 390                 395                 400

Asp Val Arg Arg Thr Asn Val Thr Thr Gln Val Arg Gly Thr Met Gly
                405                 410                 415

His Ile Ala Pro Glu Cys Ile Ser Thr Gly Lys Ser Ser Glu Lys Thr
            420                 425                 430

Asp Val Phe Gly Tyr Gly Ile Met Leu Leu Glu Leu Val Thr Gly Gln
        435                 440                 445

Arg Ala Ile Asp Phe Ser Arg Leu Glu Glu Asp Val Leu Leu
    450                 455                 460

Leu Asp His Val Lys Lys Leu Glu Arg Glu Lys Arg Leu Glu Asp Ile
465                 470                 475                 480

Val Asp Lys Lys Leu Asp Glu Asp Tyr Ile Lys Glu Val Glu Met
            485                 490                 495

Met Ile Gln Val Ala Leu Leu Cys Thr Gln Ala Ala Pro Glu Glu Arg
        500                 505                 510
```

```
Pro Ala Met Ser Glu Val Val Arg Met Leu Glu Gly Glu Gly Leu Ala
            515                 520                 525

Glu Arg Trp Glu Glu Trp Gln Asn Leu Glu Val Thr Arg Gln Glu Glu
        530                 535                 540

Phe Gln Arg Leu Gln Arg Arg Phe Asp Trp Gly Glu Asp Ser Ile Asn
545                 550                 555                 560

Asn Gln Asp Ala Ile Glu Leu Ser Gly Gly Arg
            565                 570

<210> SEQ ID NO 25
<211> LENGTH: 578
<212> TYPE: PRT
<213> ORGANISM: Arabidopsis thaliana
<220> FEATURE:
<223> OTHER INFORMATION: /note="Predicted protein domain RKS-3 of the
      RKS subfamily I"

<400> SEQUENCE: 25

Met Ala Leu Ala Phe Val Gly Ile Thr Ser Ser Thr Thr Gln Pro Asp
  1               5                  10                  15

Ile Glu Gly Gly Ala Leu Leu Gln Leu Arg Asp Ser Leu Asn Asp Ser
             20                  25                  30

Ser Asn Arg Leu Lys Trp Thr Arg Asp Phe Val Ser Pro Cys Tyr Ser
         35                  40                  45

Trp Ser Tyr Val Thr Cys Arg Gly Gln Ser Val Ala Leu Asn Leu
     50                  55                  60

Ala Ser Ser Gly Phe Thr Gly Thr Leu Ser Pro Ala Ile Thr Lys Leu
 65                  70                  75                  80

Lys Phe Leu Val Thr Leu Glu Leu Gln Asn Asn Ser Leu Ser Gly Ala
                 85                  90                  95

Leu Pro Asp Ser Leu Gly Asn Met Val Asn Leu Gln Thr Leu Asn Leu
            100                 105                 110

Ser Val Asn Ser Phe Ser Gly Ser Ile Pro Ala Ser Trp Ser Gln Leu
        115                 120                 125

Ser Asn Leu Lys His Leu Asp Leu Ser Ser Asn Asn Leu Thr Gly Ser
    130                 135                 140

Ile Pro Thr Gln Phe Phe Ser Ile Pro Thr Phe Glu Phe Ser Gly Thr
145                 150                 155                 160

Gln Leu Ile Cys Gly Lys Ser Leu Asn Gln Pro Cys Ser Ser Ser Arg
                165                 170                 175

Leu Pro Val Thr Ser Ser Lys Lys Lys Leu Arg Asp Ile Thr Leu Thr
            180                 185                 190

Ala Ser Cys Val Ala Ser Ile Ile Leu Phe Leu Gly Ala Met Val Met
        195                 200                 205

Tyr His His His Arg Val Arg Arg Thr Lys Tyr Asp Ile Phe Phe Asp
    210                 215                 220

Val Ala Gly Glu Asp Asp Arg Lys Ile Ser Phe Gly Gln Leu Lys Arg
225                 230                 235                 240

Phe Ser Leu Arg Glu Ile Gln Leu Ala Thr Asp Ser Phe Asn Glu Ser
                245                 250                 255

Asn Leu Ile Gly Gln Gly Gly Phe Gly Lys Val Tyr Arg Gly Leu Leu
            260                 265                 270

Pro Asp Lys Thr Lys Val Ala Val Lys Arg Leu Ala Asp Tyr Phe Ser
        275                 280                 285

Pro Gly Gly Glu Ala Ala Phe Gln Arg Glu Ile Gln Leu Ile Ser Val
```

-continued

```
                290                 295                 300
Ala Val His Lys Asn Leu Leu Arg Leu Ile Gly Phe Cys Thr Thr Ser
305                 310                 315                 320

Ser Glu Arg Ile Leu Val Tyr Pro Tyr Met Glu Asn Leu Ser Val Ala
                325                 330                 335

Tyr Arg Leu Arg Asp Leu Lys Ala Gly Glu Glu Gly Leu Asp Trp Pro
                340                 345                 350

Thr Arg Lys Arg Val Ala Phe Gly Ser Ala His Gly Leu Glu Tyr Leu
                355                 360                 365

His Glu His Cys Asn Pro Lys Ile Ile His Arg Asp Leu Lys Ala Ala
                370                 375                 380

Asn Ile Leu Leu Asp Asn Asn Phe Glu Pro Val Leu Gly Asp Phe Gly
385                 390                 395                 400

Leu Ala Lys Leu Val Asp Thr Ser Leu Thr His Val Thr Thr Gln Val
                405                 410                 415

Arg Gly Thr Met Gly His Ile Ala Pro Glu Tyr Leu Cys Thr Gly Lys
                420                 425                 430

Ser Ser Glu Lys Thr Asp Val Phe Gly Tyr Gly Ile Thr Leu Leu Glu
                435                 440                 445

Leu Val Thr Gly Gln Arg Ala Ile Asp Phe Ser Arg Leu Glu Glu Glu
                450                 455                 460

Glu Asn Ile Leu Leu Leu Asp His Ile Lys Lys Leu Leu Arg Glu Gln
465                 470                 475                 480

Arg Leu Arg Asp Ile Val Asp Ser Asn Leu Thr Thr Tyr Asp Ser Lys
                485                 490                 495

Glu Val Glu Thr Ile Val Gln Val Ala Leu Leu Cys Thr Gln Gly Ser
                500                 505                 510

Pro Glu Asp Arg Pro Ala Met Ser Glu Val Val Lys Met Leu Gln Gly
                515                 520                 525

Thr Gly Gly Leu Ala Glu Lys Trp Thr Glu Trp Gln Leu Glu Glu
                530                 535                 540

Val Arg Asn Lys Glu Ala Leu Leu Pro Thr Leu Pro Ala Thr Trp
545                 550                 555                 560

Asp Glu Glu Glu Thr Thr Val Asp Gln Glu Ser Ile Arg Leu Ser Thr
                565                 570                 575

Ala Arg

<210> SEQ ID NO 26
<211> LENGTH: 633
<212> TYPE: PRT
<213> ORGANISM: Arabidopsis thaliana
<220> FEATURE:
<223> OTHER INFORMATION: /note="Predicted protein domain RKS-4 of the
      RKS subfamily II"

<400> SEQUENCE: 26

Met Val Val Met Lys Leu Ile Thr Met Lys Ile Phe Ser Val Leu Leu
1               5                   10                  15

Leu Leu Cys Phe Phe Val Thr Cys Ser Leu Ser Ser Glu Pro Arg Asn
                20                  25                  30

Pro Glu Val Glu Ala Leu Ile Asn Ile Lys Asn Glu Leu His Asp Pro
                35                  40                  45

His Gly Val Phe Lys Asn Trp Asp Glu Phe Ser Val Asp Pro Cys Ser
                50                  55                  60

Trp Thr Met Ile Ser Cys Ser Ser Asp Asn Leu Val Ile Gly Leu Gly
```

-continued

```
                65                  70                  75                  80
Ala Pro Ser Gln Ser Leu Ser Gly Thr Leu Ser Gly Ser Ile Gly Asn
                        85                  90                  95
Leu Thr Asn Leu Arg Gln Val Ser Leu Gln Asn Asn Asn Ile Ser Gly
                100                 105                 110
Lys Ile Pro Pro Glu Ile Cys Ser Leu Pro Lys Leu Gln Thr Leu Asp
            115                 120                 125
Leu Ser Asn Asn Arg Phe Ser Gly Glu Ile Pro Gly Ser Val Asn Gln
        130                 135                 140
Leu Ser Asn Leu Gln Tyr Leu Arg Leu Asn Asn Ser Leu Ser Gly
    145                 150                 155                 160
Pro Phe Pro Ala Ser Leu Ser Gln Ile Pro His Leu Ser Phe Leu Asp
                165                 170                 175
Leu Ser Tyr Asn Asn Leu Arg Gly Pro Val Pro Lys Phe Pro Ala Arg
                180                 185                 190
Thr Phe Asn Val Ala Gly Asn Pro Leu Ile Cys Lys Asn Ser Leu Pro
            195                 200                 205
Glu Ile Cys Ser Gly Ser Ile Ser Ala Ser Pro Leu Ser Val Ser Leu
        210                 215                 220
Arg Ser Ser Ser Gly Arg Arg Asn Ile Leu Ala Val Ala Leu Gly Val
225                 230                 235                 240
Ser Leu Gly Phe Ala Val Ser Val Ile Leu Ser Leu Gly Phe Ile Trp
                245                 250                 255
Tyr Arg Lys Lys Gln Arg Arg Leu Thr Met Leu Arg Ile Ser Asp Lys
                260                 265                 270
Gln Glu Glu Gly Leu Leu Gly Leu Gly Asn Leu Arg Ser Phe Thr Phe
            275                 280                 285
Arg Glu Leu His Val Ala Thr Asp Gly Phe Ser Ser Lys Ser Ile Leu
        290                 295                 300
Gly Ala Gly Gly Phe Gly Asn Val Tyr Arg Gly Lys Phe Gly Asp Gly
305                 310                 315                 320
Thr Val Val Ala Val Lys Arg Leu Lys Asp Val Asn Gly Thr Ser Gly
                325                 330                 335
Asn Ser Gln Phe Arg Thr Glu Leu Glu Met Ile Ser Leu Ala Val His
            340                 345                 350
Arg Asn Leu Leu Arg Leu Ile Gly Tyr Cys Ala Ser Ser Ser Glu Arg
        355                 360                 365
Leu Leu Val Tyr Pro Tyr Met Ser Asn Gly Ser Val Ala Ser Arg Leu
    370                 375                 380
Lys Ala Lys Pro Ala Leu Asp Trp Asn Thr Arg Lys Lys Ile Ala Ile
385                 390                 395                 400
Gly Ala Ala Arg Gly Leu Phe Tyr Leu His Glu Gln Cys Asp Pro Lys
                405                 410                 415
Ile Ile His Arg Asp Val Lys Ala Ala Asn Ile Leu Leu Asp Glu Tyr
            420                 425                 430
Phe Glu Ala Val Val Gly Asp Phe Gly Leu Ala Lys Leu Leu Asn His
        435                 440                 445
Glu Asp Ser His Val Thr Thr Ala Val Arg Gly Thr Val Gly His Ile
    450                 455                 460
Ala Pro Glu Tyr Leu Ser Thr Gly Gln Ser Ser Glu Lys Thr Asp Val
465                 470                 475                 480
Phe Gly Phe Gly Ile Leu Leu Leu Glu Leu Ile Thr Gly Met Arg Ala
                485                 490                 495
```

```
Leu Glu Phe Gly Lys Ser Val Ser Gln Lys Gly Ala Met Leu Glu Trp
                500                 505                 510

Val Arg Lys Leu His Lys Glu Met Lys Val Glu Glu Leu Val Asp Arg
            515                 520                 525

Glu Leu Gly Thr Thr Tyr Asp Arg Ile Glu Val Gly Glu Met Leu Gln
        530                 535                 540

Val Ala Leu Leu Cys Thr Gln Phe Leu Pro Ala His Arg Pro Lys Met
545                 550                 555                 560

Ser Glu Val Val Gln Met Leu Glu Gly Asp Gly Leu Ala Glu Arg Trp
                565                 570                 575

Ala Ala Ser His Asp His Ser His Phe Tyr His Ala Asn Met Ser Tyr
            580                 585                 590

Arg Thr Ile Thr Ser Thr Asp Gly Asn Asn Gln Thr Lys His Leu Phe
        595                 600                 605

Gly Ser Ser Gly Phe Glu Asp Glu Asp Asn Gln Ala Leu Asp Ser
610                 615                 620

Phe Ala Met Glu Leu Ser Gly Pro Arg
625                 630

<210> SEQ ID NO 27
<211> LENGTH: 588
<212> TYPE: PRT
<213> ORGANISM: Arabidopsis thaliana
<220> FEATURE:
<223> OTHER INFORMATION: /note="Predicted protein domain RKS-1 of the
      RKS subfamily II"

<400> SEQUENCE: 27

Met Glu Gly Val Arg Phe Val Val Trp Arg Leu Gly Phe Leu Val Phe
1               5                   10                  15

Val Trp Phe Phe Asp Ile Ser Ser Ala Thr Leu Ser Pro Thr Gly Val
                20                  25                  30

Asn Tyr Glu Val Thr Ala Leu Val Ala Val Lys Asn Glu Leu Asn Asp
            35                  40                  45

Pro Tyr Lys Val Leu Glu Asn Trp Asp Val Asn Ser Val Asp Pro Cys
        50                  55                  60

Ser Trp Arg Met Val Ser Cys Thr Asp Gly Tyr Val Ser Ser Leu Val
65                  70                  75                  80

Leu Gln Asn Asn Ala Ile Thr Gly Pro Ile Pro Glu Thr Ile Gly Arg
                85                  90                  95

Leu Glu Lys Leu Gln Ser Leu Asp Leu Ser Asn Asn Ser Phe Thr Gly
            100                 105                 110

Glu Ile Pro Ala Ser Leu Gly Glu Leu Lys Asn Leu Asn Tyr Leu Arg
        115                 120                 125

Leu Asn Asn Asn Ser Leu Ile Gly Thr Cys Pro Glu Ser Leu Ser Lys
130                 135                 140

Ile Glu Gly Leu Thr Leu Val Val Ile Gly Asn Ala Leu Ile Cys Gly
145                 150                 155                 160

Pro Lys Ala Val Ser Asn Cys Ser Ala Val Pro Glu Pro Leu Thr Leu
                165                 170                 175

Pro Gln Asp Gly Pro Asp Glu Ser Gly Thr Arg Thr Asn Gly His His
            180                 185                 190

Val Ala Leu Ala Phe Ala Ala Ser Phe Ser Ala Ala Phe Phe Val Phe
        195                 200                 205

Phe Thr Ser Gly Met Phe Leu Trp Trp Arg Tyr Arg Arg Asn Lys Gln
```

```
            210                 215                 220
Ile Phe Asp Val Asn Glu Gln Tyr Asp Pro Glu Val Ser Leu Gly
225                 230                 235                 240

His Leu Lys Arg Tyr Thr Phe Lys Glu Leu Arg Ser Ala Thr Asn His
                245                 250                 255

Phe Asn Ser Lys Asn Ile Leu Gly Arg Gly Gly Tyr Gly Ile Val Tyr
                260                 265                 270

Lys Gly His Leu Asn Asp Gly Thr Leu Val Ala Val Lys Arg Leu Lys
                275                 280                 285

Asp Cys Asn Ile Ala Gly Gly Glu Val Gln Phe Gln Thr Glu Val Glu
            290                 295                 300

Thr Ile Ser Leu Ala Leu His Arg Asn Leu Leu Arg Leu Arg Gly Phe
305                 310                 315                 320

Cys Ser Ser Asn Gln Glu Arg Ile Leu Val Tyr Pro Tyr Met Pro Asn
                325                 330                 335

Gly Ser Val Ala Ser Arg Leu Lys Asp Asn Ile Arg Gly Glu Pro Ala
                340                 345                 350

Leu Asp Trp Ser Arg Arg Lys Lys Ile Ala Val Gly Thr Ala Arg Gly
                355                 360                 365

Leu Val Tyr Leu His Glu Gln Cys Asp Pro Lys Ile Ile His Arg Asp
370                 375                 380

Val Lys Ala Ala Asn Ile Leu Leu Asp Glu Asp Phe Glu Ala Val Val
385                 390                 395                 400

Gly Asp Phe Gly Leu Ala Lys Leu Leu Asp His Arg Asp Ser His Val
                405                 410                 415

Thr Thr Ala Val Arg Gly Thr Val Gly His Ile Ala Pro Glu Tyr Leu
                420                 425                 430

Ser Thr Gly Gln Ser Ser Glu Lys Thr Asp Val Phe Gly Phe Gly Ile
                435                 440                 445

Leu Leu Leu Glu Leu Ile Thr Gly Gln Lys Ala Leu Asp Phe Gly Arg
                450                 455                 460

Ser Ala His Gln Lys Gly Val Met Leu Asp Trp Val Lys Lys Leu His
465                 470                 475                 480

Gln Glu Gly Lys Leu Lys Gln Leu Ile Asp Lys Asp Leu Asn Asp Lys
                485                 490                 495

Phe Asp Arg Val Glu Leu Glu Ile Val Gln Val Ala Leu Leu Cys
                500                 505                 510

Thr Gln Phe Asn Pro Ser His Arg Pro Lys Met Ser Glu Val Met Lys
                515                 520                 525

Met Leu Glu Gly Asp Gly Leu Ala Glu Arg Trp Glu Ala Thr Gln Asn
530                 535                 540

Gly Thr Gly Glu His Gln Pro Pro Leu Pro Pro Gly Met Val Ser
545                 550                 555                 560

Ser Ser Pro Arg Val Arg Tyr Tyr Ser Asp Tyr Ile Gln Glu Ser Ser
                565                 570                 575

Leu Val Val Glu Ala Ile Glu Leu Ser Gly Pro Arg
                580                 585
```

<210> SEQ ID NO 28
<211> LENGTH: 634
<212> TYPE: PRT
<213> ORGANISM: Arabidopsis thaliana
<220> FEATURE:
<223> OTHER INFORMATION: /note="Predicted protein domain RKS-5 of the RKS subfamily II"

<400> SEQUENCE: 28

```
Met Glu Ile Ser Leu Met Lys Phe Leu Phe Leu Gly Ile Trp Val Tyr
 1               5                  10                  15

Tyr Tyr Ser Val Leu Asp Ser Val Ser Ala Met Asp Ser Leu Leu Ser
            20                  25                  30

Pro Lys Trp Ala Ala Leu Met Ser Val Lys Asn Lys Met Lys Asp Glu
        35                  40                  45

Lys Glu Val Leu Ser Gly Trp Asp Ile Asn Ser Val Asp Pro Cys Thr
 50                  55                  60

Trp Asn Met Val Gly Cys Ser Ser Glu Gly Phe Val Val Ser Leu Leu
 65                  70                  75                  80

Leu Gln Asn Asn Gln Leu Thr Gly Pro Ile Pro Ser Glu Leu Gly Gln
                85                  90                  95

Leu Ser Glu Leu Glu Thr Leu Asp Leu Ser Gly Asn Arg Phe Ser Gly
            100                 105                 110

Glu Ile Pro Ala Ser Leu Gly Phe Leu Thr His Leu Asn Tyr Leu Arg
        115                 120                 125

Leu Ser Arg Asn Leu Leu Ser Gly Gln Val Pro His Leu Val Ala Gly
    130                 135                 140

Leu Ser Gly Leu Ser Phe Leu Asp Leu Ser Phe Asn Asn Leu Ser Gly
145                 150                 155                 160

Pro Thr Pro Asn Ile Ser Ala Lys Asp Tyr Arg Ile Val Gly Asn Ala
                165                 170                 175

Phe Leu Cys Gly Pro Ala Ser Gln Glu Leu Cys Ser Asp Ala Thr Pro
            180                 185                 190

Val Arg Asn Gly Met Leu Leu Arg Lys Phe Phe Ala Lys Leu Tyr Leu
        195                 200                 205

Lys His Gly Phe Val Tyr Leu Thr Ser Cys Asn Arg Ser Ala Ala Thr
    210                 215                 220

Gly Leu Ser Glu Lys Asp Asn Ser Lys His His Ser Leu Val Leu Ser
225                 230                 235                 240

Phe Ala Phe Gly Ile Val Val Ala Phe Ile Ile Ser Leu Met Phe Leu
                245                 250                 255

Phe Phe Trp Val Leu Trp His Arg Ser Arg Leu Ser Arg Ser His Gly
            260                 265                 270

Thr Tyr Leu Ile Val Ser Leu Cys Leu Ser Tyr Thr Ile Tyr Val Lys
        275                 280                 285

Thr Leu Leu Lys Ser Ala Leu Leu Phe Met Asp Phe Leu Val Gln Gln
    290                 295                 300

Asp Tyr Glu Phe Glu Ile Gly His Leu Lys Arg Phe Ser Phe Arg Glu
305                 310                 315                 320

Ile Gln Thr Ala Thr Ser Asn Phe Ser Pro Lys Asn Ile Leu Gly Gln
                325                 330                 335

Gly Gly Phe Gly Met Val Tyr Lys Gly Tyr Leu Pro Asn Gly Thr Val
            340                 345                 350

Val Ala Val Lys Arg Leu Lys Asp Pro Ile Tyr Thr Gly Glu Val Gln
        355                 360                 365

Phe Gln Thr Glu Val Glu Met Ile Gly Leu Ala Val His Arg Asn Leu
    370                 375                 380

Leu Arg Leu Phe Gly Phe Cys Met Thr Pro Glu Glu Arg Met Leu Val
385                 390                 395                 400

Tyr Pro Tyr Met Pro Asn Gly Ser Val Ala Asp Arg Leu Arg Asp Trp
```

```
                    405                 410                 415
Asn Arg Arg Ile Ser Ile Ala Leu Gly Ala Ala Arg Gly Leu Val Tyr
            420                 425                 430

Leu His Glu Gln Cys Asn Pro Lys Ile Ile His Arg Asp Val Lys Ala
            435                 440                 445

Ala Asn Ile Leu Leu Asp Glu Ser Phe Glu Ala Ile Val Gly Asp Phe
            450                 455                 460

Gly Leu Ala Lys Leu Leu Asp Gln Arg Asp Ser His Val Thr Thr Ala
465                 470                 475                 480

Val Arg Gly Thr Ile Gly His Ile Ala Pro Glu Tyr Leu Ser Thr Gly
            485                 490                 495

Gln Ser Ser Glu Lys Thr Asp Val Phe Gly Phe Gly Val Leu Ile Leu
            500                 505                 510

Glu Leu Ile Thr Gly His Lys Met Ile Asp Gln Gly Asn Gly Gln Val
            515                 520                 525

Arg Lys Gly Met Ile Leu Ser Trp Val Arg Thr Leu Lys Ala Glu Lys
            530                 535                 540

Arg Phe Ala Glu Met Val Asp Arg Asp Leu Lys Gly Glu Phe Asp Asp
545                 550                 555                 560

Leu Val Leu Glu Glu Val Val Glu Leu Ala Leu Leu Cys Thr Gln Pro
            565                 570                 575

His Pro Asn Leu Arg Pro Arg Met Ser Gln Val Leu Lys Val Leu Glu
            580                 585                 590

Gly Leu Val Glu Gln Cys Glu Gly Gly Tyr Glu Ala Arg Ala Pro Ala
            595                 600                 605

Ser Val Ser Arg Asn Tyr Ser Asn Gly His Glu Glu Gln Ser Phe Ile
            610                 615                 620

Ile Glu Ala Ile Glu Leu Ser Gly Pro Arg
625                 630

<210> SEQ ID NO 29
<211> LENGTH: 603
<212> TYPE: PRT
<213> ORGANISM: Arabidopsis thaliana
<220> FEATURE:
<223> OTHER INFORMATION: /note="Predicted protein domain RK-7 of the RKS
      subfamily II"

<400> SEQUENCE: 29

Met Leu Gln Gly Arg Arg Glu Ala Lys Lys Ser Tyr Ala Leu Phe Ser
1               5                   10                  15

Ser Thr Phe Phe Phe Phe Ile Cys Phe Leu Ser Ser Ser Ser Ala
            20                  25                  30

Glu Leu Thr Asp Lys Val Val Ala Leu Ile Gly Ile Lys Ser Ser Leu
            35                  40                  45

Thr Asp Pro His Gly Val Leu Met Asn Trp Asp Thr Ala Val Asp
            50                  55                  60

Pro Cys Ser Trp Asn Met Ile Thr Cys Ser Asp Gly Phe Val Ile Arg
65                  70                  75                  80

Leu Tyr Arg Leu Leu Gln Asn Asn Tyr Ile Thr Gly Asn Ile Pro His
            85                  90                  95

Glu Ile Gly Lys Leu Met Lys Leu Lys Thr Leu Asp Leu Ser Thr Asn
            100                 105                 110

Asn Pro Thr Gly Gln Ile Pro Phe Thr Leu Ser Tyr Ser Lys Asn Leu
            115                 120                 125
```

-continued

```
His Arg Arg Val Asn Asn Ser Leu Thr Gly Thr Ile Pro Ser Ser
    130                 135                 140

Leu Ala Asn Met Thr Gln Leu Thr Phe Leu Leu Asp Leu Ser Tyr Asn
145                 150                 155                 160

Asn Leu Ser Gly Pro Val Pro Arg Ser Leu Ala Lys Thr Phe Asn Val
                165                 170                 175

Met Gly Asn Ser Gln Ile Cys Pro Thr Gly Thr Glu Lys Asp Cys Asn
            180                 185                 190

Gly Thr Gln Pro Lys Pro Met Ser Ile Thr Leu Asn Ser Ser Gln Arg
        195                 200                 205

Gly Thr Lys Asn Arg Lys Ile Ala Val Val Phe Gly Val Ser Leu Thr
    210                 215                 220

Cys Val Cys Leu Leu Ile Ile Gly Phe Gly Phe Leu Leu Trp Trp Arg
225                 230                 235                 240

Arg Arg His Asn Lys Gln Val Leu Phe Phe Asp Ile Asn Glu Gln Asn
                245                 250                 255

Lys Glu Glu Met Cys Leu Gly Asn Leu Arg Arg Phe Asn Phe Lys Glu
            260                 265                 270

Leu Gln Ser Ala Thr Ser Asn Phe Ser Ser Lys Asn Leu Val Gly Lys
        275                 280                 285

Gly Gly Phe Gly Asn Val Tyr Lys Gly Cys Leu His Asp Gly Ser Ile
    290                 295                 300

Ile Ala Val Lys Arg Leu Lys Asp Ile Asn Asn Gly Gly Gly Glu Val
305                 310                 315                 320

Gln Phe Gln Thr Glu Leu Glu Met Ile Ser Leu Ala Val Glu Arg Asn
                325                 330                 335

Leu Leu Arg Leu Tyr Gly Phe Cys Thr Thr Ser Ser Glu Arg Leu Leu
            340                 345                 350

Val Tyr Pro Tyr Met Ser Asn Gly Ser Val Ala Ser Arg Leu Lys Ala
        355                 360                 365

Lys Pro Val Leu Asp Trp Gly Thr Arg Lys Arg Ile Ala Leu Gly Ala
    370                 375                 380

Gly Arg Gly Leu Leu Tyr Leu His Glu Gln Cys Asp Pro Lys Ile Ile
385                 390                 395                 400

His Arg Asp Val Lys Ala Ala Asn Ile Leu Leu Asp Asp Tyr Phe Glu
                405                 410                 415

Ala Val Val Gly Asp Phe Gly Leu Ala Lys Leu Leu Asp His Glu Glu
            420                 425                 430

Ser His Val Thr Thr Ala Val Arg Gly Thr Val Gly His Ile Ala Pro
        435                 440                 445

Glu Tyr Leu Ser Thr Gly Gln Ser Ser Glu Lys Thr Asp Val Phe Gly
    450                 455                 460

Phe Gly Ile Leu Leu Leu Glu Leu Ile Thr Gly Leu Arg Ala Leu Glu
465                 470                 475                 480

Phe Gly Lys Ala Ala Asn Gln Arg Gly Ala Ile Leu Asp Trp Val Lys
                485                 490                 495

Lys Leu Gln Gln Glu Lys Lys Leu Glu Gln Ile Val Asp Lys Asp Leu
            500                 505                 510

Lys Ser Asn Tyr Asp Arg Ile Glu Val Glu Glu Met Val Gln Val Ala
        515                 520                 525

Leu Leu Cys Thr Gln Tyr Leu Pro Ile His Arg Pro Lys Met Ser Glu
    530                 535                 540

Val Val Arg Met Leu Glu Gly Asp Gly Leu Val Glu Lys Trp Glu Ala
```

```
                545                 550                 555                 560

Ser Ser Gln Arg Ala Glu Thr Asn Arg Ser Tyr Ser Lys Pro Asn Glu
                565                 570                 575

Phe Ser Ser Ser Glu Arg Tyr Ser Asp Leu Thr Asp Asp Ser Ser Val
                580                 585                 590

Leu Val Gln Ala Met Glu Leu Ser Gly Pro Arg
            595                 600

<210> SEQ ID NO 30
<211> LENGTH: 628
<212> TYPE: PRT
<213> ORGANISM: Arabidopsis thaliana
<220> FEATURE:
<223> OTHER INFORMATION: /note="Predicted protein domain RKS-8 of the
      RKS subfamily III"

<400> SEQUENCE: 30

Met Gly Arg Lys Lys Phe Glu Ala Phe Gly Phe Val Cys Leu Ile Ser
  1               5                  10                  15

Leu Leu Leu Leu Phe Asn Ser Leu Trp Leu Ala Ser Ser Asn Met Glu
             20                  25                  30

Gly Asp Ala Leu His Ser Leu Arg Ala Asn Leu Val Asp Pro Asn Asn
         35                  40                  45

Val Leu Gln Ser Trp Asp Pro Thr Leu Val Asn Pro Cys Thr Trp Phe
     50                  55                  60

His Val Thr Cys Asn Asn Glu Asn Ser Val Ile Arg Val Asp Leu Gly
 65                  70                  75                  80

Asn Ala Asp Leu Ser Gly Gln Leu Val Pro Gln Leu Gly Gln Leu Lys
                 85                  90                  95

Asn Leu Gln Tyr Leu Glu Leu Tyr Ser Asn Asn Ile Thr Gly Pro Val
            100                 105                 110

Pro Ser Asp Leu Gly Asn Leu Thr Asn Leu Val Ser Leu Asp Leu Tyr
        115                 120                 125

Leu Asn Ser Phe Thr Gly Pro Ile Pro Asp Ser Leu Gly Lys Leu Phe
130                 135                 140

Lys Leu Arg Phe Leu Arg Leu Asn Asn Asn Ser Leu Thr Gly Pro Ile
145                 150                 155                 160

Pro Met Ser Leu Thr Asn Ile Met Thr Leu Gln Val Leu Asp Leu Ser
                165                 170                 175

Asn Asn Arg Leu Ser Gly Ser Val Pro Asp Asn Gly Ser Phe Ser Leu
            180                 185                 190

Phe Thr Pro Ile Ser Phe Ala Asn Asn Leu Asp Leu Cys Gly Pro Val
        195                 200                 205

Thr Leu Arg Pro Cys Pro Gly Ser Pro Phe Ser Pro Pro Pro
210                 215                 220

Phe Ile Pro Pro Ile Val Pro Thr Pro Gly Gly Tyr Ser Ala Thr
225                 230                 235                 240

Gly Ala Ile Ala Gly Gly Val Ala Ala Gly Ala Ala Leu Leu Phe Ala
                245                 250                 255

Ala Pro Ala Leu Ala Phe Ala Trp Trp Arg Arg Arg Lys Pro Gln Glu
            260                 265                 270

Phe Phe Phe Asp Val Pro Ala Glu Glu Asp Pro Glu Val His Leu Gly
        275                 280                 285

Gln Leu Lys Arg Phe Ser Leu Arg Glu Leu Gln Val Ala Thr Asp Ser
    290                 295                 300
```

Phe Ser Asn Lys Asn Ile Leu Gly Arg Gly Gly Phe Gly Lys Val Tyr
305                 310                 315                 320

Lys Gly Arg Leu Ala Asp Gly Thr Leu Val Ala Val Lys Arg Leu Lys
            325                 330                 335

Glu Glu Arg Thr Pro Gly Gly Glu Leu Gln Phe Gln Thr Glu Val Glu
            340                 345                 350

Met Ile Ser Met Ala Val His Arg Asn Leu Leu Arg Leu Arg Gly Phe
        355                 360                 365

Cys Met Thr Pro Thr Glu Arg Leu Leu Val Tyr Pro Tyr Met Ala Asn
    370                 375                 380

Gly Ser Val Ala Ser Cys Leu Arg Glu Arg Pro Ser Gln Leu Pro
385                 390                 395                 400

Leu Ala Trp Ser Ile Arg Gln Gln Ile Ala Leu Gly Ser Ala Arg Gly
                405                 410                 415

Leu Ser Tyr Leu His Asp His Cys Asp Pro Lys Ile Ile His Arg Asp
            420                 425                 430

Val Lys Ala Ala Asn Ile Leu Leu Asp Glu Glu Phe Glu Ala Val Val
        435                 440                 445

Gly Asp Phe Gly Leu Ala Arg Leu Met Asp Tyr Lys Asp Thr His Val
    450                 455                 460

Thr Thr Ala Val Arg Gly Thr Ile Gly His Ile Ala Pro Glu Tyr Leu
465                 470                 475                 480

Ser Thr Gly Lys Ser Ser Glu Lys Thr Asp Val Phe Gly Tyr Gly Ile
                485                 490                 495

Met Leu Leu Glu Leu Ile Thr Gly Gln Arg Ala Phe Asp Leu Ala Arg
            500                 505                 510

Leu Ala Asn Asp Asp Val Met Leu Leu Asp Trp Val Lys Gly Leu
        515                 520                 525

Leu Lys Glu Lys Lys Leu Glu Met Leu Val Asp Pro Asp Leu Gln Ser
    530                 535                 540

Asn Tyr Thr Glu Ala Glu Val Glu Gln Leu Ile Gln Val Ala Leu Leu
545                 550                 555                 560

Cys Thr Gln Ser Ser Pro Met Glu Arg Pro Lys Met Ser Glu Val Val
                565                 570                 575

Arg Met Leu Glu Gly Asp Gly Leu Ala Glu Lys Trp Asp Glu Trp Gln
            580                 585                 590

Lys Val Glu Val Leu Arg Gln Glu Val Glu Leu Ser Ser His Pro Thr
        595                 600                 605

Ser Asp Trp Ile Leu Asp Ser Thr Asp Asn Leu His Ala Met Glu Leu
    610                 615                 620

Ser Gly Pro Arg
625

<210> SEQ ID NO 31
<211> LENGTH: 591
<212> TYPE: PRT
<213> ORGANISM: Arabidopsis thaliana
<220> FEATURE:
<223> OTHER INFORMATION: /note="Predicted protein domain RKS-10 of the
      RKS subfamily III"

<400> SEQUENCE: 31

Met Glu Arg Arg Leu Met Ile Pro Cys Phe Phe Trp Leu Ile Leu Val
1               5                   10                  15

Leu Asp Leu Val Leu Arg Val Ser Gly Asn Ala Glu Gly Asp Ala Leu
            20                  25                  30

```
Ser Ala Leu Lys Asn Ser Leu Ala Asp Pro Asn Lys Val Leu Gln Ser
        35                  40                  45

Trp Asp Ala Thr Leu Val Thr Pro Cys Thr Trp Phe His Val Thr Cys
 50                  55                  60

Asn Ser Asp Asn Ser Val Thr Arg Val Asp Leu Gly Asn Ala Asn Leu
 65                  70                  75                  80

Ser Gly Gln Leu Val Met Gln Leu Gly Gln Leu Pro Asn Leu Gln Tyr
                85                  90                  95

Leu Glu Leu Tyr Ser Asn Asn Ile Thr Gly Thr Ile Pro Glu Gln Leu
            100                 105                 110

Gly Asn Leu Thr Glu Leu Val Ser Leu Asp Leu Tyr Leu Asn Asn Leu
            115                 120                 125

Ser Gly Pro Ile Pro Ser Thr Leu Gly Arg Leu Lys Lys Leu Arg Phe
        130                 135                 140

Leu Arg Leu Asn Asn Asn Ser Leu Ser Gly Glu Ile Pro Arg Ser Leu
145                 150                 155                 160

Thr Ala Val Leu Thr Leu Gln Val Leu Phe Ala Asn Thr Lys Leu Thr
                165                 170                 175

Pro Leu Pro Ala Ser Pro Pro Pro Ile Ser Pro Thr Pro Pro Ser
                180                 185                 190

Pro Ala Gly Ser Asn Arg Ile Thr Gly Ala Ile Ala Gly Gly Val Ala
        195                 200                 205

Ala Gly Ala Ala Leu Leu Phe Ala Val Pro Ala Ile Ala Leu Ala Trp
    210                 215                 220

Trp Arg Arg Lys Lys Pro Gln Asp His Phe Phe Asp Val Pro Ala Glu
225                 230                 235                 240

Glu Asp Pro Glu Val His Leu Gly Gln Leu Lys Arg Phe Ser Leu Arg
                245                 250                 255

Glu Leu Gln Val Ala Ser Asp Asn Phe Ser Asn Lys Asn Ile Leu Gly
            260                 265                 270

Arg Gly Gly Phe Gly Lys Val Tyr Lys Gly Arg Leu Ala Asp Gly Thr
        275                 280                 285

Leu Val Ala Val Lys Arg Leu Lys Glu Glu Arg Thr Gln Gly Gly Glu
    290                 295                 300

Leu Gln Phe Gln Thr Glu Val Glu Met Ile Ser Met Ala Val His Arg
305                 310                 315                 320

Asn Leu Leu Arg Leu Arg Gly Phe Cys Met Thr Pro Thr Glu Arg Leu
                325                 330                 335

Leu Val Tyr Pro Tyr Met Ala Asn Gly Ser Val Ala Ser Cys Leu Arg
            340                 345                 350

Glu Arg Pro Glu Ser Gln Pro Leu Asp Trp Pro Lys Arg Gln Arg
        355                 360                 365

Ile Ala Leu Gly Ser Ala Arg Gly Leu Ala Tyr Leu His Asp His Cys
    370                 375                 380

Asp Pro Lys Ile Ile His Arg Asp Val Lys Ala Ala Asn Ile Leu Leu
385                 390                 395                 400

Asp Glu Glu Phe Glu Ala Val Val Gly Asp Phe Gly Leu Ala Lys Leu
                405                 410                 415

Met Asp Tyr Lys Asp Thr His Val Thr Thr Ala Val Arg Gly Thr Ile
            420                 425                 430

Gly His Ile Ala Pro Glu Tyr Leu Ser Thr Gly Lys Ser Ser Glu Lys
        435                 440                 445
```

```
Thr Asp Val Phe Gly Tyr Gly Val Met Leu Leu Glu Leu Ile Thr Gly
    450                 455                 460

Gln Arg Ala Phe Asp Leu Ala Arg Leu Ala Asn Asp Asp Val Met
465                 470                 475                 480

Leu Leu Asp Trp Val Lys Gly Leu Leu Lys Glu Lys Lys Leu Glu Ala
                485                 490                 495

Leu Val Asp Val Asp Leu Gln Gly Asn Tyr Lys Asp Glu Val Glu
                500                 505                 510

Gln Leu Ile Gln Val Ala Leu Leu Cys Thr Gln Ser Ser Pro Met Glu
            515                 520                 525

Arg Pro Lys Met Ser Glu Val Val Arg Met Leu Glu Gly Asp Gly Leu
        530                 535                 540

Ala Glu Arg Trp Glu Glu Trp Gln Lys Glu Glu Met Phe Arg Gln Asp
545                 550                 555                 560

Phe Asn Tyr Pro Thr His His Pro Ala Val Ser Gly Trp Ile Ile Gly
                565                 570                 575

Asp Ser Thr Ser Gln Ile Glu Asn Glu Tyr Pro Ser Gly Pro Arg
                580                 585                 590

<210> SEQ ID NO 32
<211> LENGTH: 579
<212> TYPE: PRT
<213> ORGANISM: Arabidopsis thaliana
<220> FEATURE:
<223> OTHER INFORMATION: /note="Predicted protein domain RKS-12 of the
      RKS subfamily III"

<400> SEQUENCE: 32

Met Glu His Gly Ser Ser Arg Gly Phe Ile Trp Leu Ile Leu Phe Leu
1               5                   10                  15

Asp Phe Val Ser Arg Val Thr Gly Lys Thr Gln Val Asp Ala Leu Ile
                20                  25                  30

Ala Leu Arg Ser Ser Leu Ser Ser Gly Asp His Thr Asn Asn Ile Leu
            35                  40                  45

Gln Ser Trp Asn Ala Thr His Val Thr Pro Cys Ser Trp Phe His Val
        50                  55                  60

Thr Cys Asn Thr Glu Asn Ser Val Thr Arg Leu Glu Leu Phe Asn Asn
65                  70                  75                  80

Asn Ile Thr Gly Glu Ile Pro Glu Glu Leu Gly Asp Leu Met Glu Leu
                85                  90                  95

Val Ser Leu Asp Leu Phe Ala Asn Asn Ile Ser Gly Pro Ile Pro Ser
                100                 105                 110

Ser Leu Gly Lys Leu Gly Lys Leu Arg Phe Leu Arg Leu Tyr Asn Asn
            115                 120                 125

Ser Leu Ser Gly Glu Ile Pro Arg Ser Leu Thr Ala Leu Pro Leu Asp
        130                 135                 140

Val Leu Asp Ile Ser Asn Asn Arg Leu Ser Gly Asp Ile Pro Val Asn
145                 150                 155                 160

Gly Ser Phe Ser Gln Phe Thr Ser Met Arg Phe Ala Asn Asn Lys Leu
                165                 170                 175

Arg Pro Arg Pro Ala Ser Pro Ser Pro Ser Pro Ser Gly Gly Thr Ser
                180                 185                 190

Ala Ala Ile Val Val Gly Val Ala Ala Gly Ala Ala Leu Leu Phe Ala
            195                 200                 205

Leu Ala Trp Trp Leu Arg Arg Lys Leu Gln Gly His Phe Leu Asp Val
        210                 215                 220
```

Pro Ala Ala Glu Glu Asp Pro Glu Val Tyr Leu Gly Gln Phe Lys Arg
225                 230                 235                 240

Phe Ser Leu Arg Glu Leu Val Ala Thr Glu Lys Phe Ser Lys Arg
        245                 250                 255

Asn Val Leu Gly Lys Gly Arg Phe Gly Ile Leu Tyr Lys Gly Arg Leu
        260                 265                 270

Ala Asp Asp Thr Leu Val Ala Val Lys Arg Leu Asn Glu Glu Arg Thr
            275                 280                 285

Lys Gly Gly Glu Leu Gln Phe Gln Thr Glu Val Glu Met Ile Ser Met
        290                 295                 300

Ala Val His Arg Asn Leu Leu Arg Leu Arg Gly Phe Cys Met Thr Pro
305                 310                 315                 320

Thr Glu Arg Leu Leu Val Tyr Pro Tyr Met Ala Asn Gly Ser Val Ala
            325                 330                 335

Ser Cys Leu Arg Glu Arg Pro Glu Gly Asn Pro Ala Leu Asp Trp Pro
            340                 345                 350

Lys Arg Lys His Ile Ala Leu Gly Ser Ala Arg Gly Leu Ala Tyr Leu
        355                 360                 365

His Asp His Cys Asp Gln Lys Ile Ile His Leu Asp Val Lys Ala Ala
        370                 375                 380

Asn Ile Leu Leu Asp Glu Glu Phe Glu Ala Val Val Gly Asp Phe Gly
385                 390                 395                 400

Leu Ala Lys Leu Met Asn Tyr Asn Asp Ser His Val Thr Thr Ala Val
            405                 410                 415

Arg Gly Thr Ile Gly His Ile Ala Pro Glu Tyr Leu Ser Thr Gly Lys
            420                 425                 430

Ser Ser Glu Lys Thr Asp Val Phe Gly Tyr Gly Val Met Leu Leu Glu
        435                 440                 445

Leu Ile Thr Gly Gln Lys Ala Phe Asp Leu Ala Arg Leu Ala Asn Asp
450                 455                 460

Asp Asp Ile Met Leu Leu Asp Trp Val Lys Glu Val Leu Lys Glu Lys
465                 470                 475                 480

Lys Leu Glu Ser Leu Val Asp Ala Glu Leu Glu Gly Lys Tyr Val Glu
            485                 490                 495

Thr Glu Val Glu Gln Leu Ile Gln Met Ala Leu Leu Cys Thr Gln Ser
        500                 505                 510

Ser Ala Met Glu Arg Pro Lys Met Ser Glu Val Val Arg Met Leu Glu
        515                 520                 525

Gly Asp Gly Leu Ala Glu Arg Trp Glu Glu Trp Gln Lys Glu Glu Met
530                 535                 540

Pro Ile His Asp Phe Asn Tyr Gln Ala Tyr Pro His Ala Gly Thr Asp
545                 550                 555                 560

Trp Leu Ile Pro Tyr Ser Asn Ser Leu Ile Glu Asn Asp Tyr Pro Ser
            565                 570                 575

Gly Pro Arg

<210> SEQ ID NO 33
<211> LENGTH: 592
<212> TYPE: PRT
<213> ORGANISM: Arabidopsis thaliana
<220> FEATURE:
<223> OTHER INFORMATION: /note="Predicted protein domain RKS-13 of the
      RKS subfamily III"

<400> SEQUENCE: 33

```
Met Glu Gln Arg Ser Leu Leu Cys Phe Leu Tyr Leu Leu Leu Phe
 1               5                  10                  15

Asn Phe Thr Leu Arg Val Ala Gly Asn Ala Glu Gly Asp Ala Leu Thr
             20                  25                  30

Gln Leu Lys Asn Ser Leu Ser Ser Gly Asp Pro Ala Asn Asn Val Leu
             35                  40                  45

Gln Ser Trp Asp Ala Thr Leu Val Thr Pro Cys Thr Trp Phe His Val
 50                  55                  60

Thr Cys Asn Pro Glu Asn Lys Val Thr Arg Val Glu Leu Tyr Ser Asn
 65                  70                  75                  80

Asn Ile Thr Gly Glu Ile Pro Glu Glu Leu Gly Asp Leu Val Glu Leu
                 85                  90                  95

Val Ser Leu Asp Leu Tyr Ala Asn Ser Ile Ser Gly Pro Ile Pro Ser
                 100                 105                 110

Ser Leu Gly Lys Leu Gly Lys Leu Arg Phe Leu Arg Leu Asn Asn Asn
                 115                 120                 125

Ser Leu Ser Gly Glu Ile Pro Met Thr Leu Thr Ser Val Gln Leu Gln
         130                 135                 140

Val Leu Asp Ile Ser Asn Asn Arg Leu Ser Gly Asp Ile Pro Val Asn
145                 150                 155                 160

Gly Ser Phe Ser Leu Phe Thr Pro Ile Ser Phe Ala Asn Asn Ser Leu
                 165                 170                 175

Thr Asp Leu Pro Glu Pro Pro Thr Ser Thr Ser Pro Thr Pro Pro
         180                 185                 190

Pro Pro Ser Gly Gly Gln Met Thr Ala Ala Ile Ala Gly Gly Val Ala
         195                 200                 205

Ala Gly Ala Ala Leu Leu Phe Ala Val Pro Ala Ile Ala Phe Ala Trp
     210                 215                 220

Trp Leu Arg Arg Lys Pro Gln Asp His Phe Phe Asp Val Pro Gly Ala
225                 230                 235                 240

Glu Glu Asp Pro Glu Val His Leu Gly Gln Leu Lys Arg Phe Thr Leu
                 245                 250                 255

Arg Glu Leu Leu Val Ala Thr Asp Asn Phe Ser Asn Lys Asn Val Leu
                 260                 265                 270

Gly Arg Gly Gly Phe Gly Lys Val Tyr Lys Gly Arg Leu Ala Asp Gly
         275                 280                 285

Asn Leu Val Ala Val Lys Arg Leu Lys Glu Glu Arg Thr Lys Gly Gly
     290                 295                 300

Glu Leu Gln Phe Gln Thr Glu Val Glu Met Ile Ser Met Ala Val His
305                 310                 315                 320

Arg Asn Leu Leu Arg Leu Arg Gly Phe Cys Met Thr Pro Thr Glu Arg
                 325                 330                 335

Leu Leu Val Tyr Pro Tyr Met Ala Asn Gly Ser Val Ala Ser Cys Leu
                 340                 345                 350

Arg Glu Arg Pro Glu Gly Asn Pro Ala Leu Asp Trp Pro Lys Arg Lys
         355                 360                 365

His Ile Ala Leu Gly Ser Ala Arg Gly Leu Ala Tyr Leu His Asp His
     370                 375                 380

Cys Asp Gln Lys Ile Ile His Arg Asp Val Lys Ala Ala Asn Ile Leu
385                 390                 395                 400

Leu Asp Glu Glu Phe Glu Ala Val Val Gly Asp Phe Gly Leu Ala Lys
                 405                 410                 415
```

```
Leu Met Asn Tyr Asn Asp Ser His Val Thr Thr Ala Val Arg Gly Thr
            420                 425                 430

Ile Gly His Ile Ala Pro Glu Tyr Leu Ser Thr Gly Lys Ser Ser Glu
        435                 440                 445

Lys Thr Asp Val Phe Gly Tyr Gly Val Met Leu Leu Glu Leu Ile Thr
450                 455                 460

Gly Gln Lys Ala Phe Asp Leu Ala Arg Leu Ala Asn Asp Asp Asp Ile
465                 470                 475                 480

Met Leu Leu Asp Trp Val Lys Glu Val Leu Glu Lys Lys Leu Glu
                485                 490                 495

Ser Leu Val Asp Ala Glu Leu Glu Gly Lys Tyr Val Glu Thr Glu Val
            500                 505                 510

Glu Gln Leu Ile Gln Met Ala Leu Leu Cys Thr Gln Ser Ser Ala Met
        515                 520                 525

Glu Arg Pro Lys Met Ser Glu Val Val Arg Met Leu Glu Gly Asp Gly
    530                 535                 540

Leu Ala Glu Arg Trp Glu Glu Trp Gln Lys Glu Met Pro Ile His
545                 550                 555                 560

Asp Phe Asn Tyr Gln Ala Tyr Pro His Ala Gly Thr Asp Trp Leu Ile
                565                 570                 575

Pro Tyr Ser Asn Ser Leu Ile Glu Asn Asp Tyr Pro Ser Gly Pro Arg
            580                 585                 590

<210> SEQ ID NO 34
<211> LENGTH: 1794
<212> TYPE: DNA
<213> ORGANISM: Arabidopsis thaliana
<220> FEATURE:
<221> NAME/KEY: CDS
<222> LOCATION: (28)..(1791)
<223> OTHER INFORMATION: /note="Arabidopsis thaliana RKS1 cDNA"

<400> SEQUENCE: 34
ccaaagttga ttgctttaag aagggat atg gaa ggt gtg aga ttt gtg gtg tgg        54
                              Met Glu Gly Val Arg Phe Val Val Trp
                                1               5 aga tta gga ttt ctg gtt ttt gta tgg ttc ttt gat atc tct tct gct       102
Arg Leu Gly Phe Leu Val Phe Val Trp Phe Phe Asp Ile Ser Ser Ala
 10                  15                  20                  25 aca ctt tct cct act ggt gta aac tat gaa gtg aca gct ttg gtt gct       150
Thr Leu Ser Pro Thr Gly Val Asn Tyr Glu Val Thr Ala Leu Val Ala
                 30                  35                  40 gtg aag aat gaa ttg aat gat ccg tac aaa gtt ctt gag aat tgg gat       198
Val Lys Asn Glu Leu Asn Asp Pro Tyr Lys Val Leu Glu Asn Trp Asp
             45                  50                  55 gtg aat tca gtt gat cct tgt agc tgg aga atg gtt tct tgc act gat       246
Val Asn Ser Val Asp Pro Cys Ser Trp Arg Met Val Ser Cys Thr Asp
         60                  65                  70 ggc tat gtc tct tca ctg gtg ttg caa aac aat gca atc act ggt cca       294
Gly Tyr Val Ser Ser Leu Val Leu Gln Asn Asn Ala Ile Thr Gly Pro
     75                  80                  85 att ccg gaa acg att ggg agg ttg gag aag ctt cag tca ctt gat ctt       342
Ile Pro Glu Thr Ile Gly Arg Leu Glu Lys Leu Gln Ser Leu Asp Leu
 90                  95                 100                 105 tcg aac aat tca ttc acc ggg gag ata ccg gcc tca ctt gga gaa ctc       390
Ser Asn Asn Ser Phe Thr Gly Glu Ile Pro Ala Ser Leu Gly Glu Leu
                110                 115                 120 aag aac ttg aat tac ttg cgg tta aac aat aac agt ctt ata gga act       438
Lys Asn Leu Asn Tyr Leu Arg Leu Asn Asn Asn Ser Leu Ile Gly Thr
```

-continued

```
              125                 130                 135
tgc cct gag tct cta tcc aag att gag gga ctc act cta gtg gta att       486
Cys Pro Glu Ser Leu Ser Lys Ile Glu Gly Leu Thr Leu Val Val Ile
        140                 145                 150 ggt aat gcg tta atc tgt ggc cca aaa gct gtt tca aac tgt tct gct       534
Gly Asn Ala Leu Ile Cys Gly Pro Lys Ala Val Ser Asn Cys Ser Ala
155                 160                 165 gtt ccc gag cct ctc acg ctt cca caa gat ggt cca gat gaa tca gga       582
Val Pro Glu Pro Leu Thr Leu Pro Gln Asp Gly Pro Asp Glu Ser Gly
170                 175                 180                 185 act cgt acc aat ggc cat cac gtt gct ctt gca ttt gcc gca agc ttc       630
Thr Arg Thr Asn Gly His His Val Ala Leu Ala Phe Ala Ala Ser Phe
        190                 195                 200 agt gca gca ttt ttt gtt ttc ttt aca agc gga atg ttt ctt tgg tgg       678
Ser Ala Ala Phe Phe Val Phe Phe Thr Ser Gly Met Phe Leu Trp Trp
        205                 210                 215 aga tat cgc cgt aac aag caa ata ttt ttt gac gtt aat gaa caa tat       726
Arg Tyr Arg Arg Asn Lys Gln Ile Phe Phe Asp Val Asn Glu Gln Tyr
        220                 225                 230 gat cca gaa gtg agt tta ggg cac ttg aag agg tat aca ttc aaa gag       774
Asp Pro Glu Val Ser Leu Gly His Leu Lys Arg Tyr Thr Phe Lys Glu
235                 240                 245 ctt aga tct gcc acc aat cat ttc aac tcg aag aac att ctc gga aga       822
Leu Arg Ser Ala Thr Asn His Phe Asn Ser Lys Asn Ile Leu Gly Arg
250                 255                 260                 265 ggc gga tac ggg att gtg tac aaa gga cac tta aac gat gga act ttg       870
Gly Gly Tyr Gly Ile Val Tyr Lys Gly His Leu Asn Asp Gly Thr Leu
                270                 275                 280 gtg gct gtc aaa cgt ctc aag gac tgt aac att gcg ggt gga gaa gtc       918
Val Ala Val Lys Arg Leu Lys Asp Cys Asn Ile Ala Gly Gly Glu Val
            285                 290                 295 cag ttt cag aca gaa gta gag act ata agt ttg gct ctt cat cgc aat       966
Gln Phe Gln Thr Glu Val Glu Thr Ile Ser Leu Ala Leu His Arg Asn
        300                 305                 310 ctc ctc cgg ctc cgc ggt ttc tgt agt agc aac cag gag aga att tta      1014
Leu Leu Arg Leu Arg Gly Phe Cys Ser Ser Asn Gln Glu Arg Ile Leu
        315                 320                 325 gtc tac cct tac atg cca aat ggg agt gtc gca tca cgc tta aaa gat      1062
Val Tyr Pro Tyr Met Pro Asn Gly Ser Val Ala Ser Arg Leu Lys Asp
330                 335                 340                 345 aat atc cgt gga gag cca gca tta gac tgg tcg aga agg aag aag ata      1110
Asn Ile Arg Gly Glu Pro Ala Leu Asp Trp Ser Arg Arg Lys Lys Ile
                350                 355                 360 gcg gtt ggg aca gcg aga gga cta gtt tac cta cac gag caa tgt gac      1158
Ala Val Gly Thr Ala Arg Gly Leu Val Tyr Leu His Glu Gln Cys Asp
            365                 370                 375 ccg aag att ata cac cgc gat gtg aaa gca gct aac att ctg tta gat      1206
Pro Lys Ile Ile His Arg Asp Val Lys Ala Ala Asn Ile Leu Leu Asp
        380                 385                 390 gag gac ttc gaa gca gtt gtt ggt gat ttt ggg tta gct aag ctt cta      1254
Glu Asp Phe Glu Ala Val Val Gly Asp Phe Gly Leu Ala Lys Leu Leu
395                 400                 405 gac cat aga gac tct cat gtc aca act gca gtc cgt gga act gtt ggc      1302
Asp His Arg Asp Ser His Val Thr Thr Ala Val Arg Gly Thr Val Gly
410                 415                 420                 425 cac att gca cct gag tac tta tcc acg ggt cag tcc tca gag aag act      1350
His Ile Ala Pro Glu Tyr Leu Ser Thr Gly Gln Ser Ser Glu Lys Thr
                430                 435                 440 gat gtc ttt ggc ttt ggc ata ctt ctc ctt gag ctc att act ggt cag      1398
Asp Val Phe Gly Phe Gly Ile Leu Leu Leu Glu Leu Ile Thr Gly Gln
```

```
Asp Val Phe Gly Phe Gly Ile Leu Leu Glu Leu Ile Thr Gly Gln
            445                 450                 455 aaa gct ctt gat ttt ggc aga tcc gca cac cag aaa ggt gta atg ctt     1446
Lys Ala Leu Asp Phe Gly Arg Ser Ala His Gln Lys Gly Val Met Leu
            460                 465                 470 gac tgg gtg aag aag ctg cac caa gaa ggg aaa cta aag cag tta ata     1494
Asp Trp Val Lys Lys Leu His Gln Glu Gly Lys Leu Lys Gln Leu Ile
475                 480                 485 gac aaa gat cta aat gac aag ttc gat aga gta gaa ctc gaa gaa atc     1542
Asp Lys Asp Leu Asn Asp Lys Phe Asp Arg Val Glu Leu Glu Glu Ile
490                 495                 500                 505 gtt caa gtt gcg cta ctc tgc act caa ttc aat cca tct cat cga ccg     1590
Val Gln Val Ala Leu Leu Cys Thr Gln Phe Asn Pro Ser His Arg Pro
            510                 515                 520 aaa atg tca gaa gtt atg aag atg ctt gaa ggt gac ggt ttg gct gag     1638
Lys Met Ser Glu Val Met Lys Met Leu Glu Gly Asp Gly Leu Ala Glu
            525                 530                 535 aga tgg gaa gcg acg cag aac ggt act ggt gag cat cag cca ccg cca     1686
Arg Trp Glu Ala Thr Gln Asn Gly Thr Gly Glu His Gln Pro Pro Pro
            540                 545                 550 ttg cca ccg ggg atg gtg agt tct tcg ccg cgt gtg agg tat tac tcg     1734
Leu Pro Pro Gly Met Val Ser Ser Pro Arg Val Arg Tyr Tyr Ser
555                 560                 565 gat tat att cag gaa tcg tct ctt gta gta gaa gcc att gag ctc tcg     1782
Asp Tyr Ile Gln Glu Ser Ser Leu Val Val Glu Ala Ile Glu Leu Ser
570                 575                 580                 585 ggt cct cga tga                                                      1794
Gly Pro Arg <210> SEQ ID NO 35
<211> LENGTH: 588
<212> TYPE: PRT
<213> ORGANISM: Arabidopsis thaliana

<400> SEQUENCE: 35

Met Glu Gly Val Arg Phe Val Val Trp Arg Leu Gly Phe Leu Val Phe
1               5                   10                  15

Val Trp Phe Phe Asp Ile Ser Ser Ala Thr Leu Ser Pro Thr Gly Val
                20                  25                  30

Asn Tyr Glu Val Thr Ala Leu Val Ala Val Lys Asn Glu Leu Asn Asp
            35                  40                  45

Pro Tyr Lys Val Leu Glu Asn Trp Asp Val Asn Ser Val Asp Pro Cys
        50                  55                  60

Ser Trp Arg Met Val Ser Cys Thr Asp Gly Tyr Val Ser Ser Leu Val
65                  70                  75                  80

Leu Gln Asn Asn Ala Ile Thr Gly Pro Ile Pro Glu Thr Ile Gly Arg
                85                  90                  95

Leu Glu Lys Leu Gln Ser Leu Asp Leu Ser Asn Ser Phe Thr Gly
            100                 105                 110

Glu Ile Pro Ala Ser Leu Gly Glu Leu Lys Asn Leu Asn Tyr Leu Arg
        115                 120                 125

Leu Asn Asn Asn Ser Leu Ile Gly Thr Cys Pro Glu Ser Leu Ser Lys
    130                 135                 140

Ile Glu Gly Leu Thr Leu Val Val Ile Gly Asn Ala Leu Ile Cys Gly
145                 150                 155                 160

Pro Lys Ala Val Ser Asn Cys Ser Ala Val Pro Glu Pro Leu Thr Leu
                165                 170                 175
```

-continued

```
Pro Gln Asp Gly Pro Asp Glu Ser Gly Thr Arg Thr Asn Gly His His
            180                 185                 190

Val Ala Leu Ala Phe Ala Ala Ser Phe Ser Ala Ala Phe Phe Val Phe
        195                 200                 205

Phe Thr Ser Gly Met Phe Leu Trp Trp Arg Tyr Arg Arg Asn Lys Gln
        210                 215                 220

Ile Phe Phe Asp Val Asn Glu Gln Tyr Asp Pro Glu Val Ser Leu Gly
225                 230                 235                 240

His Leu Lys Arg Tyr Thr Phe Lys Glu Leu Arg Ser Ala Thr Asn His
                245                 250                 255

Phe Asn Ser Lys Asn Ile Leu Gly Arg Gly Tyr Gly Ile Val Tyr
            260                 265                 270

Lys Gly His Leu Asn Asp Gly Thr Leu Val Ala Val Lys Arg Leu Lys
        275                 280                 285

Asp Cys Asn Ile Ala Gly Gly Glu Val Gln Phe Gln Thr Glu Val Glu
        290                 295                 300

Thr Ile Ser Leu Ala Leu His Arg Asn Leu Leu Arg Leu Arg Gly Phe
305                 310                 315                 320

Cys Ser Ser Asn Gln Glu Arg Ile Leu Val Tyr Pro Tyr Met Pro Asn
                325                 330                 335

Gly Ser Val Ala Ser Arg Leu Lys Asp Asn Ile Arg Gly Glu Pro Ala
            340                 345                 350

Leu Asp Trp Ser Arg Arg Lys Lys Ile Ala Val Gly Thr Ala Arg Gly
        355                 360                 365

Leu Val Tyr Leu His Glu Gln Cys Asp Pro Lys Ile Ile His Arg Asp
        370                 375                 380

Val Lys Ala Ala Asn Ile Leu Leu Asp Glu Asp Phe Glu Ala Val Val
385                 390                 395                 400

Gly Asp Phe Gly Leu Ala Lys Leu Leu Asp His Arg Asp Ser His Val
                405                 410                 415

Thr Thr Ala Val Arg Gly Thr Val Gly His Ile Ala Pro Glu Tyr Leu
            420                 425                 430

Ser Thr Gly Gln Ser Ser Glu Lys Thr Asp Val Phe Gly Phe Gly Ile
        435                 440                 445

Leu Leu Leu Glu Leu Ile Thr Gly Gln Lys Ala Leu Asp Phe Gly Arg
450                 455                 460

Ser Ala His Gln Lys Gly Val Met Leu Asp Trp Val Lys Lys Leu His
465                 470                 475                 480

Gln Glu Gly Lys Leu Lys Gln Leu Ile Asp Lys Asp Leu Asn Asp Lys
                485                 490                 495

Phe Asp Arg Val Glu Leu Glu Glu Ile Val Gln Val Ala Leu Leu Cys
            500                 505                 510

Thr Gln Phe Asn Pro Ser His Arg Pro Lys Met Ser Glu Val Met Lys
        515                 520                 525

Met Leu Glu Gly Asp Gly Leu Ala Glu Arg Trp Glu Ala Thr Gln Asn
        530                 535                 540

Gly Thr Gly Glu His Gln Pro Pro Leu Pro Gly Met Val Ser
545                 550                 555                 560

Ser Ser Pro Arg Val Arg Tyr Tyr Ser Asp Tyr Ile Gln Glu Ser Ser
                565                 570                 575

Leu Val Val Glu Ala Ile Glu Leu Ser Gly Pro Arg
            580                 585
```

<210> SEQ ID NO 36
<211> LENGTH: 1740
<212> TYPE: DNA
<213> ORGANISM: Arabidopsis thaliana
<220> FEATURE:
<221> NAME/KEY: CDS
<222> LOCATION: (25)..(1737)
<223> OTHER INFORMATION: /note="Arabidopsis thaliana RKS2 cDNA"

<400> SEQUENCE: 36

```
tcaattttgg tagctcttag aaaa atg gct ctg ctt att atc act gcc tta        51
                          Met Ala Leu Leu Ile Ile Thr Ala Leu
                            1               5 gtt ttt agt agt tta tgg tca tct gtg tca cca gat gct caa ggg gat       99
Val Phe Ser Ser Leu Trp Ser Ser Val Ser Pro Asp Ala Gln Gly Asp
 10              15                  20                  25 gca tta ttt gcg ttg agg agc tcg tta cgt gca tct cct gaa cag ctt      147
Ala Leu Phe Ala Leu Arg Ser Ser Leu Arg Ala Ser Pro Glu Gln Leu
             30                  35                  40 agt gat tgg aac cag aat caa gtc gat cct tgt act tgg tct caa gtt      195
Ser Asp Trp Asn Gln Asn Gln Val Asp Pro Cys Thr Trp Ser Gln Val
         45                  50                  55 att tgt gat gac aag aaa cat gtt act tct gta acc ttg tct tac atg      243
Ile Cys Asp Asp Lys Lys His Val Thr Ser Val Thr Leu Ser Tyr Met
     60                  65                  70 aac ttc tcc tcg gga aca ctg tct tca gga ata gga atc ttg aca act      291
Asn Phe Ser Ser Gly Thr Leu Ser Ser Gly Ile Gly Ile Leu Thr Thr
 75                  80                  85 ctc aag act ctt aca ttg aag gga aat gga ata atg ggt gga ata cca      339
Leu Lys Thr Leu Thr Leu Lys Gly Asn Gly Ile Met Gly Gly Ile Pro
 90                  95                 100                 105 gaa tcc att gga aat ctg tct agc ttg acc agc tta gat ttg gag gat      387
Glu Ser Ile Gly Asn Leu Ser Ser Leu Thr Ser Leu Asp Leu Glu Asp
            110                 115                 120 aat cac tta act gat cgc att cca tcc act ctc ggt aat ctc aag aat      435
Asn His Leu Thr Asp Arg Ile Pro Ser Thr Leu Gly Asn Leu Lys Asn
        125                 130                 135 cta cag ttc ttt ttc aca gca aac aac ttg agc tgt ggt ggc act ttc      483
Leu Gln Phe Phe Phe Thr Ala Asn Asn Leu Ser Cys Gly Gly Thr Phe
    140                 145                 150 ccg caa cct tgt gta acc gag tcc agt cct tca ggt gat tca agc agt      531
Pro Gln Pro Cys Val Thr Glu Ser Ser Pro Ser Gly Asp Ser Ser Ser
155                 160                 165 aga aaa act gga atc atc gct gga gtt gtt agc gga ata gcg gtt att      579
Arg Lys Thr Gly Ile Ile Ala Gly Val Val Ser Gly Ile Ala Val Ile
170                 175                 180                 185 cta cta gga ttc ttc ttc ttt ttc ttc tgc aag gat aaa cat aaa gga      627
Leu Leu Gly Phe Phe Phe Phe Phe Phe Cys Lys Asp Lys His Lys Gly
                190                 195                 200 tat aaa cga gac gta ttt gtg gat gtt gca gga acg aac ttt aaa aaa      675
Tyr Lys Arg Asp Val Phe Val Asp Val Ala Gly Thr Asn Phe Lys Lys
            205                 210                 215 ggt ttg att tca ggt gaa gtg gac aga agg att gct ttt gga cag ttg      723
Gly Leu Ile Ser Gly Glu Val Asp Arg Arg Ile Ala Phe Gly Gln Leu
        220                 225                 230 aga aga ttt gca tgg aga gag ctt cag ttg gct aca gat gag ttc agt      771
Arg Arg Phe Ala Trp Arg Glu Leu Gln Leu Ala Thr Asp Glu Phe Ser
    235                 240                 245 gaa aag aat gtt ctc gga caa gga ggc ttt ggg aaa gtt tac aaa gga      819
Glu Lys Asn Val Leu Gly Gln Gly Gly Phe Gly Lys Val Tyr Lys Gly
250                 255                 260                 265
```

```
ttg ctt tcg gat ggc acc aaa gtc gct gta aaa aga ttg act gat ttt    867
Leu Leu Ser Asp Gly Thr Lys Val Ala Val Lys Arg Leu Thr Asp Phe
                270                 275                 280 gaa cgt cca gga gga gat gaa gct ttc cag aga gaa gtt gag atg ata    915
Glu Arg Pro Gly Gly Asp Glu Ala Phe Gln Arg Glu Val Glu Met Ile
            285                 290                 295 agt gta gct gtt cat agg aat ctg ctt cgc ctt atc ggc ttt tgt aca    963
Ser Val Ala Val His Arg Asn Leu Leu Arg Leu Ile Gly Phe Cys Thr
        300                 305                 310 aca caa act gaa cga ctt ttg gtg tat cct ttc atg cag aat cta agt   1011
Thr Gln Thr Glu Arg Leu Leu Val Tyr Pro Phe Met Gln Asn Leu Ser
    315                 320                 325 gtt gca tat tgc tta aga gag att aaa ccc ggg gat cca gtt ctg gat   1059
Val Ala Tyr Cys Leu Arg Glu Ile Lys Pro Gly Asp Pro Val Leu Asp
330                 335                 340                 345 tgg ttc agg agg aaa cag att gcg tta ggt gca gca cga gga ctc gaa   1107
Trp Phe Arg Arg Lys Gln Ile Ala Leu Gly Ala Ala Arg Gly Leu Glu
                350                 355                 360 tat ctt cat gaa cat tgc aac ccg aag atc ata cac aga gat gtg aaa   1155
Tyr Leu His Glu His Cys Asn Pro Lys Ile Ile His Arg Asp Val Lys
            365                 370                 375 gct gca aat gtg tta cta gat gaa gac ttt gaa gca gtg gtt ggt gat   1203
Ala Ala Asn Val Leu Leu Asp Glu Asp Phe Glu Ala Val Val Gly Asp
        380                 385                 390 ttt ggt tta gcc aag ttg gta gat gtt aga agg act aat gta acc act   1251
Phe Gly Leu Ala Lys Leu Val Asp Val Arg Arg Thr Asn Val Thr Thr
    395                 400                 405 cag gtc cga gga aca atg ggt cat att gca cca gaa tgt ata tcc aca   1299
Gln Val Arg Gly Thr Met Gly His Ile Ala Pro Glu Cys Ile Ser Thr
410                 415                 420                 425 ggg aaa tcg tca gag aaa acc gat gtt ttc ggg tac gga att atg ctt   1347
Gly Lys Ser Ser Glu Lys Thr Asp Val Phe Gly Tyr Gly Ile Met Leu
                430                 435                 440 ctg gag ctt gta act gga caa aga gca att gat ttc tcg cgg tta gag   1395
Leu Glu Leu Val Thr Gly Gln Arg Ala Ile Asp Phe Ser Arg Leu Glu
            445                 450                 455 gaa gaa gat gat gtc tta ttg cta gac cat gtg aag aaa ctg gaa aga   1443
Glu Glu Asp Asp Val Leu Leu Leu Asp His Val Lys Lys Leu Glu Arg
        460                 465                 470 gag aag aga tta gaa gac ata gta gat aag aag ctt gat gag gat tat   1491
Glu Lys Arg Leu Glu Asp Ile Val Asp Lys Lys Leu Asp Glu Asp Tyr
    475                 480                 485 ata aag gaa gaa gtt gaa atg atg ata caa gta gct ctg cta tgc aca   1539
Ile Lys Glu Glu Val Glu Met Met Ile Gln Val Ala Leu Leu Cys Thr
490                 495                 500                 505 caa gca gca ccg gaa gaa cga cca gcg atg tcg gaa gta gta aga atg   1587
Gln Ala Ala Pro Glu Glu Arg Pro Ala Met Ser Glu Val Val Arg Met
                510                 515                 520 cta gaa gga gaa ggg ctt gca gag aga tgg gaa gag tgg cag aat ctt   1635
Leu Glu Gly Glu Gly Leu Ala Glu Arg Trp Glu Glu Trp Gln Asn Leu
            525                 530                 535 gaa gtg acg aga caa gaa gag ttt cag agg ttg cag agg aga ttt gat   1683
Glu Val Thr Arg Gln Glu Glu Phe Gln Arg Leu Gln Arg Arg Phe Asp
        540                 545                 550 tgg ggt gaa gat tcc att aat aat caa gat gct att gaa tta tct ggt   1731
Trp Gly Glu Asp Ser Ile Asn Asn Gln Asp Ala Ile Glu Leu Ser Gly
    555                 560                 565 gga aga tag                                                        1740
Gly Arg
```

-continued

570

<210> SEQ ID NO 37
<211> LENGTH: 571
<212> TYPE: PRT
<213> ORGANISM: Arabidopsis thaliana

<400> SEQUENCE: 37

Met Ala Leu Leu Ile Ile Thr Ala Leu Val Phe Ser Ser Leu Trp Ser
1               5                   10                  15

Ser Val Ser Pro Asp Ala Gln Gly Asp Ala Leu Phe Ala Leu Arg Ser
            20                  25                  30

Ser Leu Arg Ala Ser Pro Glu Gln Leu Ser Asp Trp Asn Gln Asn Gln
        35                  40                  45

Val Asp Pro Cys Thr Trp Ser Gln Val Ile Cys Asp Asp Lys Lys His
    50                  55                  60

Val Thr Ser Val Thr Leu Ser Tyr Met Asn Phe Ser Ser Gly Thr Leu
65                  70                  75                  80

Ser Ser Gly Ile Gly Ile Leu Thr Thr Leu Lys Thr Leu Thr Leu Lys
                85                  90                  95

Gly Asn Gly Ile Met Gly Gly Ile Pro Glu Ser Ile Gly Asn Leu Ser
            100                 105                 110

Ser Leu Thr Ser Leu Asp Leu Glu Asp Asn His Leu Thr Asp Arg Ile
        115                 120                 125

Pro Ser Thr Leu Gly Asn Leu Lys Asn Leu Gln Phe Phe Thr Ala
    130                 135                 140

Asn Asn Leu Ser Cys Gly Gly Thr Phe Pro Gln Pro Cys Val Thr Glu
145                 150                 155                 160

Ser Ser Pro Ser Gly Asp Ser Ser Arg Lys Thr Gly Ile Ile Ala
                165                 170                 175

Gly Val Val Ser Gly Ile Ala Val Ile Leu Leu Gly Phe Phe Phe
            180                 185                 190

Phe Phe Cys Lys Asp Lys His Lys Gly Tyr Lys Arg Asp Val Phe Val
        195                 200                 205

Asp Val Ala Gly Thr Asn Phe Lys Lys Gly Leu Ile Ser Gly Glu Val
    210                 215                 220

Asp Arg Arg Ile Ala Phe Gly Gln Leu Arg Arg Phe Ala Trp Arg Glu
225                 230                 235                 240

Leu Gln Leu Ala Thr Asp Glu Phe Ser Glu Lys Asn Val Leu Gly Gln
                245                 250                 255

Gly Gly Phe Gly Lys Val Tyr Lys Gly Leu Leu Ser Asp Gly Thr Lys
            260                 265                 270

Val Ala Val Lys Arg Leu Thr Asp Phe Glu Arg Pro Gly Gly Asp Glu
        275                 280                 285

Ala Phe Gln Arg Glu Val Glu Met Ile Ser Val Ala Val His Arg Asn
    290                 295                 300

Leu Leu Arg Leu Ile Gly Phe Cys Thr Thr Gln Thr Glu Arg Leu Leu
305                 310                 315                 320

Val Tyr Pro Phe Met Gln Asn Leu Ser Val Ala Tyr Cys Leu Arg Glu
                325                 330                 335

Ile Lys Pro Gly Asp Pro Val Leu Asp Trp Phe Arg Arg Lys Gln Ile
            340                 345                 350

Ala Leu Gly Ala Ala Arg Gly Leu Glu Tyr Leu His Glu His Cys Asn
        355                 360                 365

```
Pro Lys Ile Ile His Arg Asp Val Lys Ala Ala Asn Val Leu Leu Asp
    370                 375                 380

Glu Asp Phe Glu Ala Val Val Gly Asp Phe Gly Leu Ala Lys Leu Val
385                 390                 395                 400

Asp Val Arg Arg Thr Asn Val Thr Thr Gln Val Arg Gly Thr Met Gly
                405                 410                 415

His Ile Ala Pro Glu Cys Ile Ser Thr Gly Lys Ser Ser Glu Lys Thr
                420                 425                 430

Asp Val Phe Gly Tyr Gly Ile Met Leu Leu Glu Leu Val Thr Gly Gln
            435                 440                 445

Arg Ala Ile Asp Phe Ser Arg Leu Glu Glu Glu Asp Asp Val Leu Leu
        450                 455                 460

Leu Asp His Val Lys Lys Leu Glu Arg Glu Lys Arg Leu Glu Asp Ile
465                 470                 475                 480

Val Asp Lys Lys Leu Asp Glu Asp Tyr Ile Lys Glu Glu Val Glu Met
                485                 490                 495

Met Ile Gln Val Ala Leu Leu Cys Thr Gln Ala Ala Pro Glu Glu Arg
                500                 505                 510

Pro Ala Met Ser Glu Val Val Arg Met Leu Glu Gly Glu Gly Leu Ala
            515                 520                 525

Glu Arg Trp Glu Glu Trp Gln Asn Leu Glu Val Thr Arg Gln Glu Glu
530                 535                 540

Phe Gln Arg Leu Gln Arg Arg Phe Asp Trp Gly Glu Asp Ser Ile Asn
545                 550                 555                 560

Asn Gln Asp Ala Ile Glu Leu Ser Gly Gly Arg
                565                 570

<210> SEQ ID NO 38
<211> LENGTH: 1830
<212> TYPE: DNA
<213> ORGANISM: Arabidopsis thaliana
<220> FEATURE:
<221> NAME/KEY: CDS
<222> LOCATION: (91)..(1827)
<223> OTHER INFORMATION: /note="Arabidopsis thaliana RKS3 cDNA"

<400> SEQUENCE: 38
aacggtgaaa gtttccatga tcctcttcga ggattcattc aaagaaattg ctttagatgg      60
aacaatcaga aattgatctt acaatgtttc atg gcc tta gct ttt gtg gga atc     114
                                   Met Ala Leu Ala Phe Val Gly Ile
                                     1               5 act tcg tca aca act caa cca gat atc gaa gga gga gct ctg ttg cag     162
Thr Ser Ser Thr Thr Gln Pro Asp Ile Glu Gly Gly Ala Leu Leu Gln
        10                  15                  20 ctc aga gat tcg ctt aat gat tcg agc aat cgt cta aaa tgg aca cgc     210
Leu Arg Asp Ser Leu Asn Asp Ser Ser Asn Arg Leu Lys Trp Thr Arg
 25                  30                  35                  40 gat ttt gtg agc cct tgc tat agt tgg tct tat gtt acc tgc aga ggc     258
Asp Phe Val Ser Pro Cys Tyr Ser Trp Ser Tyr Val Thr Cys Arg Gly
                 45                  50                  55 cag agt gtt gtg gct cta aat ctt gcc tcg agt gga ttc aca gga aca     306
Gln Ser Val Val Ala Leu Asn Leu Ala Ser Ser Gly Phe Thr Gly Thr
             60                  65                  70 ctc tct cca gct att aca aaa ctg aag ttc ttg gtt acc tta gag tta     354
Leu Ser Pro Ala Ile Thr Lys Leu Lys Phe Leu Val Thr Leu Glu Leu
         75                  80                  85 cag aac aat agt tta tct ggt gcc tta cca gat tct ctt ggg aac atg     402
Gln Asn Asn Ser Leu Ser Gly Ala Leu Pro Asp Ser Leu Gly Asn Met
```

```
                                     -continued

Gln Asn Asn Ser Leu Ser Gly Ala Leu Pro Asp Ser Leu Gly Asn Met
     90                  95                 100 gtt aat cta cag act tta aac cta tca gtg aat agt ttc agc gga tcg      450
Val Asn Leu Gln Thr Leu Asn Leu Ser Val Asn Ser Phe Ser Gly Ser
105                 110                 115                 120 ata cca gcg agc tgg agt cag ctc tcg aat cta aag cac ttg gat ctc      498
Ile Pro Ala Ser Trp Ser Gln Leu Ser Asn Leu Lys His Leu Asp Leu
                125                 130                 135 tca tcc aat aat tta aca gga agc atc cca aca caa ttc ttc tca atc      546
Ser Ser Asn Asn Leu Thr Gly Ser Ile Pro Thr Gln Phe Phe Ser Ile
                140                 145                 150 cca aca ttc gat ttt tca gga act cag ctt ata tgc ggt aaa agt ttg      594
Pro Thr Phe Asp Phe Ser Gly Thr Gln Leu Ile Cys Gly Lys Ser Leu
            155                 160                 165 aat cag cct tgt tct tca agt tct cgt ctt cca gtc aca tcc tcc aag      642
Asn Gln Pro Cys Ser Ser Ser Ser Arg Leu Pro Val Thr Ser Ser Lys
170                 175                 180 aaa aag ctg aga gac att act ttg act gca agt tgt gtt gct tct ata      690
Lys Lys Leu Arg Asp Ile Thr Leu Thr Ala Ser Cys Val Ala Ser Ile
185                 190                 195                 200 atc tta ttc ctt gga gca atg gtt atg tat cat cac cat cgc gtc cgc      738
Ile Leu Phe Leu Gly Ala Met Val Met Tyr His His His Arg Val Arg
                205                 210                 215 aga acc aaa tac gac atc ttt ttt gat gta gct ggg gaa gat gac agg      786
Arg Thr Lys Tyr Asp Ile Phe Phe Asp Val Ala Gly Glu Asp Asp Arg
                220                 225                 230 aag att tcc ttt gga caa cta aaa cga ttc tct tta cgt gaa atc cag      834
Lys Ile Ser Phe Gly Gln Leu Lys Arg Phe Ser Leu Arg Glu Ile Gln
            235                 240                 245 ctc gca aca gat agt ttc aac gag agc aat ttg ata gga caa gga gga      882
Leu Ala Thr Asp Ser Phe Asn Glu Ser Asn Leu Ile Gly Gln Gly Gly
        250                 255                 260 ttt ggt aaa gta tac aga ggt ttg ctt cca gac aaa aca aaa gtt gca      930
Phe Gly Lys Val Tyr Arg Gly Leu Leu Pro Asp Lys Thr Lys Val Ala
265                 270                 275                 280 gtg aaa cgc ctt gcg gat tac ttc agt cct gga gga gaa gct gct ttc      978
Val Lys Arg Leu Ala Asp Tyr Phe Ser Pro Gly Gly Glu Ala Ala Phe
                285                 290                 295 caa aga gag att cag ctc ata agc gtt gcg gtt cat aaa aat ctc tta     1026
Gln Arg Glu Ile Gln Leu Ile Ser Val Ala Val His Lys Asn Leu Leu
                300                 305                 310 cgc ctt att ggc ttc tgc aca act tcc tct gag aga atc ctt gtt tat     1074
Arg Leu Ile Gly Phe Cys Thr Thr Ser Ser Glu Arg Ile Leu Val Tyr
            315                 320                 325 cca tac atg gaa aat ctt agt gtt gca tat cga cta aga gat ttg aaa     1122
Pro Tyr Met Glu Asn Leu Ser Val Ala Tyr Arg Leu Arg Asp Leu Lys
        330                 335                 340 gcg gga gag gaa gga tta gac tgg cca aca agg aag cgt gta gct ttt     1170
Ala Gly Glu Glu Gly Leu Asp Trp Pro Thr Arg Lys Arg Val Ala Phe
345                 350                 355                 360 ggt tca gct cac ggt tta gag tat cta cac gaa cat tgt aac ccg aag     1218
Gly Ser Ala His Gly Leu Glu Tyr Leu His Glu His Cys Asn Pro Lys
                365                 370                 375 atc ata cac cgc gat ctc aag gct gca aac ata ctt tta gac aac aat     1266
Ile Ile His Arg Asp Leu Lys Ala Ala Asn Ile Leu Leu Asp Asn Asn
                380                 385                 390 ttt gag cca gtt ctt gga gat ttc ggt tta gct aag ctt gtg gac aca     1314
Phe Glu Pro Val Leu Gly Asp Phe Gly Leu Ala Lys Leu Val Asp Thr
            395                 400                 405
```

```
tct ctg act cat gtc aca act caa gtc cga ggc aca atg ggt cac att      1362
Ser Leu Thr His Val Thr Thr Gln Val Arg Gly Thr Met Gly His Ile
    410                 415                 420 gcg cca gag tat ctc tgc aca gga aaa tca tct gaa aaa acc gat gtt      1410
Ala Pro Glu Tyr Leu Cys Thr Gly Lys Ser Ser Glu Lys Thr Asp Val
425                 430                 435                 440 ttt ggt tac ggt ata acg ctt ctt gag ctt gtt act ggt cag cgc gca      1458
Phe Gly Tyr Gly Ile Thr Leu Leu Glu Leu Val Thr Gly Gln Arg Ala
                445                 450                 455 atc gat ttt tca cgc ttg gaa gaa gag gaa aat att ctc ttg ctt gat      1506
Ile Asp Phe Ser Arg Leu Glu Glu Glu Glu Asn Ile Leu Leu Leu Asp
            460                 465                 470 cat ata aag aag ttg ctt aga gaa cag aga ctt aga gac att gtt gat      1554
His Ile Lys Lys Leu Leu Arg Glu Gln Arg Leu Arg Asp Ile Val Asp
        475                 480                 485 agc aat ttg act aca tat gac tcc aaa gaa gtt gaa aca atc gtt caa      1602
Ser Asn Leu Thr Thr Tyr Asp Ser Lys Glu Val Glu Thr Ile Val Gln
    490                 495                 500 gtg gct ctt ctc tgc aca caa ggc tca cca gaa gat aga cca gcg atg      1650
Val Ala Leu Leu Cys Thr Gln Gly Ser Pro Glu Asp Arg Pro Ala Met
505                 510                 515                 520 tct gaa gtg gtc aaa atg ctt caa ggg act ggt ggt ttg gct gag aaa      1698
Ser Glu Val Val Lys Met Leu Gln Gly Thr Gly Gly Leu Ala Glu Lys
                525                 530                 535 tgg act gaa tgg gaa caa ctt gaa gaa gtt agg aac aaa gaa gca ttg      1746
Trp Thr Glu Trp Glu Gln Leu Glu Glu Val Arg Asn Lys Glu Ala Leu
            540                 545                 550 ttg ctt ccg act tta ccg gct act tgg gat gaa gaa gaa acc acc gtt      1794
Leu Leu Pro Thr Leu Pro Ala Thr Trp Asp Glu Glu Glu Thr Thr Val
        555                 560                 565 gat caa gaa tct atc cga tta tcg aca gca aga tga                      1830
Asp Gln Glu Ser Ile Arg Leu Ser Thr Ala Arg
    570                 575

<210> SEQ ID NO 39
<211> LENGTH: 579
<212> TYPE: PRT
<213> ORGANISM: Arabidopsis thaliana

<400> SEQUENCE: 39

Met Ala Leu Ala Phe Val Gly Ile Thr Ser Ser Thr Thr Gln Pro Asp
 1               5                  10                  15

Ile Glu Gly Gly Ala Leu Leu Gln Leu Arg Asp Ser Leu Asn Asp Ser
            20                  25                  30

Ser Asn Arg Leu Lys Trp Thr Arg Asp Phe Val Ser Pro Cys Tyr Ser
        35                  40                  45

Trp Ser Tyr Val Thr Cys Arg Gly Gln Ser Val Val Ala Leu Asn Leu
    50                  55                  60

Ala Ser Ser Gly Phe Thr Gly Thr Leu Ser Pro Ala Ile Thr Lys Leu
65                  70                  75                  80

Lys Phe Leu Val Thr Leu Glu Leu Gln Asn Asn Ser Leu Ser Gly Ala
                85                  90                  95

Leu Pro Asp Ser Leu Gly Asn Met Val Asn Leu Gln Thr Leu Asn Leu
            100                 105                 110

Ser Val Asn Ser Phe Ser Gly Ser Ile Pro Ala Ser Trp Ser Gln Leu
        115                 120                 125

Ser Asn Leu Lys His Leu Asp Leu Ser Ser Asn Asn Leu Thr Gly Ser
    130                 135                 140
```

-continued

```
Ile Pro Thr Gln Phe Phe Ser Ile Pro Thr Phe Asp Phe Ser Gly Thr
145                 150                 155                 160

Gln Leu Ile Cys Gly Lys Ser Leu Asn Gln Pro Cys Ser Ser Ser Ser
            165                 170                 175

Arg Leu Pro Val Thr Ser Ser Lys Lys Lys Leu Arg Asp Ile Thr Leu
        180                 185                 190

Thr Ala Ser Cys Val Ala Ser Ile Ile Leu Phe Leu Gly Ala Met Val
    195                 200                 205

Met Tyr His His His Arg Val Arg Arg Thr Lys Tyr Asp Ile Phe Phe
210                 215                 220

Asp Val Ala Gly Glu Asp Arg Lys Ile Ser Phe Gly Gln Leu Lys
225                 230                 235                 240

Arg Phe Ser Leu Arg Glu Ile Gln Leu Ala Thr Asp Ser Phe Asn Glu
                245                 250                 255

Ser Asn Leu Ile Gly Gln Gly Gly Phe Gly Lys Val Tyr Arg Gly Leu
            260                 265                 270

Leu Pro Asp Lys Thr Lys Val Ala Val Lys Arg Leu Ala Asp Tyr Phe
        275                 280                 285

Ser Pro Gly Gly Glu Ala Ala Phe Gln Arg Glu Ile Gln Leu Ile Ser
    290                 295                 300

Val Ala Val His Lys Asn Leu Leu Arg Leu Ile Gly Phe Cys Thr Thr
305                 310                 315                 320

Ser Ser Glu Arg Ile Leu Val Tyr Pro Tyr Met Glu Asn Leu Ser Val
                325                 330                 335

Ala Tyr Arg Leu Arg Asp Leu Lys Ala Gly Glu Gly Leu Asp Trp
            340                 345                 350

Pro Thr Arg Lys Arg Val Ala Phe Gly Ser Ala His Gly Leu Glu Tyr
        355                 360                 365

Leu His Glu His Cys Asn Pro Lys Ile Ile His Arg Asp Leu Lys Ala
    370                 375                 380

Ala Asn Ile Leu Leu Asp Asn Asn Phe Glu Pro Val Leu Gly Asp Phe
385                 390                 395                 400

Gly Leu Ala Lys Leu Val Asp Thr Ser Leu Thr His Val Thr Thr Gln
                405                 410                 415

Val Arg Gly Thr Met Gly His Ile Ala Pro Glu Tyr Leu Cys Thr Gly
            420                 425                 430

Lys Ser Ser Glu Lys Thr Asp Val Phe Gly Tyr Gly Ile Thr Leu Leu
        435                 440                 445

Glu Leu Val Thr Gly Gln Arg Ala Ile Asp Phe Ser Arg Leu Glu Glu
    450                 455                 460

Glu Glu Asn Ile Leu Leu Leu Asp His Ile Lys Lys Leu Leu Arg Glu
465                 470                 475                 480

Gln Arg Leu Arg Asp Ile Val Asp Ser Asn Leu Thr Thr Tyr Asp Ser
                485                 490                 495

Lys Glu Val Glu Thr Ile Val Gln Val Ala Leu Leu Cys Thr Gln Gly
            500                 505                 510

Ser Pro Glu Asp Arg Pro Ala Met Ser Glu Val Val Lys Met Leu Gln
        515                 520                 525

Gly Thr Gly Gly Leu Ala Glu Lys Trp Thr Trp Glu Gln Leu Glu
    530                 535                 540

Glu Val Arg Asn Lys Glu Ala Leu Leu Pro Thr Leu Pro Ala Thr
545                 550                 555                 560

Trp Asp Glu Glu Glu Thr Thr Val Asp Gln Glu Ser Ile Arg Leu Ser
```

-continued

```
                     565                 570                 575
Thr Ala Arg

<210> SEQ ID NO 40
<211> LENGTH: 1587
<212> TYPE: DNA
<213> ORGANISM: Arabidopsis thaliana
<220> FEATURE:
<221> NAME/KEY: CDS
<222> LOCATION: (40)..(1584)
<223> OTHER INFORMATION: /note="Arabidopsis thaliana RKS4 cDNA"

<400> SEQUENCE: 40
tcttccttct ccttctggta atctaatcta aagcttttc atg gtg gtg atg aag       54
                                            Met Val Val Met Lys
                                            1               5 ata ttc tct gtt ctg tta cta cta tgt ttc ttc gtt act tgt tct ctc      102
Ile Phe Ser Val Leu Leu Leu Leu Cys Phe Phe Val Thr Cys Ser Leu
            10                  15                  20 tct tct gaa ccc aga aac cct gaa gtc att aat ggt gac aaa ttc ttc      150
Ser Ser Glu Pro Arg Asn Pro Glu Val Ile Asn Gly Asp Lys Phe Phe
        25                  30                  35 atc ttt gtt ttg ttt ttt ccc aat tcc aga gga gct cca agt cag tct      198
Ile Phe Val Leu Phe Phe Pro Asn Ser Arg Gly Ala Pro Ser Gln Ser
    40                  45                  50 ctt tca gga act tta tct ggg tct att gga aat ctc act aat ctt cga      246
Leu Ser Gly Thr Leu Ser Gly Ser Ile Gly Asn Leu Thr Asn Leu Arg
55                  60                  65 caa gtg tca tta cag aac aat aac atc tcc ggt aaa atc cca ccg gag      294
Gln Val Ser Leu Gln Asn Asn Asn Ile Ser Gly Lys Ile Pro Pro Glu
 70                 75                  80                  85 att tgt tct ctt ccc aaa tta cag act ctg gat tta tcc aat aac cgg      342
Ile Cys Ser Leu Pro Lys Leu Gln Thr Leu Asp Leu Ser Asn Asn Arg
                90                  95                 100 ttc tcc ggt gaa atc ccc ggt tct gtt aac cag ctg agt aat ctc caa      390
Phe Ser Gly Glu Ile Pro Gly Ser Val Asn Gln Leu Ser Asn Leu Gln
            105                 110                 115 tat ctt gtt gct ggg aac cct ttg att tgt aaa aac agc cta ccg gag      438
Tyr Leu Val Ala Gly Asn Pro Leu Ile Cys Lys Asn Ser Leu Pro Glu
        120                 125                 130 att tgt tca gga tca atc agt gca agc cct ctt tct gtc tct tta cgt      486
Ile Cys Ser Gly Ser Ile Ser Ala Ser Pro Leu Ser Val Ser Leu Arg
    135                 140                 145 tct tca tca gac aag caa gag gaa ggg tta ctt ggg ttg gga aat cta      534
Ser Ser Ser Asp Lys Gln Glu Glu Gly Leu Leu Gly Leu Gly Asn Leu
150                 155                 160                 165 aga agc ttc aca ttc agg gaa ctt cat gta gct acg gat ggt ttt agt      582
Arg Ser Phe Thr Phe Arg Glu Leu His Val Ala Thr Asp Gly Phe Ser
                170                 175                 180 tcc aag agt att ctt ggt gct ggt ggg ttt ggt aat gtc tac aga gga      630
Ser Lys Ser Ile Leu Gly Ala Gly Gly Phe Gly Asn Val Tyr Arg Gly
            185                 190                 195 aaa ttc ggg gat ggg aca gtg gtt gca gtg aaa cga ttg aaa gat gtg      678
Lys Phe Gly Asp Gly Thr Val Val Ala Val Lys Arg Leu Lys Asp Val
        200                 205                 210 aat gga acc tcc ggg aac tca cag ttt cgt act gag ctt gag atg atc      726
Asn Gly Thr Ser Gly Asn Ser Gln Phe Arg Thr Glu Leu Glu Met Ile
    215                 220                 225 agc tta gct gtt cat agg aat ttg ctt cgg tta atc ggt tat tgt gcg      774
Ser Leu Ala Val His Arg Asn Leu Leu Arg Leu Ile Gly Tyr Cys Ala
```

```
                230                 235                 240                 245
agt tct agc gaa aga ctt ctt gtt tac cct tac atg tcc aat ggc agc      822
Ser Ser Ser Glu Arg Leu Leu Val Tyr Pro Tyr Met Ser Asn Gly Ser
            250                 255                 260 gtc gcc tct agg ctc aaa gct aag cca gcg ttg gac tgg aac aca agg      870
Val Ala Ser Arg Leu Lys Ala Lys Pro Ala Leu Asp Trp Asn Thr Arg
        265                 270                 275 aag aag ata gcg att gga gct gca aga ggg ttg ttt tat cta cac gag      918
Lys Lys Ile Ala Ile Gly Ala Ala Arg Gly Leu Phe Tyr Leu His Glu
            280                 285                 290 caa tgc gat ccc aag att att cac cga gat gtc aag gca gca aac att      966
Gln Cys Asp Pro Lys Ile Ile His Arg Asp Val Lys Ala Ala Asn Ile
        295                 300                 305 ctc cta gat gag tat ttt gaa gca gtt gtt ggg gat ttt gga cta gca     1014
Leu Leu Asp Glu Tyr Phe Glu Ala Val Val Gly Asp Phe Gly Leu Ala
310                 315                 320                 325 aag cta ctc aac cac gag gat tca cat gtc aca acc gcg gtt aga gga     1062
Lys Leu Leu Asn His Glu Asp Ser His Val Thr Thr Ala Val Arg Gly
            330                 335                 340 act gtt ggt cac att gca cct gag tat ctc tcc acc ggt cag tca tct     1110
Thr Val Gly His Ile Ala Pro Glu Tyr Leu Ser Thr Gly Gln Ser Ser
        345                 350                 355 gag aaa acc gat gtc ttt ggg ttc ggt ata ctt ttg cta gag ctc atc     1158
Glu Lys Thr Asp Val Phe Gly Phe Gly Ile Leu Leu Leu Glu Leu Ile
            360                 365                 370 aca gga atg aga gct ctc gag ttt ggc aag tct gtt agc cag aaa gga     1206
Thr Gly Met Arg Ala Leu Glu Phe Gly Lys Ser Val Ser Gln Lys Gly
        375                 380                 385 gct atg cta gaa tgg gtg agg aag cta cac aag gaa atg aaa gta gag     1254
Ala Met Leu Glu Trp Val Arg Lys Leu His Lys Glu Met Lys Val Glu
390                 395                 400                 405 gag cta gta gac cga gaa ctg ggg aca acc tac gat aga ata gaa gtt     1302
Glu Leu Val Asp Arg Glu Leu Gly Thr Thr Tyr Asp Arg Ile Glu Val
            410                 415                 420 gga gag atg cta caa gtg gca ctg ctc tgc act cag ttt ctt cca gct     1350
Gly Glu Met Leu Gln Val Ala Leu Leu Cys Thr Gln Phe Leu Pro Ala
        425                 430                 435 cac aga ccc aaa atg tct gaa gta gtt cag atg ctt gaa gga gat gga     1398
His Arg Pro Lys Met Ser Glu Val Val Gln Met Leu Glu Gly Asp Gly
            440                 445                 450 tta gct gag aga tgg gct gct tca cat gac cat tca cat ttc tac cat     1446
Leu Ala Glu Arg Trp Ala Ala Ser His Asp His Ser His Phe Tyr His
        455                 460                 465 gcc aac atg tct tac agg act att acc tct act gat ggc aac aac caa     1494
Ala Asn Met Ser Tyr Arg Thr Ile Thr Ser Thr Asp Gly Asn Asn Gln
470                 475                 480                 485 acc aaa cat ctg ttt ggc tcc tca gga ttt gaa gat gaa gat gat aat     1542
Thr Lys His Leu Phe Gly Ser Ser Gly Phe Glu Asp Glu Asp Asp Asn
            490                 495                 500 caa gcg tta gat tca ttc gcc atg gaa cta tct ggt cca agg tag        1587
Gln Ala Leu Asp Ser Phe Ala Met Glu Leu Ser Gly Pro Arg
        505                 510                 515

<210> SEQ ID NO 41
<211> LENGTH: 515
<212> TYPE: PRT
<213> ORGANISM: Arabidopsis thaliana

<400> SEQUENCE: 41

Met Val Val Met Lys Ile Phe Ser Val Leu Leu Leu Leu Cys Phe Phe
```

-continued

```
  1               5              10              15
Val Thr Cys Ser Leu Ser Ser Glu Pro Arg Asn Pro Glu Val Ile Asn
            20                  25                  30
Gly Asp Lys Phe Phe Ile Phe Val Leu Phe Phe Pro Asn Ser Arg Gly
            35                  40                  45
Ala Pro Ser Gln Ser Leu Ser Gly Thr Leu Ser Gly Ser Ile Gly Asn
            50                  55                  60
Leu Thr Asn Leu Arg Gln Val Ser Leu Gln Asn Asn Ile Ser Gly
 65                 70                  75                  80
Lys Ile Pro Pro Glu Ile Cys Ser Leu Pro Lys Leu Gln Thr Leu Asp
            85                  90                  95
Leu Ser Asn Asn Arg Phe Ser Gly Glu Ile Pro Gly Ser Val Asn Gln
           100                 105                 110
Leu Ser Asn Leu Gln Tyr Leu Val Ala Gly Asn Pro Leu Ile Cys Lys
           115                 120                 125
Asn Ser Leu Pro Glu Ile Cys Ser Gly Ser Ile Ser Ala Ser Pro Leu
           130                 135                 140
Ser Val Ser Leu Arg Ser Ser Ser Asp Lys Gln Glu Glu Gly Leu Leu
145                 150                 155                 160
Gly Leu Gly Asn Leu Arg Ser Phe Thr Phe Arg Glu Leu His Val Ala
           165                 170                 175
Thr Asp Gly Phe Ser Ser Lys Ser Ile Leu Gly Ala Gly Phe Gly
           180                 185                 190
Asn Val Tyr Arg Gly Lys Phe Gly Asp Gly Thr Val Val Ala Val Lys
           195                 200                 205
Arg Leu Lys Asp Val Asn Gly Thr Ser Gly Asn Ser Gln Phe Arg Thr
           210                 215                 220
Glu Leu Glu Met Ile Ser Leu Ala Val His Arg Asn Leu Leu Arg Leu
225                 230                 235                 240
Ile Gly Tyr Cys Ala Ser Ser Ser Glu Arg Leu Leu Val Tyr Pro Tyr
           245                 250                 255
Met Ser Asn Gly Ser Val Ala Ser Arg Leu Lys Ala Lys Pro Ala Leu
           260                 265                 270
Asp Trp Asn Thr Arg Lys Lys Ile Ala Ile Gly Ala Ala Arg Gly Leu
           275                 280                 285
Phe Tyr Leu His Glu Gln Cys Asp Pro Lys Ile Ile His Arg Asp Val
           290                 295                 300
Lys Ala Ala Asn Ile Leu Leu Asp Glu Tyr Phe Glu Ala Val Val Gly
305                 310                 315                 320
Asp Phe Gly Leu Ala Lys Leu Leu Asn His Glu Asp Ser His Val Thr
           325                 330                 335
Thr Ala Val Arg Gly Thr Val Gly His Ile Ala Pro Glu Tyr Leu Ser
           340                 345                 350
Thr Gly Gln Ser Ser Glu Lys Thr Asp Val Phe Gly Phe Gly Ile Leu
           355                 360                 365
Leu Leu Glu Leu Ile Thr Gly Met Arg Ala Leu Glu Phe Gly Lys Ser
           370                 375                 380
Val Ser Gln Lys Gly Ala Met Leu Glu Trp Arg Lys Leu His Lys
385                 390                 395                 400
Glu Met Lys Val Glu Glu Leu Val Asp Arg Glu Leu Gly Thr Thr Tyr
           405                 410                 415
Asp Arg Ile Glu Val Gly Glu Met Leu Gln Val Ala Leu Leu Cys Thr
           420                 425                 430
```

-continued

```
Gln Phe Leu Pro Ala His Arg Pro Lys Met Ser Glu Val Val Gln Met
        435                 440                 445

Leu Glu Gly Asp Gly Leu Ala Glu Arg Trp Ala Ala Ser His Asp His
    450                 455                 460

Ser His Phe Tyr His Ala Asn Met Ser Tyr Arg Thr Ile Thr Ser Thr
465                 470                 475                 480

Asp Gly Asn Asn Gln Thr Lys His Leu Phe Gly Ser Ser Gly Phe Glu
                485                 490                 495

Asp Glu Asp Asp Asn Gln Ala Leu Asp Ser Phe Ala Met Glu Leu Ser
            500                 505                 510

Gly Pro Arg
        515

<210> SEQ ID NO 42
<211> LENGTH: 1629
<212> TYPE: DNA
<213> ORGANISM: Arabidopsis thaliana
<220> FEATURE:
<221> NAME/KEY: CDS
<222> LOCATION: (28)..(1623)
<223> OTHER INFORMATION: /note="Arabidopsis thaliana RKS5 cDNA"

<400> SEQUENCE: 42
ctagagaatt cttatacttt ttctacg atg gag att tct ttg atg aag ttt ctg      54
                                Met Glu Ile Ser Leu Met Lys Phe Leu
                                 1               5 ttt tta gga atc tgg gtt tat tat tac tct gtt ctt gac tct gtt tct     102
Phe Leu Gly Ile Trp Val Tyr Tyr Tyr Ser Val Leu Asp Ser Val Ser
 10              15                  20                  25 gcc atg gat agt ctt tta tct ccc aag ggt gtt aac tat gaa gtg gct     150
Ala Met Asp Ser Leu Leu Ser Pro Lys Gly Val Asn Tyr Glu Val Ala
                 30                  35                  40 gcg tta atg tca gtg aag aac aag atg aaa gat gag aaa gag gtt ttg     198
Ala Leu Met Ser Val Lys Asn Lys Met Lys Asp Glu Lys Glu Val Leu
             45                  50                  55 tct ggt tgg gat att aac tct gtt gat cct tgt act tgg aac atg gtt     246
Ser Gly Trp Asp Ile Asn Ser Val Asp Pro Cys Thr Trp Asn Met Val
         60                  65                  70 ggt tgt tct tct gaa ggt ttt gtg gtt tct ctg tta ctt cag aat aat     294
Gly Cys Ser Ser Glu Gly Phe Val Val Ser Leu Leu Leu Gln Asn Asn
     75                  80                  85 cag tta act ggt ccg att cct tct gag tta ggc caa ctc tct gag ctt     342
Gln Leu Thr Gly Pro Ile Pro Ser Glu Leu Gly Gln Leu Ser Glu Leu
 90                  95                 100                 105 gaa acg ctt gat tta tcg ggg aat cgg ttt agt ggt gaa atc cca gct     390
Glu Thr Leu Asp Leu Ser Gly Asn Arg Phe Ser Gly Glu Ile Pro Ala
                110                 115                 120 tct tta ggg ttc tta act cac tta aac tac ttg cgg ctt agc agg aat     438
Ser Leu Gly Phe Leu Thr His Leu Asn Tyr Leu Arg Leu Ser Arg Asn
            125                 130                 135 ctt tta tct ggg caa gtc cct cac ctc gtc gct ggc ctc tca ggt ctt     486
Leu Leu Ser Gly Gln Val Pro His Leu Val Ala Gly Leu Ser Gly Leu
        140                 145                 150 tct ttc ttg gat cta tct ttc aac aat cta agc gga cca act ccg aat     534
Ser Phe Leu Asp Leu Ser Phe Asn Asn Leu Ser Gly Pro Thr Pro Asn
    155                 160                 165 ata tca gca aaa gat tac agg att gta gga aat gca ttt ctt tgt ggt     582
Ile Ser Ala Lys Asp Tyr Arg Ile Val Gly Asn Ala Phe Leu Cys Gly
170                 175                 180                 185
```

```
cca gct tcc caa gag ctt tgc tca gat gct aca cct gtg aga aat gtg      630
Pro Ala Ser Gln Glu Leu Cys Ser Asp Ala Thr Pro Val Arg Asn Val
                190                 195                 200 cag caa gac tac gaa ttt gaa atc ggc cat ctg aaa agg ttc agt ttt      678
Gln Gln Asp Tyr Glu Phe Glu Ile Gly His Leu Lys Arg Phe Ser Phe
        205                 210                 215 cgc gaa ata caa acc gca aca agc aat ttt agt cca aag aac att ttg      726
Arg Glu Ile Gln Thr Ala Thr Ser Asn Phe Ser Pro Lys Asn Ile Leu
                220                 225                 230 gga caa gga ggg ttt ggg atg gtt tat aaa ggg tat ctc cca aat gga      774
Gly Gln Gly Gly Phe Gly Met Val Tyr Lys Gly Tyr Leu Pro Asn Gly
        235                 240                 245 act gtg gtg gca gtt aaa aga ttg aaa gat ccg att tat aca gga gaa      822
Thr Val Val Ala Val Lys Arg Leu Lys Asp Pro Ile Tyr Thr Gly Glu
250                 255                 260                 265 gtt cag ttt caa acc gaa gta gag atg att ggc tta gct gtt cac cgt      870
Val Gln Phe Gln Thr Glu Val Glu Met Ile Gly Leu Ala Val His Arg
            270                 275                 280 aac ctt tta cgc ctc ttt gga ttc tgt atg acc ccg gaa gag aga atg      918
Asn Leu Leu Arg Leu Phe Gly Phe Cys Met Thr Pro Glu Glu Arg Met
                285                 290                 295 ctt gtg tat ccg tac atg cca aat gga agc gta gct gat cgt ctg aga      966
Leu Val Tyr Pro Tyr Met Pro Asn Gly Ser Val Ala Asp Arg Leu Arg
        300                 305                 310 gat tgg aat cgg agg ata agc att gca ctc ggc gca gct cga gga ctt     1014
Asp Trp Asn Arg Arg Ile Ser Ile Ala Leu Gly Ala Ala Arg Gly Leu
                315                 320                 325 gtt tac ttg cac gag caa tgc aat cca aag att att cac aga gac gtc     1062
Val Tyr Leu His Glu Gln Cys Asn Pro Lys Ile Ile His Arg Asp Val
330                 335                 340                 345 aaa gct gca aat att cta ctt gat gag agc ttt gaa gca ata gtt ggc     1110
Lys Ala Ala Asn Ile Leu Leu Asp Glu Ser Phe Glu Ala Ile Val Gly
            350                 355                 360 gat ttt ggt cta gca aag ctt tta gac cag aga gat tca cat gtc act     1158
Asp Phe Gly Leu Ala Lys Leu Leu Asp Gln Arg Asp Ser His Val Thr
                365                 370                 375 acc gca gtc cga gga acc att gga cac atc gct ccc gag tac ctt tcc     1206
Thr Ala Val Arg Gly Thr Ile Gly His Ile Ala Pro Glu Tyr Leu Ser
        380                 385                 390 act gga cag tcc tca gag aaa acc gat gtt ttc gga ttc gga gta cta     1254
Thr Gly Gln Ser Ser Glu Lys Thr Asp Val Phe Gly Phe Gly Val Leu
                395                 400                 405 atc ctt gaa ctc ata aca ggt cat aag atg att gat caa ggc aat ggt     1302
Ile Leu Glu Leu Ile Thr Gly His Lys Met Ile Asp Gln Gly Asn Gly
410                 415                 420                 425 caa gtt cga aaa gga atg ata ttg agc tgg gta agg aca ttg aaa gca     1350
Gln Val Arg Lys Gly Met Ile Leu Ser Trp Val Arg Thr Leu Lys Ala
            430                 435                 440 gag aag aga ttt gca gag atg gtg gac aga gat ttg aag gga gag ttt     1398
Glu Lys Arg Phe Ala Glu Met Val Asp Arg Asp Leu Lys Gly Glu Phe
                445                 450                 455 gat gat ttg gtg ttg gag gaa gta gtg gaa ttg gct ttg ctt tgt aca     1446
Asp Asp Leu Val Leu Glu Glu Val Val Glu Leu Ala Leu Leu Cys Thr
        460                 465                 470 cag cca cat ccg aat cta aga ccg agg atg tct caa gtg ttg aag gta     1494
Gln Pro His Pro Asn Leu Arg Pro Arg Met Ser Gln Val Leu Lys Val
475                 480                 485 cta gaa ggt tta gtg gaa cag tgt gaa gga ggg tat gaa gct aga gct     1542
Leu Glu Gly Leu Val Glu Gln Cys Glu Gly Gly Tyr Glu Ala Arg Ala
```

```
                490              495              500              505
cca agt gtc tct agg aac tac agt aat ggt cat gaa gag cag tcc ttt    1590
Pro Ser Val Ser Arg Asn Tyr Ser Asn Gly His Glu Glu Gln Ser Phe
                510                          515              520 att att gaa gcc att gag ctc tct gga cca cga tgatag                 1629
Ile Ile Glu Ala Ile Glu Leu Ser Gly Pro Arg
            525              530

<210> SEQ ID NO 43
<211> LENGTH: 532
<212> TYPE: PRT
<213> ORGANISM: Arabidopsis thaliana

<400> SEQUENCE: 43

Met Glu Ile Ser Leu Met Lys Phe Leu Phe Leu Gly Ile Trp Val Tyr
 1               5                  10                  15

Tyr Tyr Ser Val Leu Asp Ser Val Ser Ala Met Asp Ser Leu Leu Ser
            20                  25                  30

Pro Lys Gly Val Asn Tyr Glu Val Ala Ala Leu Met Ser Val Lys Asn
        35                  40                  45

Lys Met Lys Asp Glu Lys Glu Val Leu Ser Gly Trp Asp Ile Asn Ser
 50                  55                  60

Val Asp Pro Cys Thr Trp Asn Met Val Gly Cys Ser Ser Glu Gly Phe
 65                  70                  75                  80

Val Val Ser Leu Leu Leu Gln Asn Asn Gln Leu Thr Gly Pro Ile Pro
                85                  90                  95

Ser Glu Leu Gly Gln Leu Ser Glu Leu Glu Thr Leu Asp Leu Ser Gly
            100                 105                 110

Asn Arg Phe Ser Gly Glu Ile Pro Ala Ser Leu Gly Phe Leu Thr His
        115                 120                 125

Leu Asn Tyr Leu Arg Leu Ser Arg Asn Leu Leu Ser Gly Gln Val Pro
130                 135                 140

His Leu Val Ala Gly Leu Ser Gly Leu Ser Phe Leu Asp Leu Ser Phe
145                 150                 155                 160

Asn Asn Leu Ser Gly Pro Thr Pro Asn Ile Ser Ala Lys Asp Tyr Arg
                165                 170                 175

Ile Val Gly Asn Ala Phe Leu Cys Gly Pro Ala Ser Gln Glu Leu Cys
            180                 185                 190

Ser Asp Ala Thr Pro Val Arg Asn Val Gln Gln Asp Tyr Glu Phe Glu
        195                 200                 205

Ile Gly His Leu Lys Arg Phe Ser Phe Arg Glu Ile Gln Thr Ala Thr
    210                 215                 220

Ser Asn Phe Ser Pro Lys Asn Ile Leu Gly Gln Gly Gly Phe Gly Met
225                 230                 235                 240

Val Tyr Lys Gly Tyr Leu Pro Asn Gly Thr Val Val Ala Val Lys Arg
                245                 250                 255

Leu Lys Asp Pro Ile Tyr Thr Gly Glu Val Gln Phe Gln Thr Glu Val
            260                 265                 270

Glu Met Ile Gly Leu Ala Val His Arg Asn Leu Leu Arg Leu Phe Gly
        275                 280                 285

Phe Cys Met Thr Pro Glu Glu Arg Met Leu Val Tyr Pro Tyr Met Pro
    290                 295                 300

Asn Gly Ser Val Ala Asp Arg Leu Arg Asp Trp Asn Arg Arg Ile Ser
305                 310                 315                 320

Ile Ala Leu Gly Ala Ala Arg Gly Leu Val Tyr Leu His Glu Gln Cys
```

```
                325                 330                 335
Asn Pro Lys Ile Ile His Arg Asp Val Lys Ala Ala Asn Ile Leu Leu
            340                 345                 350

Asp Glu Ser Phe Glu Ala Ile Val Gly Asp Phe Gly Leu Ala Lys Leu
        355                 360                 365

Leu Asp Gln Arg Asp Ser His Val Thr Thr Ala Val Arg Gly Thr Ile
    370                 375                 380

Gly His Ile Ala Pro Glu Tyr Leu Ser Thr Gly Gln Ser Ser Glu Lys
385                 390                 395                 400

Thr Asp Val Phe Gly Phe Gly Val Leu Ile Leu Glu Leu Ile Thr Gly
                405                 410                 415

His Lys Met Ile Asp Gln Gly Asn Gly Gln Val Arg Lys Gly Met Ile
            420                 425                 430

Leu Ser Trp Val Arg Thr Leu Lys Ala Glu Lys Arg Phe Ala Glu Met
        435                 440                 445

Val Asp Arg Asp Leu Lys Gly Glu Phe Asp Asp Leu Val Leu Glu Glu
    450                 455                 460

Val Val Glu Leu Ala Leu Leu Cys Thr Gln Pro His Pro Asn Leu Arg
465                 470                 475                 480

Pro Arg Met Ser Gln Val Leu Lys Val Leu Glu Gly Leu Val Glu Gln
                485                 490                 495

Cys Glu Gly Gly Tyr Glu Ala Arg Ala Pro Ser Val Ser Arg Asn Tyr
            500                 505                 510

Ser Asn Gly His Glu Gln Ser Phe Ile Ile Glu Ala Ile Glu Leu
        515                 520                 525

Ser Gly Pro Arg
    530

<210> SEQ ID NO 44
<211> LENGTH: 1920
<212> TYPE: DNA
<213> ORGANISM: Arabidopsis thaliana
<220> FEATURE:
<221> NAME/KEY: CDS
<222> LOCATION: (61)..(1899)
<223> OTHER INFORMATION: /note="Arabidopsis thaliana RKS6 cDNA"

<400> SEQUENCE: 44
attgtttcct tcttttggga ttttctcctt ggatggaacc agctcaatta atgagatgag    60 atg aga atg ttc agc ttg cag aag atg gct atg gct ttt act ctc ttg   108
Met Arg Met Phe Ser Leu Gln Lys Met Ala Met Ala Phe Thr Leu Leu
  1               5                  10                  15 ttt ttt gcc tgt tta tgc tca ttt gtg tct cca gat gct caa ggg gat   156
Phe Phe Ala Cys Leu Cys Ser Phe Val Ser Pro Asp Ala Gln Gly Asp
              20                  25                  30 gca ctg ttt gcg ttg agg atc tcc tta cgt gca tta ccg aat cag cta   204
Ala Leu Phe Ala Leu Arg Ile Ser Leu Arg Ala Leu Pro Asn Gln Leu
          35                  40                  45 agt gac tgg aat cag aac caa gtt aat cct tgc act tgg tcc caa gtt   252
Ser Asp Trp Asn Gln Asn Gln Val Asn Pro Cys Thr Trp Ser Gln Val
     50                  55                  60 att tgt gat gac aaa aac ttt gtc act tct ctt aca ttg tca gat atg   300
Ile Cys Asp Asp Lys Asn Phe Val Thr Ser Leu Thr Leu Ser Asp Met
 65                  70                  75                  80 aac ttc tcg gga acc ttg tct tca aga gta gga atc cta gaa aat ctc   348
Asn Phe Ser Gly Thr Leu Ser Ser Arg Val Gly Ile Leu Glu Asn Leu
                 85                  90                  95
```

```
aag act ctt act tta aag gga aat gga att acg ggt gaa ata cca gaa    396
Lys Thr Leu Thr Leu Lys Gly Asn Gly Ile Thr Gly Glu Ile Pro Glu
            100                 105                 110 gac ttt gga aat ctg act agc ttg act agt ttg gat ttg gag gac aat    444
Asp Phe Gly Asn Leu Thr Ser Leu Thr Ser Leu Asp Leu Glu Asp Asn
        115                 120                 125 cag cta act ggt cgt ata cca tcc act atc ggt aat ctc aag aaa ctt    492
Gln Leu Thr Gly Arg Ile Pro Ser Thr Ile Gly Asn Leu Lys Lys Leu
    130                 135                 140 cag ttc ttg acc ttg agt agg aac aaa ctt aat ggg act att ccg gag    540
Gln Phe Leu Thr Leu Ser Arg Asn Lys Leu Asn Gly Thr Ile Pro Glu
145                 150                 155                 160 tca ctc act ggt ctt cca aac ctg tta aac ctg ctg ctt gat tcc aat    588
Ser Leu Thr Gly Leu Pro Asn Leu Leu Asn Leu Leu Leu Asp Ser Asn
                165                 170                 175 agt ctc agt ggt cag att cct caa agt ctg ttt gag atc cca aaa tat    636
Ser Leu Ser Gly Gln Ile Pro Gln Ser Leu Phe Glu Ile Pro Lys Tyr
            180                 185                 190 aat ttc acg tca aac aac ttg aat tgt ggc ggt cgt caa cct cac cct    684
Asn Phe Thr Ser Asn Asn Leu Asn Cys Gly Gly Arg Gln Pro His Pro
        195                 200                 205 tgt gta tcc gcg gtt gcc cat tca ggt gat tca agc aag cct aaa act    732
Cys Val Ser Ala Val Ala His Ser Gly Asp Ser Ser Lys Pro Lys Thr
    210                 215                 220 ggc att att gct gga gtt gtt gct gga gtt aca gtt gtt ctc ttt gga    780
Gly Ile Ile Ala Gly Val Val Ala Gly Val Thr Val Val Leu Phe Gly
225                 230                 235                 240 atc ttg ttg ttt ctg ttc tgc aag gat agg cat aaa gga tat aga cgt    828
Ile Leu Leu Phe Leu Phe Cys Lys Asp Arg His Lys Gly Tyr Arg Arg
                245                 250                 255 gat gtg ttt gtg gat gtt gca ggt gaa gtg gac agg aga att gca ttt    876
Asp Val Phe Val Asp Val Ala Gly Glu Val Asp Arg Arg Ile Ala Phe
            260                 265                 270 gga cag ttg aaa agg ttt gca tgg aga gag ctc cag tta gcg aca gat    924
Gly Gln Leu Lys Arg Phe Ala Trp Arg Glu Leu Gln Leu Ala Thr Asp
        275                 280                 285 aac ttc agc gaa aag aat gta ctt ggt caa gga ggc ttt ggg aaa gtt    972
Asn Phe Ser Glu Lys Asn Val Leu Gly Gln Gly Gly Phe Gly Lys Val
    290                 295                 300 tac aaa gga gtg ctt ccg gat aca ccc aaa gtt gct gtg aag aga ttg   1020
Tyr Lys Gly Val Leu Pro Asp Thr Pro Lys Val Ala Val Lys Arg Leu
305                 310                 315                 320 acg gat ttc gaa agt cct ggt gga gat gct gct ttc caa agg gaa gta   1068
Thr Asp Phe Glu Ser Pro Gly Gly Asp Ala Ala Phe Gln Arg Glu Val
                325                 330                 335 gag atg ata agt gta gct gtt cat agg aat cta ctc cgt ctt atc ggg   1116
Glu Met Ile Ser Val Ala Val His Arg Asn Leu Leu Arg Leu Ile Gly
            340                 345                 350 ttc tgc acc aca caa aca gaa cgc ctt ttg gtt tat ccc ttc atg cag   1164
Phe Cys Thr Thr Gln Thr Glu Arg Leu Leu Val Tyr Pro Phe Met Gln
        355                 360                 365 aat cta agt ctt gca cat cgt ctg aga gag atc aaa gca ggc gac ccg   1212
Asn Leu Ser Leu Ala His Arg Leu Arg Glu Ile Lys Ala Gly Asp Pro
    370                 375                 380 gtt cta gat tgg gag acg agg aaa cgg att gcc tta gga gca gcg cgt   1260
Val Leu Asp Trp Glu Thr Arg Lys Arg Ile Ala Leu Gly Ala Ala Arg
385                 390                 395                 400 ggt ttt gag tat ctt cat gaa cat tgc aat ccg aag atc ata cat cgt   1308
Gly Phe Glu Tyr Leu His Glu His Cys Asn Pro Lys Ile Ile His Arg
                405                 410                 415
```

```
gat gtg aaa gca gct aat gtg tta cta gat gaa gat ttt gaa gca gtg      1356
Asp Val Lys Ala Ala Asn Val Leu Leu Asp Glu Asp Phe Glu Ala Val
        420                 425                 430 gtt ggt gat ttt ggt tta gcc aag cta gta gat gtt aga agg act aat      1404
Val Gly Asp Phe Gly Leu Ala Lys Leu Val Asp Val Arg Arg Thr Asn
                435                 440                 445 gtg act act caa gtt cga gga aca atg ggt cac att gca cca gaa tat      1452
Val Thr Thr Gln Val Arg Gly Thr Met Gly His Ile Ala Pro Glu Tyr
450                 455                 460 tta tca aca ggg aaa tca tca gag aga acc gat gtt ttc ggg tat gga      1500
Leu Ser Thr Gly Lys Ser Ser Glu Arg Thr Asp Val Phe Gly Tyr Gly
465                 470                 475                 480 att atg ctt ctt gag ctt gtt aca gga caa cgc gca ata gac ttt tca      1548
Ile Met Leu Leu Glu Leu Val Thr Gly Gln Arg Ala Ile Asp Phe Ser
                485                 490                 495 cgt ttg gag gaa gaa gat gat gtc ttg tta ctt gac cac gtg aag aaa      1596
Arg Leu Glu Glu Glu Asp Asp Val Leu Leu Leu Asp His Val Lys Lys
            500                 505                 510 ctg gaa aga gag aag aga tta gga gca atc gta gat aag aat ttg gat      1644
Leu Glu Arg Glu Lys Arg Leu Gly Ala Ile Val Asp Lys Asn Leu Asp
        515                 520                 525 gga gag tat ata aaa gaa gaa gta gag atg atg ata caa gtg gct ttg      1692
Gly Glu Tyr Ile Lys Glu Glu Val Glu Met Met Ile Gln Val Ala Leu
    530                 535                 540 ctt tgt aca caa ggt tca cca gaa gac cga cca gtg atg tct gaa gtt      1740
Leu Cys Thr Gln Gly Ser Pro Glu Asp Arg Pro Val Met Ser Glu Val
545                 550                 555                 560 gtg agg atg tta gaa gga gaa ggg ctt gcg gag aga tgg gaa gag tgg      1788
Val Arg Met Leu Glu Gly Glu Gly Leu Ala Glu Arg Trp Glu Glu Trp
                565                 570                 575 caa aac gtg gaa gtc acg aga cgt cat gag ttt gaa cgg ttg cag agg      1836
Gln Asn Val Glu Val Thr Arg Arg His Glu Phe Glu Arg Leu Gln Arg
            580                 585                 590 aga ttt gat tgg ggt gaa gat tct atg cat aac caa gat gcc att gaa      1884
Arg Phe Asp Trp Gly Glu Asp Ser Met His Asn Gln Asp Ala Ile Glu
        595                 600                 605 tta tct ggt gga aga tgaccaaaaa catcaaacct t                          1920
Leu Ser Gly Gly Arg
    610

<210> SEQ ID NO 45
<211> LENGTH: 613
<212> TYPE: PRT
<213> ORGANISM: Arabidopsis thaliana

<400> SEQUENCE: 45

Met Arg Met Phe Ser Leu Gln Lys Met Ala Met Ala Phe Thr Leu Leu
  1               5                  10                  15

Phe Phe Ala Cys Leu Cys Ser Phe Val Ser Pro Asp Ala Gln Gly Asp
                20                  25                  30

Ala Leu Phe Ala Leu Arg Ile Ser Leu Arg Ala Leu Pro Asn Gln Leu
            35                  40                  45

Ser Asp Trp Asn Gln Asn Gln Val Asn Pro Cys Thr Trp Ser Gln Val
        50                  55                  60

Ile Cys Asp Asp Lys Asn Phe Val Thr Ser Leu Thr Leu Ser Asp Met
 65                  70                  75                  80

Asn Phe Ser Gly Thr Leu Ser Ser Arg Val Gly Ile Leu Glu Asn Leu
                85                  90                  95
```

```
Lys Thr Leu Thr Leu Lys Gly Asn Gly Ile Thr Gly Glu Ile Pro Glu
            100                 105                 110

Asp Phe Gly Asn Leu Thr Ser Leu Thr Ser Leu Asp Leu Glu Asp Asn
            115                 120                 125

Gln Leu Thr Gly Arg Ile Pro Ser Thr Ile Gly Asn Leu Lys Lys Leu
        130                 135                 140

Gln Phe Leu Thr Leu Ser Arg Asn Lys Leu Asn Gly Thr Ile Pro Glu
145                 150                 155                 160

Ser Leu Thr Gly Leu Pro Asn Leu Leu Asn Leu Leu Asp Ser Asn
                165                 170                 175

Ser Leu Ser Gly Gln Ile Pro Gln Ser Leu Phe Glu Ile Pro Lys Tyr
            180                 185                 190

Asn Phe Thr Ser Asn Asn Leu Asn Cys Gly Gly Arg Gln Pro His Pro
            195                 200                 205

Cys Val Ser Ala Val Ala His Ser Gly Asp Ser Ser Lys Pro Lys Thr
            210                 215                 220

Gly Ile Ile Ala Gly Val Val Ala Gly Val Thr Val Val Leu Phe Gly
225                 230                 235                 240

Ile Leu Leu Phe Leu Phe Cys Lys Asp Arg His Lys Gly Tyr Arg Arg
                245                 250                 255

Asp Val Phe Val Asp Val Ala Gly Glu Val Asp Arg Arg Ile Ala Phe
            260                 265                 270

Gly Gln Leu Lys Arg Phe Ala Trp Arg Glu Leu Gln Leu Ala Thr Asp
        275                 280                 285

Asn Phe Ser Glu Lys Asn Val Leu Gly Gln Gly Gly Phe Gly Lys Val
            290                 295                 300

Tyr Lys Gly Val Leu Pro Asp Thr Pro Lys Val Ala Val Lys Arg Leu
305                 310                 315                 320

Thr Asp Phe Glu Ser Pro Gly Gly Asp Ala Ala Phe Gln Arg Glu Val
                325                 330                 335

Glu Met Ile Ser Val Ala Val His Arg Asn Leu Leu Arg Leu Ile Gly
            340                 345                 350

Phe Cys Thr Thr Gln Thr Glu Arg Leu Leu Val Tyr Pro Phe Met Gln
            355                 360                 365

Asn Leu Ser Leu Ala His Arg Leu Arg Glu Ile Lys Ala Gly Asp Pro
            370                 375                 380

Val Leu Asp Trp Glu Thr Arg Lys Arg Ile Ala Leu Gly Ala Ala Arg
385                 390                 395                 400

Gly Phe Glu Tyr Leu His Glu His Cys Asn Pro Lys Ile Ile His Arg
                405                 410                 415

Asp Val Lys Ala Ala Asn Val Leu Leu Asp Glu Asp Phe Glu Ala Val
            420                 425                 430

Val Gly Asp Phe Gly Leu Ala Lys Leu Val Asp Val Arg Arg Thr Asn
            435                 440                 445

Val Thr Thr Gln Val Arg Gly Thr Met Gly His Ile Ala Pro Glu Tyr
        450                 455                 460

Leu Ser Thr Gly Lys Ser Ser Glu Arg Thr Asp Val Phe Gly Tyr Gly
465                 470                 475                 480

Ile Met Leu Leu Glu Leu Val Thr Gly Gln Arg Ala Ile Asp Phe Ser
                485                 490                 495

Arg Leu Glu Glu Glu Asp Asp Val Leu Leu Leu Asp His Val Lys Lys
            500                 505                 510

Leu Glu Arg Glu Lys Arg Leu Gly Ala Ile Val Asp Lys Asn Leu Asp
```

```
                515                 520                 525
Gly Glu Tyr Ile Lys Glu Val Glu Met Met Ile Gln Val Ala Leu
        530                 535                 540

Leu Cys Thr Gln Gly Ser Pro Glu Asp Arg Pro Val Met Ser Glu Val
545                 550                 555                 560

Val Arg Met Leu Glu Gly Gly Leu Ala Glu Arg Trp Glu Glu Trp
                565                 570                 575

Gln Asn Val Glu Val Thr Arg Arg His Glu Phe Glu Arg Leu Gln Arg
                580                 585                 590

Arg Phe Asp Trp Gly Asp Ser Met His Asn Gln Asp Ala Ile Glu
        595                 600                 605

Leu Ser Gly Gly Arg
        610

<210> SEQ ID NO 46
<211> LENGTH: 1949
<212> TYPE: DNA
<213> ORGANISM: Arabidopsis thaliana
<220> FEATURE:
<221> NAME/KEY: CDS
<222> LOCATION: (61)..(1944)
<223> OTHER INFORMATION: /note="Arabidopsis thaliana RKS8 cDNA"

<400> SEQUENCE: 46 gtttttttttt tttaccctc ttggaggatc tgggaggaga aatttgcttt ttttggtaa        60 atg ggg aga aaa aag ttt gaa gct ttt ggt ttt gtc tgc tta atc tca      108
Met Gly Arg Lys Lys Phe Glu Ala Phe Gly Phe Val Cys Leu Ile Ser
  1               5                  10                  15 ctg ctt ctt ctg ttt aat tcg tta tgg ctt gcc tct tct aac atg gaa      156
Leu Leu Leu Leu Phe Asn Ser Leu Trp Leu Ala Ser Ser Asn Met Glu
             20                  25                  30 ggt gat gca ctg cac agt ttg aga gct aat cta gtt gat cca aat aat      204
Gly Asp Ala Leu His Ser Leu Arg Ala Asn Leu Val Asp Pro Asn Asn
         35                  40                  45 gtc ttg caa agc tgg gat cct acg ctt gtt aat ccg tgt act tgg ttt      252
Val Leu Gln Ser Trp Asp Pro Thr Leu Val Asn Pro Cys Thr Trp Phe
     50                  55                  60 cac gta acg tgt aac aac gag aac agt gtt ata aga gtc gat ctt ggg      300
His Val Thr Cys Asn Asn Glu Asn Ser Val Ile Arg Val Asp Leu Gly
 65                  70                  75                  80 aat gca gac ttg tct ggt cag ttg gtt cct cag cta ggt cag ctc aag      348
Asn Ala Asp Leu Ser Gly Gln Leu Val Pro Gln Leu Gly Gln Leu Lys
                 85                  90                  95 aac ttg cag tac ttg gag ctt tat agt aat aac ata acc ggg ccg gtt      396
Asn Leu Gln Tyr Leu Glu Leu Tyr Ser Asn Asn Ile Thr Gly Pro Val
            100                 105                 110 cca agc gat ctt ggg aat ctg aca aac tta gtg agc ttg gat ctt tac      444
Pro Ser Asp Leu Gly Asn Leu Thr Asn Leu Val Ser Leu Asp Leu Tyr
        115                 120                 125 ttg aac agc ttc act ggt cca att cca gat tct cta gga aag cta ttc      492
Leu Asn Ser Phe Thr Gly Pro Ile Pro Asp Ser Leu Gly Lys Leu Phe
    130                 135                 140 aag ctt cgc ttt ctt cgg ctc aac aat aac agt ctc acc gga cca att      540
Lys Leu Arg Phe Leu Arg Leu Asn Asn Asn Ser Leu Thr Gly Pro Ile
145                 150                 155                 160 ccc atg tca ttg act aat atc atg acc ctt caa gtt ttg gat ctg tcg      588
Pro Met Ser Leu Thr Asn Ile Met Thr Leu Gln Val Leu Asp Leu Ser
                165                 170                 175 aac aac cga tta tcc gga tct gtt cct gat aat ggt tcc ttc tcg ctc      636
```

```
                Asn Asn Arg Leu Ser Gly Ser Val Pro Asp Asn Gly Ser Phe Ser Leu
                            180                 185                 190 ttc act ccc atc agt ttt gct aac aac ttg gat cta tgc ggc cca gtt        684
Phe Thr Pro Ile Ser Phe Ala Asn Asn Leu Asp Leu Cys Gly Pro Val
        195                 200                 205 act agc cgt cct tgt cct gga tct ccc ccg ttt tct cct cca cca cct        732
Thr Ser Arg Pro Cys Pro Gly Ser Pro Pro Phe Ser Pro Pro Pro Pro
        210                 215                 220 ttt ata cca cct ccc ata gtt cct aca cca ggt ggg tat agt gct act        780
Phe Ile Pro Pro Pro Ile Val Pro Thr Pro Gly Gly Tyr Ser Ala Thr
225                 230                 235                 240 gga gcc att gcg gga gga gtt gct gct ggt gct gct tta cta ttt gct        828
Gly Ala Ile Ala Gly Gly Val Ala Ala Gly Ala Ala Leu Leu Phe Ala
                245                 250                 255 gcc cct gct tta gct ttt gct tgg tgg cgt aga aga aaa cct caa gaa        876
Ala Pro Ala Leu Ala Phe Ala Trp Trp Arg Arg Arg Lys Pro Gln Glu
            260                 265                 270 ttc ttc ttt gat gtt cct gcc gaa gag gac cct gag gtt cac ttg ggg        924
Phe Phe Phe Asp Val Pro Ala Glu Glu Asp Pro Glu Val His Leu Gly
            275                 280                 285 cag ctt aag cgg ttc tct cta cgg gaa ctt caa gta gca act gat agc        972
Gln Leu Lys Arg Phe Ser Leu Arg Glu Leu Gln Val Ala Thr Asp Ser
        290                 295                 300 ttc agc aac aag aac att ttg ggc cga ggt ggg ttc gga aaa gtc tac       1020
Phe Ser Asn Lys Asn Ile Leu Gly Arg Gly Gly Phe Gly Lys Val Tyr
305                 310                 315                 320 aaa ggc cgt ctt gct gat gga aca ctt gtt gca gtc aaa cgg ctt aaa       1068
Lys Gly Arg Leu Ala Asp Gly Thr Leu Val Ala Val Lys Arg Leu Lys
                325                 330                 335 gaa gag cga acc cca ggt ggc gag ctc cag ttt cag aca gaa gtg gag       1116
Glu Glu Arg Thr Pro Gly Gly Glu Leu Gln Phe Gln Thr Glu Val Glu
            340                 345                 350 atg ata agc atg gcc gtt cac aga aat ctc ctc agg cta cgc ggt ttc       1164
Met Ile Ser Met Ala Val His Arg Asn Leu Leu Arg Leu Arg Gly Phe
        355                 360                 365 tgt atg acc cct acc gag aga ttg ctt gtt tat cct tac atg gct aat       1212
Cys Met Thr Pro Thr Glu Arg Leu Leu Val Tyr Pro Tyr Met Ala Asn
370                 375                 380 gga agt gtc gct tcc tgt ttg aga gaa cgt cca cca tca cag ttg cct       1260
Gly Ser Val Ala Ser Cys Leu Arg Glu Arg Pro Pro Ser Gln Leu Pro
385                 390                 395                 400 cta gcc tgg tca ata aga cag caa atc gcg cta gga tca gcg agg ggt       1308
Leu Ala Trp Ser Ile Arg Gln Gln Ile Ala Leu Gly Ser Ala Arg Gly
                405                 410                 415 ttg tct tat ctt cat gat cat tgc gac ccc aaa att att cac cgt gat       1356
Leu Ser Tyr Leu His Asp His Cys Asp Pro Lys Ile Ile His Arg Asp
            420                 425                 430 gtg aaa gct gct aat att ctg ttg gac gag gaa ttt gag gcg gtg gta       1404
Val Lys Ala Ala Asn Ile Leu Leu Asp Glu Glu Phe Glu Ala Val Val
        435                 440                 445 ggt gat ttc ggg tta gct aga ctt atg gac tat aaa gat act cat gtc       1452
Gly Asp Phe Gly Leu Ala Arg Leu Met Asp Tyr Lys Asp Thr His Val
450                 455                 460 aca acg gct gtg cgt ggg act att gga cac att gct cct gag tat ctc       1500
Thr Thr Ala Val Arg Gly Thr Ile Gly His Ile Ala Pro Glu Tyr Leu
465                 470                 475                 480 tca act gga aaa tct tca gag aaa act gat gtt ttt ggc tac ggg atc       1548
Ser Thr Gly Lys Ser Ser Glu Lys Thr Asp Val Phe Gly Tyr Gly Ile
                485                 490                 495
```

```
atg ctt ttg gaa ctg att aca ggt cag aga gct ttt gat ctt gca aga      1596
Met Leu Leu Glu Leu Ile Thr Gly Gln Arg Ala Phe Asp Leu Ala Arg
        500                 505                 510 ctg gcg aat gac gat gac gtt atg ctc cta gat tgg gtg aaa ggg ctt      1644
Leu Ala Asn Asp Asp Asp Val Met Leu Leu Asp Trp Val Lys Gly Leu
    515                 520                 525 ttg aag gag aag aag ctg gag atg ctt gtg gat cct gac ctg caa agc      1692
Leu Lys Glu Lys Lys Leu Glu Met Leu Val Asp Pro Asp Leu Gln Ser
530                 535                 540 aat tac aca gaa gca gaa gta gaa cag ctc ata caa gtg gct ctt ctc      1740
Asn Tyr Thr Glu Ala Glu Val Glu Gln Leu Ile Gln Val Ala Leu Leu
545                 550                 555                 560 tgc aca cag agc tca cct atg gaa cga cct aag atg tct gag gtt gtt      1788
Cys Thr Gln Ser Ser Pro Met Glu Arg Pro Lys Met Ser Glu Val Val
                565                 570                 575 cga atg ctt gaa ggt gac ggt tta gcg gag aaa tgg gac gag tgg cag      1836
Arg Met Leu Glu Gly Asp Gly Leu Ala Glu Lys Trp Asp Glu Trp Gln
            580                 585                 590 aaa gtg gaa gtt ctc agg caa gaa gtg gag ctc tct tct cac ccc acc      1884
Lys Val Glu Val Leu Arg Gln Glu Val Glu Leu Ser Ser His Pro Thr
        595                 600                 605 tct gac tgg atc ctt gat tcg act gat aat ctt cat gct atg gag ttg      1932
Ser Asp Trp Ile Leu Asp Ser Thr Asp Asn Leu His Ala Met Glu Leu
    610                 615                 620 tct ggt cca aga taaac                                                 1949
Ser Gly Pro Arg
625

<210> SEQ ID NO 47
<211> LENGTH: 628
<212> TYPE: PRT
<213> ORGANISM: Arabidopsis thaliana

<400> SEQUENCE: 47

Met Gly Arg Lys Lys Phe Glu Ala Phe Gly Phe Val Cys Leu Ile Ser
  1               5                  10                  15

Leu Leu Leu Leu Phe Asn Ser Leu Trp Leu Ala Ser Ser Asn Met Glu
             20                  25                  30

Gly Asp Ala Leu His Ser Leu Arg Ala Asn Leu Val Asp Pro Asn Asn
         35                  40                  45

Val Leu Gln Ser Trp Asp Pro Thr Leu Val Asn Pro Cys Thr Trp Phe
     50                  55                  60

His Val Thr Cys Asn Asn Glu Asn Ser Val Ile Arg Val Asp Leu Gly
 65                  70                  75                  80

Asn Ala Asp Leu Ser Gly Gln Leu Val Pro Gln Leu Gly Gln Leu Lys
                 85                  90                  95

Asn Leu Gln Tyr Leu Glu Leu Tyr Ser Asn Asn Ile Thr Gly Pro Val
            100                 105                 110

Pro Ser Asp Leu Gly Asn Leu Thr Asn Leu Val Ser Leu Asp Leu Tyr
        115                 120                 125

Leu Asn Ser Phe Thr Gly Pro Ile Pro Asp Ser Leu Gly Lys Leu Phe
    130                 135                 140

Lys Leu Arg Phe Leu Arg Leu Asn Asn Asn Ser Leu Thr Gly Pro Ile
145                 150                 155                 160

Pro Met Ser Leu Thr Asn Ile Met Thr Leu Gln Val Leu Asp Leu Ser
                165                 170                 175

Asn Asn Arg Leu Ser Gly Ser Val Pro Asp Asn Gly Ser Phe Ser Leu
            180                 185                 190
```

```
Phe Thr Pro Ile Ser Phe Ala Asn Asn Leu Asp Leu Cys Gly Pro Val
            195                 200                 205

Thr Ser Arg Pro Cys Pro Gly Ser Pro Pro Phe Ser Pro Pro Pro Pro
    210                 215                 220

Phe Ile Pro Pro Pro Ile Val Pro Thr Pro Gly Gly Tyr Ser Ala Thr
225                 230                 235                 240

Gly Ala Ile Ala Gly Gly Val Ala Ala Gly Ala Ala Leu Leu Phe Ala
            245                 250                 255

Ala Pro Ala Leu Ala Phe Ala Trp Trp Arg Arg Lys Pro Gln Glu
            260                 265                 270

Phe Phe Phe Asp Val Pro Ala Glu Glu Asp Pro Glu Val His Leu Gly
            275                 280                 285

Gln Leu Lys Arg Phe Ser Leu Arg Glu Leu Gln Val Ala Thr Asp Ser
            290                 295                 300

Phe Ser Asn Lys Asn Ile Leu Gly Arg Gly Gly Phe Gly Lys Val Tyr
305                 310                 315                 320

Lys Gly Arg Leu Ala Asp Gly Thr Leu Val Ala Val Lys Arg Leu Lys
            325                 330                 335

Glu Glu Arg Thr Pro Gly Gly Glu Leu Gln Phe Gln Thr Glu Val Glu
            340                 345                 350

Met Ile Ser Met Ala Val His Arg Asn Leu Leu Arg Leu Arg Gly Phe
            355                 360                 365

Cys Met Thr Pro Thr Glu Arg Leu Leu Val Tyr Pro Tyr Met Ala Asn
            370                 375                 380

Gly Ser Val Ala Ser Cys Leu Arg Glu Arg Pro Pro Ser Gln Leu Pro
385                 390                 395                 400

Leu Ala Trp Ser Ile Arg Gln Gln Ile Ala Leu Gly Ser Ala Arg Gly
            405                 410                 415

Leu Ser Tyr Leu His Asp His Cys Asp Pro Lys Ile Ile His Arg Asp
            420                 425                 430

Val Lys Ala Ala Asn Ile Leu Leu Asp Glu Glu Phe Glu Ala Val Val
            435                 440                 445

Gly Asp Phe Gly Leu Ala Arg Leu Met Asp Tyr Lys Asp Thr His Val
            450                 455                 460

Thr Thr Ala Val Arg Gly Thr Ile Gly His Ile Ala Pro Glu Tyr Leu
465                 470                 475                 480

Ser Thr Gly Lys Ser Ser Glu Lys Thr Asp Val Phe Gly Tyr Gly Ile
            485                 490                 495

Met Leu Leu Glu Leu Ile Thr Gly Gln Arg Ala Phe Asp Leu Ala Arg
            500                 505                 510

Leu Ala Asn Asp Asp Asp Val Met Leu Leu Asp Trp Val Lys Gly Leu
            515                 520                 525

Leu Lys Glu Lys Lys Leu Glu Met Leu Val Asp Pro Asp Leu Gln Ser
            530                 535                 540

Asn Tyr Thr Glu Ala Glu Val Glu Gln Leu Ile Gln Val Ala Leu Leu
545                 550                 555                 560

Cys Thr Gln Ser Ser Pro Met Glu Arg Pro Lys Met Ser Glu Val Val
            565                 570                 575

Arg Met Leu Glu Gly Asp Gly Leu Ala Glu Lys Trp Asp Glu Trp Gln
            580                 585                 590

Lys Val Glu Val Leu Arg Gln Glu Val Glu Leu Ser Ser His Pro Thr
            595                 600                 605
```

-continued

```
Ser Asp Trp Ile Leu Asp Ser Thr Asp Asn Leu His Ala Met Glu Leu
    610                 615                 620
Ser Gly Pro Arg
625

<210> SEQ ID NO 48
<211> LENGTH: 1920
<212> TYPE: DNA
<213> ORGANISM: Arabidopsis thaliana
<220> FEATURE:
<221> NAME/KEY: CDS
<222> LOCATION: (79)..(1851)
<223> OTHER INFORMATION: /note="Arabidopsis thaliana RKS10 cDNA"

<400> SEQUENCE: 48
atcaggggtt ttaacaatga tggattttct ctgatgaggg atagttctag ggtttgtttt        60
taatctcttg aggataaa atg gaa cga aga tta atg atc cct tgc ttc ttt       111
                   Met Glu Arg Arg Leu Met Ile Pro Cys Phe Phe
                    1               5                  10 tgg ttg att ctc gtt ttg gat ttg gtt ctc aga gtc tcg ggc aac gcc       159
Trp Leu Ile Leu Val Leu Asp Leu Val Leu Arg Val Ser Gly Asn Ala
         15                  20                  25 gaa ggt gat gct cta agt gca ctg aaa aac agt tta gcc gac cct aat       207
Glu Gly Asp Ala Leu Ser Ala Leu Lys Asn Ser Leu Ala Asp Pro Asn
     30                  35                  40 aag gtg ctt caa agt tgg gat gct act ctt gtt act cca tgt aca tgg       255
Lys Val Leu Gln Ser Trp Asp Ala Thr Leu Val Thr Pro Cys Thr Trp
 45                  50                  55 ttt cat gtt act tgc aat agc gac aat agt gtt aca cgt gtt gac ctt       303
Phe His Val Thr Cys Asn Ser Asp Asn Ser Val Thr Arg Val Asp Leu
             60                  65                  70                  75 ggg aat gca aat cta tct gga cag ctc gta atg caa ctt ggt cag ctt       351
Gly Asn Ala Asn Leu Ser Gly Gln Leu Val Met Gln Leu Gly Gln Leu
                 80                  85                  90 cca aac ttg cag tac ttg gag ctt tat agc aat aac att act ggg aca       399
Pro Asn Leu Gln Tyr Leu Glu Leu Tyr Ser Asn Asn Ile Thr Gly Thr
             95                 100                 105 atc cca gaa cag ctt gga aat ctg acg gaa ttg gtg agc ttg gat ctt       447
Ile Pro Glu Gln Leu Gly Asn Leu Thr Glu Leu Val Ser Leu Asp Leu
        110                 115                 120 tac ttg aac aat tta agc ggg cct att cca tca act ctc ggc cga ctt       495
Tyr Leu Asn Asn Leu Ser Gly Pro Ile Pro Ser Thr Leu Gly Arg Leu
    125                 130                 135 aag aaa ctc cgt ttc ttg cgt ctt aat aac aat agc tta tct gga gaa       543
Lys Lys Leu Arg Phe Leu Arg Leu Asn Asn Asn Ser Leu Ser Gly Glu
140                 145                 150                 155 att cca agg tct ttg act gct gtc ctg acg cta caa gtt ctt ttt gcc       591
Ile Pro Arg Ser Leu Thr Ala Val Leu Thr Leu Gln Val Leu Phe Ala
                160                 165                 170 aac acc aag ttg act ccc ctt cct gca tct cca ccg cct cct atc tct       639
Asn Thr Lys Leu Thr Pro Leu Pro Ala Ser Pro Pro Pro Pro Ile Ser
            175                 180                 185 cct aca ccg cca tca cct gca ggg agt aat aga att act gga gcg att       687
Pro Thr Pro Pro Ser Pro Ala Gly Ser Asn Arg Ile Thr Gly Ala Ile
        190                 195                 200 gcg gga gga gtt gct gca ggt gct gca ctt cta ttt gct gtt ccg gcc       735
Ala Gly Gly Val Ala Ala Gly Ala Ala Leu Leu Phe Ala Val Pro Ala
    205                 210                 215 att gca cta gct tgg tgg cga agg aaa aag ccg cag gac cac ttc ttt       783
Ile Ala Leu Ala Trp Trp Arg Arg Lys Lys Pro Gln Asp His Phe Phe
220                 225                 230
```

```
              220             225             230             235
gat gta cca gct gaa gag gac cca gaa gtt cat tta gga caa ctg aag    831
Asp Val Pro Ala Glu Glu Asp Pro Glu Val His Leu Gly Gln Leu Lys
                240             245             250 agg ttt tca ttg cgt gaa cta caa gtt gct tcg gat aat ttt agc aac    879
Arg Phe Ser Leu Arg Glu Leu Gln Val Ala Ser Asp Asn Phe Ser Asn
            255             260             265 aag aac ata ttg ggt aga ggt ggt ttt ggt aaa gtt tat aaa gga cgg    927
Lys Asn Ile Leu Gly Arg Gly Gly Phe Gly Lys Val Tyr Lys Gly Arg
        270             275             280 tta gct gat ggt act tta gtg gcc gtt aaa agg cta aaa gag gag cgc    975
Leu Ala Asp Gly Thr Leu Val Ala Val Lys Arg Leu Lys Glu Glu Arg
    285             290             295 acc caa ggt ggc gaa ctg cag ttc cag aca gag gtt gag atg att agt   1023
Thr Gln Gly Gly Glu Leu Gln Phe Gln Thr Glu Val Glu Met Ile Ser
300             305             310             315 atg gcg gtt cac aga aac ttg ctt cgg ctt cgt gga ttt tgc atg act   1071
Met Ala Val His Arg Asn Leu Leu Arg Leu Arg Gly Phe Cys Met Thr
                320             325             330 cca acc gaa aga ttg ctt gtt tat ccc tac atg gct aat gga agt gtt   1119
Pro Thr Glu Arg Leu Leu Val Tyr Pro Tyr Met Ala Asn Gly Ser Val
            335             340             345 gcc tcc tgt tta aga gaa cgt ccc gag tcc cag cca cca ctt gat tgg   1167
Ala Ser Cys Leu Arg Glu Arg Pro Glu Ser Gln Pro Pro Leu Asp Trp
        350             355             360 cca aag aga cag cgt att gcg ttg gga tct gca aga ggg ctt gcg tat   1215
Pro Lys Arg Gln Arg Ile Ala Leu Gly Ser Ala Arg Gly Leu Ala Tyr
    365             370             375 tta cat gat cat tgc gac cca aag att att cat cga gat gtg aaa gct   1263
Leu His Asp His Cys Asp Pro Lys Ile Ile His Arg Asp Val Lys Ala
380             385             390             395 gca aat att ttg ttg gat gaa gag ttt gaa gcc gtg gtt ggg gat ttt   1311
Ala Asn Ile Leu Leu Asp Glu Glu Phe Glu Ala Val Val Gly Asp Phe
                400             405             410 gga ctt gca aaa ctc atg gac tac aaa gac aca cat gtg aca acc gca   1359
Gly Leu Ala Lys Leu Met Asp Tyr Lys Asp Thr His Val Thr Thr Ala
            415             420             425 gtg cgt ggg aca att ggt cat ata gcc cct gag tac ctt tcc act gga   1407
Val Arg Gly Thr Ile Gly His Ile Ala Pro Glu Tyr Leu Ser Thr Gly
        430             435             440 aaa tca tca gag aaa acc gat gtc ttt ggg tat gga gtc atg ctt ctt   1455
Lys Ser Ser Glu Lys Thr Asp Val Phe Gly Tyr Gly Val Met Leu Leu
    445             450             455 gag ctt atc act gga caa agg gct ttt gat ctt gct cgc ctc gcg aat   1503
Glu Leu Ile Thr Gly Gln Arg Ala Phe Asp Leu Ala Arg Leu Ala Asn
460             465             470             475 gat gat gat gtc atg tta cta gac tgg gtg aaa ggg ttg tta aaa gag   1551
Asp Asp Asp Val Met Leu Leu Asp Trp Val Lys Gly Leu Leu Lys Glu
                480             485             490 aag aaa ttg gaa gca cta gta gat gtt gat ctt cag ggt aat tac aaa   1599
Lys Lys Leu Glu Ala Leu Val Asp Val Asp Leu Gln Gly Asn Tyr Lys
            495             500             505 gac gaa gaa gtg gag cag cta atc caa gtg gct tta ctc tgc act cag   1647
Asp Glu Glu Val Glu Gln Leu Ile Gln Val Ala Leu Leu Cys Thr Gln
        510             515             520 agt tca cca atg gaa aga ccc aaa atg tct gaa gtt gta aga atg ctt   1695
Ser Ser Pro Met Glu Arg Pro Lys Met Ser Glu Val Val Arg Met Leu
    525             530             535 gaa gga gat ggt tta gct gag aga tgg gaa gag tgg caa aag gag gaa   1743
```

```
Glu Gly Asp Gly Leu Ala Glu Arg Trp Glu Glu Trp Gln Lys Glu Glu
540                 545                 550                 555 atg ttc aga caa gat ttc aac tac cca acc cac cat cca gcc gtg tct      1791
Met Phe Arg Gln Asp Phe Asn Tyr Pro Thr His His Pro Ala Val Ser
                560                 565                 570 ggc tgg atc att ggc gat tcc act tcc cag atc gaa aac gaa tac ccc      1839
Gly Trp Ile Ile Gly Asp Ser Thr Ser Gln Ile Glu Asn Glu Tyr Pro
            575                 580                 585 tcg ggt cca aga taagattcga aacacgaatg ttttttctgt attttgtttt          1891
Ser Gly Pro Arg
        590 tctctgtatt tattgagggt tttagcttc                                      1920

<210> SEQ ID NO 49
<211> LENGTH: 591
<212> TYPE: PRT
<213> ORGANISM: Arabidopsis thaliana

<400> SEQUENCE: 49

Met Glu Arg Arg Leu Met Ile Pro Cys Phe Phe Trp Leu Ile Leu Val
 1                5                  10                  15

Leu Asp Leu Val Leu Arg Val Ser Gly Asn Ala Glu Gly Asp Ala Leu
                20                  25                  30

Ser Ala Leu Lys Asn Ser Leu Ala Asp Pro Asn Lys Val Leu Gln Ser
            35                  40                  45

Trp Asp Ala Thr Leu Val Thr Pro Cys Thr Trp Phe His Val Thr Cys
        50                  55                  60

Asn Ser Asp Asn Ser Val Thr Arg Val Asp Leu Gly Asn Ala Asn Leu
65                  70                  75                  80

Ser Gly Gln Leu Val Met Gln Leu Gly Gln Leu Pro Asn Leu Gln Tyr
                85                  90                  95

Leu Glu Leu Tyr Ser Asn Asn Ile Thr Gly Thr Ile Pro Glu Gln Leu
            100                 105                 110

Gly Asn Leu Thr Glu Leu Val Ser Leu Asp Leu Tyr Leu Asn Asn Leu
        115                 120                 125

Ser Gly Pro Ile Pro Ser Thr Leu Gly Arg Leu Lys Lys Leu Arg Phe
130                 135                 140

Leu Arg Leu Asn Asn Ser Leu Ser Gly Glu Ile Pro Arg Ser Leu
145                 150                 155                 160

Thr Ala Val Leu Thr Leu Gln Val Leu Phe Ala Asn Thr Lys Leu Thr
                165                 170                 175

Pro Leu Pro Ala Ser Pro Pro Pro Ile Ser Pro Thr Pro Pro Ser
            180                 185                 190

Pro Ala Gly Ser Asn Arg Ile Thr Gly Ala Ile Ala Gly Gly Val Ala
        195                 200                 205

Ala Gly Ala Ala Leu Leu Phe Ala Val Pro Ala Ile Ala Leu Ala Trp
210                 215                 220

Trp Arg Arg Lys Lys Pro Gln Asp His Phe Phe Asp Val Pro Ala Glu
225                 230                 235                 240

Glu Asp Pro Glu Val His Leu Gly Gln Leu Lys Arg Phe Ser Leu Arg
                245                 250                 255

Glu Leu Gln Val Ala Ser Asp Asn Phe Ser Asn Lys Asn Ile Leu Gly
            260                 265                 270

Arg Gly Gly Phe Gly Lys Val Tyr Lys Gly Arg Leu Ala Asp Gly Thr
        275                 280                 285
```

```
Leu Val Ala Val Lys Arg Leu Lys Glu Glu Arg Thr Gln Gly Gly Glu
    290                 295                 300

Leu Gln Phe Gln Thr Glu Val Glu Met Ile Ser Met Ala Val His Arg
305                 310                 315                 320

Asn Leu Leu Arg Leu Arg Gly Phe Cys Met Thr Pro Thr Glu Arg Leu
                325                 330                 335

Leu Val Tyr Pro Tyr Met Ala Asn Gly Ser Val Ala Ser Cys Leu Arg
            340                 345                 350

Glu Arg Pro Glu Ser Gln Pro Pro Leu Asp Trp Pro Lys Arg Gln Arg
        355                 360                 365

Ile Ala Leu Gly Ser Ala Arg Gly Leu Ala Tyr Leu His Asp His Cys
370                 375                 380

Asp Pro Lys Ile Ile His Arg Asp Val Lys Ala Ala Asn Ile Leu Leu
385                 390                 395                 400

Asp Glu Glu Phe Glu Ala Val Val Gly Asp Phe Gly Leu Ala Lys Leu
                405                 410                 415

Met Asp Tyr Lys Asp Thr His Val Thr Thr Ala Val Arg Gly Thr Ile
            420                 425                 430

Gly His Ile Ala Pro Glu Tyr Leu Ser Thr Gly Lys Ser Ser Glu Lys
        435                 440                 445

Thr Asp Val Phe Gly Tyr Gly Val Met Leu Leu Glu Leu Ile Thr Gly
450                 455                 460

Gln Arg Ala Phe Asp Leu Ala Arg Leu Ala Asn Asp Asp Val Met
465                 470                 475                 480

Leu Leu Asp Trp Val Lys Gly Leu Leu Lys Glu Lys Lys Leu Glu Ala
                485                 490                 495

Leu Val Asp Val Asp Leu Gln Gly Asn Tyr Lys Asp Glu Val Glu
            500                 505                 510

Gln Leu Ile Gln Val Ala Leu Leu Cys Thr Gln Ser Ser Pro Met Glu
        515                 520                 525

Arg Pro Lys Met Ser Glu Val Val Arg Met Leu Glu Gly Asp Gly Leu
530                 535                 540

Ala Glu Arg Trp Glu Glu Trp Gln Lys Glu Glu Met Phe Arg Gln Asp
545                 550                 555                 560

Phe Asn Tyr Pro Thr His His Pro Ala Val Ser Gly Trp Ile Ile Gly
                565                 570                 575

Asp Ser Thr Ser Gln Ile Glu Asn Glu Tyr Pro Ser Gly Pro Arg
            580                 585                 590

<210> SEQ ID NO 50
<211> LENGTH: 1779
<212> TYPE: DNA
<213> ORGANISM: Arabidopsis thaliana
<220> FEATURE:
<221> NAME/KEY: CDS
<222> LOCATION: (29)..(1747)
<223> OTHER INFORMATION: /note="Arabidopsis thaliana RKS11 cDNA"

<400> SEQUENCE: 50
tgttaacctc tcgtaactaa aatcttcc atg aag att caa att cat ctc ctt      52
                                Met Lys Ile Gln Ile His Leu Leu
                                 1               5 tac tcg ttc ttg ttc ctc tgt ttc tct act ctc act cta tct tct gag   100
Tyr Ser Phe Leu Phe Leu Cys Phe Ser Thr Leu Thr Leu Ser Ser Glu
         10                  15                  20 ccc aga aac cct gaa gtt gag gcg ttg ata agt ata agg aac aat ttg   148
```

```
Pro Arg Asn Pro Glu Val Glu Ala Leu Ile Ser Ile Arg Asn Asn Leu
 25                  30                  35                  40 cat gat cct cat gga gct ttg aac aat tgg gac gag ttt tca gtt gat    196
His Asp Pro His Gly Ala Leu Asn Asn Trp Asp Glu Phe Ser Val Asp
                 45                  50                  55 cct tgt agc tgg gct atg atc act tgc tct ccc gac aac ctc gtc att    244
Pro Cys Ser Trp Ala Met Ile Thr Cys Ser Pro Asp Asn Leu Val Ile
             60                  65                  70 gga ctg tca ttg caa aat aac aac atc tcc ggc aaa att cca ccg gag    292
Gly Leu Ser Leu Gln Asn Asn Asn Ile Ser Gly Lys Ile Pro Pro Glu
         75                  80                  85 ctc ggt ttt cta ccc aaa tta caa acc ttg gat ctt tcc aac aac cga    340
Leu Gly Phe Leu Pro Lys Leu Gln Thr Leu Asp Leu Ser Asn Asn Arg
     90                  95                 100 ttc tcc ggt gac atc cct gtt tcc atc gac cag cta agc agc ctt caa    388
Phe Ser Gly Asp Ile Pro Val Ser Ile Asp Gln Leu Ser Ser Leu Gln
105                 110                 115                 120 tat ctg aga ctc aac aac aac tct ttg tct ggg ccc ttc cct gct tct    436
Tyr Leu Arg Leu Asn Asn Asn Ser Leu Ser Gly Pro Phe Pro Ala Ser
                125                 130                 135 ttg tcc caa att cct cac ctc tcc ttc ttg gac ttg tct tac aac aat    484
Leu Ser Gln Ile Pro His Leu Ser Phe Leu Asp Leu Ser Tyr Asn Asn
            140                 145                 150 ctc agt ggc cct gtt cct aaa ttc cca gca agg act ttc aac gtt gct    532
Leu Ser Gly Pro Val Pro Lys Phe Pro Ala Arg Thr Phe Asn Val Ala
        155                 160                 165 ggt aat cct ttg att tgt aga agc aac cca cct gag att tgt tct gga    580
Gly Asn Pro Leu Ile Cys Arg Ser Asn Pro Pro Glu Ile Cys Ser Gly
170                 175                 180 tca atc aat gca agt cca ctt tct gtt tct ttg agc tct tca tca gca    628
Ser Ile Asn Ala Ser Pro Leu Ser Val Ser Leu Ser Ser Ser Ser Ala
185                 190                 195                 200 gat aaa caa gag gaa ggg ctt caa gga ctt ggg aat cta aga agc ttc    676
Asp Lys Gln Glu Glu Gly Leu Gln Gly Leu Gly Asn Leu Arg Ser Phe
                205                 210                 215 aca ttc aga gaa ctc cat gtt tat aca gat ggt ttc agt tcc aag aac    724
Thr Phe Arg Glu Leu His Val Tyr Thr Asp Gly Phe Ser Ser Lys Asn
            220                 225                 230 att ctc ggc gct ggt gga ttc ggt aat gtg tac aga ggc aag ctt gga    772
Ile Leu Gly Ala Gly Gly Phe Gly Asn Val Tyr Arg Gly Lys Leu Gly
        235                 240                 245 gat ggg aca atg gtg gca gtg aaa cgg ttg aag gat att aat gga acc    820
Asp Gly Thr Met Val Ala Val Lys Arg Leu Lys Asp Ile Asn Gly Thr
250                 255                 260 tca ggg gat tca cag ttt cgt atg gag cta gag atg att agc tta gct    868
Ser Gly Asp Ser Gln Phe Arg Met Glu Leu Glu Met Ile Ser Leu Ala
265                 270                 275                 280 gtt cat aag aat ctg ctt cgg tta att ggt tat tgc gca act tct ggt    916
Val His Lys Asn Leu Leu Arg Leu Ile Gly Tyr Cys Ala Thr Ser Gly
                285                 290                 295 gaa agg ctt ctt gtt tac cct tac atg cct aat gga agc gtc gcc tct    964
Glu Arg Leu Leu Val Tyr Pro Tyr Met Pro Asn Gly Ser Val Ala Ser
            300                 305                 310 aag ctt aaa tct aaa ccg gca ttg gac tgg aac atg agg aag agg ata   1012
Lys Leu Lys Ser Lys Pro Ala Leu Asp Trp Asn Met Arg Lys Arg Ile
        315                 320                 325 gca att ggt gca gcg aga ggt ttg ttg tat cta cat gag caa tgt gat   1060
Ala Ile Gly Ala Ala Arg Gly Leu Leu Tyr Leu His Glu Gln Cys Asp
330                 335                 340
```

```
ccc aag atc att cat aga gat gta aag gca gct aat att ctc tta gac    1108
Pro Lys Ile Ile His Arg Asp Val Lys Ala Ala Asn Ile Leu Leu Asp
345                 350                 355                 360 gag tgc ttt gaa gct gtt gtt ggt gac ttt gga ctc gca aag ctc ctt    1156
Glu Cys Phe Glu Ala Val Val Gly Asp Phe Gly Leu Ala Lys Leu Leu
            365                 370                 375 aac cat gcg gat tct cat gtc aca act gcg gtc cgt ggt acg gtt ggc    1204
Asn His Ala Asp Ser His Val Thr Thr Ala Val Arg Gly Thr Val Gly
        380                 385                 390 cac att gca cct gaa tat ctc tcc act ggt cag tct tct gag aaa acc    1252
His Ile Ala Pro Glu Tyr Leu Ser Thr Gly Gln Ser Ser Glu Lys Thr
    395                 400                 405 gat gtg ttt ggg ttc ggt ata cta ttg ctc gag ctc ata acc gga ctg    1300
Asp Val Phe Gly Phe Gly Ile Leu Leu Leu Glu Leu Ile Thr Gly Leu
410                 415                 420 aga gct ctt gag ttt ggt aaa acc gtt agc cag aaa gga gct atg ctt    1348
Arg Ala Leu Glu Phe Gly Lys Thr Val Ser Gln Lys Gly Ala Met Leu
425                 430                 435                 440 gaa tgg gtg agg aaa tta cat gaa gag atg aaa gta gag gaa cta ttg    1396
Glu Trp Val Arg Lys Leu His Glu Glu Met Lys Val Glu Glu Leu Leu
            445                 450                 455 gat cga gaa ctc gga act aac tac gat aag att gaa gtt gga gag atg    1444
Asp Arg Glu Leu Gly Thr Asn Tyr Asp Lys Ile Glu Val Gly Glu Met
        460                 465                 470 ttg caa gtg gct ttg cta tgc aca caa tat ctg cca gct cat cgt cct    1492
Leu Gln Val Ala Leu Leu Cys Thr Gln Tyr Leu Pro Ala His Arg Pro
    475                 480                 485 aaa atg tct gaa gtt gtt ttg atg ctt gaa ggc gat gga tta gcc gag    1540
Lys Met Ser Glu Val Val Leu Met Leu Glu Gly Asp Gly Leu Ala Glu
490                 495                 500 aga tgg gct gct tcg cat aac cat tca cat ttc tac cat gcc aat atc    1588
Arg Trp Ala Ala Ser His Asn His Ser His Phe Tyr His Ala Asn Ile
505                 510                 515                 520 tct ttc aag aca atc tct tct ctg tct act act tct gtc tca agg ctt    1636
Ser Phe Lys Thr Ile Ser Ser Leu Ser Thr Thr Ser Val Ser Arg Leu
            525                 530                 535 gac gca cat tgc aat gat cca act tat caa atg ttt gga tct tcg gct    1684
Asp Ala His Cys Asn Asp Pro Thr Tyr Gln Met Phe Gly Ser Ser Ala
        540                 545                 550 ttc gat gat gac gat gat cat cag cct tta gat tcc ttt gcc atg gaa    1732
Phe Asp Asp Asp Asp Asp His Gln Pro Leu Asp Ser Phe Ala Met Glu
    555                 560                 565 cta tcc ggt cca aga taacacaatg aaaaaaaaaa aaaaaaaaaa aa           1779
Leu Ser Gly Pro Arg
    570

<210> SEQ ID NO 51
<211> LENGTH: 573
<212> TYPE: PRT
<213> ORGANISM: Arabidopsis thaliana

<400> SEQUENCE: 51

Met Lys Ile Gln Ile His Leu Leu Tyr Ser Phe Leu Phe Leu Cys Phe
1               5                   10                  15

Ser Thr Leu Thr Leu Ser Ser Glu Pro Arg Asn Pro Glu Val Glu Ala
            20                  25                  30

Leu Ile Ser Ile Arg Asn Asn Leu His Asp Pro His Gly Ala Leu Asn
        35                  40                  45

Asn Trp Asp Glu Phe Ser Val Asp Pro Cys Ser Trp Ala Met Ile Thr
    50                  55                  60
```

```
Cys Ser Pro Asp Asn Leu Val Ile Gly Leu Ser Leu Gln Asn Asn Asn
 65                  70                  75                  80

Ile Ser Gly Lys Ile Pro Pro Glu Leu Gly Phe Leu Pro Lys Leu Gln
             85                  90                  95

Thr Leu Asp Leu Ser Asn Asn Arg Phe Ser Gly Asp Ile Pro Val Ser
        100                 105                 110

Ile Asp Gln Leu Ser Ser Leu Gln Tyr Leu Arg Leu Asn Asn Asn Ser
        115                 120                 125

Leu Ser Gly Pro Phe Pro Ala Ser Leu Ser Gln Ile Pro His Leu Ser
    130                 135                 140

Phe Leu Asp Leu Ser Tyr Asn Asn Leu Ser Gly Pro Val Pro Lys Phe
145                 150                 155                 160

Pro Ala Arg Thr Phe Asn Val Ala Gly Asn Pro Leu Ile Cys Arg Ser
                165                 170                 175

Asn Pro Pro Glu Ile Cys Ser Gly Ser Ile Asn Ala Ser Pro Leu Ser
            180                 185                 190

Val Ser Leu Ser Ser Ser Ala Asp Lys Gln Glu Glu Gly Leu Gln
        195                 200                 205

Gly Leu Gly Asn Leu Arg Ser Phe Thr Phe Arg Glu Leu His Val Tyr
        210                 215                 220

Thr Asp Gly Phe Ser Ser Lys Asn Ile Leu Gly Ala Gly Gly Phe Gly
225                 230                 235                 240

Asn Val Tyr Arg Gly Lys Leu Gly Asp Gly Thr Met Val Ala Val Lys
                245                 250                 255

Arg Leu Lys Asp Ile Asn Gly Thr Ser Gly Asp Ser Gln Phe Arg Met
            260                 265                 270

Glu Leu Glu Met Ile Ser Leu Ala Val His Lys Asn Leu Leu Arg Leu
        275                 280                 285

Ile Gly Tyr Cys Ala Thr Ser Gly Glu Arg Leu Leu Val Tyr Pro Tyr
        290                 295                 300

Met Pro Asn Gly Ser Val Ala Ser Lys Leu Lys Ser Lys Pro Ala Leu
305                 310                 315                 320

Asp Trp Asn Met Arg Lys Arg Ile Ala Ile Gly Ala Ala Arg Gly Leu
                325                 330                 335

Leu Tyr Leu His Glu Gln Cys Asp Pro Lys Ile Ile His Arg Asp Val
            340                 345                 350

Lys Ala Ala Asn Ile Leu Leu Asp Glu Cys Phe Glu Ala Val Val Gly
        355                 360                 365

Asp Phe Gly Leu Ala Lys Leu Leu Asn His Ala Asp Ser His Val Thr
    370                 375                 380

Thr Ala Val Arg Gly Thr Val Gly His Ile Ala Pro Glu Tyr Leu Ser
385                 390                 395                 400

Thr Gly Gln Ser Ser Glu Lys Thr Asp Val Phe Gly Phe Gly Ile Leu
                405                 410                 415

Leu Leu Glu Leu Ile Thr Gly Leu Arg Ala Leu Glu Phe Gly Lys Thr
            420                 425                 430

Val Ser Gln Lys Gly Ala Met Leu Glu Trp Val Arg Lys Leu His Glu
        435                 440                 445

Glu Met Lys Val Glu Glu Leu Asp Arg Glu Leu Gly Thr Asn Tyr
        450                 455                 460

Asp Lys Ile Glu Val Gly Glu Met Leu Gln Val Ala Leu Leu Cys Thr
465                 470                 475                 480
```

```
Gln Tyr Leu Pro Ala His Arg Pro Lys Met Ser Glu Val Val Leu Met
                485                 490                 495

Leu Glu Gly Asp Gly Leu Ala Glu Arg Trp Ala Ala Ser His Asn His
            500                 505                 510

Ser His Phe Tyr His Ala Asn Ile Ser Phe Lys Thr Ile Ser Ser Leu
        515                 520                 525

Ser Thr Thr Ser Val Ser Arg Leu Asp Ala His Cys Asn Asp Pro Thr
    530                 535                 540

Tyr Gln Met Phe Gly Ser Ser Ala Phe Asp Asp Asp Asp His Gln
545                 550                 555                 560

Pro Leu Asp Ser Phe Ala Met Glu Leu Ser Gly Pro Arg
                565                 570

<210> SEQ ID NO 52
<211> LENGTH: 1925
<212> TYPE: DNA
<213> ORGANISM: Arabidopsis thaliana
<220> FEATURE:
<221> NAME/KEY: CDS
<222> LOCATION: (61)..(1791)
<223> OTHER INFORMATION: /note="Arabidopsis thaliana RKS12 cDNA"

<400> SEQUENCE: 52
tttaaaaacc ttgctagttc tcaattctca tgactttgct tttagtctta gaagtggaaa      60 atg gaa cat gga tca tcc cgt ggc ttt att tgg ctg att cta ttt ctc      108
Met Glu His Gly Ser Ser Arg Gly Phe Ile Trp Leu Ile Leu Phe Leu
 1               5                  10                  15 gat ttt gtt tcc aga gtc acc gga aaa aca caa gtt gat gct ctc att      156
Asp Phe Val Ser Arg Val Thr Gly Lys Thr Gln Val Asp Ala Leu Ile
             20                  25                  30 gct cta aga agc agt tta tca tca ggt gac cat aca aac aat ata ctc      204
Ala Leu Arg Ser Ser Leu Ser Ser Gly Asp His Thr Asn Asn Ile Leu
         35                  40                  45 caa agc tgg aat gcc act cac gtt act cca tgt tca tgg ttt cat gtt      252
Gln Ser Trp Asn Ala Thr His Val Thr Pro Cys Ser Trp Phe His Val
     50                  55                  60 act tgc aat act gaa aac agt gtt act cgt ctg gaa ctt ttt aac aat      300
Thr Cys Asn Thr Glu Asn Ser Val Thr Arg Leu Glu Leu Phe Asn Asn
 65                  70                  75                  80 aat att act ggg gag ata cct gag gag ctt ggc gac ttg atg gaa cta      348
Asn Ile Thr Gly Glu Ile Pro Glu Glu Leu Gly Asp Leu Met Glu Leu
                 85                  90                  95 gta agc ttg gac ctt ttt gca aac aac ata agc ggt ccc atc cct tcc      396
Val Ser Leu Asp Leu Phe Ala Asn Asn Ile Ser Gly Pro Ile Pro Ser
            100                 105                 110 tct ctt ggc aaa cta gga aaa ctc cgc ttc ttg cgt ctt tat aac aac      444
Ser Leu Gly Lys Leu Gly Lys Leu Arg Phe Leu Arg Leu Tyr Asn Asn
        115                 120                 125 agc tta tct gga gaa att cca agg tct ttg act gct ctg ccg ctg gat      492
Ser Leu Ser Gly Glu Ile Pro Arg Ser Leu Thr Ala Leu Pro Leu Asp
    130                 135                 140 gtt ctt gat atc tca aac aat cgg ctc agt gga gat att cct gtt aat      540
Val Leu Asp Ile Ser Asn Asn Arg Leu Ser Gly Asp Ile Pro Val Asn
145                 150                 155                 160 ggt tcc ttt tcg cag ttc act tct atg agt ttt gcc aat aat aaa tta      588
Gly Ser Phe Ser Gln Phe Thr Ser Met Ser Phe Ala Asn Asn Lys Leu
                165                 170                 175 agg ccg cga cct gca tct cct tca cca tca cct tca gga acg tct gca      636
Arg Pro Arg Pro Ala Ser Pro Ser Pro Ser Pro Ser Gly Thr Ser Ala
            180                 185                 190
```

-continued

| | |
|---|---|
| gca ata gta gtg gga gtt gct gcg ggt gca gca ctt cta ttt gcg ctt<br>Ala Ile Val Val Gly Val Ala Ala Gly Ala Ala Leu Leu Phe Ala Leu<br>      195                  200                205 | 684 |
| gct tgg tgg ctg aga aga aaa ctg cag ggt cac ttt ctt gat gta cct<br>Ala Trp Trp Leu Arg Arg Lys Leu Gln Gly His Phe Leu Asp Val Pro<br>210                  215                  220 | 732 |
| gct gaa gaa gac cca gag gtt tat tta gga caa ttt aaa agg ttc tcc<br>Ala Glu Glu Asp Pro Glu Val Tyr Leu Gly Gln Phe Lys Arg Phe Ser<br>225                  230                235              240 | 780 |
| ttg cgt gaa ctg cta gtt gct aca gag aaa ttt agc aaa aga aat gta<br>Leu Arg Glu Leu Leu Val Ala Thr Glu Lys Phe Ser Lys Arg Asn Val<br>              245                250              255 | 828 |
| ttg ggc aaa gga cgt ttt ggt ata ttg tat aaa gga cgt tta gct gat<br>Leu Gly Lys Gly Arg Phe Gly Ile Leu Tyr Lys Gly Arg Leu Ala Asp<br>      260                265              270 | 876 |
| gac act cta gtg gct gtg aaa cgg cta aat gaa gaa cgt acc aag ggt<br>Asp Thr Leu Val Ala Val Lys Arg Leu Asn Glu Glu Arg Thr Lys Gly<br>275                280                285 | 924 |
| ggg gaa ctg cag ttt caa acc gaa gtt gag atg atc agt atg gcc gtt<br>Gly Glu Leu Gln Phe Gln Thr Glu Val Glu Met Ile Ser Met Ala Val<br>290                  295                300 | 972 |
| cat agg aac ttg ctt cgg ctt cgt ggc ttt tgc atg act cca act gaa<br>His Arg Asn Leu Leu Arg Leu Arg Gly Phe Cys Met Thr Pro Thr Glu<br>305                310                315              320 | 1020 |
| aga tta ctt gtt tat ccc tac atg gct aat gga agt gtt gct tct tgt<br>Arg Leu Leu Val Tyr Pro Tyr Met Ala Asn Gly Ser Val Ala Ser Cys<br>              325                330              335 | 1068 |
| tta aga gag cgt cct gaa ggc aat cca gcc ctt gac tgg cca aaa aga<br>Leu Arg Glu Arg Pro Glu Gly Asn Pro Ala Leu Asp Trp Pro Lys Arg<br>      340                345              350 | 1116 |
| aag cat att gct ctg gga tca gca agg ggg ctc gca tat tta cac gat<br>Lys His Ile Ala Leu Gly Ser Ala Arg Gly Leu Ala Tyr Leu His Asp<br>355                360                365 | 1164 |
| cat tgc gac caa aag atc att cac ctg gat gtg aaa gct gca aat ata<br>His Cys Asp Gln Lys Ile Ile His Leu Asp Val Lys Ala Ala Asn Ile<br>370                375                380 | 1212 |
| ctg tta gat gaa gag ttt gaa gct gtt gtt gga gat ttt ggg cta gca<br>Leu Leu Asp Glu Glu Phe Glu Ala Val Val Gly Asp Phe Gly Leu Ala<br>385                390                395              400 | 1260 |
| aaa tta atg aat tat aac gac tcc cat gtg aca act gct gta cgg ggt<br>Lys Leu Met Asn Tyr Asn Asp Ser His Val Thr Thr Ala Val Arg Gly<br>              405                410              415 | 1308 |
| acg att ggc cat ata gcg ccc gag tac ctc tcg aca gga aaa tct tct<br>Thr Ile Gly His Ile Ala Pro Glu Tyr Leu Ser Thr Gly Lys Ser Ser<br>      420                425              430 | 1356 |
| gag aag act gat gtt ttt ggg tac ggg gtc atg ctt ctc gag ctc atc<br>Glu Lys Thr Asp Val Phe Gly Tyr Gly Val Met Leu Leu Glu Leu Ile<br>435                440                445 | 1404 |
| act gga caa aag gct ttc gat ctt gct cgg ctt gca aat gat gat gat<br>Thr Gly Gln Lys Ala Phe Asp Leu Ala Arg Leu Ala Asn Asp Asp Asp<br>450                455                460 | 1452 |
| atc atg tta ctc gac tgg gtg aaa gag gtt ttg aaa gag aag aag ttg<br>Ile Met Leu Leu Asp Trp Val Lys Glu Val Leu Lys Glu Lys Lys Leu<br>465                470                475              480 | 1500 |
| gaa agc ctt gtg gat gca gaa ctc gaa gga aag tac gtg gaa aca gaa<br>Glu Ser Leu Val Asp Ala Glu Leu Glu Gly Lys Tyr Val Glu Thr Glu<br>              485                490              495 | 1548 |
| gtg gag cag ctg ata caa atg gct ctg ctc tgc act caa agt tct gca<br>Val Glu Gln Leu Ile Gln Met Ala Leu Leu Cys Thr Gln Ser Ser Ala | 1596 |

```
                    500              505              510
atg gaa cgt cca aag atg tca gaa gta gtg aga atg ctg gaa gga gat      1644
Met Glu Arg Pro Lys Met Ser Glu Val Val Arg Met Leu Glu Gly Asp
        515              520              525 ggt tta gct gag aga tgg gaa gaa tgg caa aag gag gag atg cca ata      1692
Gly Leu Ala Glu Arg Trp Glu Glu Trp Gln Lys Glu Glu Met Pro Ile
530              535              540 cat gat ttt aac tat caa gcc tat cct cat gct ggc act gac tgg ctc      1740
His Asp Phe Asn Tyr Gln Ala Tyr Pro His Ala Gly Thr Asp Trp Leu
545              550              555              560 atc ccc tat tcc aat tcc ctt atc gaa aac gat tac ccc tcg ggg cca      1788
Ile Pro Tyr Ser Asn Ser Leu Ile Glu Asn Asp Tyr Pro Ser Gly Pro
                565              570              575 aga taaccttta gaaagggtca tttcttgtgg gttcttcaac aagtatatat            1841
Arg
ataggtagtg aagttgtaag aagcaaaacc ccacattcac ctttgaatat cactactcta    1901
taaaaaaaaa aaaaaaaaaa aaaa                                           1925
```

<210> SEQ ID NO 53
<211> LENGTH: 577
<212> TYPE: PRT
<213> ORGANISM: Arabidopsis thaliana

<400> SEQUENCE: 53

```
Met Glu His Gly Ser Ser Arg Gly Phe Ile Trp Leu Ile Leu Phe Leu
1               5                   10                  15

Asp Phe Val Ser Arg Val Thr Gly Lys Thr Gln Val Asp Ala Leu Ile
            20                  25                  30

Ala Leu Arg Ser Ser Leu Ser Ser Gly Asp His Thr Asn Asn Ile Leu
        35                  40                  45

Gln Ser Trp Asn Ala Thr His Val Thr Pro Cys Ser Trp Phe His Val
    50                  55                  60

Thr Cys Asn Thr Glu Asn Ser Val Thr Arg Leu Glu Leu Phe Asn Asn
65                  70                  75                  80

Asn Ile Thr Gly Glu Ile Pro Glu Glu Leu Gly Asp Leu Met Glu Leu
                85                  90                  95

Val Ser Leu Asp Leu Phe Ala Asn Asn Ile Ser Gly Pro Ile Pro Ser
            100                 105                 110

Ser Leu Gly Lys Leu Gly Lys Leu Arg Phe Leu Arg Leu Tyr Asn Asn
        115                 120                 125

Ser Leu Ser Gly Glu Ile Pro Arg Ser Leu Thr Ala Leu Pro Leu Asp
    130                 135                 140

Val Leu Asp Ile Ser Asn Asn Arg Leu Ser Gly Asp Ile Pro Val Asn
145                 150                 155                 160

Gly Ser Phe Ser Gln Phe Thr Ser Met Ser Phe Ala Asn Asn Lys Leu
                165                 170                 175

Arg Pro Arg Pro Ala Ser Pro Ser Pro Ser Pro Gly Thr Ser Ala
            180                 185                 190

Ala Ile Val Val Gly Val Ala Gly Ala Ala Leu Leu Phe Ala Leu
        195                 200                 205

Ala Trp Trp Leu Arg Arg Lys Leu Gln Gly His Phe Leu Asp Val Pro
    210                 215                 220

Ala Glu Glu Asp Pro Glu Val Tyr Leu Gly Gln Phe Lys Arg Phe Ser
225                 230                 235                 240

Leu Arg Glu Leu Leu Val Ala Thr Glu Lys Phe Ser Lys Arg Asn Val
                245                 250                 255
```

```
Leu Gly Lys Gly Arg Phe Gly Ile Leu Tyr Lys Gly Arg Leu Ala Asp
            260                 265                 270

Asp Thr Leu Val Ala Val Lys Arg Leu Asn Glu Glu Arg Thr Lys Gly
            275                 280                 285

Gly Glu Leu Gln Phe Gln Thr Glu Val Glu Met Ile Ser Met Ala Val
            290                 295                 300

His Arg Asn Leu Leu Arg Leu Arg Gly Phe Cys Met Thr Pro Thr Glu
305                 310                 315                 320

Arg Leu Leu Val Tyr Pro Tyr Met Ala Asn Gly Ser Val Ala Ser Cys
                325                 330                 335

Leu Arg Glu Arg Pro Glu Gly Asn Pro Ala Leu Asp Trp Pro Lys Arg
            340                 345                 350

Lys His Ile Ala Leu Gly Ser Ala Arg Gly Leu Ala Tyr Leu His Asp
            355                 360                 365

His Cys Asp Gln Lys Ile Ile His Leu Asp Val Lys Ala Ala Asn Ile
370                 375                 380

Leu Leu Asp Glu Glu Phe Glu Ala Val Val Gly Asp Phe Gly Leu Ala
385                 390                 395                 400

Lys Leu Met Asn Tyr Asn Asp Ser His Val Thr Ala Val Arg Gly
                405                 410                 415

Thr Ile Gly His Ile Ala Pro Glu Tyr Leu Ser Thr Gly Lys Ser Ser
                420                 425                 430

Glu Lys Thr Asp Val Phe Gly Tyr Gly Val Met Leu Leu Glu Leu Ile
            435                 440                 445

Thr Gly Gln Lys Ala Phe Asp Leu Ala Arg Leu Ala Asn Asp Asp
            450                 455                 460

Ile Met Leu Leu Asp Trp Val Lys Glu Val Leu Lys Glu Lys Lys Leu
465                 470                 475                 480

Glu Ser Leu Val Asp Ala Glu Leu Glu Gly Lys Tyr Val Glu Thr Glu
                485                 490                 495

Val Glu Gln Leu Ile Gln Met Ala Leu Leu Cys Thr Gln Ser Ser Ala
            500                 505                 510

Met Glu Arg Pro Lys Met Ser Glu Val Val Arg Met Leu Glu Gly Asp
            515                 520                 525

Gly Leu Ala Glu Arg Trp Glu Glu Trp Gln Lys Glu Glu Met Pro Ile
            530                 535                 540

His Asp Phe Asn Tyr Gln Ala Tyr Pro His Ala Gly Thr Asp Trp Leu
545                 550                 555                 560

Ile Pro Tyr Ser Asn Ser Leu Ile Glu Asn Asp Tyr Pro Ser Gly Pro
                565                 570                 575

Arg
```

<210> SEQ ID NO 54
<211> LENGTH: 1910
<212> TYPE: DNA
<213> ORGANISM: Arabidopsis thaliana
<220> FEATURE:
<221> NAME/KEY: CDS
<222> LOCATION: (40)..(1827)
<223> OTHER INFORMATION: /note="Arabidopsis thaliana RKS13 cDNA"

<400> SEQUENCE: 54

```
taataaacct ctaataataa tggctttgct tttactctg atg aca agt tca aaa      54
                                            Met Thr Ser Ser Lys
                                              1               5
```

```
atg gaa caa aga tca ctc ctt tgc ttc ctt tat ctg ctc cta cta ttc    102
Met Glu Gln Arg Ser Leu Leu Cys Phe Leu Tyr Leu Leu Leu Leu Phe
              10                  15                  20 aat ttc act ctc aga gtc gct gga aac gct gaa ggt gat gct ttg act    150
Asn Phe Thr Leu Arg Val Ala Gly Asn Ala Glu Gly Asp Ala Leu Thr
          25                  30                  35 cag ctg aaa aac agt ttg tca tca ggt gac cct gca aac aat gta ctc    198
Gln Leu Lys Asn Ser Leu Ser Ser Gly Asp Pro Ala Asn Asn Val Leu
      40                  45                  50 caa agc tgg gat gct act ctt gtt act cca tgt act tgg ttt cat gtt    246
Gln Ser Trp Asp Ala Thr Leu Val Thr Pro Cys Thr Trp Phe His Val
  55                  60                  65 act tgc aat cct gag aat aaa gtt act cgt gtg gag ctt tat agc aat    294
Thr Cys Asn Pro Glu Asn Lys Val Thr Arg Val Glu Leu Tyr Ser Asn
70                  75                  80                  85 aac att aca ggg gag ata cct gag gag ctt ggc gac ttg gtg gaa cta    342
Asn Ile Thr Gly Glu Ile Pro Glu Glu Leu Gly Asp Leu Val Glu Leu
              90                  95                 100 gta agc ttg gat ctt tac gca aac agc ata agc ggt ccc atc cct tcg    390
Val Ser Leu Asp Leu Tyr Ala Asn Ser Ile Ser Gly Pro Ile Pro Ser
         105                 110                 115 tct ctt ggc aaa cta gga aaa ctc cgg ttc ttg cgt ctt aac aac aat    438
Ser Leu Gly Lys Leu Gly Lys Leu Arg Phe Leu Arg Leu Asn Asn Asn
     120                 125                 130 agc tta tca ggg gaa att cca atg act ttg act tct gtg cag ctg caa    486
Ser Leu Ser Gly Glu Ile Pro Met Thr Leu Thr Ser Val Gln Leu Gln
 135                 140                 145 gtt ctg gat atc tca aac aat cgg ctc agt gga gat att cct gtt aat    534
Val Leu Asp Ile Ser Asn Asn Arg Leu Ser Gly Asp Ile Pro Val Asn
150                 155                 160                 165 ggt tct ttt tcg ctc ttc act cct atc agt ttt gcg aat aat agc tta    582
Gly Ser Phe Ser Leu Phe Thr Pro Ile Ser Phe Ala Asn Asn Ser Leu
             170                 175                 180 acg gat ctt ccc gaa cct ccg cct act tct acc tct cct acg cca cca    630
Thr Asp Leu Pro Glu Pro Pro Pro Thr Ser Thr Ser Pro Thr Pro Pro
         185                 190                 195 cca cct tca ggg ggg caa atg act gca gca ata gca ggg gga gtt gct    678
Pro Pro Ser Gly Gly Gln Met Thr Ala Ala Ile Ala Gly Gly Val Ala
     200                 205                 210 gca ggt gca gca ctt cta ttt gct gtt cca gcc att gcg ttt gct tgg    726
Ala Gly Ala Ala Leu Leu Phe Ala Val Pro Ala Ile Ala Phe Ala Trp
 215                 220                 225 tgg ctc aga aga aaa cca cag gac cac ttt ttt gat gta cct gct gaa    774
Trp Leu Arg Arg Lys Pro Gln Asp His Phe Phe Asp Val Pro Ala Glu
230                 235                 240                 245 gaa gac cca gag gtt cat tta gga caa ctc aaa agg ttt acc ttg cgt    822
Glu Asp Pro Glu Val His Leu Gly Gln Leu Lys Arg Phe Thr Leu Arg
             250                 255                 260 gaa ctg tta gtt gct act gat aac ttt agc aat aaa aat gta ttg ggt    870
Glu Leu Leu Val Ala Thr Asp Asn Phe Ser Asn Lys Asn Val Leu Gly
         265                 270                 275 aga ggt ggt ttt ggt aaa gtg tat aaa gga cgt tta gcc gat ggc aat    918
Arg Gly Gly Phe Gly Lys Val Tyr Lys Gly Arg Leu Ala Asp Gly Asn
     280                 285                 290 cta gtg gct gtc aaa agg cta aaa gaa gaa cgt acc aag ggt ggg gaa    966
Leu Val Ala Val Lys Arg Leu Lys Glu Glu Arg Thr Lys Gly Gly Glu
 295                 300                 305 ctg cag ttt caa acc gaa gtt gag atg atc agt atg gcc gtt cat agg   1014
Leu Gln Phe Gln Thr Glu Val Glu Met Ile Ser Met Ala Val His Arg
```

```
                310                 315                 320                 325
aac ttg ctt cgg ctt cgt ggc ttt tgc atg act cca act gaa aga tta     1062
Asn Leu Leu Arg Leu Arg Gly Phe Cys Met Thr Pro Thr Glu Arg Leu
                330                 335                 340 ctt gtt tat ccc tac atg gct aat gga agt gtt gct tct tgt tta aga     1110
Leu Val Tyr Pro Tyr Met Ala Asn Gly Ser Val Ala Ser Cys Leu Arg
            345                 350                 355 gag cgt cct gaa ggc aat cca gca ctt gat tgg cca aaa aga aag cat     1158
Glu Arg Pro Glu Gly Asn Pro Ala Leu Asp Trp Pro Lys Arg Lys His
        360                 365                 370 att gct ctg gga tca gca agg ggg ctt gcg tat tta cat gat cat tgc     1206
Ile Ala Leu Gly Ser Ala Arg Gly Leu Ala Tyr Leu His Asp His Cys
    375                 380                 385 gac caa aaa atc att cac cgg gat gtt aaa gct gct aat ata ttg tta     1254
Asp Gln Lys Ile Ile His Arg Asp Val Lys Ala Ala Asn Ile Leu Leu
390                 395                 400                 405 gat gaa gag ttt gaa gct gtt gtt gga gat ttt ggg ctc gca aaa tta     1302
Asp Glu Glu Phe Glu Ala Val Val Gly Asp Phe Gly Leu Ala Lys Leu
                410                 415                 420 atg aat tat aat gac tcc cat gtg aca act gct gta cgc ggt aca att     1350
Met Asn Tyr Asn Asp Ser His Val Thr Thr Ala Val Arg Gly Thr Ile
            425                 430                 435 ggc cat ata gcg ccc gag tac ctc tcg aca gga aaa tct tct gag aag     1398
Gly His Ile Ala Pro Glu Tyr Leu Ser Thr Gly Lys Ser Ser Glu Lys
        440                 445                 450 act gat gtt ttt ggg tac ggg gtc atg ctt ctc gag ctc atc act gga     1446
Thr Asp Val Phe Gly Tyr Gly Val Met Leu Leu Glu Leu Ile Thr Gly
    455                 460                 465 caa aag gct ttc gat ctt gct cgg ctt gca aat gat gat gat atc atg     1494
Gln Lys Ala Phe Asp Leu Ala Arg Leu Ala Asn Asp Asp Asp Ile Met
470                 475                 480                 485 tta ctc gac tgg gtg aaa gag gtt ttg aaa gag aag aag ttg gaa agc     1542
Leu Leu Asp Trp Val Lys Glu Val Leu Lys Glu Lys Lys Leu Glu Ser
                490                 495                 500 ctt gtg gat gca gaa ctc gaa gga aag tac gtg gaa aca gaa gtg gag     1590
Leu Val Asp Ala Glu Leu Glu Gly Lys Tyr Val Glu Thr Glu Val Glu
            505                 510                 515 cag ctg ata caa atg gct ctg ctc tgc act caa agt tct gca atg gaa     1638
Gln Leu Ile Gln Met Ala Leu Leu Cys Thr Gln Ser Ser Ala Met Glu
        520                 525                 530 cgt cca aag atg tca gaa gta gtg aga atg ctg gaa gga gat ggt tta     1686
Arg Pro Lys Met Ser Glu Val Val Arg Met Leu Glu Gly Asp Gly Leu
    535                 540                 545 gct gag aga tgg gaa gaa tgg caa aag gag gag atg cca ata cat gat     1734
Ala Glu Arg Trp Glu Glu Trp Gln Lys Glu Glu Met Pro Ile His Asp
550                 555                 560                 565 ttt aac tat caa gcc tat cct cat gct ggc act gac tgg ctc atc ccc     1782
Phe Asn Tyr Gln Ala Tyr Pro His Ala Gly Thr Asp Trp Leu Ile Pro
                570                 575                 580 tat tcc aat tcc ctt atc gaa aac gat tac ccc tcg ggt cca aga         1827
Tyr Ser Asn Ser Leu Ile Glu Asn Asp Tyr Pro Ser Gly Pro Arg
            585                 590                 595 taaccttta gaaagggtct tttcttgtgg gttcttcaac aagtatatat atagattggt    1887
gaagttttaa gatgcaaaaa aaa                                          1910

<210> SEQ ID NO 55
<211> LENGTH: 596
<212> TYPE: PRT
<213> ORGANISM: Arabidopsis thaliana
```

<400> SEQUENCE: 55

```
Met Thr Ser Ser Lys Met Glu Gln Arg Ser Leu Leu Cys Phe Leu Tyr
1               5                   10                  15
Leu Leu Leu Leu Phe Asn Phe Thr Leu Arg Val Ala Gly Asn Ala Glu
            20                  25                  30
Gly Asp Ala Leu Thr Gln Leu Lys Asn Ser Leu Ser Ser Gly Asp Pro
        35                  40                  45
Ala Asn Asn Val Leu Gln Ser Trp Asp Ala Thr Leu Val Thr Pro Cys
    50                  55                  60
Thr Trp Phe His Val Thr Cys Asn Pro Glu Asn Lys Val Thr Arg Val
65                  70                  75                  80
Glu Leu Tyr Ser Asn Asn Ile Thr Gly Glu Ile Pro Glu Glu Leu Gly
                85                  90                  95
Asp Leu Val Glu Leu Val Ser Leu Asp Leu Tyr Ala Asn Ser Ile Ser
            100                 105                 110
Gly Pro Ile Pro Ser Ser Leu Gly Lys Leu Gly Lys Leu Arg Phe Leu
        115                 120                 125
Arg Leu Asn Asn Asn Ser Leu Ser Gly Glu Ile Pro Met Thr Leu Thr
    130                 135                 140
Ser Val Gln Leu Gln Val Leu Asp Ile Ser Asn Asn Arg Leu Ser Gly
145                 150                 155                 160
Asp Ile Pro Val Asn Gly Ser Phe Ser Leu Phe Thr Pro Ile Ser Phe
                165                 170                 175
Ala Asn Asn Ser Leu Thr Asp Leu Pro Glu Pro Pro Thr Ser Thr
            180                 185                 190
Ser Pro Thr Pro Pro Pro Ser Gly Gly Gln Met Thr Ala Ala Ile
        195                 200                 205
Ala Gly Gly Val Ala Ala Gly Ala Ala Leu Leu Phe Ala Val Pro Ala
    210                 215                 220
Ile Ala Phe Ala Trp Trp Leu Arg Arg Lys Pro Gln Asp His Phe Phe
225                 230                 235                 240
Asp Val Pro Ala Glu Glu Asp Pro Glu Val His Leu Gly Gln Leu Lys
                245                 250                 255
Arg Phe Thr Leu Arg Glu Leu Leu Val Ala Thr Asp Asn Phe Ser Asn
            260                 265                 270
Lys Asn Val Leu Gly Arg Gly Gly Phe Gly Lys Val Tyr Lys Gly Arg
        275                 280                 285
Leu Ala Asp Gly Asn Leu Val Ala Val Lys Arg Leu Lys Glu Glu Arg
    290                 295                 300
Thr Lys Gly Gly Glu Leu Gln Phe Gln Thr Glu Val Glu Met Ile Ser
305                 310                 315                 320
Met Ala Val His Arg Asn Leu Leu Arg Leu Arg Gly Phe Cys Met Thr
                325                 330                 335
Pro Thr Glu Arg Leu Leu Val Tyr Pro Tyr Met Ala Asn Gly Ser Val
            340                 345                 350
Ala Ser Cys Leu Arg Glu Arg Pro Glu Gly Asn Pro Ala Leu Asp Trp
        355                 360                 365
Pro Lys Arg Lys His Ile Ala Leu Gly Ser Ala Arg Gly Leu Ala Tyr
    370                 375                 380
Leu His Asp His Cys Asp Gln Lys Ile Ile His Arg Asp Val Lys Ala
385                 390                 395                 400
Ala Asn Ile Leu Leu Asp Glu Glu Phe Glu Ala Val Val Gly Asp Phe
```

-continued

```
                    405                 410                 415
Gly Leu Ala Lys Leu Met Asn Tyr Asn Asp Ser His Val Thr Thr Ala
            420                 425                 430

Val Arg Gly Thr Ile Gly His Ile Ala Pro Glu Tyr Leu Ser Thr Gly
            435                 440                 445

Lys Ser Ser Glu Lys Thr Asp Val Phe Gly Tyr Gly Val Met Leu Leu
            450                 455                 460

Glu Leu Ile Thr Gly Gln Lys Ala Phe Asp Leu Ala Arg Leu Ala Asn
465                 470                 475                 480

Asp Asp Asp Ile Met Leu Leu Asp Trp Val Lys Glu Val Leu Lys Glu
                485                 490                 495

Lys Lys Leu Glu Ser Leu Val Asp Ala Glu Leu Glu Gly Lys Tyr Val
            500                 505                 510

Glu Thr Glu Val Glu Gln Leu Ile Gln Met Ala Leu Leu Cys Thr Gln
            515                 520                 525

Ser Ser Ala Met Glu Arg Pro Lys Met Ser Glu Val Val Arg Met Leu
            530                 535                 540

Glu Gly Asp Gly Leu Ala Glu Arg Trp Glu Glu Trp Gln Lys Glu Glu
545                 550                 555                 560

Met Pro Ile His Asp Phe Asn Tyr Gln Ala Tyr Pro His Ala Gly Thr
                565                 570                 575

Asp Trp Leu Ile Pro Tyr Ser Asn Ser Leu Ile Glu Asn Asp Tyr Pro
            580                 585                 590

Ser Gly Pro Arg
        595

<210> SEQ ID NO 56
<211> LENGTH: 1899
<212> TYPE: DNA
<213> ORGANISM: Arabidopsis thaliana
<220> FEATURE:
<221> NAME/KEY: CDS
<222> LOCATION: (55)..(1857)
<223> OTHER INFORMATION: /note="Arabidopsis thaliana RKS14 cDNA"

<400> SEQUENCE: 56 ctgcaccta gagattaata ctctcaagaa aaacaagttt tgattcggac aaag atg        57
                                                             Met
                                                              1 ttg caa gga aga aga gaa gca aaa aag agt tat gct ttg ttc tct tca      105
Leu Gln Gly Arg Arg Glu Ala Lys Lys Ser Tyr Ala Leu Phe Ser Ser
         5                  10                  15 act ttc ttc ttc ttc ttt atc tgt ttt ctt tct tct tct tct gca gaa     153
Thr Phe Phe Phe Phe Phe Ile Cys Phe Leu Ser Ser Ser Ser Ala Glu
                20                  25                  30 ctc aca gac aaa gtt gtt gcc tta ata gga atc aaa agc tca ctg act     201
Leu Thr Asp Lys Val Val Ala Leu Ile Gly Ile Lys Ser Ser Leu Thr
        35                  40                  45 gat cct cat gga gtt cta atg aat tgg gat gac aca gca gtt gat cca     249
Asp Pro His Gly Val Leu Met Asn Trp Asp Asp Thr Ala Val Asp Pro
 50                  55                  60                  65 tgt agc tgg aac atg atc act tgt tct gat ggt ttt gtc ata agg cta     297
Cys Ser Trp Asn Met Ile Thr Cys Ser Asp Gly Phe Val Ile Arg Leu
                 70                  75                  80 tac agg tta ttg cag aac aat tac ata aca gga aac atc cct cat gag     345
Tyr Arg Leu Leu Gln Asn Asn Tyr Ile Thr Gly Asn Ile Pro His Glu
             85                  90                  95
```

-continued

```
att ggg aaa ttg atg aaa ctc aaa aca ctt gat ctc tct acc aat aac    393
Ile Gly Lys Leu Met Lys Leu Lys Thr Leu Asp Leu Ser Thr Asn Asn
        100                 105                 110 ttc act ggt caa atc cca ttc act ctt tct tac tcc aaa aat ctt cac    441
Phe Thr Gly Gln Ile Pro Phe Thr Leu Ser Tyr Ser Lys Asn Leu His
115                 120                 125 agg agg gtt aat aat aac agc ctg aca gga aca att cct agc tca ttg    489
Arg Arg Val Asn Asn Asn Ser Leu Thr Gly Thr Ile Pro Ser Ser Leu
130                 135                 140                 145 gca aac atg acc caa ctc act ttt ttg gat ttg tcg tat aat aac ttg    537
Ala Asn Met Thr Gln Leu Thr Phe Leu Asp Leu Ser Tyr Asn Asn Leu
                150                 155                 160 agt gga cca gtt cca aga tca ctt gcc aaa aca ttc aat gtt atg ggc    585
Ser Gly Pro Val Pro Arg Ser Leu Ala Lys Thr Phe Asn Val Met Gly
            165                 170                 175 aat tct cag att tgt cca aca gga act gag aaa gac tgt aat ggg act    633
Asn Ser Gln Ile Cys Pro Thr Gly Thr Glu Lys Asp Cys Asn Gly Thr
        180                 185                 190 cag cct aag cca atg tca atc acc ttg aac agt tct caa aga act aaa    681
Gln Pro Lys Pro Met Ser Ile Thr Leu Asn Ser Ser Gln Arg Thr Lys
195                 200                 205 aac cgg aaa atc gcg gta gtc ttc ggt gta agc ttg aca tgt gtt tgc    729
Asn Arg Lys Ile Ala Val Val Phe Gly Val Ser Leu Thr Cys Val Cys
210                 215                 220                 225 ttg ttg atc att ggc ttt ggt ttt ctt ctt tgg tgg aga aga aga cat    777
Leu Leu Ile Ile Gly Phe Gly Phe Leu Leu Trp Trp Arg Arg Arg His
                230                 235                 240 aac aaa caa gta tta ttc ttt gac att aat gag caa aac aag gaa gaa    825
Asn Lys Gln Val Leu Phe Phe Asp Ile Asn Glu Gln Asn Lys Glu Glu
            245                 250                 255 atg tgt cta ggg aat cta agg agg ttt aat ttc aaa gaa ctt caa tcc    873
Met Cys Leu Gly Asn Leu Arg Arg Phe Asn Phe Lys Glu Leu Gln Ser
        260                 265                 270 gca act agt aac ttc agc agc aag aat ctg gtc gga aaa gga ggg ttt    921
Ala Thr Ser Asn Phe Ser Ser Lys Asn Leu Val Gly Lys Gly Gly Phe
275                 280                 285 gga aat gtg tat aaa ggt tgt ctt cat gat gga agt atc atc gcg gtg    969
Gly Asn Val Tyr Lys Gly Cys Leu His Asp Gly Ser Ile Ile Ala Val
290                 295                 300                 305 aag aga tta aag gat ata aac aat ggt ggt gga gag gtt cag ttt cag   1017
Lys Arg Leu Lys Asp Ile Asn Asn Gly Gly Gly Glu Val Gln Phe Gln
                310                 315                 320 aca gag ctt gaa atg ata agc ctt gcc gtc cac cgg aat ctc ctc cgc   1065
Thr Glu Leu Glu Met Ile Ser Leu Ala Val His Arg Asn Leu Leu Arg
            325                 330                 335 tta tac ggt ttc tgt act act tcc tct gaa cgg ctt ctc gtt tat cct   1113
Leu Tyr Gly Phe Cys Thr Thr Ser Ser Glu Arg Leu Leu Val Tyr Pro
        340                 345                 350 tac atg tcc aat ggc agt gtc gct tct cgt ctc aaa gct aaa ccg gta   1161
Tyr Met Ser Asn Gly Ser Val Ala Ser Arg Leu Lys Ala Lys Pro Val
355                 360                 365 ttg gat tgg ggc aca aga aag cga ata gca tta gga gca gga aga ggg   1209
Leu Asp Trp Gly Thr Arg Lys Arg Ile Ala Leu Gly Ala Gly Arg Gly
370                 375                 380                 385 ttg ctg tat ttg cat gag caa tgt gat cca aag atc att cac cgt gat   1257
Leu Leu Tyr Leu His Glu Gln Cys Asp Pro Lys Ile Ile His Arg Asp
                390                 395                 400 gtc aaa gct gcg aac ata ctt ctt gac gat tac ttt gaa gct gtt gtc   1305
Val Lys Ala Ala Asn Ile Leu Leu Asp Asp Tyr Phe Glu Ala Val Val
            405                 410                 415
```

```
gga gat ttc ggg ttg gct aag ctt ttg gat cat gag gag tcg cat gtg      1353
Gly Asp Phe Gly Leu Ala Lys Leu Leu Asp His Glu Glu Ser His Val
        420                 425                 430 aca acc gcc gtg aga gga aca gtg ggt cac att gca cct gag tat ctc      1401
Thr Thr Ala Val Arg Gly Thr Val Gly His Ile Ala Pro Glu Tyr Leu
    435                 440                 445 tca aca gga caa tct tct gag aag aca gat gtg ttc ggt ttc ggg att      1449
Ser Thr Gly Gln Ser Ser Glu Lys Thr Asp Val Phe Gly Phe Gly Ile
450                 455                 460                 465 ctt ctt ctc gaa ttg att act gga ttg aga gct ctt gaa ttc gga aaa      1497
Leu Leu Leu Glu Leu Ile Thr Gly Leu Arg Ala Leu Glu Phe Gly Lys
            470                 475                 480 gca gca aac caa aga gga gcg ata ctt gat tgg gta aag aaa cta caa      1545
Ala Ala Asn Gln Arg Gly Ala Ile Leu Asp Trp Val Lys Lys Leu Gln
        485                 490                 495 caa gag aag aag cta gaa cag ata gta gac aag gat ttg aag agc aac      1593
Gln Glu Lys Lys Leu Glu Gln Ile Val Asp Lys Asp Leu Lys Ser Asn
    500                 505                 510 tac gat aga ata gaa gtg gaa gaa atg gtt caa gtg gct ttg ctt tgt      1641
Tyr Asp Arg Ile Glu Val Glu Glu Met Val Gln Val Ala Leu Leu Cys
515                 520                 525 aca cag tat ctt ccc att cac cgt cct aag atg tct gaa gtt gtg aga      1689
Thr Gln Tyr Leu Pro Ile His Arg Pro Lys Met Ser Glu Val Val Arg
530                 535                 540                 545 atg ctt gaa ggc gat ggt ctt gtt gag aaa tgg gaa gct tct tct cag      1737
Met Leu Glu Gly Asp Gly Leu Val Glu Lys Trp Glu Ala Ser Ser Gln
            550                 555                 560 aga gca gaa acc aat aga agt tac agt aaa cct aac gag ttt tct tcc      1785
Arg Ala Glu Thr Asn Arg Ser Tyr Ser Lys Pro Asn Glu Phe Ser Ser
        565                 570                 575 tct gaa cgt tat tcg gat ctt aca gat gat tcc tcg gtg ctg gtt caa      1833
Ser Glu Arg Tyr Ser Asp Leu Thr Asp Asp Ser Ser Val Leu Val Gln
    580                 585                 590 gcc atg gag tta tca ggt cca aga tgacaagaga aactatatga atggctttgg    1887
Ala Met Glu Leu Ser Gly Pro Arg
595                 600 gtttgtaaaa aa                                                        1899

<210> SEQ ID NO 57
<211> LENGTH: 601
<212> TYPE: PRT
<213> ORGANISM: Arabidopsis thaliana

<400> SEQUENCE: 57

Met Leu Gln Gly Arg Arg Glu Ala Lys Lys Ser Tyr Ala Leu Phe Ser
1               5                   10                  15

Ser Thr Phe Phe Phe Phe Ile Cys Phe Leu Ser Ser Ser Ser Ala
            20                  25                  30

Glu Leu Thr Asp Lys Val Val Ala Leu Ile Gly Ile Lys Ser Ser Leu
        35                  40                  45

Thr Asp Pro His Gly Val Leu Met Asn Trp Asp Thr Ala Val Asp
    50                  55                  60

Pro Cys Ser Trp Asn Met Ile Thr Cys Ser Asp Gly Phe Val Ile Arg
65                  70                  75                  80

Leu Tyr Arg Leu Leu Gln Asn Asn Tyr Ile Thr Gly Asn Ile Pro His
            85                  90                  95

Glu Ile Gly Lys Leu Met Lys Leu Lys Thr Leu Asp Leu Ser Thr Asn
            100                 105                 110
```

```
Asn Phe Thr Gly Gln Ile Pro Phe Thr Leu Ser Tyr Ser Lys Asn Leu
            115                 120                 125

His Arg Arg Val Asn Asn Ser Leu Thr Gly Thr Ile Pro Ser Ser
        130                 135                 140

Leu Ala Asn Met Thr Gln Leu Thr Phe Leu Asp Leu Ser Tyr Asn Asn
145                 150                 155                 160

Leu Ser Gly Pro Val Pro Arg Ser Leu Ala Lys Thr Phe Asn Val Met
                165                 170                 175

Gly Asn Ser Gln Ile Cys Pro Thr Gly Thr Glu Lys Asp Cys Asn Gly
            180                 185                 190

Thr Gln Pro Lys Pro Met Ser Ile Thr Leu Asn Ser Ser Gln Arg Thr
        195                 200                 205

Lys Asn Arg Lys Ile Ala Val Val Phe Gly Val Ser Leu Thr Cys Val
        210                 215                 220

Cys Leu Leu Ile Ile Gly Phe Gly Phe Leu Leu Trp Trp Arg Arg Arg
225                 230                 235                 240

His Asn Lys Gln Val Leu Phe Phe Asp Ile Asn Glu Gln Asn Lys Glu
            245                 250                 255

Glu Met Cys Leu Gly Asn Leu Arg Arg Phe Asn Phe Lys Glu Leu Gln
            260                 265                 270

Ser Ala Thr Ser Asn Phe Ser Ser Lys Asn Leu Val Gly Lys Gly Gly
        275                 280                 285

Phe Gly Asn Val Tyr Lys Gly Cys Leu His Asp Gly Ser Ile Ile Ala
        290                 295                 300

Val Lys Arg Leu Lys Asp Ile Asn Asn Gly Gly Gly Glu Val Gln Phe
305                 310                 315                 320

Gln Thr Glu Leu Glu Met Ile Ser Leu Ala Val His Arg Asn Leu Leu
            325                 330                 335

Arg Leu Tyr Gly Phe Cys Thr Thr Ser Ser Glu Arg Leu Leu Val Tyr
                340                 345                 350

Pro Tyr Met Ser Asn Gly Ser Val Ala Ser Arg Leu Lys Ala Lys Pro
        355                 360                 365

Val Leu Asp Trp Gly Thr Arg Lys Arg Ile Ala Leu Gly Ala Gly Arg
370                 375                 380

Gly Leu Leu Tyr Leu His Glu Gln Cys Asp Pro Lys Ile Ile His Arg
385                 390                 395                 400

Asp Val Lys Ala Ala Asn Ile Leu Leu Asp Asp Tyr Phe Glu Ala Val
                405                 410                 415

Val Gly Asp Phe Gly Leu Ala Lys Leu Leu Asp His Glu Ser His
            420                 425                 430

Val Thr Thr Ala Val Arg Gly Thr Val Gly His Ile Ala Pro Glu Tyr
        435                 440                 445

Leu Ser Thr Gly Gln Ser Ser Glu Lys Thr Asp Val Phe Gly Phe Gly
        450                 455                 460

Ile Leu Leu Leu Glu Leu Ile Thr Gly Leu Arg Ala Leu Glu Phe Gly
465                 470                 475                 480

Lys Ala Ala Asn Gln Arg Gly Ala Ile Leu Asp Trp Val Lys Lys Leu
            485                 490                 495

Gln Gln Glu Lys Lys Leu Glu Gln Ile Val Asp Lys Asp Leu Lys Ser
        500                 505                 510

Asn Tyr Asp Arg Ile Glu Val Glu Glu Met Val Gln Val Ala Leu Leu
        515                 520                 525
```

```
Cys Thr Gln Tyr Leu Pro Ile His Arg Pro Lys Met Ser Glu Val Val
        530                 535                 540

Arg Met Leu Glu Gly Asp Gly Leu Val Glu Lys Trp Glu Ala Ser Ser
545                 550                 555                 560

Gln Arg Ala Glu Thr Asn Arg Ser Tyr Ser Lys Pro Asn Glu Phe Ser
                565                 570                 575

Ser Ser Glu Arg Tyr Ser Asp Leu Thr Asp Asp Ser Ser Val Leu Val
            580                 585                 590

Gln Ala Met Glu Leu Ser Gly Pro Arg
        595                 600

<210> SEQ ID NO 58
<211> LENGTH: 154
<212> TYPE: DNA
<213> ORGANISM: Arabidopsis thaliana
<220> FEATURE:
<223> OTHER INFORMATION: /note="Arabidopsis thaliana RKS7 partial cDNA
      sequence"

<400> SEQUENCE: 58
agcgaatata cttcttgatg actactgtga agctgtggtt ggcgattttg gtttagctaa      60
actcttggat catcaagatt ctcatgtgac aaccgcggtt agaggcacgg tgggtcacat     120
tgctccagag tatctctcaa ctggtcaatc ctct                                 154

<210> SEQ ID NO 59
<211> LENGTH: 692
<212> TYPE: DNA
<213> ORGANISM: Arabidopsis thaliana
<220> FEATURE:
<223> OTHER INFORMATION: /note="Arabidopsis thaliana RKS7 partial cDNA
      sequence"

<400> SEQUENCE: 59
aacagatgtt ttttggcttt gggattcttc ttcttgagct tgtaaccgga caaggagctt      60
ttgagtctgt taaagcggct aaccggaaag gtgtgatgct tgattgggtt aaaaagattc     120
atcaagagaa gaaacttgag ctacttgtgg ataaagagtt gttgaagaag aagagctacg     180
atgagattga gttagacgaa atggtaagag tagctttgtt gtgcacacag tacctgccag     240
gacatagacc aaaaatgtct gaagttgttc gaatgctgga aggagatgga cttgcagaga     300
aatgggaagc ttctcaaaga tcagacagtg tttcaaaatg tagcaacagg ataaatgaat     360
tgatgtcatc ttcagacaga tactctgatc ttaccgatga ctctagttta cttgtgcaag     420
caatggagct ctctggtcct agatgaaatc tatacatgaa tctgaagaag aagaagaaca     480
tgcatctgtt tcttgaatca agagggattc ttgttttttt gtataataga gaggtttttt     540
ggagggaaat gttgtgtctc tgtaactgta taggcttgtt gtgtaagaag ttattactgc     600
acttagggtt aattcaaagt tctttacata aaaaatgatt agttgcgttg aatagaggga     660
acactttggg agatttcatg tatgaaattt gg                                   692

<210> SEQ ID NO 60
<211> LENGTH: 51
<212> TYPE: PRT
<213> ORGANISM: Arabidopsis thaliana
<220> FEATURE:
<223> OTHER INFORMATION: /note="Arabidopsis thaliana RKS-7 partial protein
      sequence"

<400> SEQUENCE: 60

Ala Asn Ile Leu Leu Asp Asp Tyr Cys Glu Ala Val Val Gly Asp Phe
```

```
                1               5                  10                  15
Gly Leu Ala Lys Leu Leu Asp His Gln Asp Ser His Val Thr Thr Ala
                            20                  25                  30

Val Arg Gly Thr Val Gly His Ile Ala Pro Glu Tyr Leu Ser Thr Gly
                35                  40                  45

Gln Ser Ser
    50

<210> SEQ ID NO 61
<211> LENGTH: 147
<212> TYPE: PRT
<213> ORGANISM: Arabidopsis thaliana
<220> FEATURE:
<223> OTHER INFORMATION: /note="Arabidopsis thaliana RKS-7 partial protein
      sequence"

<400> SEQUENCE: 61

Gln Met Phe Phe Gly Phe Gly Ile Leu Leu Glu Leu Val Thr Gly
 1               5                  10                  15

Gln Gly Ala Phe Glu Ser Val Lys Ala Ala Asn Arg Lys Gly Val Met
                20                  25                  30

Leu Asp Trp Val Lys Lys Ile His Gln Glu Lys Lys Leu Glu Leu Leu
            35                  40                  45

Val Asp Lys Glu Leu Leu Lys Lys Lys Ser Tyr Asp Glu Ile Glu Leu
    50                  55                  60

Asp Glu Met Val Arg Val Ala Leu Leu Cys Thr Gln Tyr Leu Pro Gly
 65                  70                  75                  80

His Arg Pro Lys Met Ser Glu Val Val Arg Met Leu Glu Gly Asp Gly
                85                  90                  95

Leu Ala Glu Lys Trp Glu Ala Ser Gln Arg Ser Asp Ser Val Ser Lys
            100                 105                 110

Cys Ser Asn Arg Ile Asn Glu Leu Met Ser Ser Ser Asp Arg Tyr Ser
        115                 120                 125

Asp Leu Thr Asp Asp Ser Ser Leu Leu Val Gln Ala Met Glu Leu Ser
    130                 135                 140

Gly Pro Arg
145

<210> SEQ ID NO 62
<211> LENGTH: 534
<212> TYPE: DNA
<213> ORGANISM: Arabidopsis thaliana
<220> FEATURE:
<223> OTHER INFORMATION: /note="Arabidopsis thaliana RKS-9 partial cDNA
      sequence"

<400> SEQUENCE: 62
gaaatggtaa gagtagcttt gttgtgcaca cagtacctgc caggacatag accaagagtg     60
tctgaagttg ttcgaatgct ggaaggagat ggacttgcag agaagtggga agcttctcaa    120
ggatcagaca gtgtttcaaa atgtagcaac aggataaatg aagtgatgtc atcttcagac    180
agatactctg atgttaccga tgactctagt ttacgtgtgc aagcaatgga gctctctggt    240
cctagatgaa gtctatacat gaatctgaag aagaagaaga acatgcatct gtttcttgaa    300
tcaagaggga ttcttgtttt tttgtataat agagaggttt tttggaggga aatgttgtgt    360
ctctgtaact gtataggctt gttgtgtaag aagttattac tgcacttagg gttaagtcaa    420
agttctttac ataaggggggg attagttgcg ttgaatagag gaacactttt gggagatttc    480
```

```
atgtgtgaaa gttgggaagt catgtttgag aatgaaggtt atcttattat tgaa         534
```

<210> SEQ ID NO 63
<211> LENGTH: 99
<212> TYPE: PRT
<213> ORGANISM: Arabidopsis thaliana
<220> FEATURE:
<223> OTHER INFORMATION: /note="Arabidopsis thaliana RKS-9 partial protein sequence"

<400> SEQUENCE: 63

```
Val Asp Lys Glu Leu Leu Lys Lys Ser Tyr Asp Glu Ile Glu Leu
 1               5                  10                  15

Asp Glu Met Val Arg Val Ala Leu Leu Cys Thr Gln Tyr Leu Pro Gly
                20                  25                  30

His Arg Pro Arg Val Ser Glu Val Val Arg Met Leu Glu Gly Asp Gly
            35                  40                  45

Leu Ala Glu Lys Trp Glu Ala Ser Gln Gly Ser Asp Ser Val Ser Lys
        50                  55                  60

Cys Ser Asn Arg Ile Asn Glu Val Met Ser Ser Ser Asp Arg Tyr Ser
65                  70                  75                  80

Asp Val Thr Asp Asp Ser Ser Leu Arg Val Gln Ala Met Glu Leu Ser
                85                  90                  95

Gly Pro Arg
```

<210> SEQ ID NO 64
<211> LENGTH: 586
<212> TYPE: DNA
<213> ORGANISM: Arabidopsis thaliana
<220> FEATURE:
<223> OTHER INFORMATION: /note="Arabidopsis thaliana RKS-15 partial cDNA sequence"

<400> SEQUENCE: 64

```
gtggataaag agttgttgaa gaagaagagc tacgatgaga ttgagttaga cgaaatggta    60
agagtagctt tgttgtgcac acagtacctg ccaggacata gaccaagagt gtctgaagtt   120
gttcgaatgc tggaaggaga tggacttgca gagaagtggg aagcttctc aaggatcaga   180
cagtgtttca aaatgtagca acaggataaa tgaagtgatg tcatcttcag acagatactc   240
tgatgttacc gatgactcta gtttacgtgt gcaagcaatg gagctctctg gtcctagatg   300
aagtctatac atgaatctga agaagaagaa gaacatgcat ctgtttcttg aatcaagagg   360
gattcttgtt tttttgtata atagagaggt tttttggagg gaaatgttgt gtctctgtaa   420
ctgtataggc ttgttgtgta agaagttatt actgcactta gggttaagtc aaagttcttt   480
acataagggg ggattagttg cgttgaatag agggaacact ttgggagatt tcatgtgtga   540
aagttgggaa gtcatgtttg agaatgaagg ttatcttatt attgaa              586
```

<210> SEQ ID NO 65
<211> LENGTH: 99
<212> TYPE: PRT
<213> ORGANISM: Arabidopsis thaliana
<220> FEATURE:
<223> OTHER INFORMATION: /note="Arabidopsis thaliana RKS-15 partial protein sequence"

<400> SEQUENCE: 65

```
Val Asp Lys Glu Leu Leu Lys Lys Ser Tyr Lys Glu Ile Glu Leu
 1               5                  10                  15

Asp Glu Met Val Arg Val Ala Leu Leu Cys Thr Gln Tyr Leu Pro Gly
```

```
                    20                  25                  30

His Arg Pro Arg Val Ser Glu Val Arg Met Leu Glu Gly Asp Gly
            35                  40                  45

Leu Ala Glu Lys Trp Glu Ala Ser Gln Gly Ser Asp Ser Val Ser Lys
 50                  55                  60

Cys Ser Asn Arg Ile Asn Glu Val Met Ser Ser Asp Arg Tyr Ser
 65                  70                  75                  80

Asp Val Thr Asp Ser Ser Leu Arg Val Gln Ala Met Glu Leu Ser
                85                  90                  95

Gly Pro Arg

<210> SEQ ID NO 66
<211> LENGTH: 396
<212> TYPE: DNA
<213> ORGANISM: Arabidopsis thaliana
<220> FEATURE:
<223> OTHER INFORMATION: /note="Arabidopsis thaliana RKS-16 partial cDNA
      sequence"

<400> SEQUENCE: 66
aaagtacgtg gaagcagaag tggagcagct gatacgaatg gctctgctct gcactcaaag      60
ttctgcaatg gaacgtccaa agatgtcaga agtagtgaga atgctggaag gagatggttt     120
agctgagaga tgggaagaat ggcaaaagga ggagatgcca atacatgatt ttaactatca     180
agcctatcct catgctggca ctgactggct catcccctat tccaagtccc ttatcgaagg     240
cgattacccc tcgggtccaa gataacctttt tagaaagggt ctttttcttgt gggttcttca    300 acaagtatat atatagattg gtgaagttttt aagatgcaag agggggccat gcacttttga    360
atatcacctc ctctataagt agtattgtgt ctcttg                                396

<210> SEQ ID NO 67
<211> LENGTH: 87
<212> TYPE: PRT
<213> ORGANISM: Arabidopsis thaliana
<220> FEATURE:
<223> OTHER INFORMATION: /note="Arabidopsis thaliana RKS-16 partial protein
      sequence"

<400> SEQUENCE: 67

Lys Tyr Val Glu Ala Glu Val Glu Gln Leu Ile Arg Met Ala Leu Leu
 1               5                  10                  15

Cys Thr Gln Ser Ser Ala Met Glu Arg Pro Lys Met Ser Glu Val Val
                20                  25                  30

Arg Met Leu Glu Gly Asp Gly Leu Ala Glu Arg Trp Glu Glu Trp Gln
            35                  40                  45

Lys Glu Glu Met Pro Ile His Asp Phe Asn Tyr Gln Ala Tyr Pro His
 50                  55                  60

Ala Gly Thr Asp Trp Leu Ile Pro Tyr Ser Lys Ser Leu Ile Glu Gly
 65                  70                  75                  80

Asp Tyr Pro Ser Gly Pro Arg
                85
```

REGENERATION

This application is a divisional of, and claims priority to, application Ser. No. 10/111,018 filed Sep. 9, 2002 now abandoned, which claims priority to PCT/NL00/00765 filed Oct. 22, 1999.

BACKGROUND OF THE INVENTION

The invention relates to the field of regeneration of cells, self-renewal of (micro)-organisms, the vegetative propagation of plant parts such as plant tissues or organs thereof, for example cells grown in tissue or organ culture, and more in particular to the seedless propagation of plants.

Renewal of plant and animal cells into more cells, tissues, organs and even whole plants and organisms is a process central to life that has been set to men's whims and desires already for a long time. Self-renewal of specific micro-organism starter cultures are used to ferment foods and drinks. Yet other cultures are useful for the metabolites they produce per se, such as produced by modern day's large scale fermentor cultures for the production of antibiotics or enzymes. Within the realm of animal cells, use of the renewed cultured cells, although being of fairly recent date, has taken great flight with the production of for example viral vaccines in cell- or tissue culture. Even more recent is the use of donor cells harvested from an individual, and grown and/or differentiated in culture, for transplantation purposes. Such cells (take for example bone marrow cells) are, after having been sufficiently regenerated and differentiated, proliferated or equipped with the desired characteristics, transplanted into a recipient for medical purposes. Shortly, such therapies will even include transgenic cells, transformed with modern recombinant techniques, that are thereby equipped with the desired characteristics and transplanted.

Regeneration is very well studied in plants, where it is crucial in vegetative propagation. In principle, plants can be propagated in two ways, via seeds or vegetatively without using seeds as starting material to obtain the desired plant. Both types of propagation may be impossible or undesirable under certain conditions. When propagation via seeds is unsatisfactory (when no seeds or too few of the desired seeds are formed or the desired seeds quickly loose their germination viability) then seedless propagation is often adopted. Also, when due to sexually crossing a very heterogenous progeny is or may be obtained due to its strong heterozygosity, propagation via seeds is often also considered unsatisfactory. Of course, seedless propagation of essentially seedless starting material may in a later phase give rise to the desired seeds, which can further be used to obtain the desired plants.

Within seedless propagation of plants two major fields can be distinguished: In vivo and in vitro vegetative propagation. In vivo vegetative propagation (via for example cuttings, splitting or division, layering, earthing up, grafting or budding, and other methods known to the gardener or horticulturist), has for many years played an important role in agriculture; e.g. with potatoes, apples, pears, many ornamental bulbs and tuberous plants like potatoes, many arboricultural crops, carnations, chrysanthemums, etc. Vegetative propagation is also very important in plant breeding: parent lines have to be maintained and propagated vegetatively for seed production; cloning is often required for setting up gene banks; adventitious shoot formation is needed to obtain solid mutants after mutation induction.

However, the classical methods of in vivo vegetative propagation often fall short (to slow, too difficult or too expensive) of that required or are completely impossible. In the last couple of decades, since the discovery that plants can be more rapidly cloned in vitro than in vivo, knowledge concerning vegetative propagation has grown quickly; this holds equally true for plants from temperate, subtropical as well as tropical regions. It has now even become possible to clone species by in vitro culture techniques that are impossible to clone in vivo. Different methods of in vitro vegetative or seedless propagation from plant starting material are for example using single-node cuttings, axillary branching, regeneration of adventitious organs (roots or shoots) on starting material such as explants or callus tissue and regeneration of plants from suspensions of, or even single, cells or protoplasts used as starting material. For the generation of transformed or transgenic plants, in vitro propagation is even considered a prerequisite, since it is the totipotency of individual plant cells that underlies most plant transformation systems.

To propagate plants from starting material in vitro, it is in principle necessary that at least one cell in the starting material is capable of regeneration. The ability to regenerate is for example determined by the genotype, the environmental conditions (nutrient supply, regulators and physical conditions) or the developmental stage of the plant, or combinations of these. It is well known that some families and genera have high regeneration ability: Solanacea (*Solanum, Nicotiana, Petunia, Datura,* and *Lycopersion*), Crucifera (*Lunaria, Brassica, Arabidopsis*), Generiaceae (*Achimenes, Saintpaulia, Streptocarpus*) Compositae (*Chicornum, Lactuca, Chrysantemum*), Liliaceae (*Litium, Haworthia*) Allium, *Ornithogalum*) but others, such as many decorative plants, woody species such as shrubs, conifers or trees, especially fruit trees, *Rosacea, Alstroemeria, Euphorbia*, and bulbs such as *Tulipa*, and others are notoriously difficult, even with in vitro techniques.

As indicated above, regeneration (self-renewal of (micro-) organisms and self-renewal of plants, animals or parts thereof, i.e. vegetative reproduction/propagation) can also be considered a repair strategy observed throughout the realm of micro-organisms, animal and plant species. Regeneration in plants for example comprises the formation of new tissues containing both root and shoot meristems, separate shoot or root meristems, plant organs or organ primordia from individual cells or groups of cells. Regeneration in general mimics the process of normal cellular and organ differentiation that takes place during plant development and results in the formation of the different plant organs. In normal development, early in ontogony, cells and tissues of common lineage diverge into often contrasting paths of development as they respond to developmental signals. This ability to develop in response to a specific signal is also known as cellular competence or cellular potentiality. As competent cells become committed to particular paths of differentiation, they are not readily diverted into other pathways; this restriction of the developmental potentiality of cells is referred to as determination.

Plant cells or groups of cells that under normal conditions are unable to initiate the formation of certain plant organs, meristems or organ primordia can often be stimulated by extracellular stimuli modifying the differentiation stage of the cell. Extracellular diffusible factors have shown to be essential for cellular redifferentiation in plant cells (Siegel and Verbeke, 1989 Science 244, 580-582). The perception of these signals at the cellular surface and the intracellular signal transduction that finally result in changes in transcriptional regulation provides cells with the ability to respond to such extracellular stimuli. Regeneration can result in the formation of either a shoot alone or a root alone or both together. Only after redifferentiation of a cell or tissue, regeneration is possible that results in differentiated tissue that again comprises the necessary three-dimensional layout of the emerging plant, the apical-basal or shoot-root body plan from which the mature desired plant can develop.

Indeed, central in in vitro techniques for seedless propagation are phytohormones and other factors often added to the culture medium that mimic these extracellular stimuli. For the process of regeneration of the original starting cell into a multicellular totipotent tissue underlying and preceding somatic embryogenesis or organogenesis in vitro in cell, tissue or explant cultures which lead to a fully differentiated plant again, in general a well balanced, and per plant species often different, phytohormone addition to the culture is required. Overall, a balance is required between auxins on the one hand and cytokinin on the other. After exogenous exposure to auxin (such as 2,4-dichlorophenoxyacetic acid (2,4-D), chloramben or dicamba) or cytokinin (such as 6-benzylaminopurine or zeatine) or both, cells or tissue react by development of the shoot-root body plan, for example by forming shoots and/or roots, sometimes readily, sometimes erratically especially when the proper balance between the hormones is not properly selected.

Regeneration in vitro and especially the manipulatable nature of in vitro culture thus depends mainly on the application of these two types of hormones, and also on the ability of the tissue to respond to phytohormonal changes during culture. In general, three phases of regeneration are recognisable. In the first phase, cells in the culture acquire "competence", which is defined as the ability (not capacity) to respond to hormonal signals of organ induction. The process of acquisition of said organogenic competence is often referred to as "dedifferentiation" of differentiated cells to acquire organogenic competence. The competent cells in the culture are canalised and determined for specific tissue and organ formation for re-entry of quiescent cells into cell cycle, and organisation of cell division along the lines of the shoot-root body plan to form specific primordia and meristems under the influence of the phytohormone balance through the second phase. Especially auxin is thought to be involved in specific regenerative signal transduction pathways for adventitious root initiation, whereas cytokinin is thought to be involved in specific regenerative signal transduction pathways for adventitious shoot initiation.

Then the morphogenesis, the growing of the plant to its fully differentiated state, proceeds independently of the exogenously supplied hormones during the third phase.

Although the general principles governing regeneration via addition of exogenous phytohormones are thus fairly well understood, designing working in vitro culture protocols finding the right balance, the right time of administration or the right type or subtype of said hormones for a great many individual species is still more or less a process of trial-and-error. However, as already indicated above, for in vitro regeneration or seedless propagation of a great many plant species is a large interest, especially for those that are in general hard to propagate.

The invention provides a culture method for propagation of a plant from plant starting material wherein, especially in the phase of the development of the shoot-root body plan, root or shoot initiation is stimulated by introducing at least one recombinant gene product or functional fragment thereof in said starting material, for example by stimulating at least one signal transduction pathway for root or shoot initiation, said gene product or gene products for example derived from a gene or genes involved in the regulation of plant development, allowing reducing or omitting exogenous phytohormone addition to said culture in the regeneration process. In a preferred embodiment the invention provides a culture method for vegetative propagation of plants from plant starting material comprising regeneration of said starting material wherein during regeneration of said starting material at least one specific signal transduction pathway for adventitious root or shoot initiation is endogenously stimulated allowing reducing or omitting exogenous phytohormone addition to said culture, in particular wherein said pathway is endogenously stimulated by a recombinant gene product derived from a gene involved in the developmental regulation of regeneration, such as a gene or gene product involved in hormone production, a gene or gene product giving feed back on hormone production, or involved in the cascade of events leading to regeneration.

Preferably, the method as provided by the invention comprises at least one step of in vitro culture, since it is in in vitro culture that the auxins or cytokinins are most widely used, in the regeneration process, especially for plants that are notoriously difficult to regenerate for vegetative propagation such as many decorative plants, woody species such as shrubs, conifers or trees, especially fruit trees, *Rosacea, Alstroemeria, Euphorbia*, and bulbs such as *Tulipa*. However, clearly, said hormones are also commonly used in in vivo cultures as well, (in vivo cultures essentially being all crop or plant culture methods traditionally used in agriculture) where such hormones are commonly added by (root or stem) dipping, spraying or watering. Especially those plants that are propagated in an essential seedless way can now be regenerated or propagated more easily, consequently, in a preferred embodiment, the invention provides a culture method for essentially seedless propagation of plants from plant starting material comprising regeneration of said starting material wherein during regeneration at least one specific signal transduction pathway for adventitious root or shoot initiation endogenously is stimulated, e.g. by above mentioned gene product, allowing reducing or omitting exogenous phytohormone addition to said culture.

SUMMARY OF THE INVENTION

Essentially seedless propagation herein is defined in that said starting material essentially comprises no seeds, or at least that seed possibly present in said starting material does not lay at the basis of the regeneration of said starting material or does not develop into the desired plant. However, as one aspect of the culture method comprising regeneration as provided by the invention, during or after the process of regeneration or propagation according to the invention seed may be formed, from which even a desired plant may develop, which is a result of the propagation according to the invention, rather than that it lays at the basis thereof.

In particular, the invention provides a culture method wherein said starting material comprises an individual plant cell or protoplast or explant or plant tissue, materials which are commonly used in in vitro culture methods whereby the addition of phytohormones was thought to be axiomatic. Now such addition is no longer necessary or can be reduced, providing an easier way of in vitro culture, wherein not such an intricate balance between the addition of the various hormones has to be sought.

The invention provides manipulation of propagation characteristics of for example plant tissue. Numerous plant species are propagated in tissue culture in order to obtain large amounts in a relative short period of time. Using the invention it is relatively easy to increase the multiplication factor several times. For several notoriously difficult species, like shrubs, trees en various bulbous species it is now also possible to use esssentially seedless propagation, and especially in vitro culture, when using the invention. The regeneration capacity of cells or tissue isolated from these plants is increased significantly, thereby increasing the multiplication factor by introducing of certain bioactive molecules, like nucleic acid or (modified) protein. The nucleic acids or proteins may be introduced by the methods known in art, like particle gun bombardment, electroporation, micro-injection or other techniques described in the introduction. The introduced molecules are either nucleic acid, being RNA, or naked DNA with a small chance of becoming integrated in the genome, or (modified) protein product. The molecules will in general be lost during the regeneration process and are therefore only transiently present. The nucleic acids that may be used encode or produce proteins that stimulate the regeneration process and reduce or eliminate the use of exogenously added planthormones. The proteins that may be added are the protein products of these nucleic acids or their modified forms. Examples of molecules with the above described characteristics are proteins or genes coding for proteins involved in the regulation of plant development or perception of plant hormones. By using the invention the multiplication factor can be increased so much that it will be possible to use in vitro propagation techniques in a broader sense and also for the more difficult species, Also, by using the invention it is relatively easy to permanently increase the propagation characteristics for these plants. The regeneration capacity of these plants can be increased significantly if these plants are made transgenic by introducing a gene coding for proteins involved in the regulation of plant development or perception of plant hormones or more specific a gene coding for a product stimulating or inducing one signal transduction pathway for root or shoot initiation or even more specific a gene coding for a representative of the plant receptor kinase family RKS. Transformation can be achieved using the techniques known in the field like *Agrobacterium* mediated transformation, particle gun bombardment, the above described marker-free transformation system or others and select for non-lethal expressors of the gene.

In one preferred embodiment, the invention provides a culture method according to the invention wherein said starting material comprises a desired somatic mutation. Mutations can occur in any cell of a living organism, but are only transferred to the offspring when this mutation occurred in those cells from which gametophytic cells of that organism are derived. Somatic mutations are usually lost unless the tissue in which the mutation is apparent is vegetatively propagated or if cells in this tissue are regenerated to form an intact new organism. Using the technology described in this invention the rescue of somatic mutations in plants is provided. Somatic, but also generative tissue is stimulated to regenerate by the introduction of bioactive molecules, like nucleic acid or (modified) protein as provided by the invention. The nucleic acids or proteins may be introduced by the methods known in art, like particle gun bombardment, electroporation, micro-injection or other techniques described. The introduced molecules are either nucleic acid, being RNA, or naked DNA with a (not necessarily) small chance of becoming integrated in the genome, or (modified) protein product. The molecules will in general be lost during the regeneration process and are therefore in general only transiently present. The nucleic acids that may be used encode proteins that stimulate the regeneration process and reduce or eliminate the use of exogenously added planthormones. The proteins that may be added are the protein products of these nucleic acids or their modified forms. Examples of molecules with the above described characteristics are proteins or genes coding for proteins involved in the regulation of plant development or perception of plant hormones. Alternatively somatic mutations may have been created by treatment of seeds with mutagenic agents, like colchicines, EMS, radiation or carcinogenic substances etc. The sectors in these mosaic plants grown from these treated seeds will be screened for desirable phenotypes. The interesting sectors will subsequently be isolated and used as starting material for regeneration by the above-described invention in order to obtain clonal propagation of these desired traits.

In another preferred embodiment, the invention provides a culture method according to the invention wherein said starting material comprises transgenic material. These days transgenic plants are being produced rapidly, albeit often in only limited numbers. To rapidly acquire sufficient numbers of plants for further propagation under field conditions, in vitro culture techniques are widely used. The invention now provides a method wherein little or no attention has to be given to phytohormone levels in such transgenic plants cultures.

In particular, the invention provided a method wherein said starting material additionally comprises starting material comprising a recombinant nucleic acid encoding a desired trait. The invention herewith provides essentially marker-free transformation, or at least it provides plants that after transformation and propagation are essentially marker-free. A recombinant nucleic acid encoding a desired trait, that one would like to integrate in a plant's genome is provided to at least part of said starting material with gene delivery vehicles or methods, such as vectors, particle bombardment, electroporation, micro-injection or other techniques described in the art. Cells comprising said recombinant nucleic acid are also provided according to the invention with at least one recombinant gene product or functional fragment thereof, for example by stimulating at least one signal transduction pathway for root or shoot initiation, said gene product or gene products for example derived from a gene or genes involved in the regulation of plant development, allowing reducing or omitting exogenous phytohormone addition to said culture.

In particular, the invention provides a culture method for vegetative propagation of plants from plant starting material having been provided with a recombinant nucleic acid encoding a desired trait comprising regeneration of said starting material wherein during regeneration of said starting material at least one specific signal transduction pathway for adventitious root or shoot initiation is endogenously stimulated allowing reducing or omitting exogenous phytohormone addition to said culture, in particular wherein said pathway is endogenously stimulated by a recombinant gene product derived from a gene involved in the developmental regulation of regeneration, such as a gene or gene product involved in hormone production, a gene or gene product giving feed back on hormone production, or involved in the cascade of events leading to regeneration.

In a preferred embodiment, said recombinant nucleic acid encoding a desired trait has additionally been provided with means for nuclear targeting and/or integration in a plant genome. Such means can be nucleic acid signals incorporated with the recombinant nucleic acid encoding the desired trait, or proteinaceous substances such as transposases, or viral or bacterial proteins (such as Vir-proteins) to protect the recombinant nucleic acid inside the cell, taking care of proper targeting towards the nucleus and/or stimulating proper integration.

Even more preferred, the invention provides a method wherein said starting material comprises a to be transformed individual plant cell or protoplast or explant or plant tissue comprising recombinant nucleic acid encoding a desired trait among other, non-transformed starting material from which the transformed material has to be selected.

In general, as a part of the process of for example plant transformation, dominant selectable markers are used to select transgenic cells from which transgenic plants can be regenerated. For one thing, these marker genes are generally superfluous once an intact transgenic plant has been established. Furthermore, selectable marker genes conferring for example antibiotic or herbicide resistance, used to introduce economically valuable genes into crop plants have major problems: detoxification of the selective agent by expression of a modifying enzyme can enable untransformed cells to escape, dying untransformed cells release products which are toxic and inhibit the regeneration of transformed cells, the selective agents may have negative effects on proliferation and differentiation of cells, there is uncertainty regarding the environmental impact of many selectable genes, and it is difficult to perform recurrent transformations using the same selectable marker to pyramid desirable genes. The invention now provides a method reducing or omitting selective agent addition to said culture.

Attempts have been made earlier to design transformation systems allowing marker gene elimination to obtain marker-free transformants of diverse plant species whereby the marker gene used is removed from the transformed cell after it has performed its task. One method involves co-transformation of cells mediated by *Agrobacterium tumefaciens* with binary vectors carrying two separate T-DNAs, one for example comprising a drug-resistance selection marker gene, another comprising the desired gene, followed by conventional out-breeding the undesired drug-resistance gene, that is thought to localise at a different locus than the desired gene. Although drug sensitive transformants comprising the desired gene may be thus obtained it is not clear whether all these transformants are indeed totally free of (non or partly functional) selection marker-gene or fragments thereof. Also, the selective agent initially used still has the unwanted negative effects on proliferation and differentiation of plant cell during the transformation process. Furthermore, the method requires sexual crossing which limits it to plant species where sexual crossing, and not vegetative reproduction, is the practical method of reproduction, and practically limits it even further to those plant species with a sufficient short generation time.

One strategy currently available to eliminate the superfluous marker after the cell has been transformed without the need to sexually cross plants is the MAT vector system. However, said system relies on intrinsic post-transformational excision of the selection gene which is comprised in a transposable element, an event which only haphazardly occurs and reduces the final efficiency of the transformation process.

Yet another strategy involves site specific recombination such as seen with the Cre-Lox system whereby in a first transformation the selection-marker gene is inserted at a previously determined specific site, allowing selection of transformed cells, after which in a second transformation comprising the introduction of a site specific recombinase, the selection-marker gene is again excised from the genome.

Needless to say that, apart from other problems, the prerequisite of having a suitable site in the to be transformed cell available restricts said method to those organisms of which the genome is well known. The invention now provides a method to obtain transformed plants by in vitro culture wherein said transgenic material is devoid of a selectable marker gene conferring resistance to an selective agent. Resistance to selective agents is no longer needed since according to the invention the transformed material is equipped with the necessary recombinant gene product or gene products or functional fragment(s) thereof derived from a gene involved in the regulation of plant development allowing reducing or omitting exogenous phytohormone addition to said culture, thereby giving preferred growth conditions to the transformed cells over those non-transformed cells that have not been provided with said gene product or functional fragment thereof. In particular, the invention provides a culture method for vegetative propagation of plants from transformed plant starting material comprising regeneration of said starting material wherein during regeneration of said transformed starting material at least one specific signal transduction pathway for adventitious root or shoot initiation is endogenously stimulated allowing reducing or omitting exogenous phytohormone addition to said culture, in particular wherein said pathway is endogenously stimulated by a recombinant gene product derived from a gene involved in the developmental regulation of regeneration. The beauty of it is that no selectable marker gene conferring resistance to a selective agent has to be introduced in said material at all, thereby obviating the need to deplete the transformed material of such marker genes afterwards. In particular, the invention thus does not make use of resistance to antibiotic or herbicides, and does nor carry all the disadvantages associated herewith.

In short, most plant transformation systems are based on the selection for herbicide or antibiotic resistance or selection for transformants is based on the presence of an additional selection marker besides the trait itself. Using the technology described in this invention, markerless transformation in plants is provided. This new transformation/regeneration (t/r) system for example consist of two components (FIG. 20). A first component in this example is the trait, which may be present between the borders of Agrobacterial T-DNA, but apart from a suitable promoter no other DNA is needed. This first component may be single or double stranded DNA and may be in vitro coated with the VirE2 protein and/or a molecule of VirD2 (preferentially covalently attached to the 5'-end of this DNA). The Vir-proteins may be present to protect the DNA inside the plant cell, take care of proper targeting towards the nucleus and will stimulate proper integration into plant DNA. Tissue will be stimulated to regenerate by the introduction of certain bioactive molecules. These bioactive molecules act as the second component. The second component is either nucleic acid, being RNA, or naked DNA with a small chance of becoming integrated in the genome, or (modified) protein product.

The nucleic acids or proteins (second component) may be introduced mixed with the first component by the methods known in art, like particle gun bombardment, electroporation, micro-injection or other techniques described in the introduction. Both components have to be present in the plant cell together in sufficient quantities, but the ratio between the two components may vary depending on the species and the preferred number of integration's of the trait in the plant DNA. The second component will preferably be lost during the regeneration process and is therefore only transiently present, whereas the first component has a high change of becoming integrated into the plant genome. The second component is a nucleic acid or a mixture of nucleic acids that will produce proteins that stimulate the regeneration process and reduce or eliminate the use of exogenously added planthormones or is the protein product or a mixture of products of these nucleic acids or their modified forms or a mixture of both. Examples of molecules with the above described characteristics are proteins, or genes coding for proteins involved in the regulation of plant development or perception of plant hormones.

The main advantages of the this t/r-system are, as explained with the example of FIG. 20:

only the trait is introduced into the plant DNA; apart from the T-DNA borders (Only in the case when VIR proteins are used, it is necessary to include T-DNA borders onto the trait DNA), if present, no other unwanted DNA, like a selection marker, is present. In order to allow the process of homologous recombination of the trait DNA into the corresponding endogenous DNA on the plant genome, genes or gene products encoding At R51, AtRAD51 or RecA or gene products with similar function can be applied in the second component in order to result in transient expression of the recombinase. After targeting and localized integration of the trait DNA, the recombinase is lost.

the principle of regeneration is universally applicable the amount of exogenous plant hormones for regeneration can be reduced or omitted active selection is not necessary as mainly transformed cells will regenerate.

Said gene involved in the regulation of plant development can be selected from a great many genes already known, or yet to be determined, to be involved in regeneration. Examples of such genes are clavata (Clark et al., 1997, Cell 89, 575-585) and primordia timing genes (Mordhorst et al. 1998 Genetics 149, 549-563), which are stimulating regeneration when inactivated, leafy-Cotelydon gene (LEC, Lotan et al., 1998, Cell 93, 1195-1205), the KAPP gene (Stone et al., 1994, Science 266, 793-795; Stone et al., 1998, Plant Physiol. 117, 1217-1225), IPT (Morris, R. O., 1986 Annu. Rev. Plant Physiol. 37, 509-538), WUSCHEL (Mayer et al. 1998 Cell 95, 805-815; Schoof et al. 2000 Cell 100, 635-644), KNAT1&2 (the *Arabidopsis* kn1-like gene) (Chuck et al. 1996. Plant Cell 8, 1277-1289; Lincoln et al. 1994 The Plant Cell 6, 1859-1876), SHOOT MERISTEMLESS gene (Endrizzi et al. 1996 Plant J. 10, 967-979), CUP-SHAPED COTYLEDON (Aida et al. 1999 Development 126, 1563-1570), CYCLIN D (Cockcroft et al. 2000 Nature 405, 575-579; Riou-Khamlichi et al. 1999 Science 283, 1541-1544), CKI1 (Kakimoto 1996 Science 274, 982-985), AINTEGUMENTA (Mizukami and Fischer 2000 PNAS 97, 942-947; Krizek 1999 Dev. Genetics 25, 224-236), SBP-box proteins (Cardon et al. 1999 Gene 237, 91-104), CDC2a (Hemerly et al. 1993 The Plant Cell 5, 1711-1723), which are genes that stimulate regeneration when induced or overexpressed, or antagonists thereof or others that are involved in the regulation of plant development in the broadest sense, such as can be found by studying plant embryogenesis or organogenesis on the molecular level. In particular, a population of gene products involved in regeneration is represented by the intracellular signal transduction factors that are directly phosphorylated by RKS protein and thereby activated.

In a preferred embodiment, the invention provides a method according to the invention wherein said gene involved in the regulation of plant development encodes a leucine-rich repeat containing receptor-like kinase, such as present in plant database collections, with homology to the extracellular domain of the *Arabidopsis* RKS protein family, such as:

GB:AW011134 AW011134 ST17B03 *Pinus taeda*
GB:LELRPGENE X95269 *L. esculentum*
GB:AI775448 AI775448 EST256548 *Lycopersicon esculentum*
GB:AI496325 AI496325 sb05c09.y1 Gm-c1004 Glycine
GB:AI487272 AI487272 EST245594 *Lycopersicon esculentum*
GB:AI441759 AI441759 sa82d08.y1 Gm-c1004 Glycine max
GB:AI782010 AI782010 EST262889 *Lycopersicon esculentum*
GB:AI772079 AI772079 EST253179 *Lycopersicon esculentum*
GB:SBU62279 U62279 *Sorghum bicolor*
GB:C22645 C22645 C22645 *Oryza sativa*
GB:D49016 D49016 RICS15625A *Oryza sativa*
GB:AI776399 AI776399 EST257499 *Lycopersicon esculentum*
GB:AI776208 AI776208 EST257308 *Lycopersicon esculentum*
GB:AI352795 AI352795 MB61-10D PZ204.BNlib *Brassica napus*
GB:AQ578072 AQ578072 nbxb0092C18f *Oryza sativa*
GB:C95313 C95313 C95313 *Citrus unshiu Miyagawa*
GB:AI162893 AI162893 A026P38U *Hybrid aspen*
GB:AI782076 AI782076 EST262955 *Lycopersicon esculentum*
GB:AI726177 AI726177 BNLGHi5165 *Cotton*
GB:AI777982 AI777982 EST258861 *Lycopersicon esculentum*
GB:AI774881 AI774881 EST255981 *Lycopersicon esculentum*
GB:AI896737 AI896737 EST266180 *Lycopersicon esculentum*
GB:AI676939 AI676939 605047A07.x1 *Zea mays*
GB:D40598 D40598 RICS2674A *Oryza sativa*
GB:OSU82168 U82168 *Oryza sativa*
GB:SBRLK1 Y14600 *Sorghum bicolor*
GB:AI495359 AI495359 sa97a09.y1 Gm-c1004 Glycine max
GB:C96041 C96041 C96041 *Marchantia polymorpha*, or such as present in plant database collections, with homology to the intracellular domain of the *Arabidopsis* RKS protein family, such as:

GB:AI896277 AI896277 EXT2657200 *Lycopersicon esculentum*
GB:AU056335 AU056335 AU056335 *Oryza sativa*
GB:AA738546 AA738546 SbRLK4 *Sorghum bicolor*
GB:AA738544 AA738544 SbRLK2 *Sorghum bicolor*
GB:AA738545 AA738545 SbRLK3 *Sorghum bicolor*
GB:SBRLK1 Y14600 *Sorghum bicolor*
GB:AI729090 AI729090 *Gossypium hirsutum*
GB:AI920205 AI920205 *Pinus taeda*
GB:AI89183 AI896183 EST265626 *Lycopersicon esculentum*
GB:AI967314 AI967314 *Lotus japonicus*
GB:AI730535 AI730535 *Gossypium hirsutum*
GB:AF078082 AF078082 *Phaseolus vulgaris*
GB:CRPK1 Z73295 *C. roseus*
GB:C22536 C22536 C22536 *Oryza sativa*
GB:C22530 C22530 C22530 *Oryza sativa*
GB:ZMA010166 AJ010166 *Zea mays* mRNA
GB:AQ271213 AQ271213 *Oryza sativa*, or known from Schmidt et al (1997, Development 124, 2049-2062, WO 97/43427), where for example stable transformation, but not regeneration, nor transient expression nor use in selection, of plants with SERK (RKS0) is considered. Also applicable in a method according to the invention are bacterial genes or fragments thereof such as the AK-6b gene (Wabiko et al, Plant Physiol. 1996, 939-951) or the rolABC genes (Jasik J, Plant Science, 1997, 57-68), however, where only regeneration by stable transformation is intended, plant genes such as those disclosed herein are preferred.

Figure 3:
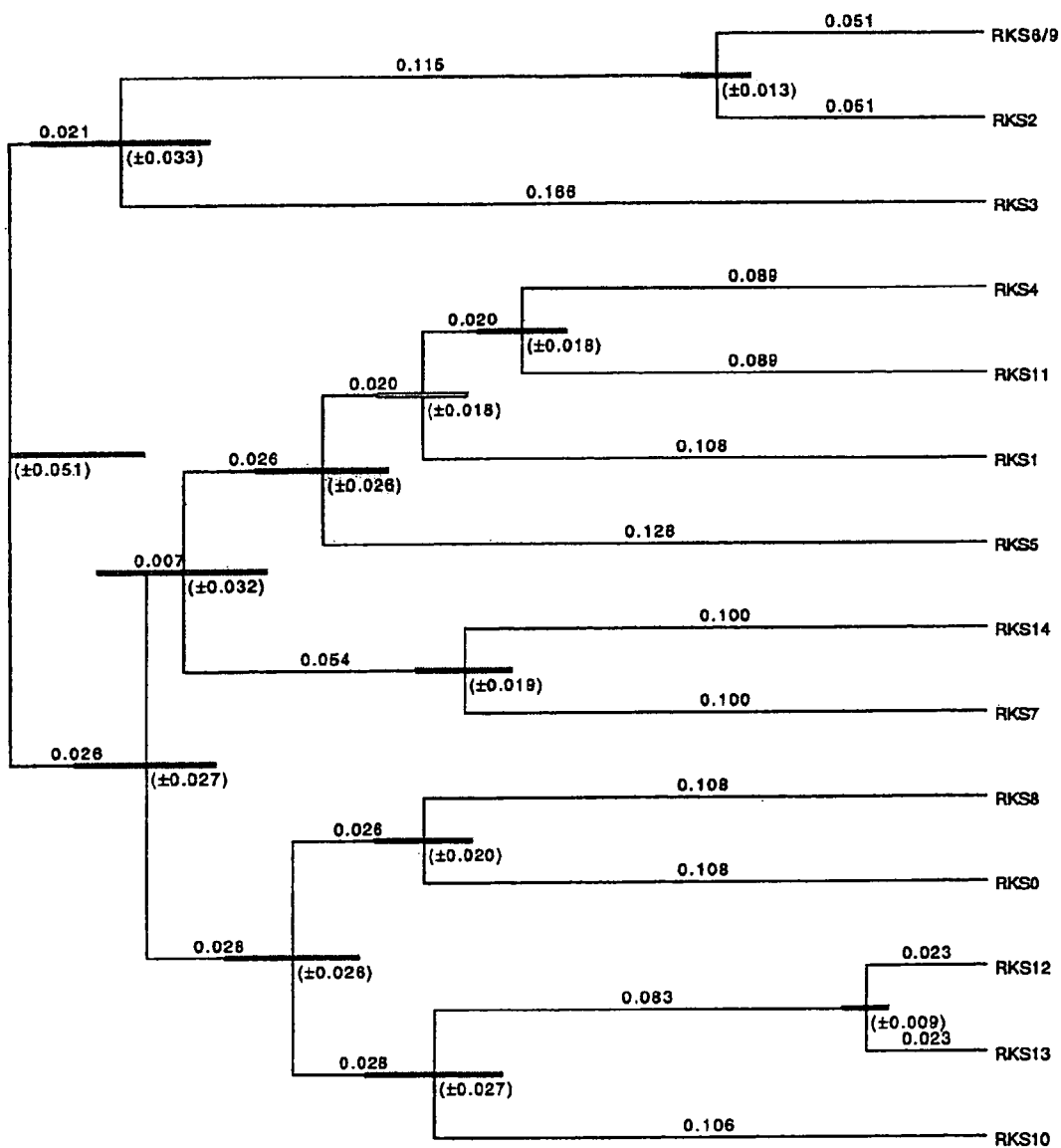

In a preferred embodiment, the invention provides a method according to the invention wherein said gene involved in the regulation of plant development encodes a leucine-rich repeat containing receptor-like kinase, wherein said receptor-like kinase is a representative of a plant receptor kinase family RKS such as shown in FIG. 3.

In particular, the invention provides a method wherein said gene product or functional fragment thereof is derived from a receptor-like kinase that comprises an N-terminal signal sequence, an extracellular region comprising a leucine zipper domain, a disulphate bridge domain, a leucine rich repeat domain comprising 3-5 leucine rich repeats, a transmembrane domain, an intracellular region comprising an anchor domain, a serine/threonine kinase domain and/or a C-terminal leucine rich repeat domain.

These genes encode membrane spanning proteins having a particular function in signal transduction, thereby being prime candidate genes to provide gene products or functional fragments thereof to be employed in a method of the current invention.

In particular, the invention provides a method wherein said receptor-like kinase is encoded by a nucleic acid which in *Arabidopsis thaliana* comprises a sequence as shown in anyone of FIG. 4 or 8 to 20. Suitable receptor kinase-like genes from plants other than *Arabidopsis thaliana*, such as *Daucus carota, Rosa, Gerbera, Chrysanthemum, Alstroumeria, Lilium, Tulipa, Dyanthus, Cymbidium, Gypsopays, Ficus, Calangoe, Begonia, Phalasnopsis, Rhonondendrum, Spatiphilus*, Cucubitaceae, Solanaceae, and grasses such as cereals are easily found using the *Arabidopsis thaliana* sequences provided herein by methods known in the art. In general for each RKS gene identified in *Arabidopsis thaliana* a corresponding RKS gene is present in individual species of both monocotyledon as well as in dicotyledon plants. The invention provides a method wherein said receptor-like kinase is encoded by a plant derived nucleic acid corresponding or homologous to a nucleic acid which in *Arabidopsis thaliana* comprises a sequence as shown in anyone of FIG. 4 or 8 to 20. Corresponding or homologous RKS genes and gene products in plant species other than *Arabidopsis thaliana* are isolated by various approaches. For example by screening of cDNA and genomic libraries using *Arabidopsis* RKS cDNA probes under low stringency hybridisation/washing conditions as described above, alternatively by the use of degenerated RKS primers (for example primer combination RKS B forward and RKS E reverse as shown herein in order to amplify an exon fragment of the desired gene. Full length cDNA clones can further be obtained by race and tail PCR approaches Also, the generation of antibodies recognising conserved or distinct and specific regions within different members of RKS gene family within a plant species allow the desired isolation. Alternatively, specific antibodies are generated that recognise one specific RKS gene product in a variety of plant species. These antibodies are used to screen cDNA expression libraries of plant species. Furthermore, it is possible to screen for RKS-homologous sequences in electronic databases. Searches are performed both on nucleotide and on amino acid level. Additionally, RKS genes and gene products in plant species other than *Arabidopsis thaliana* are isolated for example by two or three hybrid screenings in yeast with RKS clones in other to isolate (hetero) dimerizing members of this RKS family in similar or unrelated plant species.

In one embodiment, the invention provides a method for propagation of a plant from plant starting material wherein during regeneration of said starting material at least one signal transduction pathway for root or shoot initiation is stimulated by a recombinant gene product or functional fragment thereof derived from a gene involved in the regulation of plant development allowing reducing or omitting exogenous phytohormone addition to said culture, wherein said gene product or functional fragment thereof is introduced in at least a part of the starting material by transformation. The invention also provides the introduction of regenerating gene constructs into cells which can lead to the regeneration of the cell itself or to the induction of regeneration processes in neighbouring cells, even somatic embryos resulting from said induced cells are provided herewith. Individual transformed cells are generated that are essential for the differentiation state of surrounding cells. Introduction of such an inducing regenerator as provided herewith into plant cells results in the formation of a proliferation of neighbouring cells and the formation of new plants or parts thereof from these proliferating cell masses. The originally transformed plant is not necessarily included in the proliferation process itself an is therefore not necessarily part in the resulting regenerating plants or parts thereof This specific from of induced regeneration of neighbouring cells provide herewith gives the option to regenerate plants that do not contain the introduced gene or gene product, and therefore represents a method to induce regeneration without the necessity to introduce gene products into an originating cell population and having to maintain these gene products or nucleic acids encoding therefore. An example of the process of induced induction is shown in FIG. 6F, where a single GUS positive cell marks the original introduction site for the bombarded DNA constructs. Above this cell, a proliferating cell mass has been formed that is clearly GUS negative. On top of this induced proliferated cell mass, we could detect several structures that morphologically represent somatic embryos. These somatic embryos develop from the borders of the proliferating cell mass as previously described (Schmidt et al. 1997, Development 124, 12049-2062). Somatic embryos provide an excellent source of regenerating plant since all the organs and plant parts are formed by similar processes as take place during zygotic embryogenesis. This observation clearly indicates the potential of this class of regenerating molecules to induce a proliferating, non-transformed cell mass from which new plantlets can be regenerated. It provides the means to induce somatic embryos directly on living plant tissues, even without the prior need to introduce an in vitro culture procedure.

Again, transformation as provided here can be thus either in a stable fashion where the introduced genetic information or nucleic acid is integrated into the nuclear, chloroplast or mitochondrial genome, and is either constitutively or inducibly expressed but preferably is transient, wherein the nucleic acid is not introduced into the genome and gets lost after a certain period after introduction. Transformation of recombinant DNA or RNA into the cell or protoplast can take place in various ways using protocols known in the art, such as by particle bombardment, micro-injection, *Agrobacterium*-mediated transformation, viral-mediated transformation, bacterial conjugation, electroporation, osmotic shock, vesicle transport or by direct gene transfer, with or without the addition of a proteinaceous substance bound to the nucleic acid molecule. Integration of a proteinaceous substance into cells or protoplast can be facilitated along the lines of the transformation protocols as described above. A cell or protoplast thus having been provided with a gene product (i.e. a DNA, RNA or proteinaceous substance or functional fragment thereof) derived from a gene involved in the regulation of plant development can now regenerate on its own, allowing reducing or omitting exogenous phytohormone addition to the culture that comprises that cell or protoplast. The process of vegetative propagation is hereby very much simplified, large numbers of plants with an identical genetic background can now be obtained staring from starting material with the desired characteristics.

In a preferred embodiment, the present invention provides a method for propagation of a plant from plant starting material wherein said starting material comprises a cell or protoplast transformed with a desired nucleic acid sequence intended to provide the resulting transgenic plant arising from that cell or protoplast with desirable characteristics. Such a cell or protoplast, according to the invention having been provided with a gene product (i.e. a DNA, RNA or proteinaceous substance or functional fragment thereof), for example derived from a gene involved in the regulation of plant development can now regenerate on its own, allowing reducing or omitting exogenous phytohormone addition to the culture that comprises that transformed cell or protoplast. Selection for regenerating cells or tissues after the transformation of the desired sequence together with the regenerating gene product results in the recovery of only those plants or plant material that contain the desired nucleic acid sequence, preferably integrated in a stable fashion in the plant's genome, and the regenerating gene product, thereby providing a selection of the desired transgenic plant based on the selective regeneration of the transformed starting material.

In a preferred embodiment, the invention provides a method wherein the regenerating gene product is only transiently expressed, wherein the regenerating gene product or its coding sequence is not introduced into the genome and gets lost after a certain period after introduction, hereby providing an essentially marker-free transgenic plant as end-product, containing only the desired transgenic nucleic acid, and not the nucleic acid encoding the selection marker used: the regenerating gene product.

Furthermore, the invention provides plant or plant material obtainable by a method according to the invention, propagated along the lines or using a method herein disclosed. In particular, the invention provides a plant or plant material obtainable by in vitro vegetative or seedless propagation according to the invention from plant starting material, for example using single-node cuttings, axillary branching, regeneration of adventitious organs (roots or shoots), or staring material such as explants or callus tissue or suspensions of, or even single, cells or protoplasts, in particular wherein said starting material comprises transgenic material, said transgenic plant or plant material according to the invention preferably being free of a selection marker gene.

The invention furthermore provides an isolated and/or recombinant nucleic acid encoding a receptor-like kinase or a functional fragment or functional equivalent thereof, corresponding to or capable of hybridising to a nucleic acid molecule as shown in anyone of FIG. 8, 9, 10, 11, 12, 13, 14, 15, 16, 17, 18, 19 or 20, or its complementary nucleic acid. Such a nucleic is obtained as described above. In a preferred embodiment, such a nucleic acid is at least 75% homologous, preferably at least 85%, more preferably at least 90%, or most preferably at least 95% homologous to a nucleic acid molecule or to a functional equivalent or functional fragment thereof, as shown in anyone of FIG. 8, 9, 10, 11, 12, 13, 14, 15, 16, 17, 18, 19 or 20, or its complementary nucleic acid, for example derived from *Arabidopsis thaliana*.

Also, the invention provides a vector comprising a nucleic acid according to the invention. Such a vector is preferably capably of providing stably or transient transformation of a cell by providing said cell with nucleic acid (DNA or RNA) or protein derived from a nucleic acid according to the invention. A variety of methods to provide cells with nucleic acid or protein are known, such as electroporation, liposome-mediated transfer, micro-injection, particle gun bombardment or bacteria-mediated transfer. RNA can for example be produced in vitro from appropriate vector constructs incorporating sites such as SP6, T7 or T3. Protein is produced in vitro in for example yeast or bacterial or insect cells, or other appropriate cells known in the art. DNA can be delivered as linear or circular DNA, possibly placed in a suitable vector for propagation.

1. Furthermore, the invention provides a host cell comprising a nucleic acid or a vector according to the invention. In a preferred embodiment, such a host cell is a transformed cell additionally comprising a desired, but most times totally unrelated, nucleic acid sequence, preferably integrated in a stable fashion in its genome. Even more preferred is a host cell according to the invention wherein the nucleic acid or vector according to the invention is only transiently expressed. Of course it is preferred to use a nucleic acid, vector or host cell according to the invention for use in a culture method as provided by the invention. The invention also provides a method for determining a developmental stage of a plant comprising detecting in said plant or parts thereof a nucleic acid or a proteinaceous substance according to the invention. Said detection is thus aimed at using receptor kinase genes or gene products belonging to the RKS family, or fragments thereof, as markers for plant development.

The invention furthermore provides an isolated or recombinant proteinaceous substance comprising an amino acid sequence as shown in anyone of FIG. 8, 9, 10, 11, 12, 13, 14, 15, 16, 17, 18, 19 or 20, or a functional equivalent or functional fragment thereof. Proteinaceous substance herein is defined as a substance comprising a peptide, polypeptide or protein, optionally having been modified by for example glycosylation, myristilation, phosphorylation, the addition of lipids, by homologous or heterologous di- or multimerization, or any other (posttranslational) modifications known in the art. Based on sequence composition, the N-terminal domain of predicted amino acid sequences of the RKS gene family represents a signal peptide, indicating that this region of the protein is extracellular. The length of this signal sequence and the predicted cleavage sites have been established using a prediction program. This domain is followed by a short domain containing a number of leucine residues, separated from each other by 7 amino acid residues. Based on the conservation of these leucines in an amphipathic helix, this domain represents a leucine zipper domain that mediates protein dimerization through formation of a short coiled-coil structure (Landschultz W H, Johnson P F, and McKnight s S L (1988) Science 240, 1759-1764). In RKS proteins, this leucine zipper domain is likely to be involved in receptor hetero/homo dimerization. The next domain contains 2 conserved cysteine residues that form a disulphate bridge. The subsequent domain represents a leucine rich repeat (LRR) region with 3-5 LRRs of approximately 24 amino acids each. In animals, this domain is known to be involved in protein-protein interactions (Kobe B and Deisenhofer J (1994) TIBS19, 415-420). In plants the extracellular LRR region is predicted to be necessary for ligand and elicitor binding. At the C-terminal part of the LRR region of most RKS proteins, another conserved couple of cysteine residues is involved in the formation of another disulphate bridge. At both ends, the LRR domain is thus surrounded by two disulphate bridges. The next domain contains a relatively high number of P and S amino acid residues, and shows similarity with cell wall proteins like extensins. Prediction server programs can be utilized to indicate the presence of multiple O-glycosylation sites within this domain. This domain might have similar functions as extensins and provide interaction sites with multiple cell wall components, thus forming a stable immobilised interaction with the cell wall in which the complete extracellular region of RKS proteins is embedded. The next domain represents a single transmembrane helical domain, as predicted by a program. The end of this domain, and the beginning of the intracellular cytoplasmic domain, contains a small number of basic K and R residues. The next domain is relatively acidic. The next large domain shows extensive homology with the family of plant seine, threonine receptor kinases. Autophosphorylation studies on SERK (Schmidt et al. 1997) have shown that this domain shows serine, threonine kinase activity. Within the kinase domain, several RKS proteins like RKS0 and RKS8 contain a putative 14-3-3 binding site represented by the core sequence RxpSxP, in which x represents any amino acid (Yaffe M B, Rittinger K, Volinia 5, Caron P R, Aitken A, Leffers H, Gamblin S J, Smerdon S J and Cantley L C (1997) Cell 91, 961-971). (Auto)phosphorylation of the S residue within this sequence as a result of ligand-mediated receptor-kinase activation would thus allow the binding and subsequent activation of 14-3-3 proteins. The next domain has an unknown function although the conservation of WD pair residues suggests a function of a docking site for other proteins. The C-terminal intracellular domain contains again part of a single LRR sequence, and might therefore be involved in protein-protein interactions. Preferably such a proteinaceous substance according to the invention is encoded by a nucleic acid according to the invention or produced by a host cell according to the invention.

In particular, the invention provides a proteinaceous substance for use in a culture method according to the invention. Introduction of a proteinaceous substance into cells or protoplast can be facilitated along the lines of the transformation protocols as known in the art. A variety of methods are known, such as micro-injection, particle gun bombardment or bacteria-mediated transfer. A cell or protoplast thus having been provided with a proteinaceous substance or functional fragment thereof derived from a gene involved in the regulation of plant development can now regenerate on its own, allowing reducing or omitting exogenous phytohormone addition to the culture that comprises that cell or protoplast. The process of vegetative propagation is hereby very much simplified, large numbers of plants with an identical genetic background can now be obtained staring from starting material with the desired characteristics. Proteins or peptides, encoded for by the RKS genes, are produced by expressing the corresponding cDNA sequences, or parts thereof in vitro or in an in vivo expression system in E. coli yeast, Baculovirus or animal cell cultures. The expressed protein sequences are purified using affinity column purification using recombinant Tag sequences attached to the proteins like (HIS)6 tags. Tags are removed after purification by proteolytic cleavage. The resulting protein sequence encodes a functionally active receptor-kinase, or a derivative thereof In a preferred embodiment, the protein contains a (constitutive) active kinase domain. The purified recombinant protein is introduced into plant cells in order to induce regeneration from these cells in a transient fashion. Proteins are introduced by methods similar as described for the introduction of nucleotide sequences, such as liposome-mediated transfer, micro-injection, electroporation, particle gun bombardment or bacteria-mediated transfer. If so desired, modification of recombinant proteins like glycosylation, disulphate bridge formation, phosphorylation etc. can be optimized in order to obtain an optimal efficiency in protein stability and activity.

Also, the invention provides an isolated or synthetic antibody specifically recognising a proteinaceous substance according to the invention. Such an antibody is for example obtainable by immunising an experimental animal with a proteinaceous substance according to the invention or an immunogenic fragment or equivalent thereof and harvesting polyclonal antibodies from said immunised animal, or obtainable by other methods known in the art such as by producing monoclonal antibodies, or (single chain) antibodies or binding proteins expressed from recombinant nucleic acid derived from a nucleic acid library, for example obtainable via phage display techniques. Such an antibody can advantageously be used in a culture method according to the invention, for example to identify cells comprising a regenerating gene product as identified above. With such an antibody, the invention also provides a proteinaceous substance specifically recognisable by such an antibody according to the invention, for example obtainable via immunoprecipitation, Western Blotting, or other immunological techniques known in the art. Also, the generation of such antibodies recognising conserved or distinct and specific regions within different members of RKS gene family within a plant species allow the desired isolation of RKS-homologues or recognise a specific RKS gene product in a variety of plant species. These antibodies are also used to screen cDNA expression libraries of plant species to screen for RKS-homologues. The invention, and use as provided of a nucleic acid, a vector, a host cell, a proteinaceous substance or an antibody according to the invention in a method according to the invention is further explained in the detailed description without limiting the invention.

DETAILED DESCRIPTION

In order to isolate genes involved in the developmental regulation of regeneration in plants, the different members of a family of genes were identified of which the expression was present in developing influorescenses. Within this tissue a large number of different organ primordia are initiated from the influorescence meristems. As a model plant species *Arabidopsis thaliana* was choosen, based on the presence of many well characterized genetic mutations and the availability of genetic information in databases.

The differentiation stage is highly stable in vivo, yet in response to nuclear transplantation or cell fusion, the nuclei of differentiated cells exhibit a remarkable capacity to change, both in animal and in plant cells (Blau, 1989).

The ability to change the differentiation stage provides cells and tissues with the ability to adapt towards their environment. Normally only a small number of stem cells have the ability to differentiate into different cell types. In plants, the only cells that are truly totipotent are the zygotes, consisting of fused egg cells and sperm. From these dipoid totipotent cells all other differentiated cell types are derived.

Regeneration is a vegetative reproduction or repair strategy observed in a large number of animal and plant species. Regeneration in plants is defined as the formation of new tissues containing both root and shoot meristems, separate shoot or root meristems, plant organs or organ primordia from individual cells or groups of cells. Regeneration mimics the process of normal cellular and organ differentiation that takes place during plant development and results in the formation of the different plant organs. However, plant cells or groups of cells that under normal conditions are unable to initiate the formation of certain plant organs, meristems or organ primordia can be stimulated by either extracellular stimuli or intracellular modification of the differentiation stage of the cell.

Regeneration can take place under either in vivo or in vitro conditions.

Regeneration does not include the process of apomixis, wherein specific forms of vegetative plant reproduction are taking place in seeds. Extracellular diffusible factors have shown to be essential for cellular redifferentiation in plant cells (Siegel and Verbeke, 1989). The perception of these signals at the cellular surface and the intracellular signal transduction that finally result in changes in transcriptional regulation provides cells with the ability to respond to such extracellular stimuli.

In a search for gene products with the ability to regulate cellular differentiation we concentrated on genes involved in perception and transmission of intercellular differentiation signalling. Extracellular signals in animal cells are normally perceived by an high affinity binding compound, the sensor molecule.

Extracellular signalling factors are further referred to as ligands and their cellular binding partners are defined as receptors. Upon binding, the extracellular signal can result in modification of the receptor, resulting in transmission of the signal over the cellular membrane. Cell surface receptors contain an extracellular ligand binding domain, a transmembrane domain and an intracellular domain involved in transmission of signals to the intracellular signal transduction components (Walker, 1994). SERK represents a member of the large group of transmembrane receptor kinases with various functions in plants and animals. Many of these gene products are known to be involved in cellular differentiation processes like Clavata 1 (Clark et al. 1997) or Erecta (Torii et al. 1996). Overexpression or mutation of these genes in plants result in morphological changes in plant organs or plant cells.

The Somatic Embryogenesis Receptor-like Kinase SERK was originally identified as a marker for embryogenic cells, both in vivo, and in vitro. (Schmidt et al. 1997a). Expression of the SERK gene was correlated with the ability to form somatic embryos, a process in which plants are formed from somatic cells through the same morphological, cytological and molecular sequence of stages of embryogenesis as zygotic embryos.

Transmembrane proteins like receptor kinases provide a set of candidate key regulator gene products that are involved in organ or cellular differentiation. In a search for gene products with the ability to modulate the differentiated we searched for receptor-kinase genes expressed in a plant tissues with a large variety of cellular differentiation processes, the influorescense meristem. In a screen for gene products involved in the regulation of the differentiation stage of cells we identified a complete family of receptor-like kinases.

Identification of a New Family of Receptor-Like Kinases in *Arabidopsis thaliana*, the RKS Gene Family.

In genomic databases of *Arabidopsis*, a small number of sequences were identified with homology to the *Arabidopsis* SERK sequence (Schmidt et al. 1997b). These sequences showed homology on nucleotide and predicted amino acid level and were further defined as Receptor Kinases-like SERK (RKS) genes. The initially identified sequences are further defined as R.5. Based on these five RKS sequences a set of degenerated DNA primers was designed that allowed amplification of possible RKS gene fragments from *Arabidopsis*.

```
Primer RKS B forward:                    (SEQ ID NO: 1)
5'-CC[C/G] AAG AT[C/T] AT[A/T] CAC CG[A/C/T] GAT
GT[A/C/G] AA[A/G] GC-3'

Primer RKS E reverse                     (SEQ ID NO: 2)
5'-CC[A/G] [A/T]A[A/C/G/T] CC[A/G] AA[A/G] ACA TCG
GTT TTC TC-3'
```

These sequences are based on conserved parts within the nucleotides encoding one exon of the kinase domain. PCR amplification reactions (60 sec. 94° C.; 60 sec. 50° C.; 90 sec. 72° C.)×40 cycli. were performed with 100 ng of genomic DNA as a template. The resulting PCR products consisted of 209 bp DNA fragments. After cloning in a pGEM-T (Promega) vector, a total of 21 different clones was analysed in order to identify the amplified nucleotide sequences. Removal of the degenerated primer sequences resulted in sequences of 154 nucleotides. Apart from the sequences of RKS1-4 and the SERK gene, a total of 4 new unidentified RKS homologous sequences were identified, further defined as RKS6-10. Sequences from the RKS5 gene were not identified in this screen.

Number of clones isolated and sequenced for different RKS genes followed by time(s) identified in genomic PCR.

| RKS1 | 1 |
|---|---|
| RKS2 | 4 |
| RKS3 | 2 |
| RKS4 | 5 |
| RKS5 | 0 |
| RKS6 | 2 |
| RKS7 | 1 |
| RKS8 | 2 |
| RKS103 | |
| SERK/RKS0 | 1 |

These results indicated the presence of at least 9 different sequences with homology to the conserved kinase domain of the predicted RKS genes (apart from SERK) on the *Arabidopsis* genome (FIG. 1). In order to confirm these data, the fragment of one of the isolated RKS genes was used as a probe in a Southern blot (FIG. 2). Low stringency hybridization confirmed the presence of a number of sequences related to the probe fragment. Under the stringency used (see Materials and Methods) a total of approximately 5 hybridizing bands could be observed, indicating the presence of a small RKS gene family in *Arabidopsis*.

RKS Gene Expression in *Arabidopsis* Inflorescence Tissues.

In order to test whether RKS genes are expressed in tissues where formation of primordia and organs is initiated, RT-PCR reactions were performed on inflorescences. The same combination of PCR primers for RKS fragment amplification was used as described for the genomic PCR reactions. Due to the absence of intron sequences in the described nucleotide fragments, the resulting product was again 209 bp. Starting from the first strand cDNA, a standard PCR reaction was performed for (60 sec. 94° C.; 60 sec. 50° C.; 90 sec. 72° C.)×40 cycli. In order to obtain a sufficient large amounts of amplified product, a reamplification was performed under similar conditions, using 10% of the mix from the first RT-PCR amplification reactionmix as a template. After cloning in a pGEM-T vector, a total of 21 different clones was sequenced in order to identify the amplified sequences. Removal of the degenerated primer sequences resulted in sequences of 154 nucleotides (FIG. 1).

Number of RT-PCR clones isolated and sequenced for different RKS genes followed by time(s) RT-PCR product identified from influorescence tissue:

| | |
|---|---|
| RKS1 | 0 |
| RKS2 | 0 |
| RKS3 | 2 |
| RKS4 | 5 |
| RKS5 | 0 |
| RKS6 | 0 |
| RKS7 | 1 |
| RKS8 | 2 |
| RKS104 | |
| RKS112 | |
| RKS123 | |
| RKS131 | |
| RKS141 | |
| SERK/RKS0 | 0 |
| RKS | 14 |

These results indicated the presence of at least 14 different sequences with homology to the conserved kinase domain of the predicted RKS genes (apart from SERK) on the *Arabidopsis* genome (FIG. 1). Within influorescenses, at least 9 RKS-like genes were expressed. Within this experiment, expression of RKS 0, 1, 2, 5 and 6 in inflorescences could not be confirmed. Homology between the different RKS sequences was performed using ALLIGMENT software from Geneworks 2.2 (FIG. 3). At least three different subgroups could be visualized of the RKS gene family, representing RKS 2 and RKS6 in subgroup 1, RKS 4, 11, 1, 5, 14 and 7 in subgroup 2 and RKS 0, 8, 10, 12 and 13 in subgroup 3. These results confirmed the hybridization patterns, observed with genomic Southerns hybridized with a member of the RKS subgroup 3 (FIG. 2). A total of 5 hybridizing bands could be observed, that were likely to represent the genes from RKS 0, 8, 10, 12 and 13.

In order to investigate whether the isolated PCR fragments represented parts of complete RKS genes, full length and partial cDNA clones homologous to these PCR fragments were isolated and characterized.

Isolation and Characterization of the RKS Gene Products in *Arabidopsis*

A cDNA library from *Arabidopsis thaliana* Colombia wild type was used to isolate cDNA clones hybridizing with the PCR amplified RKS gene fragments. The consisted of a BRL λZipLox vector containing SalI, NotI linked cDNA inserts from different plant organs (including siliques, flowers, stems, rosette leaves and roots.

Filter hybridization, purification of plaques hybridizing under stringent conditions (65.degree. C., 0.1 SSC) with the different RKS fragment probes and finally nucleotide sequence analysis resulted in the characterization of a number of RKS cDNA clones. The predicted amino acid sequences of these clones confirmed that the gene products represent members of the RKS plant receptor kinase family RKS. The sequences from the clones identified by the cDNA library were compared and combined with sequence information from the database *Arabidopsis*.org. Apart from 14 different full length cDNA clones a number of 4 different-partial clones were identified.

Overexpression of RKS Gene Products in Transgenic *Arabidopsis*

Transformation of plasmid DNA into plant cells was performed using *A. tumefaciens* C58C1. The binary vector used consisted of pGREEN, pGREEN1K or RKS expression constructs. Bacterial colonies were grown on LB agar plates containing 20 mg/L gentamycin, 50 mg/L kanamycin and 50 mg/L rifampicin. Five colonies were used to inoculate 50 ml of LB medium containing 50 mg/L kanamycin and 50 mg/L rifampicin. After 16 hours of incubation at 30° C. cells were concentrated by centrifugation and resuspended in 10 ml infiltration medium (consisting of 5% sucrose and 0.05% Silwett L-77 in water. A helper plasmid, necessary for transformation, consisted of the vector pJIC Sa-Rep and was co-transformed together with the pGREEN vector. After electroporation and incubation for 2 hours at 30° C., cells were plated onto LB plates with 50 mg/L rifampicin en 50 mg/L kanamycin. *Arabidopsis thaliana* wild-type WS cultivar was transformed following the floral dip protocol (Clough and Bent, 1998). In short, the influorescences of young *Arabidopsis* WS plants grown under long day conditions (16 hours light, 8 hours dark) were dipped for 10 seconds in 10 ml of infiltration solution. Plants were grown further under long day conditions and seeds were harvested after an additional 3-5 weeks. Seeds were surface sterilized in 4% bleach solution for 15 minutes and after extensive washing in sterile water, plated on ½MS plates with 60 mg/L kanamycin. After 10 days incubation under long day conditions, transgenic kanamycin resistant seedlings were isolated and planted on soil for further non-sterile growth under standard long day greenhouse conditions. This infiltration protocol routinely resulted in approximately 1% transformed seeds for each of the RKS gene constructs used.

Regeneration of *Arabidopsis* Plants After RKS Gene Transformation

Figure 5:
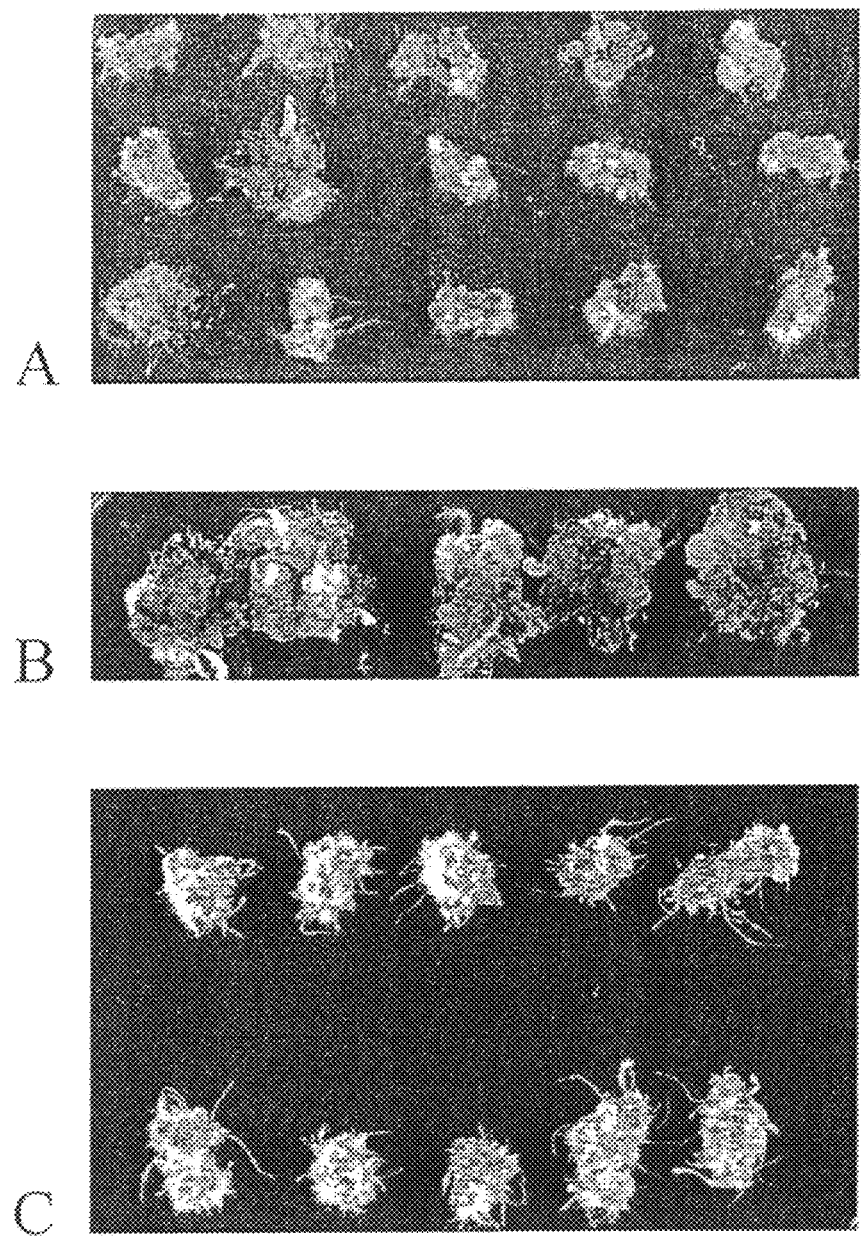

*Arabidopsis* T2 seeds; obtained from plants infiltrated with *A. tumefaciens* containing empty pGREEN vectors or pGREEN1K vectors including RKS genes under the control of a 35S promoter, were surface sterilized and added to 40 ml ½MS medium culture to which 1 mg/L 2,4-D was added. After three days of stratification at 4° C., the cultures were incubated on a shaker under long day conditions in a climate room of 20° C. for 0-18 days to induce cell proliferation. At different time intervals, seedlings were isolated from the culture, washed and transferred onto ½MS agarplates without 2,4-D or any other hormones. Incubation in the climate room was continued under long day conditions for 4 more weeks. In the absense of RKS genes in the transformed binairy vector, no regeneration of plantlets could be observed (FIG. 5C). However, in the presence of RKS gene expression, regenerating plants could be observed that originated from the proliferating cell mass (FIG. 5A,B). Different RKS gene constructs showed the ability to regenerate shoot meristems and leaves. The ability to induce regeneration varied between individual integration events and between RKS gene constructs (FIG. 5A versus 5B). At this timepoint of 4 weeks of regeneration, plantlets were transferred directly to non-sterile soil and grown for another 4-6 weeks under long day conditions. Fertile, seed setting plants could be obtained from the regenerated plantlets as shown in FIG. 5A,B.

20 µg of vector DNA for biolistic DNA delivery into *Arabidopsis* tissue was mixed with a ballistic suspension mix: 10 mg of gold (Aldrich Chem, Co. Gold 1.5-3 micron), 30 µl 5M NaCl, 5 µl 2M Tris pH 8, 965 µl water, 100 µl 0.1M spermidine, 100 µl 25% PEG, 100 µl 2.5M CaCl2. The suspension was incubated at room temp for 10 min, and centrifuged. The resulting pellet was washed twice with ethanol and resuspended into 200 µl icecold 99.8% ethanol. For each microprojectile bombardment, 10 µl of the gold-coated DNA was used. Bombardment conditions for the HELIUM GUN 461 were: helium pressure 6 bar, vacuum to 50 mbar and 9 cm distance of the tissue from the filter. 0.1 mm mesh size screen was used between tissue and filter, 3 cm distance of the screen from the filter. After bombardment, the *Arabidopsis* plants were cultured for a period of 3 weeks under long day conditions.

Figure 6A:
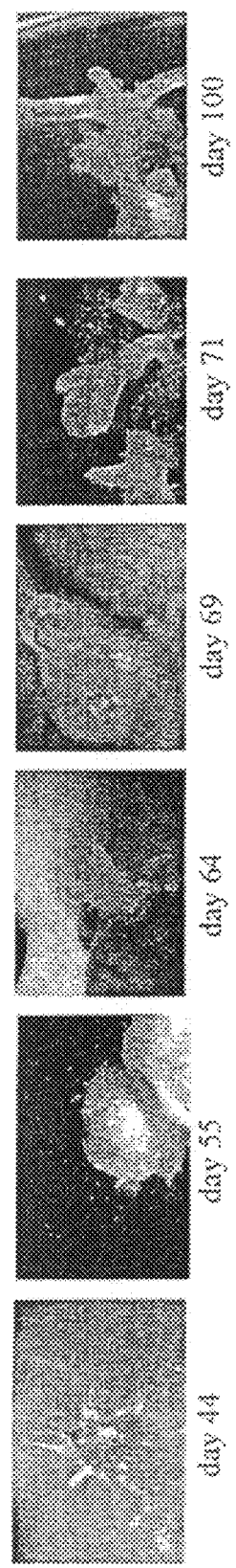
Figure 6B:
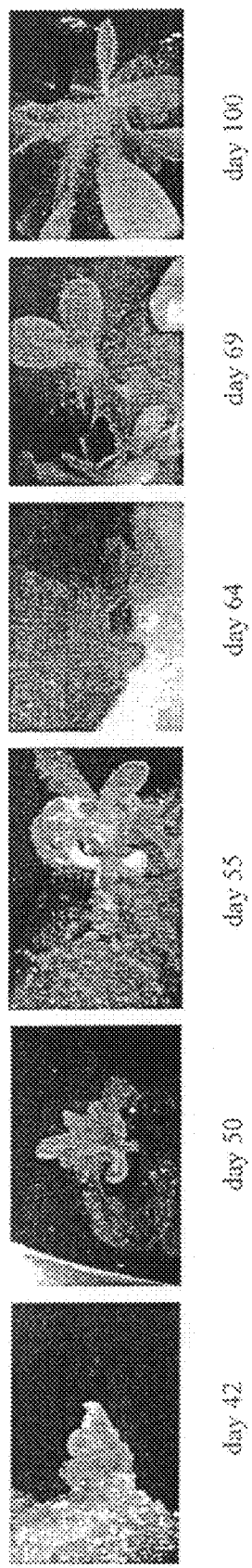
Figure 6D:
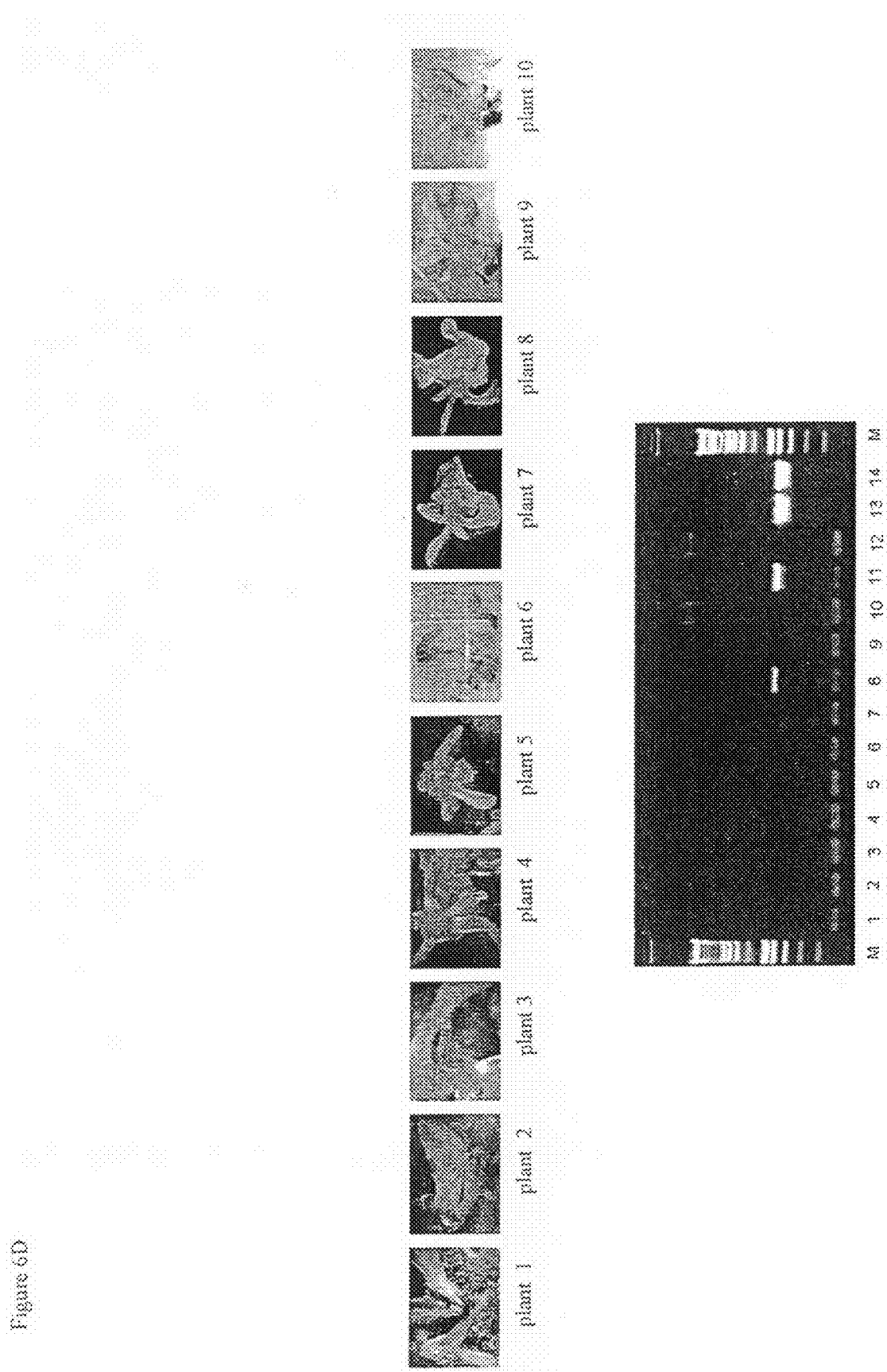
Figure 68:

Regeneration in *Nicotiana tabacum* Induced by Expression of Regeneration-Stimulating Gene Products 20 microgram of plasmid DNA was transferred into cells of tobacco (NTSR1) leaves, using biolistic bombardment with gold particles coated with DNA. Leaf discs were subsequently submerged in liquid MS30 medium (MS medium 30 g sucrose/l, Murashige and Skoog 1962) containing 1 mg/l kinetin and incubated on a rotary shaker (250 rpm) for 14 days. Leaves were then transferred to plates with MS30 plates, 0.8% agar. All incubations have been performed at 20° C. with 16 hours light, 8 hours dark. Control experiments with empty or control vectors never gave rise to shoot formation. Regenerating plantlets appeared as a result of particle bombardment with regenerating DNA constructs as shown in FIG. 6A-C. The transient nature of the introduced construct could be confirmed for 9 out of 10 different regenerants obtained from bombarded tissue (FIG. 6D).

Induction of Cell Proliferation in *Arabidopsis thaliana* Induced by Expression of Regeneration Inducing Gene Products In order to identify the earlier stages of regeneration after particle bombardment the formation of cellular proliferation was studied as a result of the activity of the regenerating gene product. Single regenerating constructs or combinations of such DNA constructs were bombarded onto two weeks old seedlings of *Arabidopsis thaliana* grown on MS agar plates. Between one and three weeks thereafter the formation of multicellular structures arising from the surface of bombarded rosette leaves could be observed (FIG. 6E-H).

Bombardments with empty control vectors never gave rise to the formation of these structures. Interestingly, the proliferating cell mass originating from bombardment with a GT-W-20S construct developed somatic embryos as a clear indication of regeneration by the process of somatic embryogenesis.

Figure 6G:
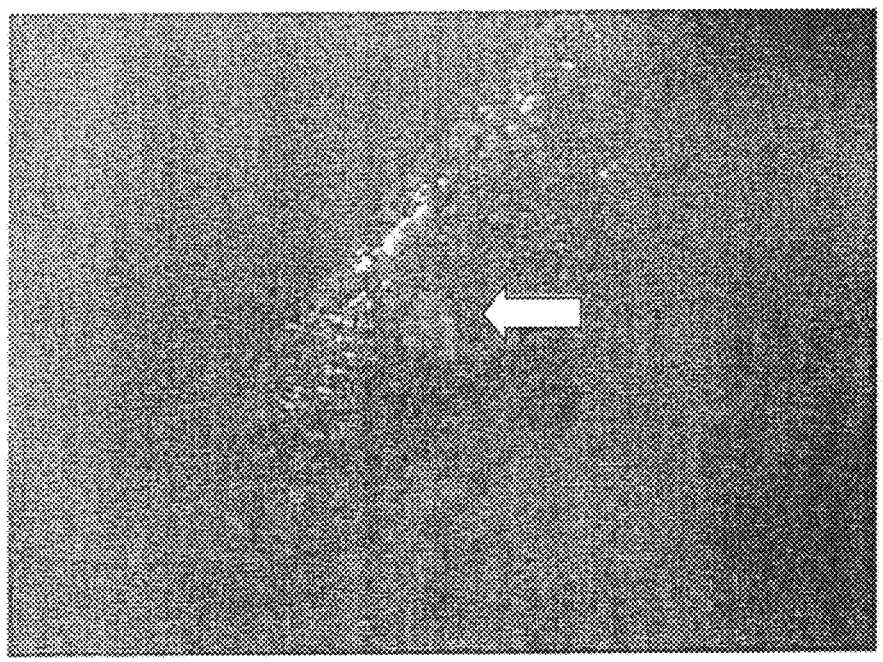
Figure 6H:
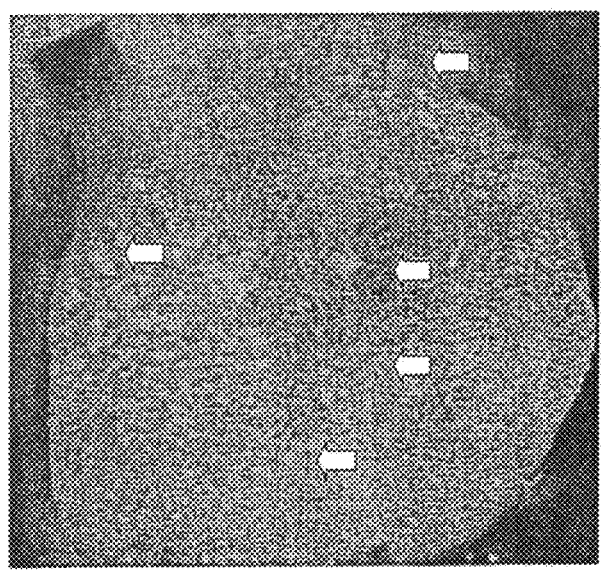

Somatic embryogenesis was hereby not depending on a tissue culture state of the originating tissue but could be directly initiated on adult leaves still attached to the parent plant. Combinations of different regenerating contructs coated on the same gold particle before bombardment allowed also the process of cellular proliferation to be initiated (FIG. 6G). Multiple loci of proliferated tissue could be observed on individual leaves after the different regenerating constructs (FIG. 6H), indicating that the frequency of regeneration was relatively high when using combinations of regenerating constructs in contrast to bombardments with individual regenerants.

Materials and Methods

Southern Blotting

10 µg of genomic DNA from *Arabidopsis thaliana* wild-type was digested with different restriction enzymes. Fragment DNA was size separated on a 0.9% agarosegel. DNA purination was performed in 0.6M NaCl with 0.4M NaOH. Capillairy blotting was performed onto Hybond N+ membranes. Membranes are hybridized overnight at 65° C. in C&G hybridization mix (Church and Gilbert, 1985) and subsequently washed at 65° C. with 5 SSC, 0.1% SDS. For detection of radioactivity, the Phosphorimager 425 (Molecular Dynamics) was used in combination with phosphoscreen exposure casettes and ImageQuaNT software.

DNA Fragment Purification

DE81 paper (Whatmann) was used for isolation of DNA fragments from agarose gels. Paper segments were introduced into the agarosegel just behind the desired DNA fragments (which were visualized under long wave UV with ethidium bromide staining). Electrophoresis was performed for 10 minutes at 10V/cm gel and the DE81 paper to which the DNA was bound was recovered from the gel. Paper fragments were washed extensively in Low Salt Buffer (LSB) and subsequently DNA was removed from the paper in a small volume of High Salt Buffer (HSB).

| LSB (Low Salt Buffer): | HSB (High Salt Buffer): |
|---|---|
| 10 mM Tris pH 7.5 | 10 mM Tris pH 7.5 |
| 1 mM EDTA | 1 mM EDTA |
| 100 mM LiCl2 | 1 M LiCl2 |
| | 20% Ethanol |

Radioactive Probes

Purified DNA fragments were radiolabelled with 32P-dCTP following a random primed labelling:

50 ng of fragment DNA in 27 µl water is denatured for 5 min. at 100° C. On ice, 21 µl of GAT mix was added: 0.67 M Hepes, 0.17 M Tris, 17 mM MgCl2, 33 mg/ml acetylated BSA, 25 mg/ml random hexamer primers, 33 mM b-mercapto-ethanol, 5 mM dNTP's (G+A+T) without dCTP. 2 µl dCTP and 2 µl Klenow (1 U/µl) was added, mixed and incubation was performed for 60 min. at 25° C.

Genomic PCR

Genomic DNA was isolated from wild type *Arabidopsis thaliana* plants using the protocol of Klimyuk et al. (1993). All PCR reactions were performed in a Thermal Cycler from Perlin Elmer.

PCR amplification reactions were performed under standard conditions using the following mix: 100 ng genomic template DNA in 5 µl water, denatured for 5 min. at 100° C. On ice the following components were added: 2 µl primer B (10 µM) en 2 ml primer E (10 µM), 1 µl dNTP's (10 mM), 5 µl 10× Taq buffer (Boehringer Mannheim), 0.1 ml Taq polymerase, 5 Units/µl (Boehringer Mannheim), 35 µl water. Paraffin oil was added to the surface in a volume of 20 µl and amplification was performed under the following conditions: (60 sec. 94° C., 60 sec. 50° C., 90 sec. 72° C.)×40 cycli. PCR products were routinely purified using the High Pure-PCR product purification kit (Boehringer Mannheim). Purified DNA was cloned in a five-fold molar excess in the PGEM-T Easy vector (Promega) following standard protocols and reaction mixes as supplied within the reaction kit.

RT-PCR

Inflorescences from *Arabidopsis thaliana* was used as source material to isolate total RNA following the protocol of Siebert and Chenchik (1993)

2.5 µg of total RNA in 10 µl of water was linearized by 1 min. incubation at 100° C., followed by the addition of the following components on ice:

```
2 µl (10 pmol) dT race primer           (SEQ ID NO: 3)
5'- GAC TCG AGT CGA CAT CGA TTT TTT TTT TTT TTT
TT - 3'
```

1 µl dNTP's (10 mM)
4 µl 5×RT buffer (Boehringer Mannheim)
0.8 µl reverse transcriptase M-MuLV Expand (Boebringer Mannheim)
2 µl 100 mM DTT Incubation was performed for 60 min. at 42° C., diluted with an equal amount of RNAse free water and stored at −20° C. 2 µl of first strand (=125 ng) was used in PCR reactions, using the RKS degenerated primers B and E. 2 µl primer B (10 µM) en 2 µl primer E (10 µM), 1 µl dNTP's (10 mM), 5 µl 10× Taq buffer (Boehringer Mannheim), 0.1 ml Taq polymerase, 5 Units/µl (Boehringer Mannheim), 38 µl water.

Paraffin oil was added to the surface in a volume of 20 µl and amplification was performed under the following conditions: (60 sec. 94° C., 60 sec. 50° C., 90 sec. 72° C.)×40 cycli. PCR products were routinely purified using the High Pure-PCR product purification kit from Boehringer Mannheim. Purified DNA was cloned in a five-fold molar excess in the pGEM-T Easy vector (Promega) following standard protocols and reaction mixes as supplied with the reaction kit.

E-coli and A. tumefaciens Transformation

Transformation of plasmid DNA into competent bacteria was performed by electroporation (Dower et al., 1988), using a Genepulser (Biorad). Conditions for electroporation were as follows: 1.5 kV, 25 mF and 200 W in standard cuvettes. Directly after transformation, cells were incubated for 90 min. at 37° C. in SOC medium (Sambrook et al. 1989). The bacterial suspension was plated on selective agar plates and incubated overnight at 37° C. (E. coli) or for two days at 30° C. (A. tumefaciens) in order to visualize transgenic bacterial colonies.

Nucleotide Sequence Analysis

Plasmid DNA was isolated from E. coli by standard boiling method protocol (Sambrook et al. 1989) followed by a subsequent purification with the PCR product purification kit from Boehringer Mannheim. Plasmids were sequenced using the ABI PRISM Dye Terminator Cycle Sequencing Core Kit van Perkin Elmer, using standard protocols as designed for the 480 DNA Thermal Cycler. After electrophoresis on polyacrylamide gels, the results were analysed using the 373A DNA Sequencer from Applied Biosystems. Data were analysed using the software programs Sequencer 3.0, Geneworks 2.2 and DNA-strider 1.2.

cDNA Library Screening

Plating of the c.lamda.ZipLox cDNA library was performed as described by the supplier protocols (GIBCO BRL), and plaque lifting and purification as described by Sambrook et al. (1989). cDNA library screening was performed using 20 duplicate filters, each containing approximately 250.000 individual plaques. Filters were screened with different RKS DNA probes representing 209 bp amplified PCR fragment. Prior to labeling, DNA fragments were isolated from the pGEM-T vector by digestion and purified twice by DE81 purification from agarose gels. Filters were hybridized under stringent conditions (0.1 SSC, 65.degree. C.). Plaques that hybridized on both filters were isolated and used for two subsequent rounds of further purification. The resulting cDNA clones were sequenced using the 17 and SP6 primers from the primer binding regions of the multiple cloning sit of the .lamda.ZipLox vector. Internal oligos were designed to sequence the complete cDNA inserts of the RKS clones. Only one cDNA clone was sequenced completely for each RKS gene product identified. An alternative approach to identify and subsequently isolate cDNA clones from RKS genes was to screen the Arabidopsis genome database for RKS homologous sequences and to amplify cDNA clones by RT-PCR approach as described above using primers specific for these RKS gene products, based on the sequence data obtained from Arabidopsis genomic. Purified RT-PCR products were cloned in a five-fold molar excess in the pGEM-T Easy vector (Promega) following standard protocols and reaction mixes as supplied with the reaction kit.

Regenerating Gene Product Expression Constructs

The CaMV 35S promoter enhanced by duplication of the −343/−90 bp region (Kay et al, 1987) was isolated from the vector pMON999 together with the NOS terminator by NotI digestion. The resulting construct was cloned into the vector pGreen (Bean et al. 1997) and the resulting binairy vector is further defined as pGreen1K RKS cDNA clones (FIG. 2) were isolated from either the pGEM-T easy vector by EcoRI digestion or from the λZipLox vector by EcoRI/BamHI digestion. The resulting cDNA fragments were cloned into respectively EcoRI digested pGreen 1K or EcoR1/BamH1 digested pGreen 1K. Nucleotide sequence analysis was performed in order to test the integrity and the orientation of the RKS cDNA in the vector pGreen1K. The resulting constructs in which the different $RKS_{0-14}$ had been ligated in the sense configuration with respect to the 35S promoter are further defined as RKS expression constructs. The other regenerating gene products as previously mentioned have been cloned in a similar fashion into the pGreen expression construct under the control of a 35S promoter Regeneration Induced by Transient Expression of RKS Gene Products Rosette leaves and shoot meristems from 3-weeks old Arabdopsis plants grown under long day conditions were surface sterilized in a 1% bleach solution for 20 min, washed extensively with sterile water and placed on ½ MS plates solidified with 0.8% agar.

Particle Bombardment

20 µg of vector DNA for biolistic DNA delivery into plant tissue was mixed with a ballistic suspension mix: 10 mg of gold (Aldrich Chem, Co. Gold 1.5-3 micron), 30 µl 5M NaCl, 5 µl 2M Tris pH 8.0, 965 µl water, 100 µl 0.1M spermidine, 100 µd 25% PEG, 100 µl 2.5M CaCl2. The suspension was incubated at room temp. for 10 min. and centrifuged. The resulting pellet was washed twice with ethanol and resuspended into 200 µl icecold 99.8% ethanol. For each microprojectile to bombardment, 10 µl opf the gold-coated DNA was used. Bombardment conditions for the HELIUM GUN 461 were: helium pressure 6 bar, vacuum to 50 mbar and 9 cm distance of the tissue from the filter. 0.1 mm mesh size screen was used between tissue and filter, 3 cm distance of the screen from the filter.

REFERENCES

Bean S J, Gooding P S, Mullineaux P M and Davies D R (1997) Plant Cell Reports 16, 513-519.
Blau H M (1989) Trends in Genetics 5, 268-272.
Church C and Gilbert K (1985) Proc. Natl. Acad. Sci USA 81, 1991-1995.
Clark S E, Williams R W and Meyerowitz (1997) Cell 89, 575-585.

Dower W J et al. (1988) Nucl. Acid Res. 16, 6127-6145.
Kay et al. (1987) Science 236, 1299-1302.
Klimyuk V I, Carroll B J, Thomas C M and Jones J D G (1993) Plant J. 3, 493-494.
Sambrook J, Fritsch E F and Maniatis T. (1989) Molecular cloning: a laboratory manual, Cold Spring Harbor Laboratory, New York.
Schmidt E D L, Hecht V, van Holst G J, de Vries S C (1997b) production of apomictic seed. International publication number WO97/43427.
Schmidt E D L, Guzzo F, Toonen M, de Vries S C (1997a) Development 124, 2049-2062.
Siebert P D and Chenchik A (1993) Nucl. Acid Res. 21, 2019-2020.
Siegel B A and Verbeke J A 1989, Science 244, 580-582.
Torii K U, Mitsukawa N, Oosumi T, Matsuura Y, Yokoyama R, Whittier R F and Komeda Y (1996) Plant Cell 8, 735-746.
Walker J C (1994) Plant Molecular Biology 26, 1599-1609.
Murashige T. and Skoog F. (1962). A revised medium for rapid growth and bioassays with tobacco tissue cultures. Physiol. Plant. 15, 473-496

FIGURE LEGENDS

FIG. 1 depicts the different 154 bp PCR fragments as amplified with the degenerated forward and reverse RKS primers B and E, as shown in Material and Methods. The sequence of the RKS0 fragment is identical with the corresponding region of the *Arabidopsis* SERK gene. The nucleotide sequences representing the primer sequences have been deleted from the original 209 bp PCR products in this figure.

FIG. 2.

Genomic Southern blot of *Arabidopsis thaliana* genomic DNA digested with different restriction enzymes. 10 μg of genomic digested DNA is loaded in each lane. Low stringency hybridization (65° C., 5SSC) is performed with a 209 bp PCR fragment encoding part of the kinase domain of RKS0.

FIG. 3.

Homologies between the 154 bp fragments as amplified from *Arabidopsis* with the degenerated RKS primers B and E, shown in FIG. 1. At least three different subgroups can be visualized of the RKS gene family, representing RKS 2 and RKS6 in subgroup 1, RKS 4, 11, 1, 5, 14 and 7 in subgroup 2 and RKS 0, 8, 10, 12 and 13 in subgroup 3. Alignments were performed using DNA Strider 1.2 software.

FIG. 4A

*Arabidopsis thaliana* RKS0 cDNA

The start codon has been indicated by bold capitals.

FIG. 4B

Predicted amino acid sequence of the *Arabidopsis thaliana* RKS-0 protein. Different domains are spaced and shown from the N-terminus towards the C-terminus. Overall domain structure is similar as described in Schmidt et al. (1997).

At the predicted extracellular domain the first domain represents a signal sequence.

The second domain contains a leucine zipper motif, containing 4 evenly spaced leucine residues, each separated by 7 other amino acids.

The third domain contains conserved cysteine residues, involved in disulphate bridge formation.

The fourth domain contains a leucine rich repeat domain, consisting of 5 complete repeats of each approximately 24 amino acid residues.

The fifth domain contains many serine and proline residues, and is likely to contain hydroxy-proline residues, and is a site for O-glycosylation.

The sixth domain contains a single transmembrane domain after which the predicted intracellular domains are positioned.

The seventh domain has an unknown function.

The eight domain represents a serine/threonine protein kinase domain (Schmidt et al. 1997), and is probably also containing sequences for protein, protein interactions.

The ninth domain has an unknown function.

The last and tenth domain at the C-terminal end represents a single leucine rich repeat, probably involved in protein, protein interactions.

FIG. 5

Proliferated cell mass of *Arabidopsis* plants transformed with different overexpressing constructs of RKS genes (A and B) or with a control pGREEN1K vector without RKS genes. After 18 days of proliferation in the presence of 2,4-D, tissues have been grown for 4 weeks in the absence of hormones. Regenerated plantlets and green shoots are dearly visible in transformed tissues A and B, but absent in the control tissues transformed with the empty pGREEN vector (C).

FIG. 6A

Ballistic bombardment of *Nicotiana tabacum* leaf discs with GT-W-20S at day 0 is followed by a two weeks submerged culture in liquid MS medium 1 mg/L kinetin. Subsequently the discs are cultured on MS agar plates without hormones. Control experiments with empty vector never gave rise to proliferation. The formation of regenerating from leaf explants is shown in days after bombardment.

FIG. 6B

Ballistic bombardment of *Nicotiana tabacum* leaf discs with GT-SBP5-16S at day 0 is followed by a two weeks submerged culture in liquid MS medium with 1 mg/L kinetin. Subsequently the leaf discs are cultured on MS agar plates without hormones. The formation of regenerating tissues from leaf explants is shown in days after bombardment. Control experiments with empty vectors never gave rise to shoot formation.

FIG. 6C

*Nicotiana tabacum* callus is bombarded with GT-SBP5-16S at day 0. Callus was generated by incubating tobacco leaves for 6 weeks on MS30, 0.8% agar supplemented with 1 mg/L 2,4-D auxin. The callus that formed on the leaves with root like characteristics (extending roots or root hairs from calli) was further cultured on MS30, 0.8% agar petri dishes. The incubation are performed at 20° C. with 16 hours light, 8 hours dark. Control experiments with empty vectors never gave rise to shoot formation. 40 days after bombardment regenerating plant can be identified on top of the bombarded callus tissue (plant 1 and plant 2).

FIG. 6D

In order to examine the presence of the bombarded DNA regeneration constructs in regenerated plant, tissue samples were taken from 10 different regenerates from the experiments described in the legends of FIG. 6A-C. Genomic DNA was isolated from all samples, as well as from two control plants. On this DNA a PRC reaction was performed using primers specific for the NptII gene: construct 1 and 3 from experiment I.

Oligo's used for NptII specific amplification:

Forward oligo: 5'-CCATGGTGAACAAGATGGATGG-3' (SEQ ID NO: 4) Reverse oligo: 5'-GGATCCTCAGAA-GAACTCGTCAAG-3' (SEQ ID NO: 5). The resulting PCR product was analysed on agarose gel. Lane 1 and 2 represent regenerates from FIG. 6C; Lane 3-6 represent regenerates from FIG. 6B. These 10 plants from which tissue material was isolated for lane 1-10 are shown below just prior to DNA isolation. Lane 11 represents a positive control plant that is stable transformed with a control vector (pG1K-GEP). Lane 12 represents a negative control, an untransformed wildtype NTSR1 plant. Lane 13 and 14 represent positive control *E. coli* purified DNA used for PCR analysis and M represent marker DNA. Results indicate that only the regenerated plant from lane 8 contained a stable intergrated NptII sequence, with all controls giving vector DNA bands.

FIG. 6E

*Arabidopsis thaliana* WS seedlings grown for 14 days on MS agar plates have bombarded with DNA coated gold particles at day 0. Plants are further incubated on the plates at 20° C. with 16 hours light, 8 hours dark. Gold particles were coated with 18 microgram of the construct GT-RKS13. In the bombardment procedure, a GUS expression vector was co-bombarded in combination with the GT-W-20S construct in a molar ration of 10% (GUS versus GT-RKS13). Prior to photography, GUS staining was performed on the bombarded tissues. Cell proliferation (arrow) is detectable on the surface of rosette leaves. Control experiments performed with empty vectors did never result in proliferating tissues.

FIG. 6F

Ballistic bombardment of *Arabidopsis thaliana* with GT-W-20S constructs results in cell proliferation on top of the rosette leaver (left).

Structures with the morphologic characteristics of somatic embryos appear on the callused structures (middle and right, white arrows). In the bombardment procedure, a GUS expression vector was co-bombarded in combination with the GT-W-20S construct in a molar ration of 10% (GUS versus GT-W-20S). The GT-W-20S construct induces cellular proliferation in neighbouring cells and is unable to induce not contain fragments of the introduced regeneration construct or the GUS expression construct. However, after GUS staining, one cell at the basis of the proliferating cell mass is clearly GUS positive (middle and right, black arrow), indicating that this basal cell has been transformed construct results in the formation of a GUS-negative proliferating cell mass on top of a basal GUS-positive cell. Bombardment studies with empty control vectors did never result in cellular proliferation.

FIG. 6G

Ballistic bombardment of *Arabidopsis thaliana* Ws with GT-CUC2-S, GT-KNAT1-S and GT-CYCD3-S. Cell proliferation becomes already clearly detectable within one week after bombardment (arrow). Control bombardment studies with empty vectors did not result in cellular proliferation.

FIG. 6H

Ballistic bombardment of *Arabidopsis thaliana* Ws with GT-CUC-2S, GT-KNAT2-S and GT-CYCD3-3S. Different regions of cell proliferation within individual rosette leaves become already clearly detectable within one week after bombardment (arrows). Control bombardment studies with empty vectors did not result in cellular proliferation.

FIG. 7

The three different RKS subfamilies I-III based on FIG. 3. The predicted protein products are shown, and alignment is based on predicted domain structures. Conserved cysteine residues in disulphate bridge formation are underlined.

From the N-terminus towards the C-terminus these domains can be defined as the signal sequence, the extracellular region consisting of respectively a leucine zipper domain, a disulphate bridge domain, an leucine rich repeat domain with 3-5 leucine rich repeats, a putative hydroxyproline domain involved in O-glycosylation, a single transmembrane domain, an intracellular region consisting of respectively an anchor domain, a serine/threonine kinase domain, a domain with unknown function and at the C-terminus a sequence resembling an intracellular leucine rich repeat.

FIG. 8A

*Arabidopsis thaliana* RKS1 cDNA

The start codon has been indicated by bold capitals.

FIG. 8B

Predicted amino acid sequence of the *Arabidopsis thaliana* RKS-1 protein. Different domains are spaced and shown from the N-terminus towards the C-terminus Overall domain structure is similar as described in Schmidt et al. (1997). At the predicted extracellular domain the first domain represents a signal sequence.

The second domain contains a leucine zipper motif, containing 3 leucine residues, each separated by 7 other amino acids. The third domain contains conserved cysteine residues, involved in disulphate bridge formation.

The fourth-domain contains a leucine rich repeat domain, consisting of 3 complete repeats of each approximately 24 amino acid residues.

The fifth domain contains many serine and proline residues, and is likely to contain hydroxy-proline residues, and to be a site for O-glycosylation.

The sixth domain contains a single transmembrane domain after which the predicted intracellular domains are positioned.

The seventh domain has an unknown function.

The eight domain represents a serine/threonine protein kinase domain (Schmidt et al. 1997), and is probably also containing sequences for protein, protein interactions.

The ninth domain has an unknown function.

The last and tenth domain at the C-terminal end represents a single leucine rich repeat, probably involved in protein, protein interactions.

FIG. 9A

*Arabidopsis thaliana* RKS2 cDNA. The start codon has been indicated by bold capitals.

FIG. 9B

Predicted amino acid sequence of the *Arabidopsis thaliana* RKS-14 protein. Different domains are spaced and shown from the N-terminus towards the C-terminus, Overall domain structure is similar as described in Schmidt et al. (1997). At the predicted extracellular domain the first domain represents a signal sequence.

The second domain contains a leucine zipper motif, containing 2 leucine residues, each separated by 7 other amino acids. The third domain contains conserved cysteine residues, involved in disulphate bridge formation.

The fourth domain contains a leucine rich repeat domain, consisting of 4 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997), and is probably also containing sequences for protein, protein interactions. The ninth domain has an unknown function. The last and tenth domain at the C-terminal end represents a single leucine rich repeat, probably involved in protein, protein interactions.

FIG. 10A

*Arabidopsis thaliana* RKS3 cDNA The start codon has been indicated by bold capitals.

FIG. 10B

Predicted amino acid sequence of the *Arabidopsis thaliana* RKS-3 protein. Different domains are spaced and shown from the N-terminus towards the C-terminus. Overall domain structure is similar as described in Schmidt et al. (1997). At the predicted extracellular domain the first domain represents a signal sequence.

The second domain contains a leucine zipper motif, containing 3 leucine evenly residues, each separated by 7 other amino acids. The third domain contains conserved cysteine residues, involved in disulphate bridge formation. The fourth domain contains a leucine rich repeat domain, consisting of 4 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997), and is probably also containing sequences for protein, protein interactions. The ninth domain has an unknown function. The last and tenth domain at the C-terminal end represents a single leucine rich repeat, probably involved in protein, protein interactions.

FIG. 11A

*Arabidopsis thaliana* RKS4 cDNA

The start codon has been indicated by bold capitals.

FIG. 11B

Predicted amino acid sequence of the *Arabidopsis thaliana* RKS-4 protein. Different domains are spaced and shown from the N-terminus towards the C-terminus. Overall domain structure is similar as described in Schmidt et al. (1997). At the predicted extracellular domain the first domain represents a signal sequence.

The second domain contains a leucine zipper motif, containing 2 leucine residues, each separated by 7 other amino acids. The third domain contains conserved cysteine residues, involved in disulphate bridge formation.

The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997), and is probably also containing sequences for protein, protein interactions. The ninth domain has an unknown function. The last and tenth domain at the C-terminal end represents a single leucine rich repeat, probably involved in protein, protein interactions.

FIG. 12A

*Arabidopsis thaliana* RKS5 cDNA. The start codon has been indicated by bold capitals.

FIG. 12B

Predicted amino acid sequence of the *Arabidopsis thaliana* RKS-5 protein. Different domains are spaced and shown from the N-terminus towards the C-terminus. Overall domain structure is similar as described in Schmidt et al. (1997). At the predicted extracellular domain the first domain represents a signal sequence.

The second domain contains a leucine zipper motif, containing 2 leucine residues, each separated by 7 other amino acids. The third domain contains conserved cysteine residues, involved in disulphate bridge formation.

The fourth domain contains a leucine rich repeat domain, consisting of 4 complete repeats of each approximately 24 amino acid residues. The fifth domain has no clear function. The sixth domain contains a single transmembrane domain after which the predicted intracellular domains are positioned. The seventh domain has an unknown function. The eight domain represents a serine/threonine protein kinase domain (Schmidt et al. 1997), and is probably also containing sequences for protein, protein interactions. The ninth domain has an unknown function. The last and tenth domain at the C-terminal end represents a single leucine rich repeat, probably involved in protein, protein interactions.

FIG. 13A

*Arabidopsis thaliana* RKS6 cDNA. The start codon has been indicated by bold capitals.

FIG. 13B

Predicted amino acid sequence of the *Arabidopsis thaliana* RKS-6 protein. Different domains are spaced and shown from the N-terminus towards the C-terminus. Overall domain structure is similar as described in Schmidt et al. (1997). At the predicted extracellular domain the first domain represents a signal sequence.

The second domain contains a leucine zipper motif, containing 3 leucine residues, each separated by 7 other amino acids. The third domain contains conserved cysteine residues, involved in disulphate bridge formation.

The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned.

The seventh domain has an unknown function. The eight domain represents a serine/threonine protein kinase domain (Schmidt et al. 1997), and is probably also containing sequences for protein, protein interactions.

The ninth domain has an unknown function.

The last and tenth domain at the C-terminal end represents a single leucine rich repeat, probably involved in protein, protein interactions.

FIG. 14A

*Arabidopsis thaliana* RKS8 cDNA.

The start codon has been indicated by bold capitals.

FIG. 14B

Predicted amino acid sequence of the *Arabidopsis thaliana* RKS-8 protein. Different domains are spaced and shown from the N-terminus towards the C-terminus. Overall domain structure is similar as described in Schmidt et al. (1997). At the predicted extracellular domain the first domain represents a signal sequence.

The second domain contains a leucine zipper motif, containing 4 leucine evenly spaced residues, each separated by 7 other amino acids. The third domain contains conserved cysteine residues, involved in disulphate bridge formation.

The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation.

The sixth domain contains a single transmembrane domain after which the predicted intracellular domains are positioned. The seventh domain has an unknown function.

The eight domain represents a serine/threonine protein kinase domain (Schmidt et al. 1997), and is probably also containing sequences for protein, protein interactions.

The ninth domain has an unknown function. The last and tenth domain at the C-terminal end represents a single leucine rich repeat, probably involved in protein, protein interactions.

FIG. 15A

Arabidopsis thaliana RKS 10 cDNA. The start codon has been indicated by bold capitals.

FIG. 15B

Predicted amino acid sequence of the Arabidopsis thaliana RKS-10 protein. Different domains are spaced and shown from the N-terminus towards the C-terminus. Overall domain structure is similar as described in Schmidt et al. (1997). At the predicted extracellular domain the first domain represents a signal sequence.

The second domain contains a leucine zipper motif, containing 4 leucine residues, each separated by 7 other amino acids. The third domain contains conserved cysteine residues, involved in disulphate bridge formation.

The fourth domain contains a leucine rich repeat domain, consisting of 4 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned.

The seventh domain has an unknown function.

The eight domain represents a serine/threonine protein kinase domain (Schmidt et al. 1997), and is probably also containing sequences for protein, protein interactions.

The ninth domain has an unknown function.

The last and tenth domain at the C-terminal end represents a single leucine rich repeat, probably involved in protein, protein interactions.

FIG. 16A

Arabidopsis thaliana RKS11 cDNA/. The start codon has been indicated by bold capitals.

FIG. 16B

Predicted amino acid sequence of the Arabidopsis thaliana RKS-11 protein. Different domains are spaced and shown from the N-terminus towards the C-terminus. Overall domain structure is similar as described in Schmidt et al. (1997). At the predicted extracellular domain the first domain represents a signal sequence. The second domain contains a leucine zipper motif, containing 3 leucine residues, each separated by 7 other amino acids.

The third domain contains conserved cysteine residues, involved in disulphate bridge formation. The fourth domain contains a leucine rich repeat domain, consisting of 3 complete repeats of each approximately 24 amino acid residues.

The fifth domain contains many serine and proline residues, and is likely to contain hydroxy-proline residues, and to be a site for O-glycosylation.

The sixth domain contains a single transmembrane domain after which the predicted intracellular domains are positioned. The seventh domain has an unknown function.

The eight domain represents a serine/threonine protein kinase domain (Schmidt et al. 1997), and is probably also containing sequences for protein, protein interactions.

The ninth domain has an unknown function. The last and tenth domain at the C-terminal end represents a single leucine rich repeat, probably involved in protein, protein interactions.

FIG. 17A

Arabidopsis thaliana RKS12 cDNA. The start codon has been indicated by bold capitals.

FIG. 17B

Predicted amino acid sequence of the Arabidopsis thaliana RKS-12 protein. Different domains are spaced and shown from the N-terminus towards the C-terminus. Overall domain structure is similar as described in Schmidt et al. (1997). At the predicted extracellular domain the first domain represents a signal sequence.

The second domain contains a leucine zipper motif, containing 2 leucine residues, each separated by 7 other amino acids. The third domain contains conserved cysteine residues, involved in disulphate bridge formation.

The fourth domain contains a leucine rich repeat domain, consisting of 4 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned.

The seventh domain has an unknown function.

The eight domain represents a serine/threonine protein kinase domain (Schmidt et al. 1997), and is probably also containing sequences for protein, protein interactions.

The ninth domain has an unknown function.

The last and tenth domain at the C-terminal end represents a single leucine rich repeat, probably involved in protein, protein interactions.

FIG. 18A

Arabidopsis thaliana RKS13 cDNA. The start codon has been indicated by bold capitals.

FIG. 18B

Predicted amino acid sequence of the Arabidopsis thaliana RKS-13 protein. Different domains are spaced and shown from the N-terminus towards the C-terminus. Overall domain structure is similar as described in Schmidt et al. (1997). At the predicted extracellular domain the first domain represents a signal sequence.

The second domain contains a leucine zipper motif, containing 4 leucine residues, each separated by 7 other amino acids. The third domain contains conserved cysteine residues, involved in disulphate bridge formation.

The fourth domain contains a leucine rich repeat domain, consisting of 4 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997), and is probably also containing sequences for protein, protein interactions. The ninth domain has an unknown function. The last and tenth domain at the C-terminal end represents a single leucine rich repeat, probably involved in protein, protein interactions.

FIG. 19A

Arabidopsis thaliana RKS14 cDNA. The start codon has been indicated by bold capitals.

FIG. 19B

Predicted amino acid sequence of the Arabidopsis thaliana RKS-14 protein. Different domains are spaced and shown from the N-terminus towards the C-terminus. Overall domain structure is similar as described in Schmidt et al. (1997). At the predicted extracellular domain the first domain represents a signal sequence. The second domain contains a leucine zipper motif, containing 2 leucine residues, each separated by 7 other amino acids.

The third domain contains conserved cysteine residues, involved in disulphate bridge formation. The fourth domain contains a leucine rich repeat domain, consisting of 4 complete repeats of each approximately 24 amino acid residues.

The fifth domain contains many serine and proline residues, and is likely to contain hydroxy-proline residues, and to be a site for O-glycosylation.

The sixth domain contains a single transmembrane domain after which the predicted intracellular domains are positioned. The seventh domain has an unknown function.

The eight domain represents a serine/threonine protein kinase domain (Schmidt et al. 1997), and is probably also containing sequences for protein, protein interactions.

The ninth domain has an unknown function. The last and tenth domain at the C-terminal end represents a single leucine rich repeat, probably involved in protein, protein interactions.

FIG. 20A

*Arabidopsis thaliana* RKS 7 partial cDNA sequence.

The 5'-end and a region between the two cDNA fragments ( . . . ) is not shown.

FIG. 20B

Predicted partial amino acid sequences of the *Arabidopsis thaliana* RKS-7 protein. Different domains are spaced and shown from the N-terminus towards the C-terminus. Overall domain structure is similar as described in Schmidt et al. (1997). The protein sequence is obtained from partial cDNA sequences. The first available domain represents part of a serine/threonine protein kinase domain (Schmidt et al. 1997), and is probably also containing sequences for protein, protein interactions. The next domain has an unknown function. The last domain at the C-terminal end represents a single leucine rich repeat, probably involved in protein, protein interactions.

FIG. 21A

*Arabidopsis thaliana* RKS 9 partial cDNA sequence.

The 5'-end is not shown.

FIG. 21B

Predicted amino acid sequence of the *Arabidopsis thaliana* RKS-9 protein. Different domains are spaced and shown from the N-terminus towards the C-terminus. Overall domain structure is similar as described in Schmidt et al. (1997). The protein sequence is obtained from partial cDNA sequences. The first available domain represents part of a serine/threonine protein kinase domain (Schmidt et al. 1997), and is probably also containing sequences for protein, protein interactions. The next domain has an unknown function. The last domain at the C-terminal end represents a single leucine rich repeat, probably involved in protein, protein interactions.

FIG. 22A

*Arabidopsis thaliana* RKS 15 partial cDNA sequence.

The 5'-end is not shown.

FIG. 22B

Predicted amino acid sequence of the *Arabidopsis thaliana* RKS-15 protein. Different domains are spaced and shown from the N-terminus towards the C-terminus. Overall domain structure is similar as described in Schmidt et al. (1997). The protein sequence is obtained from partial cDNA sequences. The first available domain represents part of a serine/threonine protein kinase domain (Schmidt et al. 1997), and is probably also containing sequences for protein, protein interactions. The next domain has an unknown function. The last domain at the C-terminal end represents a single leucine rich repeat, probably involved in protein, protein interactions.

FIG. 23A

*Arabidopsis thaliana* RKS 16 partial cDNA sequence.

The 5'-end is not shown.

FIG. 23B

Predicted amino acid sequence of the *Arabidopsis thaliana* RKS-16 protein. Different domains are spaced and shown from the N-terminus towards the C-terminus. Overall domain structure is similar as described in Schmidt et al. (1997). The protein sequence is obtained from partial cDNA sequences. The first available domain represents part of a serine/threonine protein kinase domain (Schmidt et al. 1997), and is probably also containing sequences for protein, protein interactions. The next domain has an unknown function. The last domain at the C-terminal end represents a single leucine rich repeat, probably involved in protein, protein interactions.

The invention claimed is:

1. An isolated and/or recombinant nucleic acid comprising the sequence set forth in SEQ ID NO: 40.

2. The isolated and/or recombinant nucleic acid according to claim 1, wherein said nucleic acid is derived from *Arabidopsis thaliana*.

3. A vector comprising a nucleic acid according to claim 1.

4. The vector comprising a nucleic acid according to claim 2.

5. An isolated host cell comprising a nucleic acid according to claim 1, or a vector according to claim 3.

6. A method for propagating a plant comprising:
 a) introducing the nucleic acid of claim 1 into a plant wherein the nucleic acid is operably linked to a promoter and is expressed in the plant,
 b) culturing staffing material from said plant on media lacking phytohormones and
 c) regenerating a plant from said cultured starting material.

* * * * *